United States Patent
Brodeur et al.

(10) Patent No.: US 9,840,543 B2
(45) Date of Patent: Dec. 12, 2017

(54) ANTI-BAFF ANTIBODIES

(71) Applicant: Boehringer Ingelheim International GmbH, Ingelheim am Rhein (DE)

(72) Inventors: Scott Ronald Brodeur, Guilford, CT (US); Keith Canada, Southbury, CT (US); Mlchael Dziegelewski, Newburgh, NY (US); Philip Nicholas Gorman, Prospect, CT (US); Pankaj Gupta, Scarsdale, NY (US); Ashraf Khalil, Hamden, CT (US); John James Miglietta, Bethel, CT (US); Amy Marie Nicoletti, Derby, CT (US); Qi Pan, Chappaqua, NY (US); David Presky, Goldens Bridge, NY (US); Sanjaya Singh, Sandy Hook, CT (US); Tao Wu, Danbury, CT (US); Haiguang Xiao, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 151 days.

(21) Appl. No.: 14/609,756

(22) Filed: Jan. 30, 2015

(65) Prior Publication Data
US 2015/0218267 A1   Aug. 6, 2015

Related U.S. Application Data

(60) Provisional application No. 61/934,124, filed on Jan. 31, 2014.

(51) Int. Cl.
| | |
|---|---|
| A61K 39/395 | (2006.01) |
| C07K 16/18 | (2006.01) |
| C07K 16/24 | (2006.01) |
| C07K 16/28 | (2006.01) |
| C07K 14/475 | (2006.01) |
| C07K 14/435 | (2006.01) |
| C07K 14/525 | (2006.01) |
| C07K 14/715 | (2006.01) |
| A61K 39/00 | (2006.01) |

(52) U.S. Cl.
CPC ........ *C07K 14/475* (2013.01); *A61K 39/3955* (2013.01); *C07K 16/241* (2013.01); *C07K 16/2875* (2013.01); *A61K 2039/505* (2013.01); *C07K 16/18* (2013.01); *C07K 2316/96* (2013.01); *C07K 2317/24* (2013.01); *C07K 2317/34* (2013.01); *C07K 2317/56* (2013.01); *C07K 2317/565* (2013.01); *C07K 2317/76* (2013.01); *C07K 2317/92* (2013.01)

(58) Field of Classification Search
CPC ........ A61K 2039/505; A61K 39/39558; A61K 2039/545; A61K 2039/572; A61K 39/00; A61K 39/395; A61K 39/39533; C07K 2317/92; C07K 2317/34; C07K 2317/73; C07K 2317/24; C07K 2317/732; C07K 2317/31; C07K 2317/565; C07K 2317/76; C07K 2317/56; C07K 2319/43; C07K 2316/96; C07K 16/22; C07K 16/24
See application file for complete search history.

(56) References Cited

U.S. PATENT DOCUMENTS

| | | | | |
|---|---|---|---|---|
| 6,403,770 | B1 * | 6/2002 | Yu | C07H 21/04 435/69.5 |
| 6,635,482 | B1 * | 10/2003 | Yu | C07H 21/04 435/326 |
| 6,869,605 | B2 | 3/2005 | Browning et al. | |
| 7,317,089 | B2 * | 1/2008 | Kikly | C07K 16/2875 530/351 |
| 7,846,662 | B2 | 12/2010 | Takeuchi et al. | |
| 8,303,951 | B2 * | 11/2012 | Yu | C07H 21/04 424/130.1 |
| 2005/0070694 | A1 | 3/2005 | Gelfanova et al. | |
| 2013/0280256 | A1 | 10/2013 | Allan et al. | |
| 2014/0213470 | A1 | 7/2014 | Hsu et al. | |
| 2014/0302036 | A1 | 10/2014 | Hsu et al. | |
| 2015/0218267 | A1 | 8/2015 | Brodeur et al. | |

OTHER PUBLICATIONS

Baker et al. Generation and characterization of Lymphostat-B, a human monoclonal antobdy that antagonizes the bioactivities of B Lymphocyte Stimulator. Arthritis Rheumatism 48(11): 3253-3265, 2003.*

Stohl, W. Biologic differences between various inhibitors of the BLyS/BAFF pathway: Should we expect differences between belimumab and other inhibitors in development? Curr Rheumatol Rep 14: 303-309, 2012.*

Stohl, W. Therapeutic targeting of the BAFF/APRIL axis in systemic lupus erythematosus. Expert Opin Ther Targets 18(4): 473-489, 2014.*

Vincent et al. The BAFF/APRIL system: Emerging functions beyond B cell biology and autoimmunity. Cytokine Growth Factor Reviews 24: 203-215, 2013.*

Hsu, H. et al., "A novel modality of BAFF-specific inhibitor AMG623 peptibody reduces B-cell number and improves outcomes in murine models of autoimmune disease." Clinical and Experimental Rheumatology, 2012, vol. 30, No. 2, pp. 197-201.

International Search Report and Written Opinion for PCT/US2015/013711 mailed Nov. 17, 2015.

Liu, Z. et al., "BAFF inhibition: A new class of drugs for the treatment of autoimmunity." Experimental Cell Research, 2011, vol. 317, No. 9, pp. 1270-1277.

Mackay, F. et al., "Cracking the BAFF code." The Journal of Immunology, 2009, vol. 9, No. 7, pp. 491-502.

(Continued)

*Primary Examiner* — Bridget E Bunner
(74) *Attorney, Agent, or Firm* — Marc A. Began; Atabak R. Royaee

(57) ABSTRACT

The present invention relates to anti-BAFF antibody molecules, including novel humanized anti-BAFF antibodies, therapeutic and diagnostic methods and compositions for using the same.

15 Claims, 2 Drawing Sheets

(56) References Cited

OTHER PUBLICATIONS

Manetta, J. et al., "Generation and characterization of tabalumab, a human monoclonal antibody that neutralizes both soluble and membrane-bound B-cell activating factor." Journal of Inflammation Research, 2014, pp. 121-131.
Stohl, W. et al., "Treatment of systemic lupus erythematosus patients with the BAFF antagonist "peptibody" blisibimod (AMG 623/A-623): results from randomized, double-blind phase 1a and phase 1b trials." Arthritis Research & Therapy, 2015, vol. 6, No. 1, pp. 1-14.
Karpusas, M. et al., "Crystal Structure of Extracellular Human BAFF, a TNF Family Member that Stimulates B Lymphocytes." Journal of Molecular Biology, 2002, vol. 315, pp. 1145-1154.
Al-Lazikani, Bissan et al. "Standard Conformations for the Canonical Structures of Immunoglobulins" (1997) Journal of Molecular Biology, vol. 273, 927-948.
Altschul, Stephen F. et al "Gapped BLAST and PSI-BLAST: a new generation of protein database search programs" (1997) Nucleic Acids Research, vol. 25, No. 17, 3389-3402.
Altschul, Stephen F. et al. "Basic Local Alignment Search Tool" (1990) Journal of molecular biology, vol. 215, 403-410.
Barnes, David et al. "Methods for Growth of Cultured Cells in Serum-Free Medium" (1980) Analytical Biochemistry, vol. 102, 255-270.
Brennan, Maureen et al. "Preparation of Bispecific Antibodies by Chemical Recombination of Monoclonal Immunoglobulin G1 Fragments" (1985) Science, vol. 229, 81-83.
Buchwald, Henry et al. "Long-term, continuous intravenous heparin administration by an implantable infusion pump in ambulatory patients with recurrent venous thrombosis" (1980) Surgery, 507-516.
Caron, Philip C. et al. "Engineered Humanized Dimeric Forms of IgG are More Effective Antibodies" (1992), Journal of Experimental Medicine, vol. 176, 1191-1195.
Carter, Paul et al. "High Level *Escherichia Coli* Expression and Production of a Bivalent Humanized Antibody Fragment" (1992) Nature, Biotechnology vol. 10, 163-167.
Chothia, Cyrus "Domain Association in Immunoglobulin Molecules the Packing of Variable Domains" (1985) Journal of Molecular Biology, vol. 186, 651-663.
Chothia, Cyrus et al. "Canonical Structures for the Hypervariable Regions of Immunoglobulins" (1987) Journal of Molecular Biology, vol. 196, 901-917.
Clackson, Tim et al. "Making antibody fragments using phage display libraries" (1991) Nature, vol. 352, 624-628.
Cunningham, Brian C. et al. "High-Resolution Epitope Mapping of hGH-Receptor Interactions by Alanine-Scanning Mutagenesis" (1989) Science, vol. 244, 1081-1085.
During, Matthew J. et al. "Controlled Release of Dopamine from a Polymeric Brain Implant: In Vivo Characterization" (1989) Annals of Neurology, vol. 25, No. 4, 351-356.
Edge, Albert S.B. et al. "Deglycosylation of Glycoproteins by Trifluoromethanesulfonic Acid" (1981) Analytical Biochemistry, vol. 118, 131-137.
Eppstein, Deborah A. et al. "Biological activity of liposome-encapsulated murine interferon y is mediated by a cell membrane receptor" (1985) Proc. Natl. Acad. Sci. USA, vol. 82, 3688-3692.
Evan, Gerald I. et al. "Isolation of Monoclonal Antibodies Specific for Human c-myc Proto-Oncogene Product" (1985) Molecular and Cellular Biology, vol. 5, 3610-3616.
Field, Jeffrey et al. "Purification of a RAS-Responsive Adenylyl Cyclase Complex from Saccharomyces cerevisiae by Use of an Epitope Addition Method" (1988) Molecular and Cellular Biology, vol. 8, 2159-2165.
Fleer, R. et al. "Stable Multicopy Vectors for High-Level Secretion of Recombinant Human Serum Albumin by <Kluyveromyces Yeasts" (1991) Nature Biotechnology, vol. 9, 968-975.
Graham, F.L. et al. "Characteristics of a Human Cell Line Transformed by DNA from Human Adenovirus Type 5" (1977) J. Gen. Viral., vol. 36, 59-72.
Guss, Bengt et al. "Structure of the IgG-binding regions of *streptococcal* protein G" (1986) The EMBO Journal, vol. 5, 1567-1575.
Ham, Richard G. et al. "[5] Media and Growth Requirements" (1979) Methods in Enzymology, vol. LVIII, 44-93.
Hezareh, Marjan et al "Effector Function Activities of a Panel of Mutants of a Broadly Neutralizing Antibody against Human Immunodeficiency Virus Type 1" (2001) Journal of Virology, vol. 75, No. 24, 12161-12168.
Higgins, Desmond G. et al. "[22] Using CLUSTAL for Multiple Sequence Alignments" (1996) Methods in Enzymology, vol. 266, 383-402.
Holliger, Philipp et al. "Diabodies: Small bivalent and bispecific antibody fragments" (1993) Proc. Natl. Acad. Sci. USA, vol. 90, 6444-6448.
Hwang, Karl J. et al. "Hepatic uptake and degradation of unilamellar sphingomyelin/cholesterol liposomes: A kinetic study", (1980) Proc. Natl. Acad. Sci. USA, vol. 77, No. 7, 4030-4034.
Karlin, Samuel et al. "Methods for assessing the statistical significance of molecular sequence features by using general scoring schemes" (1990) Proc. Natl. Acad. Sci. USA, vol. 87, 2264-2268.
Karlin, Samuel et al. "Applications and statistics for multiple high-scoring segments in molecular sequences" (1993), Proc. Natl. Acad. Sci. USA, vol. 90, 5873-5877.
Kohler, G. et al. "Continuous cultures of fused cells secreting antibody of predefined specificity" (1975) Nature, vol. 256, 495-497.
Langer, Robert et al. "Chemical and Physical Structure of Polymers as Carriers for Controlled Release of Bioactive Agents: A Review" (1983) Journal of Macromolecular Science, Part C, 61-126.
Langer, Robert "New Methods of Drug Delivery" (1990), Science, vol. 249, 1527-1533.
Lefranc, Marie-Paule et al. "IMGT unique numbering for immunoglobulin and T cell receptor variable domains and Ig superfamily V-like domains" (2003) Developmental and Comparative Immunology, vol. 27, 55-77.
Levy, Robert J. et al. "Inhibition of Calcification of Bioprosthetic Heart Valves by Local Controlled-Release Diphosphonate" (1985) Science, vol. 228, 190-192.
Lindmark, Roger et al. "Binding of Immunoglobulins to Protein A and Immunoglobulin Levels in Mammalian Sera" (1983) Journal of Immunological Methods, vol. 62, 1-13.
Manetta, Joseph et al. "Generation and characterization of tabalumab, a human monoclonal antibody that neutralizes both soluble and membrane-bound B-cell activating factor" (2014) Journal of Inflammation Research, vol. 7, 121-131.
Marks, James D. et al. "By-passing Immunization Human Antibodies from V-gene Libraries Displayed on Phage" (1991) Journal of Molecular Biology, vol. 222, 581-597.
Martin, Francis J. et al. "Irreversible Coupling of Immunoglobulin Fragments to Preformed Vesicles" (1982) The Journal of Biological Chemistry, vol. 257, 286-288.
Massey, R.J. et al. "Catalytic antibodies catching on" (1987) Nature, vol. 328, 457-458.
Mather, Jennie P. "Establishment and Characterization of Two Distinct Mouse Testicular Epithelial Cell Lines" (1980) Biology of Reproduction, vol. 23, 243-252.
Mather, Jennie P. et al. "Culture of Testicular Cells in Hormone-Supplemented Serum-Free Medium" (1982), Annals New York Academy of Sciences, 44-68.
Morimoto, Koichi et al. "Single-step purification of F(ab')2 fragments of mouse monoclonal antibodies (immunoglobulins G1) by hydrophobic interaction high performance liquid chromatography using TSKgel Phenyl-5PW" (1992) Journal of Biochemical and Biophysical Methods, vol. 24, 107-117.
Morrison, Sherie L. et al. "Chimeric human antibody molecules: Mouse antigen-binding domains with human constant region domains" (1984) Proc. Natl. Acad. Sci. USA, vol. 81, 6851-6855.

(56) References Cited

OTHER PUBLICATIONS

Neuberger, Michael S. et al. "Recombinant antibodies possessing novel effector functions" (1984) Nature, vol. 312, 604-608.

Nicolaou, K.C. et al. "Calicheamicin 0I1: a Rationally Designed Molecule with Extremely Potent and Selective DNA Cleaving Properties and Apoptosis Inducing Activity" (1994) Angew. Chem. Int. Ed. Engl., vol. 33, No. 2, 183-186.

Pearson, William R. et al. "Improved tools for biological sequence comparison" (1988) Proc. Natl. Acad. Sci. USA, vol. 85, 2444-2448.

Reyes, Gregory R. et al. "Expression of human β-interferon cDNA under the control of a thymidine kinase promoter from herpes simplex virus" (1982) Nature, vol. 297, 598-601.

Saudek, Christopher D. et al. "A Preliminary Trail of the Programmable Implantable Medication System for Insulin Delivery" (1989) The New England Journal of Medicine, vol. 321, No. 9, 574-579.

Sefton, Michael V. et al. "Implantable Pumps" (1989) CRC Critical Reviews in Biomedical Engineering, vol. 14, Issue 3, 201-240.

Shopes, Bob "A Genetically Engineered Human IgG Mutant with Enhanced Cytolytic Activity" (1992) The Journal of Immunology, vol. 148, 2918-2922.

Sojar, Hakimuddin T. et al. "A Chemical Method for the Deglycosylation of Proteins" (1987) Archives of Biochemistry and Biophysics, vol. 259, No. 1, 52-57.

Stinchcomb, D.T. et al. "Isolation and characterisation of a yeast chromosomal replicator" (1979) Nature, vol. 282, 39-43.

Thotakura, Nageswara R. et al. "[28] Enzymatic Deglycosylation of Glycoproteins" (1987) Methods in Enzymology, vol. 138, 350-359.

Torelli, Alberto et al. "ADVANCE and ADAM: two algorithms for the analysis of global similarity between homologous informational sequences" (1994) CABIOS, vol. 10, No. 1, 3-5.

Urlaub, Gail et al. "Isolation of Chinese hamster cell mutants deficient in dihydrofolate reductase activity" (1980) Proc. Natl. Acad. Sci. USA, vol. 77, No. 7, 4216-4220.

Vandenberg, Johan A. et al. "Kluyveromyces as a Host for Heterologous Gene Expression: Expression and Secretion of Prochymosin" (1990) Nature Biotechnology, vol. 8, 135-139.

Vitetta, Ellen S. et al. "Redesigning Nature's Poisons to Create Anti-Tumor Reagents" (1987) Science, vol. 238, 1098-1104.

Wolff, Edith A. et al. "Monoclonal Antibody Homodimers: Enhanced Antitumor Activity in Nude Mice" (1993) Cancer Research, vol. 53, 2560-2565.

Yaniv, Moshe "Enhancing elements for activation of eukaryotic promoters" (1982) Nature, vol. 297, 17-18.

\* cited by examiner

ANTI-BAFF ANTIBODIES

SEQUENCE LISTING

The instant application contains a Sequence Listing which has been submitted electronically in ASCII format and is hereby incorporated by reference in its entirety. Said ASCII copy, created on Jan. 30, 2015, is named 09-0625-US-2_SL.txt and is 256,600 bytes in size.

TECHNICAL FIELD OF THE INVENTION

This invention generally relates to anti-BAFF antibodies for diagnostic and therapeutic use. More specifically, anti-BAFF antibodies and methods for treating various diseases or disorders are disclosed. Pharmaceutical compositions and kits comprising such compounds are also disclosed.

BACKGROUND OF THE INVENTION

B-cell activating factor (BAFF) is a cytokine that belongs to the tumor necrosis factor (TNF) ligand superfamily and acts as a ligand for receptors BAFF-R (BR3), TACI (transmembrane activator and calcium modulator and cyclophilin ligand interactor) and BCMA (B-cell maturation antigen). The interaction between BAFF and its receptors triggers signals essential for the formation and maintenance of B cells, which in turn synthesizes immunoglobulins in response to invasion by a foreign substance. Appropriate levels of BAFF in a patient help maintain normal levels of immunity whereas inadequate levels can lead to immunodeficiency and excessive levels can result in abnormally high antibody production.

When a patient exhibits autoimmunity, it produces antibodies against the tissues or organs of its own body. Autoimmune diseases, including lupus erythematosus and rheumatoid arthritis, result from excessive levels of BAFF in the body. Thus it is important to modulate the production of BAFF in order to treat the patients having these diseases.

BAFF can exist in three forms: membrane bound (mbBAFF), soluble trimeric BAFF (sBAFF) and a multimeric form consisting of 60 BAFF monomers. The relative importance of the various forms of BAFF in normal and disease physiology is not well understood. As noted, BAFF binds to three receptors, BAFFR (BR3), TACI and BCMA. A proliferation-inducing ligand (APRIL), a related member of the TNF receptor ligand family, has been shown to bind with high affinity to TACI and BCMA. In contrast to the high affinity APRIL:BCMA interaction, the BAFF:BCMA interaction is of low affinity (1-2 µM) and is not believed to be play an important role in vivo (Bossen and Schneider, 2006).

Soluble BAFF is expressed at high levels in individuals with systemic lupus erythematosus (SLE) and in inflamed target organs such as the kidney. Soluble BAFF serves as a critical factor for B cell homeostasis and survival (Kalled et al., 2005; Mackay et al., 2003; Smith and Cancro, 2003; Patke et al., 2004). Autoantibody formation by BAFF-dependent B cells results in glomerular IC deposits, initially at the glomerular basement membrane (GBM), mesangium and interstitial tissue within the proximal tubular epithelial cells (PTEC). These IC deposits lead to complement fixation and neutrophil activation resulting in local kidney damage. Inflammatory mediators (e.g. IL6, IL8, MCP-1) produced by the damaged kidney cells (MC, PTEC, renal fibroblasts, endothelial cells) fuel an inflammatory cycle by increasing immune cell infiltration (e.g. B cells, T cells, dendritic cells, neutrophils and macrophages).

Anti-BAFF monoclonal antibody belimumab (Benlysta®) has demonstrated activity in the treatment of systemic lupus erythematosus (SLE) and has the demonstrated ability to decrease autoantibody formation. Belimumab is currently approved for the treatment of active SLE without kidney involvement. Belimumab, however, is not reported to bind to mbBAFF but inhibition of sBAFF only is therefore a viable path to treat excessive levels of BAFF and increased antibody production. In contrast, the anti-BAFF peptibody blisibimod (A-623) and the anti-BAFF mAb tabalumab (LY2127399) have been reported to bind both sBAFF and mbBAFF (2010 Anthera press release and 2012 Lilly press release). Given the uncertain roles for various forms of BAFF in disease, antagonist molecules against sBAFF and mbBAFF with beneficial pharmacologic properties may possess added benefit in the treatment of immunological and autoimmune diseases in humans.

BRIEF SUMMARY OF THE INVENTION

The present invention relates to novel anti-BAFF antibodies for treatment of immunological and autoimmune diseases, including, but not limited to, systemic lupus erythematosus, lupus nephritis and rheumatoid arthritis. The anti-BAFF antibodies of this invention bind to human BAFF with high affinity thus inhibiting abnormally high immunoglobulin production. In one embodiment of the invention anti-BAFF antibodies are derived from mouse hybridomas, for example monoclonal antibodies. Another embodiment includes full length anti-BAFF antibodies. In yet another embodiment, the present invention provides anti-BAFF human antibodies, including full-length humanized monoclonal anti-BAFF antibodies. Further embodiments encompass DNA molecules encoding antibodies of the present invention, expression vectors and host cells comprising such DNA molecules, and methods of making antibodies of the present invention. The present invention further provides therapeutic uses for the antibodies of the present invention, in particular immunological and autoimmune diseases.

In one embodiment, the invention provides an anti-BAFF antibody molecule comprising a light chain variable domain with a CDR1 selected from the group consisting of SEQ ID NO: 1, SEQ ID NO: 5, SEQ ID NO: 10, SEQ ID NO: 13, SEQ ID NO: 15, SEQ ID NO: 76, SEQ ID NO: 77, SEQ ID NO: 78, SEQ ID NO: 79, SEQ ID NO: 80, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274 and SEQ ID NO: 275; a CDR2 selected from the group consisting of SEQ ID NO: 2, SEQ ID NO: 6, SEQ ID NO: 8, SEQ ID NO: 11, SEQ ID NO: 16, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291 and SEQ ID NO: 292; and a CDR3 selected from the group consisting of SEQ ID NO: 3, SEQ ID NO: 4, SEQ ID NO: 7, SEQ ID NO: 9, SEQ ID NO: 12, SEQ ID NO:14, SEQ ID NO: 17, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310 and SEQ ID NO: 311; and a heavy chain variable domain with a CDR1 selected from the group consisting of SEQ ID NO: 18, SEQ ID NO: 21, SEQ ID NO: 23, SEQ ID NO: 25, SEQ ID NO: 28, SEQ ID NO: 31, SEQ ID NO: 34, SEQ ID NO: 36, SEQ ID NO: 37, SEQ ID NO: 81, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 392, SEQ ID NO: 333, SEQ ID NO: 334, SEQ ID NO: 335 and SEQ ID NO: 336; a CDR2 selected from the group consisting of SEQ ID NO: 19, SEQ ID NO: 24, SEQ ID NO: 26, SEQ ID NO: 29, SEQ ID NO: 32, SEQ ID NO: 35, SEQ ID NO: 38, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 343, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366 and SEQ ID NO: 367; and a CDR3 selected from the group consisting of SEQ ID NO: 20, SEQ ID NO: 22, SEQ ID NO: 27, SEQ ID NO: 30, SEQ ID NO: 33, SEQ ID NO. 39, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 378, SEQ ID NO: 379, SEQ ID NO:380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390 and SEQ ID NO: 391.

In other embodiments, the invention provides (a) an anti-BAFF antibody molecule where the light chain variable domain comprises a CDR1 of SEQ ID NO: 1, a CDR2 of SEQ ID NO: 2 and a CDR3 of SEQ ID NO: 3 and a heavy chain variable domain comprises a CDR1 of SEQ ID NO: 18, a CDR2 of SEQ ID NO: 19 and a CDR3 of SEQ ID NO: 20; (b) an anti-BAFF antibody molecule where the light chain variable domain comprises a CDR1 of SEQ ID NO: 1, a CDR2 of SEQ ID NO: 2 and a CDR3 of SEQ ID NO: 4 and a heavy chain variable domain comprises a CDR1 of SEQ ID NO: 21, a CDR2 of SEQ ID NO: 19 and a CDR3 of SEQ ID NO: 22; (c) an anti-BAFF antibody molecule where the light chain variable domain comprises a CDR1 of SEQ ID NO: 1, a CDR2 of SEQ ID NO: 2 and a CDR3 of SEQ ID NO: 4 and a heavy chain variable domain comprises a CDR1 of SEQ ID NO: 23, a CDR2 of SEQ ID NO: 24 and a CDR3 of SEQ ID NO: 20; (d) an anti-BAFF antibody molecule where the light chain variable domain comprises a CDR1 of SEQ ID NO: 5, a CDR2 of SEQ ID NO: 6 and a CDR3 of SEQ ID NO: 7 and a heavy chain variable domain comprises a CDR1 of SEQ ID NO: 25, a CDR2 of SEQ ID NO: 26 and a CDR3 of SEQ ID NO: 27; (e) an anti-BAFF antibody molecule where the light chain variable domain comprises a CDR1 of SEQ ID NO: 5, a CDR2 of SEQ ID NO: 8 and a CDR3 of SEQ ID NO: 9 and a heavy chain variable domain comprises a CDR1 of SEQ ID NO: 28, a CDR2 of SEQ ID NO: 29 and a CDR3 of SEQ ID NO: 30; (f) an anti-BAFF antibody molecule where the light chain variable domain comprises a CDR1 of SEQ ID NO: 10, a CDR2 of SEQ ID NO: 11 and a CDR3 of SEQ ID NO: 12 and a heavy chain variable domain comprises a CDR1 of SEQ ID NO: 31, a CDR2 of SEQ ID NO: 32 and a CDR3 of SEQ ID NO: 33; (g) an anti-BAFF antibody molecule where the light chain variable domain comprises a CDR1 of SEQ ID NO: 13, a CDR2 of SEQ ID NO: 6 and a CDR3 of SEQ ID NO: 14 and a heavy chain variable domain comprises a CDR1 of SEQ ID NO: 34, a CDR2 of SEQ ID NO: 35 and a CDR3 of SEQ ID NO: 27; (h) an anti-BAFF antibody molecule where the light chain variable domain comprises a CDR1 of SEQ ID NO: 10, a CDR2 of SEQ ID NO: 6 and a CDR3 of SEQ ID NO: 7 and a heavy chain variable domain comprises a CDR1 of SEQ ID NO: 36, a CDR2 of SEQ ID NO: 26 and a CDR3 of SEQ ID NO: 27; (i) an anti-BAFF antibody molecule where the light chain variable domain comprises a CDR1 of SEQ ID NO: 15, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (j) an anti-BAFF antibody molecule where the light chain variable domain comprises a CDR1 of SEQ ID NO: 76, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (k) an anti-BAFF antibody molecule where the light chain variable domain comprises a CDR1 of SEQ ID NO: 77, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (l) an anti-BAFF antibody molecule where the light chain variable domain comprises a CDR1 of SEQ ID NO: 78, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (m) an anti-BAFF antibody molecule where the light chain variable domain comprises a CDR1 of SEQ ID NO: 79, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (n) an anti-BAFF antibody molecule where the light chain variable domain comprises a CDR1 of SEQ ID NO: 80, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (o) an anti-BAFF antibody molecule where the light chain variable domain comprises a CDR1 of SEQ ID NO: 5, a CDR2 of SEQ ID NO: 8 and a CDR3 of SEQ ID NO: 9 and a heavy chain variable domain comprises a CDR1 of SEQ ID NO: 81, a CDR2 of SEQ ID NO: 29 and a CDR3 of SEQ ID NO: 30; (p) an anti-BAFF antibody molecule where the light chain variable domain comprises a CDR1 of SEQ ID NO: 249, a CDR2 of SEQ ID NO: 276 and a CDR3 of SEQ ID NO: 293 and a heavy chain variable domain comprises a CDR1 of SEQ ID NO: 312, a CDR2 of SEQ ID NO: 337 and a CDR3 of SEQ ID NO: 368; (q) an anti-BAFF antibody molecule where the light chain variable domain comprises a CDR1 of SEQ ID NO: 250, a CDR2 of SEQ ID NO: 276 and a CDR3 of SEQ ID NO: 293 and a heavy chain variable domain comprises a CDR1 of SEQ ID NO: 312, a CDR2 of SEQ ID NO: 337 and a CDR3 of SEQ ID NO: 368; (r) an anti-BAFF antibody molecule where the light chain variable domain comprises a CDR1 of SEQ ID NO: 251, a CDR2 of SEQ ID NO: 277 and a CDR3 of SEQ ID NO: 294 and a heavy chain variable domain comprises a CDR1 of SEQ ID NO: 313, a CDR2 of SEQ ID NO: 338 and a CDR3 of SEQ ID NO: 369; (s) an anti-BAFF antibody molecule where the light chain variable domain comprises a CDR1 of SEQ ID NO: 252, a CDR2 of SEQ ID NO: 278 and a CDR3 of SEQ ID NO: 295 and a heavy chain variable domain comprises a CDR1 of SEQ ID NO: 314, a CDR2 of SEQ ID NO: 339 and a CDR3 of SEQ ID NO: 370; (t) an anti-BAFF antibody molecule where the light chain variable domain comprises a CDR1 of SEQ ID NO: 253, a CDR2 of SEQ ID NO: 279 and a CDR3 of SEQ ID NO: 296 and a heavy chain variable domain comprises a CDR1 of SEQ ID NO: 315, a CDR2 of SEQ ID NO: 340 and a CDR3 of SEQ ID NO: 371; (u) an anti-BAFF antibody molecule where the light chain variable domain comprises a CDR1 of SEQ ID NO: 15, a CDR2 of SEQ ID NO: 16 and a CDR3 of SEQ ID NO: 297 and a heavy chain variable domain comprises a CDR1 of SEQ ID NO: 316, a CDR2 of SEQ ID NO: 341 and a CDR3 of SEQ ID NO: 39; (v) an anti-BAFF antibody molecule where the light chain variable domain comprises a CDR1 of SEQ ID NO: 254, a CDR2 of SEQ ID NO: 280 and a CDR3 of SEQ ID NO: 298 and a heavy chain variable domain comprises a CDR1 of SEQ ID NO: 317, a CDR2 of SEQ ID NO: 342 and a CDR3 of SEQ ID NO: 372; (w) an anti-BAFF antibody molecule where the light chain variable domain comprises a CDR1 of SEQ ID NO: 255, a CDR2 of SEQ ID NO: 281 and a CDR3 of SEQ ID NO: 298 and a heavy chain variable domain comprises a CDR1 of SEQ ID NO: 317, a CDR2 of SEQ ID NO: 343 and a CDR3 of SEQ ID NO: 373; (x) an anti-BAFF antibody molecule where the light chain variable domain comprises a CDR1 of SEQ ID NO: 256, a CDR2 of SEQ ID NO: 2 and a CDR3 of SEQ ID NO: 299 and a heavy chain variable domain comprises a CDR1 of SEQ ID NO: 317, a CDR2 of SEQ ID NO: 344 and a CDR3 of SEQ ID NO: 372; (y) an anti-BAFF antibody molecule where the light chain variable domain comprises a CDR1 of SEQ ID NO: 255, a CDR2 of SEQ ID NO: 281 and a CDR3 of SEQ ID NO: 298 and a heavy chain variable domain comprises a CDR1 of SEQ ID NO: 318, a CDR2 of SEQ ID NO: 343 and a CDR3 of SEQ ID NO: 374; (z) an anti-BAFF antibody molecule where the light chain variable domain comprises a CDR1 of SEQ ID NO: 257, a CDR2 of SEQ ID NO: 282 and a CDR3 of SEQ ID NO: 300 and a heavy chain variable domain comprises a CDR1 of SEQ ID NO: 319, a CDR2 of SEQ ID NO: 345 and a CDR3 of SEQ ID NO: 375; (aa) an anti-BAFF antibody molecule where the light chain variable domain comprises a CDR1 of SEQ ID NO: 258, a CDR2 of SEQ ID NO: 283 and a CDR3 of SEQ ID NO: 301 and a heavy chain variable domain comprises a CDR1 of SEQ ID NO: 320, a CDR2 of SEQ ID NO: 346 and a CDR3 of SEQ ID NO: 376; (bb) an anti-BAFF antibody molecule where the light chain variable domain comprises a CDR1 of SEQ ID NO: 259, a CDR2 of SEQ ID NO: 281 and a CDR3 of SEQ ID NO: 298 and a heavy chain variable domain comprises a CDR1 of SEQ ID NO: 317, a CDR2 of SEQ ID NO: 347 and a CDR3 of SEQ ID NO: 377; (cc) an anti-BAFF antibody molecule where the light chain variable domain comprises a CDR1 of SEQ ID NO: 260, a CDR2 of SEQ ID NO: 284 and a CDR3 of SEQ ID NO: 294 and a heavy chain variable domain comprises a CDR1 of SEQ ID NO: 321, a CDR2 of SEQ ID NO: 348 and a CDR3 of SEQ ID NO: 378; (dd) an anti-BAFF antibody molecule where the light chain variable domain comprises a CDR1 of SEQ ID NO: 254, a CDR2 of SEQ ID NO: 2 and a CDR3 of SEQ ID NO: 299 and a heavy chain variable domain comprises a CDR1 of SEQ ID NO: 322, a CDR2 of SEQ ID NO: 349 and a CDR3 of SEQ ID NO: 372; (ee) an anti-BAFF antibody molecule where the light chain variable domain comprises a CDR1 of SEQ ID NO: 261, a CDR2 of SEQ ID NO: 285 and a CDR3 of SEQ ID NO: 294 and a heavy chain variable domain comprises a CDR1 of SEQ ID NO: 323, a CDR2 of SEQ ID NO: 350 and a CDR3 of SEQ ID NO: 378; (ff) an anti-BAFF antibody molecule where the light chain variable domain comprises a CDR1 of SEQ ID NO: 262, a CDR2 of SEQ ID NO: 286 and a CDR3 of SEQ ID NO: 302 and a heavy chain variable domain comprises a CDR1 of SEQ ID NO: 324, a CDR2 of SEQ ID NO: 351 and a CDR3 of SEQ ID NO: 379; (gg) an anti-BAFF antibody molecule where the light chain variable domain comprises a CDR1 of SEQ ID NO: 263, a CDR2 of SEQ ID NO: 6 and a CDR3 of SEQ ID NO: 303 and a heavy chain variable domain comprises a CDR1 of SEQ ID NO: 317, a CDR2 of SEQ ID NO: 352 and a CDR3 of SEQ ID NO: 380; (hh) an anti-BAFF antibody molecule where the light chain variable domain comprises a CDR1 of SEQ ID NO: 264, a CDR2 of SEQ ID NO: 276 and a CDR3 of SEQ ID NO: 304 and a heavy chain variable domain comprises a CDR1 of SEQ ID NO: 325, a CDR2 of SEQ ID NO: 353 and a CDR3 of SEQ ID NO: 381; (ii) an anti-BAFF antibody molecule where the light chain variable domain comprises a CDR1 of SEQ ID NO: 265, a CDR2 of SEQ ID NO: 287 and a CDR3 of SEQ ID NO: 305 and a heavy chain variable domain comprises a CDR1 of SEQ ID NO: 326, a CDR2 of SEQ ID NO: 354 and a CDR3 of SEQ ID NO: 382; (jj) an anti-BAFF antibody molecule where the light chain variable domain comprises a CDR1 of SEQ ID NO: 266, a CDR2 of SEQ ID NO: 287 and a CDR3 of SEQ ID NO: 306 and a heavy chain variable domain comprises a CDR1 of SEQ ID NO: 326, a CDR2 of SEQ ID NO: 355 and a CDR3 of SEQ ID NO: 383; (kk) an anti-BAFF antibody molecule where the light chain variable domain comprises a CDR1 of SEQ ID NO: 267, a CDR2 of SEQ ID NO: 285 and a CDR3 of SEQ ID NO: 294 and a heavy chain variable domain comprises a CDR1 of SEQ ID NO: 327, a CDR2 of SEQ ID NO: 356 and a CDR3 of SEQ ID NO: 369; (ll) an anti-BAFF antibody molecule where the light chain variable domain comprises a CDR1 of SEQ ID NO: 268, a CDR2 of SEQ ID NO: 276 and a CDR3 of SEQ ID NO: 306 and a heavy chain variable domain comprises a CDR1 of SEQ ID NO: 328, a CDR2 of SEQ ID NO: 357 and a CDR3 of SEQ ID NO: 383; (mm) an anti-BAFF antibody molecule where the light chain variable domain comprises a CDR1 of SEQ ID NO: 269, a CDR2 of SEQ ID NO: 288 and a CDR3 of SEQ ID NO: 304 and a heavy chain variable domain comprises a CDR1 of SEQ ID NO: 329, a CDR2 of SEQ ID NO: 358 and a CDR3 of SEQ ID NO: 384; (nn) an anti-BAFF antibody molecule where the light chain variable domain comprises a CDR1 of SEQ ID NO: 270, a CDR2 of SEQ ID NO: 276 and a CDR3 of SEQ ID NO: 306 and a heavy chain variable domain comprises a CDR1 of SEQ ID NO: 330, a CDR2 of SEQ ID NO: 359 and a CDR3 of SEQ ID NO: 385; (oo) an anti-BAFF antibody molecule where the light chain variable domain comprises a CDR1 of SEQ ID NO: 271, a CDR2 of SEQ ID NO: 289 and a CDR3 of SEQ ID NO: 307 and a heavy chain variable domain comprises a CDR1 of SEQ ID NO: 331, a CDR2 of SEQ ID NO: 360 and a CDR3 of SEQ ID NO: 385; (pp) an anti-BAFF antibody molecule where the light chain variable domain comprises a CDR1 of SEQ ID NO: 261, a CDR2 of SEQ ID NO: 285 and a CDR3 of SEQ ID NO: 294 and a heavy chain variable domain comprises a CDR1 of SEQ ID NO: 332, a CDR2 of SEQ ID NO: 361 and a CDR3 of SEQ ID NO: 386; (qq) an anti-BAFF antibody molecule where the light chain variable domain comprises a CDR1 of SEQ ID NO: 272, a CDR2 of SEQ ID NO: 289 and a CDR3 of SEQ ID NO: 307 and a heavy chain variable domain comprises a CDR1 of SEQ ID NO: 331, a CDR2 of SEQ ID NO: 362 and a CDR3 of SEQ ID NO: 385; (rr) an anti-BAFF antibody molecule where the light chain variable domain comprises a CDR1 of SEQ ID NO: 266, a CDR2 of SEQ ID NO: 287 and a CDR3 of SEQ ID NO: 306 and a heavy chain variable domain comprises a CDR1 of SEQ ID NO: 326, a CDR2 of SEQ ID NO: 355 and a CDR3 of SEQ ID NO: 383; (ss) an anti-BAFF antibody molecule where the light chain variable domain comprises a CDR1 of SEQ ID NO: 270, a CDR2 of SEQ ID NO: 276 and a CDR3 of SEQ ID NO: 306 and a heavy chain variable domain comprises a CDR1 of SEQ ID NO: 330, a CDR2 of SEQ ID NO: 359 and a CDR3 of SEQ ID NO: 285; (tt) an anti-BAFF antibody molecule where the light chain variable domain comprises a CDR1 of SEQ ID NO: 270, a CDR2 of SEQ ID NO: 276 and a CDR3 of SEQ ID NO: 306 and a heavy chain variable domain comprises a CDR1 of SEQ ID NO: 392, a CDR2 of SEQ ID NO: 363 and a CDR3 of SEQ ID NO: 387; (uu) an anti-BAFF antibody molecule where the light chain variable domain comprises a CDR1 of SEQ ID NO: 273, a CDR2 of SEQ ID NO: 276 and a CDR3 of SEQ ID NO: 308 and a heavy chain variable domain comprises a CDR1 of SEQ ID NO: 333, a CDR2 of SEQ ID NO: 364 and a CDR3 of SEQ ID NO: 388; (vv) an anti-BAFF antibody molecule where the light chain variable domain comprises a CDR1 of SEQ ID NO: 274, a CDR2 of SEQ ID NO: 290 and a CDR3 of SEQ ID NO: 309 and a heavy chain variable domain comprises a CDR1 of SEQ ID NO: 334, a CDR2 of SEQ ID NO: 365 and a CDR3 of SEQ ID NO: 389; (ww) an anti-BAFF antibody molecule where the light chain variable domain comprises a CDR1 of SEQ ID NO: 275, a CDR2 of SEQ ID NO: 291 and a CDR3 of SEQ ID NO: 310 and a heavy chain variable domain comprises a CDR1 of SEQ ID NO: 335, a CDR2 of SEQ ID NO: 366 and a CDR3 of SEQ ID NO: 390; and (xx) an anti-BAFF antibody molecule where the light chain variable domain comprises a CDR1 of SEQ ID NO: 258, a CDR2 of SEQ ID NO: 292 and a CDR3 of SEQ ID NO: 311 and a heavy chain variable domain comprises a CDR1 of SEQ ID NO: 336, a CDR2 of SEQ ID NO: 367 and a CDR3 of SEQ ID NO: 391.

In another embodiment of the present invention, the anti-BAFF antibody molecule comprises a light chain variable region of any one of SEQ ID NOS: 82-97, and a heavy chain variable region of any one of SEQ ID NOS: 100-115. In a preferred embodiment, the present invention provides monoclonal antibodies with the combinations of light chain variable and heavy chain variable regions of SEQ ID NO: 82/101, 88/101, 94/112 or 93/114.

In an additional embodiment of the present invention, the anti-BAFF antibody molecule neutralizes all three forms of human BAFF, the forms of which include membrane bound (mbBAFF), soluble trimeric BAFF, and soluble 60-mer BAFF. In particular, the anti-BAFF antibody molecules of the present invention neutralize human soluble 60-mer BAFF. Furthermore, the anti-BAFF antibody molecules of the present invention neutralize human soluble trimeric BAFF. Finally, the anti-BAFF antibody molecules of the present invention neutralize human membrane-bound BAFF.

In a further embodiment, the present invention relates to an anti-BAFF antibody molecule comprising a humanized light chain variable domain comprising the CDRs of SEQ ID NO: 76, 16 and 17 and framework regions having an amino acid sequence at least 90% identical, at least 93% identical or at least 95% identical to the amino acid sequence of the framework regions of the variable domain light chain amino acid sequence of SEQ ID NO: 82 and a humanized heavy chain variable domain comprising the CDRs of SEQ ID NO: 37, 38 and 39 and framework regions having an amino acid sequence at least 90% identical, at least 93% identical or at least 95% identical to the amino acid sequence of the framework regions of the variable domain heavy chain amino acid sequence of SEQ ID NO: 101. In one embodiment, the anti-BAFF antibody molecule is a humanized monoclonal antibody.

In a further embodiment, the present invention relates to an anti-BAFF antibody molecule comprising a humanized light chain variable domain comprising the CDRs of SEQ ID NO: 15, 16 and 17 and framework regions having an amino acid sequence at least 90% identical, at least 93% identical or at least 95% identical to the amino acid sequence of the framework regions of the variable domain light chain amino acid sequence of SEQ ID NO: 88 and a humanized heavy chain variable domain comprising the CDRs of SEQ ID NO: 37, 38 and 39 and framework regions having an amino acid sequence at least 90% identical, at least 93% identical or at least 95% identical to the amino acid sequence of the framework regions of the variable domain heavy chain amino acid sequence of SEQ ID NO: 101. In one embodiment, the anti-BAFF antibody molecule is a humanized monoclonal antibody.

In a further embodiment, the present invention relates to an anti-BAFF antibody molecule comprising a humanized light chain variable domain comprising the CDRs of SEQ ID NO:5, 8 and 9 and framework regions having an amino acid sequence at least 90% identical, at least 93% identical or at least 95% identical to the amino acid sequence of the framework regions of the variable domain light chain amino acid sequence of SEQ ID NO: 94 and a humanized heavy chain variable domain comprising the CDRs of SEQ ID NO: 81, 29 and 30 and framework regions having an amino acid sequence at least 90% identical, at least 93% identical or at least 95% identical to the amino acid sequence of the framework regions of the variable domain heavy chain amino acid sequence of SEQ ID NO: 112. In one embodiment, the anti-BAFF antibody molecule is a humanized monoclonal antibody.

In a further embodiment, the present invention relates to an anti-BAFF antibody molecule comprising a humanized light chain variable domain comprising the CDRs of SEQ ID NO: 5, 8 and 9 and framework regions having an amino acid sequence at least 90% identical, at least 93% identical or at least 95% identical to the amino acid sequence of the framework regions of the variable domain light chain amino acid sequence of SEQ ID NO: 93 and a humanized heavy chain variable domain comprising the CDRs of SEQ ID NO: 81, 29 and 30 and framework regions having an amino acid sequence at least 90% identical, at least 93% identical or at least 95% identical to the amino acid sequence of the framework regions of the variable domain heavy chain amino acid sequence of SEQ ID NO: 114. In one embodiment, the anti-BAFF antibody molecule is a humanized monoclonal antibody.

In yet another embodiment, the anti-BAFF antibody molecule is a monoclonal antibody or a humanized monoclonal antibody.

The present invention also provides pharmaceutical compositions comprising an anti-BAFF antibody molecule described herein and a pharmaceutically acceptable carrier.

The present invention further provides a method for treating a subject having a BAFF-associated disorder comprising administering to the subject an anti-BAFF antibody molecule, or a pharmaceutical composition comprising an anti-BAFF antibody molecule and a pharmaceutically acceptable carrier, which anti-BAFF antibody molecule binds to human BAFF. Specifically provided in the present invention is a method for treating an inflammatory disease, an autoimmune disease, a respiratory disease, a metabolic disorder or cancer comprising administering to a subject in need thereof an effective amount of an anti-BAFF antibody molecule, or a pharmaceutical composition comprising an anti-BAFF antibody molecule and a pharmaceutically acceptable carrier. In particular, the disease to be treated may be systemic lupus erythematosus, lupus nephritis or rheumatoid arthritis.

Also provided in the invention is a method for inhibiting the binding of BAFF to one or more BAFF receptors on a mammalian cell, wherein the BAFF receptor is BAFF-R (BR3), TACI (transmembrane activator and calcium modulator and cyclophilin ligand interactor) and/or BCMA (B-cell maturation antigen), comprising administering to the cell an anti-BAFF antibody molecule, whereby signaling mediated by the BAFF receptor is inhibited.

A further embodiment encompasses a DNA molecule encoding a variable light chain region, variable heavy chain region, light chain region or heavy chain region described herein.

In one embodiment, an isolated polynucleotide comprises a sequence encoding a light chain variable region of any one of SEQ ID NOS: 82-97, or a heavy chain variable region of any one of SEQ ID NOS: 100-115. In another embodiment, the isolated polynucleotide comprises a light chain variable region is SEQ ID NO: 234 and the heavy chain variable region is SEQ ID NO: 396, the light chain variable region is SEQ ID NO: 393 and the heavy chain variable region is SEQ ID NO: 396, the light chain variable region is SEQ ID NO: 395 and the heavy chain variable region is SEQ ID NO: 397 or the light chain variable region is SEQ ID NO: 394 and the heavy chain variable region is SEQ ID NO: 398.

Another embodiment encompasses an expression vector containing a DNA molecule. A further embodiment encompasses a host cell carrying one or more expression vectors. In one embodiment, a host is a mammalian cell.

A further embodiment encompasses a method for producing an antibody molecule comprising transfecting a mammalian host cell with one or more vectors, cultivating the host cell and recovering and purifying the antibody molecule.

Another aspect of the invention relates to a method for producing an antibody molecule comprising obtaining a mammalian host cell comprising one or more of the vectors above, and cultivating the host cell. In one embodiment, the method further comprises recovering and purifying the antibody molecule.

In one embodiment, the present invention further provides an antibody molecule above for use in medicine. In one embodiment, the use is the treatment of an inflammatory disease, of an autoimmune disease, of a respiratory disease, of a metabolic disorder or of cancer. In one embodiment, the use is for the treatment of systemic lupus erythematosus, lupus nephritis or rheumatoid arthritis. In another embodiment, the use of the antibody molecule is for the preparation of a medicament for the treatment of an inflammatory disease, of an autoimmune disease, of a respiratory disease, of a metabolic disorder or of cancer, preferably for the treatment of systemic lupus erythematosus, lupus nephritis or rheumatoid arthritis. In yet another embodiment, the present invention provides a method for inhibiting the binding of BAFF to one or more BAFF receptors on a mammalian cell that is not within a human, wherein the method comprises contacting the mammalian cell with an antibody molecule according to the present invention.

DETAILED DESCRIPTION

Figure 1:
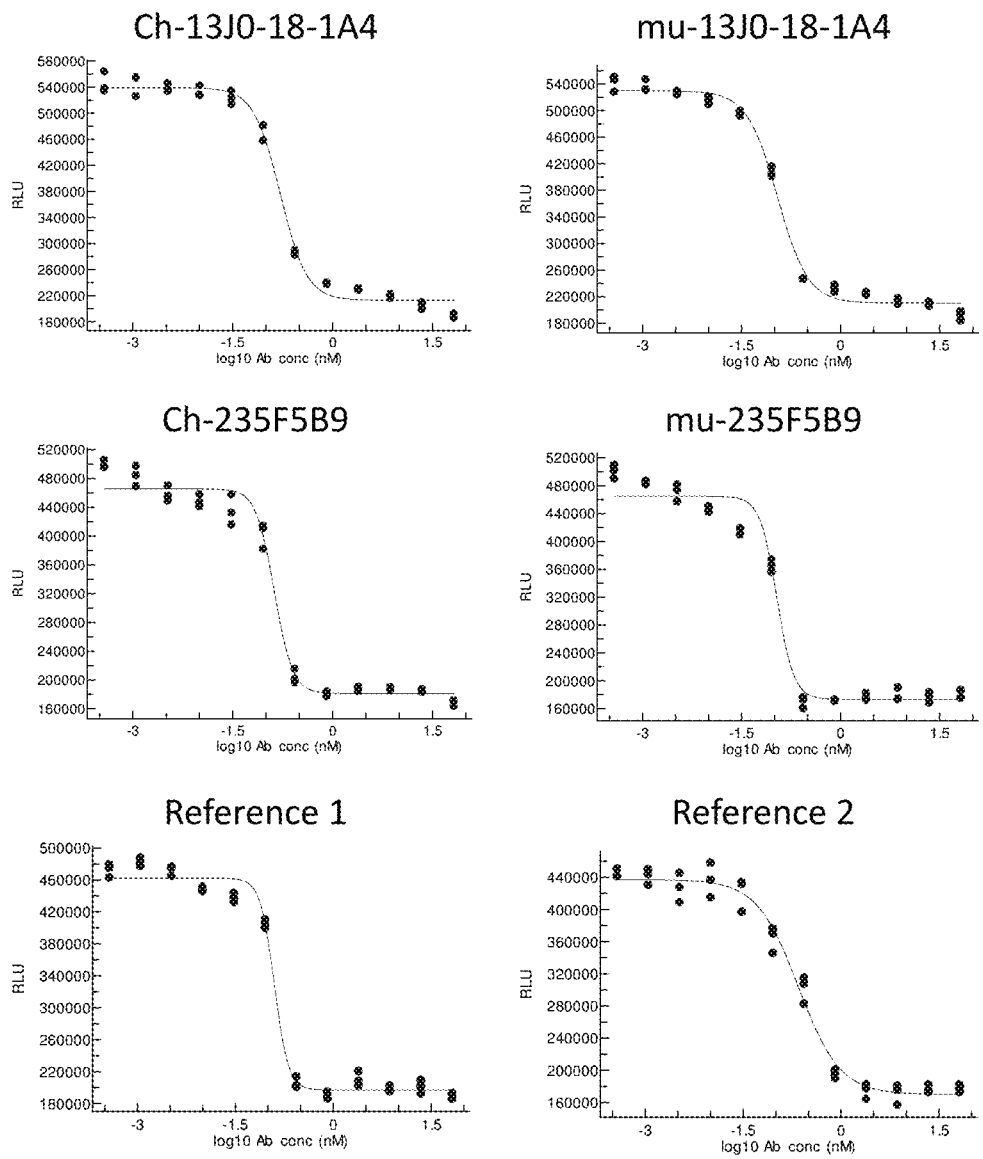
FIG. 1: Anti-BAFF monoclonal antibody potency against sBAFF: chimeric HuIgG1 KO vs. parental mouse monoclonal antibodies.

The present invention provides antibodies that bind to BAFF, in particular human BAFF. The present invention also relates to humanized antibodies. In specific embodiments, the sequence of these humanized antibodies has been identified based on the sequences of certain lead mouse antibodies.

The lead mouse antibodies of the present invention were derived from mouse hybridomas. The immunization of the mice is carried out using different techniques. For example, antibodies that are specific for human BAFF can be raised against an immunogenic antigen such as an isolated BAFF protein, and/or a portion thereof of any of the above (including synthetic peptides). Preparation of immunogenic antigens and monoclonal antibody production can be performed using any suitable technique known in the art.

The lead mouse antibodies were selected based on their high affinity to BAFF. Accordingly, in one aspect, the present invention provides an antibody that binds to human BAFF with high affinity. Selected mouse antibodies were humanized to result in humanized antibodies. The humanized antibodies of the present invention bind to human BAFF with high affinity. Accordingly, in another aspect, the present invention provides a humanized antibody that binds to human BAFF with high affinity.

Accordingly, in one embodiment, the present invention provides an anti-BAFF antibody having a $K_D$ of less than 100 pM. In a further embodiment, the present invention provides an anti-BAFF antibody having a $K_D$ of less than 10 pM. In a further embodiment, the present invention provides an anti-BAFF antibody having a $K_D$ less than 1 pM.

In a further aspect, a humanized monoclonal anti-BAFF antibody of the present invention has favorable biophysical properties, for example quality, stability, or solubility.

In one aspect, the anti-BAFF antibody is a humanized antibody. In one aspect, the anti-BAFF antibody is a monoclonal antibody. In one aspect, the anti-BAFF antibody is a full length antibody. In one aspect, the anti-BAFF antibody is a humanized monoclonal antibody, for example a full length humanized monoclonal antibody.

An anti-BAFF antibody of the present invention recognizes a specific or "BAFF epitope". Epitopes may be determined by various techniques known in the art, such as X-ray crystallography, Hydrogen/Deuterium Exchange Mass Spectrometry (HXMS), site-directed mutagenesis, alanine scanning mutagenesis, and peptide screening methods.

Definitions

The generalized structure of antibodies or immunoglobulin is well known to those of skill in the art. These molecules are heterotetrameric glycoproteins, typically of about 150,000 daltons, composed of two identical light (L) chains and two identical heavy (H) chains and are typically referred to as full length antibodies. Each light chain is covalently linked to a heavy chain by one disulfide bond to form a heterodimer, and the heterotetrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$) and a carboxy-terminal constant domain ($C_L$). The $V_L$ domain associates noncovalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663). Variable domains are also referred herein as variable regions.

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5$^{th}$ Ed. Public Health Service, National Institutes of Health, Bethesda, Md., whereas HVLs (also referred herein as CDRs) are structurally defined according to the three-dimensional structure of the variable domain, as described by Chothia and Lesk, 1987, J. Mol. Biol. 196: 901-917. These two methods result in slightly different identifications of a CDR. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The exact residue numbers that encompass a particular CDR will vary depending on the sequence and size of the CDR. Those skilled in the art can routinely determine which residues comprise a particular CDR given the variable region amino acid sequence of the antibody. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody dependent cellular cytotoxicity (ADCC), antibody dependent cellular phagocytosis (ADCP) and complement dependent cytotoxicity (CDC).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ and μ, respectively. The subunit structures and three-dimensional configurations of the classes of native immunoglobulins are well known.

The terms, "antibody", "anti-BAFF antibody", "anti-BAFF antibody molecule", "humanized anti-BAFF antibody", "humanized anti-BAFF epitope antibody", and "variant humanized anti-BAFF epitope antibody" specifically encompass monoclonal antibodies (including full length monoclonal antibodies), polyclonal antibodies, multispecific antibodies, and antibody fragments such as variable domains and other portions of antibodies that exhibit a desired biological activity, e.g., BAFF binding. The term "monoclonal antibody" (mAb) refers to an antibody that is highly specific, being directed against a single antigenic determinant, an "epitope". Therefore, the modifier "monoclonal" is indicative of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

The term "monomer" refers to a homogenous form of an antibody. For example, for a full-length antibody, monomer means a monomeric antibody having two identical heavy chains and two identical light chains.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms "antibody fragment", "anti-BAFF antibody fragment", "anti-BAFF antibody molecule", "anti-BAFF epitope antibody fragment", "humanized anti-BAFF antibody fragment", "humanized anti-BAFF epitope antibody fragment", "variant humanized anti-BAFF epitope antibody fragment" refer to a portion of a full length anti-BAFF antibody, in which a variable region or a functional capability is retained, for example, specific BAFF epitope binding. Examples of antibody fragments include, but are not limited to, a Fab, Fab', F(ab')$_2$, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produces two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a F(ab')$_2$ fragment that has two antigen-binding sites and is still capable of cross-linking antigen.

Fab' fragments differ from Fab fragments by the presence of additional residues including one or more cysteines from the antibody hinge region at the C-terminus of the $C_{H1}$ domain. F(ab')$_2$ antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

A "diabody" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). Diabodies are described more fully in, e.g., Holliger et al. (1993) Proc. Natl. Acad. Sci. USA 90: 6444-6448.

Other recognized antibody fragments include those that comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A "humanized antibody" or a "humanized antibody fragment" is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain. The present invention describes specific humanized BAFF antibodies which contain CDRs derived from the mouse monoclonal antibodies or humanized CDRs shown in Tables 3 and 4 inserted between the FRs of human germline sequence heavy and light chain variable domains. It will be understood that certain mouse FR residues may be important to the function of the humanized antibodies and therefore certain of the human germline sequence heavy and light chain variable domains residues are modified to be the same as those of the corresponding mouse sequence.

In another aspect, a humanized BAFF antibody comprises substantially all of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, all of the CDRs are mouse or humanized sequences as detailed in Tables 1 through 4 herein below and all, or substantially all, of the FRs are those of a human immunoglobulin consensus or germline sequence. In another aspect, a humanized anti-BAFF antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-BAFF antibody can be selected from any class of immunoglobulins, including IgM, IgG, IgD, IgA and IgE, and any isotype, including IgG$_1$, IgG$_2$, IgG$_3$, IgG$_4$, IgA$_1$ and IgA$_2$. For example, the constant domain can be a complement fixing constant domain where it is desired that the humanized antibody exhibit cytotoxic activity, and the isotype is typically IgG$_1$. Where such cytotoxic activity is not desirable, the constant domain may be of another isotype, e.g., IgG$_2$. An alternative humanized anti-BAFF antibody can comprise sequences from more than one immunoglobulin class or isotype, and selecting particular constant domains to optimize desired effector functions is within the ordinary skill in the art. In specific embodiments, the present invention provides antibodies that are IgG1 antibodies and more particularly, are IgG1 antibodies in which there is a knock-out of effector functions.

The FRs and CDRs, or HVLs, of a humanized anti-BAFF antibody need not correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to BAFF. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-BAFF antibodies. See, for example, U.S. Pat. Nos. 6,037,454 and 6,054,297.

Human germline sequences are found naturally in the human population. A combination of those germline genes generates antibody diversity. Germline antibody sequences for the light chain of the antibody come from conserved human germline kappa or lambda v-genes and j-genes. Similarly the heavy chain sequences come from germline v-, d- and j-genes (LeFranc, M-P, and LeFranc, G, "The Immunoglobulin Facts Book" Academic Press, 2001).

As used herein, "variant", "anti-BAFF variant", "humanized anti-BAFF variant", or "variant humanized anti-BAFF" each refers to a humanized anti-BAFF antibody having at least a light chain variable murine CDR from any of the sequences as shown in Table 1 or a heavy chain murine CDR sequence derived from the murine monoclonal antibody as shown in Table 2. Variants include those having one or more amino acid changes in one or both light chain or heavy chain variable domains, provided that the amino acid change does not substantially impair binding of the antibody to BAFF.

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

An "antibody molecule" refers to any one of the antibody definitions described above or an antigen-binding fragment thereof.

The term "antibody performance" refers to factors that contribute to antibody recognition of antigen or the effectiveness of an antibody in vivo. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half life of the antibody.

The term "neutralize" generally relates to rendering inactive via inhibition of bioactivity. The term "inhibition" generally relates to a situation where a molecule is unable to execute its function. In chemistry or biology the term "inhibit" means to limit, prevent or block the action or function, i.e., to inhibit an enzyme, or to inhibit a chemical reaction. IC50 represents the concentration of a drug that is required for 50% inhibition in vitro and IC 90 represents the concentration of a drug that is required for 90% inhibition in vitro.

The term "epitope tagged" when used herein, refers to an anti-BAFF antibody fused to an "epitope tag". An "epitope tag" is a polypeptide having a sufficient number of amino acids to provide an epitope for antibody production, yet is designed such that it does not interfere with the desired activity of the humanized anti-BAFF antibody. The epitope tag is usually sufficiently unique such that an antibody raised against the epitope tag does not substantially cross-react with other epitopes. Suitable tag polypeptides generally contain at least 6 amino acid residues and usually contain about 8 to 50 amino acid residues, or about 9 to 30 residues. Examples of epitope tags and the antibody that binds the epitope include the flu HA tag polypeptide and its antibody 12CA5 (Field et al., 1988 Mol. Cell. Biol. 8: 2159-2165; c-myc tag and 8F9, 3C7, 6E10, G4, B7 and 9E10 antibodies thereto (Evan et al., 1985, Mol. Cell. Biol. 5(12):3610-3616; and Herpes simplex virus glycoprotein D (gD) tag and its antibody (Paborsky et al. 1990, Protein Engineering 3(6): 547-553). In certain embodiments, the epitope tag is a "salvage receptor binding epitope". As used herein, the term "salvage receptor binding epitope" refers to an epitope of the Fc region of an IgG molecule (such as $IgG_1$, $IgG_2$, $IgG_3$, or $IgG_4$) that is responsible for increasing the in vivo serum half-life of the IgG molecule.

In some embodiments, the antibodies of the present invention may be conjugated to a cytotoxic agent. This is any substance that inhibits or prevents the function of cells and/or causes destruction of cells. The term is intended to include radioactive isotopes (such as $I^{131}$, $I^{125}$, $Y^{90}$, and $Re^{186}$), chemotherapeutic agents, and toxins such as enzymatically active toxins of bacterial, fungal, plant, or animal origin, and fragments thereof. Such cytotoxic agents can be coupled to the humanized antibodies of the present invention using standard procedures, and used, for example, to treat a patient indicated for therapy with the antibody.

A "chemotherapeutic agent" is a chemical compound useful in the treatment of cancer. There are numerous examples of chemotherapeutic agents that could be conjugated with the therapeutic antibodies of the present invention. Examples of such chemotherapeutic agents include alkylating agents such a thiotepa and cyclosphosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues); cryptophycines (particularly cryptophycin 1 and cryptophycin 8); dolastatin, auristatins, (including analogues monomethyl-auristatin E and monomethyl-auristatin F); duocarmycin (including the synthetic analogues, KW-2189 and CBI-TMI); eleutherobin; pancratistatin; sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calichemicin gamma1I and calicheamicin phiI1, see for example, Agnew, Chem. Intl. Ed. Engl., 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, potfiromycin, puromycine, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™) raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above. Any one or more of these agents may be conjugated to the humanized antibodies of the present invention to provide a useful therapeutic agent for the treatment of various disorders.

The antibodies also may be conjugated to prodrugs. A "prodrug" is a precursor or derivative form of a pharmaceutically active substance that is less cytotoxic to tumor cells compared to the parent drug and is capable of being enzymatically activated or converted into the more active form. See, for example, Wilman, 1986, "Prodrugs in Cancer Chemotherapy", In Biochemical Society Transactions, 14, pp. 375-382, 615th Meeting Belfast and Stella et al., 1985, "Prodrugs: A Chemical Approach to Targeted Drug Delivery, In: "Directed Drug Delivery, Borchardt et al., (ed.), pp. 247-267, Humana Press. Useful prodrugs include, but are not limited to, phosphate-containing prodrugs, thiophosphate-containing prodrugs, sulfate-containing prodrugs peptide-containing prodrugs, D-amino acid-modified prodrugs, glycosylated prodrugs, β-lactam-containing prodrugs, optionally substituted phenoxyacetamide-containing prodrugs, and optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form include, but are not limited to, those chemotherapeutic agents described above.

For diagnostic as well as therapeutic monitoring purposes, the antibodies of the invention also may be conjugated to a label, either a label alone or a label and an additional second agent (prodrug, chemotherapeutic agent and the like). A label, as distinguished from the other second agents refers to an agent that is a detectable compound or composition and it may be conjugated directly or indirectly to a humanized antibody of the present invention. The label may itself be detectable (e.g., radioisotope labels or fluorescent labels) or, in the case of an enzymatic label, may catalyze chemical alteration of a substrate compound or composition that is detectable. Labeled humanized anti-BAFF antibody can be prepared and used in various applications including in vitro and in vivo diagnostics.

The antibodies of the present invention may be formulated as part of a liposomal preparation in order to affect delivery thereof in vivo. A "liposome" is a small vesicle composed of various types of lipids, phospholipids, and/or surfactant. Liposomes are useful for delivery to a mammal of a compound or formulation, such as a humanized anti-BAFF antibody disclosed herein, optionally, coupled to or in combination with one or more pharmaceutically active agents and/or labels. The components of the liposome are commonly arranged in a bilayer formation, similar to the lipid arrangement of biological membranes.

Certain aspects of the present invention related to isolated nucleic acids that encode one or more domains of the humanized antibodies of the present invention. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is distinguished from the nucleic acid molecule as it exists in natural cells.

In various aspects of the present invention one or more domains of the humanized antibodies will be recombinantly expressed. Such recombinant expression may employ one or more control sequences, i.e., polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of humanized anti-BAFF antibody in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disorder", as used herein, is any condition that would benefit from treatment with a humanized anti-BAFF antibody described herein. This includes chronic and acute disorders or diseases including those pathological conditions that predispose the mammal to the disorder in question. Non-limiting examples or disorders to be treated herein include inflammatory, angiogenic, autoimmune and immunologic disorders, respiratory disorders, cancer, hematological malignancies, benign and malignant tumors, leukemias and lymphoid malignancies.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia.

As used herein, the term "BAFF-associated disorder" or "BAFF-associated disease" refers to a condition in which BAFF activity contributes to the disease and typically where BAFF is abnormally expressed. An BAFF-associated disorder includes diseases and disorders of the immune system, such as autoimmune disorders and inflammatory disorders. Such conditions include, but are not limited to, rheumatoid arthritis (RA), systemic lupus erythematosus (SLE), scleroderma, Sjogren's syndrome, multiple sclerosis, psoriasis, psoriatic arthritis, inflammatory bowel disease (e.g., ulcerative colitis and Crohn's disease), pulmonary inflammation, asthma, idiopathic thrombocytopenic purara (ITP) and ankylosing spondylitis.

The term "intravenous infusion" refers to introduction of an agent into the vein of an animal or human patient over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an active agent that relieves or ameliorates one or more of the symptoms of the disorder being treated. In another aspect, the therapeutically effective amount refers to a target serum concentration that has been shown to be effective in, for example, slowing disease progression. Efficacy can be measured in conventional ways, depending on the condition to be treated.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder thereby preventing or removing one or more signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the humanized anti-BAFF antibody composition, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

In one aspect, anti-BAFF antibodies are described and disclosed. Of particular importance for treating autoimmune disease in humans are humanized anti-BAFF antibodies and compositions disclosed herein. Also described are binding agents that include an antigen-binding fragment of an anti-BAFF antibody, in particular a humanized anti-BAFF antibody. The humanized anti-BAFF antibodies and binding agents can inhibit the production of BAFF-associated cytokines, which contribute to chronic autoimmune and inflammatory diseases. The humanized anti-BAFF antibodies and binding agents can thus be used in the treatment of a variety of diseases or disorders. A humanized anti-BAFF antibody and a BAFF binding agent each includes at least a portion that specifically recognizes an BAFF epitope (i.e., an antigen-binding fragment).

In the initial characterization of mouse antibodies were selected based on BAFF receptor binding characterization.

Accordingly in one aspect, an antibody of the present invention has a $K_D$ for BAFF, in particular human BAFF, of less than 100 pM. In another aspect, an antibody of the present invention has a $K_D$ of less than 10 pM. In another aspect, an antibody of the present invention has a $K_D$ of less than 1 pM.

The light chain and heavy chain CDRs of the various anti-BAFF antibodies are shown in Table 3 and Table 4, respectively. Tables 3 and 4 also show five light chain CDRs and one heavy chain CDR derived from either 1A4 or 5B9 mouse antibodies through the humanization process.

TABLE 1

Anti-BAFF Mouse Leads - Vκ Sequences

| Designation | Sequence |
|---|---|
| 206G9A10 | GACATTGTGATGACCCAGTCTCAAAAATTCATGTCCACAACAGTAGGAG ACAGGGTCAGCATCACCTGCAAGGCCAGTCAGAATGCGGGTGCTGCTGT AGCCTGGTTTCAACAGAAACCAGGACAATCTCCTAAACTACTGATTTAC TCAGCATCCAATCGGTATACTGGAGTCCCTGATCGCTTCACAGGCAGTG GATCGGGGACAGATTTCACTCTCACCATTAGCAATGTGCAGTCTGAGGA CCTGGCAGATTATATCTGTCAACAATACAGAAGCTATCCTCGGACGTTC GGAGGAGGCACCAAGCTGGAAATCAAA (SEQ ID NO: 40)<br><br>DIVMTQSQKFMSTTVGDRVSITCKASQNAGAAVAWFQQKPGQSPKLLIYS ASNRYTGVPDRFTGSGSGTDFTLTISNVQSEDLADYICQQYRSYPRTFGGGT KLEIK (SEQ ID NO: 41) |
| 227D5A7 | GACATTGTGATGACCCAGTCTCAAAAATTCATGTCCACAACAGTAGGAG ACAGGGTCAGCATCACCTGCAAGGCCAGTCAGAATGCGGGTGCTGCTGT AGCCTGGTTTCAACAGAAACCGGGACAATCTCCTAAATTACTGATTTAC TCAGCATCCAATCGGTATACTGGAGTCCCTGATCGCTTCACAGGCAGTG GATCGGGGACAGATTTCACTCTCACCATTAGCAATGTGCAGTCTGAGGA CCTGGCAGATTATATCTGTCAACAATACAGAAGCTTTCCTCGGACGTTC GGAGGAGGCACCAAGCTGGAAATCAAA (SEQ ID NO: 42)<br><br>DIVMTQSQKFMSTTVGDRVSITCKASQNAGAAVAWFQQKPGQSPKLLIYS ASNRYTGVPDRFTGSGSGTDFTLTISNVQSEDLADYICQQYRSFPRTFGGGT KLEIK (SEQ ID NO: 43) |
| 250E5A11 | GACATTGTGATGACCCAGTCTCAAAAATTCATGTCCACAACAGTAGGAG ACAGGGTCAGCATCACCTGCAAGGCCAGTCAGAATGCGGGTGCTGCTGT AGCCTGGTTTCAACAGAAACCAGGACAATCTCCTAAACTACTGATTTAC TCAGCATCCAATCGGTATACTGGAGTCCCTGATCGCTTCACAGGCAGTG GATCGGGGACAGATTTCACTCTCACCATTACCAATGTGCAGTCTGAGGA CCTGGCAGATTATATCTGTCAACAATACAGAAGCTTTCCTCGGACGTTC GGAGGAGGCACTAAGCTGGAAATCAAA (SEQ ID NO: 44)<br><br>DIVMTQSQKFMSTTVGDRVSITCKASQNAGAAVAWFQQKPGQSPKLLIYS ASNRYTGVPDRFTGSGSGTDFTLTITNVQSEDLADYICQQYRSFPRTFGGGT KLEIK (SEQ ID NO: 45) |
| 227D3B11 | GACATTGTGATGACCCAGTCTCAAAAAATCATGTCCACAACAGTGGGAG ACAGGGTCAGCATCACCTGCAAGGCCAGTCAGAATGCGGGTATTGATGT AGCCTGGTTTCAACAGAAACCAAGACAATCTCCTAAACTACTGATTTTC |

TABLE 1-continued

Anti-BAFF Mouse Leads - Vκ Sequences

Designation Sequence

TCAACATCCAATCGATATACTGGAGTCCCAGATCGCTTCGCAGGCAGTG
GATCGGGGACAGATTTCACTCTCACCATTTACAATGTGCAGTCTGAAGA
CCTGGCAGATTATTTCTGTCTGCAATATAGAAGTTATCCTCGGACGTTCG
GAGGGGGGACCAAGCTGGAAATAAAA (SEQ ID NO: 46)

DIVMTQSQKIMSTTVGDRVSITCKASQNAGIDVAWFQQKPRQSPKLLIFSTS
NRYTGVPDRFAGSGSGTDFTLTIYNVQSEDLADYFCLQYRSYPRTFGGGTK
LEIK (SEQ ID NO: 47)

235F5B9  GACATTGTGATGACCCAGTCTCAAAAAATCATGTCCACAACAGTGGGAG
ACAGGGTCAGCATCACCTGCAAGGCCAGTCAGAATGCGGGTATTGATGT
AGCCTGGTTTCAACAGAAACCAAGACAATCTCCTAAACTACTGATTTTC
TCAAAATCCAATCGATATACTGGAGTCCCAGATCGCTTCGCAGGCAGTG
GATCGGGGACAGATTTCACTCTCACCATTTACAATGTGCAGTCTGAAGA
CCTGGCAGATTATTTCTGTCTGCAATATAGAAGTTATCCTCGGACGTTCG
GAGGAGGCACCAAGCTGGAAATCAAA (SEQ ID NO: 48)

DIVMTQSQKIMSTTVGDRVSITCKASQNAGIDVAWFQQKPRQSPKLLIFSKS
NRYTGVPDRFAGSGSGTDFTLTIYNVQSEDLADYFCLQYRSYPRTFGGGTK
LEIK (SEQ ID NO: 49)

217H12A7  GACATTGTGATGACCCAGTCTCAAAAATTCATGTCCACAACAGTAGGAG
ACAGGGTCAGCATCACCTGCAAGGCCAGTCAGAATGCGGGTACTGCTGT
AGCCTGGTTTCAACAGAAACCAGGACAATCTCCTAAACTACTGATTTAC
TCAGCATTTAATCGGTATACTGGAGTCCCTGATCGCTTCACAGGCAGTG
GATCGGGGACAGATTTCACTCTCACCATTAGCAATATGCAGTCTGAAGA
CCTGGCAGATTATATCTGTCAACAATATAGAAGCTATCCTCGGACGTTC
GGAGGAGGCACCAAGCTGGAAATCAAA (SEQ ID NO: 50)

DIVMTQSQKFMSTTVGDRVSITCKASQNAGTAVAWFQQKPGQSPKLLIYSA
FNRYTGVPDRFTGSGSGTDFTLTISNMQSEDLADYICQQYRSYPRTFGGGTK
LEIK (SEQ ID NO: 51)

210D9B8  GACATTGTGATGACCCAGTCTCAAAAATTCGTGTCCACAACACTAGGGG
ACAGGGTCAGCATCACCTGCAAGGCCAGTCAGAGTGTGGGTATTGCTGT
AGCCTGGTATCAACAGAAACCAGGACATTCTCCTAACCTACTGATTTTC
TCAACATCCAATCGCTACACTGGAGTCCCTGATCGCTTCACAGGCAGCG
GATCTGGGACAGATTTCACTCTCACCATTAGCGATGTGCAGTCTGAAGA
CCTGGCAGATTATTTCTGTCAGCAATATAGCAGGTATCCTCGGACGTTC
GGTGGAGGCACCAAGCTGGAGATCAAA (SEQ ID NO: 52)

DIVMTQSQKFVSTTLGDRVSITCKASQSVGIAVAWYQQKPGHSPNLLIFSTS
NRYTGVPDRFTGSGSGTDFTLTISDVQSEDLADYFCQQYSRYPRTFGGGTK
LEIK (SEQ ID NO: 53)

214G4B7  GACATTGTGATGACCCAGTCTCAAAAATTCATGTCCACAACAGTAGGAG
ACAGGGTCAGCATCACCTGCAAGGCCAGTCAGAATGCGGGTACTGCTGT
AGCCTGGTTTCAACAGAAACCAGGACAATCTCCTAAACTACTGATTTTC
TCAACATCCAATCGGTATACTGGAGTCCCTGATCGCTTCACAGGCAGTG
GATCGGGGACAGATTTCACTCTCACCATTAGCAATATGCAGTCTGAAGA
CCTGGCAGATTATTTCTGTCTGCAATATAGAAGCTATCCTCGGACGTTCG
GAGGAGGCACCAAGCTGGAAATCAAA (SEQ ID NO: 54)

DIVMTQSQKFMSTTVGDRVSITCKASQNAGTAVAWFQQKPGQSPKLLIFST
SNRYTGVPDRFTGSGSGTDFTLTISNMQSEDLADYFCLQYRSYPRTFGGGT
KLEIK (SEQ ID NO: 55)

13J018-1A4  GACATCCAGATGACCCAGTCTCCATCCTCATTATCTGCCTCTCTGGGAGA
AAGAGTCAGTCTCACTTGTCGGGCAAGTCAAGACATTGGTAATAGGTTA
AACTGGCTTCAGCAGGAACCAGATGGAACTATTAAACGCCTGATCTACG
CCACATCCAGTTTAGATTCTGGTGTCCCCAAAAGGTTCAGTGGCAGTAG
GTCTGGGTCGGATTATTCTCTCACCATCAGCAGCCTTGAGTCTGAAGATT
TTGTAGACTATTACTGTCTACAATATGCTAGTTCTCCATTCACGTTCGGC
ACGGGGACAAAATTGGAAATAAAA (SEQ ID NO: 56)

DIQMTQSPSSLSASLGERVSLTCRASQDIGNRLNWLQQEPDGTIKRLIYATSS
LDSGVPKRFSGSRSGSDYSLTISSLESEDFVDYYCLQYASSPFTFGTGTKLEI
K (SEQ ID NO: 57)

1002E8A6  GACATCAAAATGACCCAGTCTCCATCTTCCATGTATGCATCTCTAGGAG
AGAGAGTCACTATCACTTGCAAGGCGAGTCAGGACATTAATAGCTATTT
AAACTGGTTCCAGCAGAAACCAGGGAAATCTCCTGAGACCCTGATCTAT
CGTGCAAACAGATTGGTATCTGGGGTCCCATCAAGGTTCAGTGGCAGTG
GATCTGGGCAAGATTATTCTCTCACCATCAGCAGCCTGGAATATGAAGA
TATGGGAATTTATTCTTGTCTACAGTATGATGAGTTTCCGTACACGTTCG
GAGGGGGGACCAAGCTGGAAATAAAA (SEQ ID NO: 118)

TABLE 1-continued

Anti-BAFF Mouse Leads - Vκ Sequences

| Designation | Sequence |
|---|---|
| | DIKMTQSPSSMYASLGERVTITCKASQDINSYLTWFQQKPGKSPETLIYRAN<br>RLVSGVPSRFSGSGSGQDYSLTISSLEYEDMGIYSCLQYDEFPYTFGGGTKL<br>EIK (SEQ ID NO: 119) |
| 1070A6B7 | GATGTTGTGATGACCCAAACTCCACTCTCCCTGCCTGTCAGTCTTGGAGA<br>TCAAGCCTCCATCTCTTGCAGATGTAGTCAGAGCCTTGTACACAGTAAT<br>GGAAACACGTATTTACATTGGTACCTGCAGAAGCCAGGCCAGTCTCCAA<br>AGCTCCTGATCTACAAAGTTTCCGACCGATTTTCTGGGGTCCCAGACAG<br>GTTCAGTGGCAGTGGATCAGGGACAGATTTCACACTCAGGATCAGCAGA<br>GTGGAGGCTGACGATCTGGGAGTTTATTTCTGCTCTCAAAGTACACATG<br>TTCCGCTCACGTTCGGTGCTGGGACCAAGCTGGAGCTGAAA<br>(SEQ ID NO: 120) |
| | DVVMTQTPLSLPVSLGDQASISCRCSQSLVHSNGNTYLHWYLQKPGQSPKL<br>LIYKVSDRFSGVPDRFSGSGSGTDFTLRISRVEADDLGVYFCSQSTHVPLTFG<br>AGTKLELK (SEQ ID NO: 121) |
| 1094C4E6 | GACATTGTGATGACCCAGTCTCACAAATTCATGTCCACATCAGTAGGAG<br>ACAGGGTCACCATCACCTGCAAGGCCAGTCAGGATGTGGCTACTGCTGT<br>AGCCTGGTATCAACAGAAACCAGGGCAATCTCCTAAACTACTAATTTAC<br>TGGGCATCCACCCGGCACACTGGAGTCCCTGATCGCTTCACAGGCAGTG<br>GATCTGGGACAGATTTCACTCTCACCATTAGCAATGTGCAGTCTGAAGA<br>CTTGGCAAATTATTTCTGTCAGCAATATAGCAACTATCCGTACACGTTCG<br>GAGGGGGGACCACGCTGGAAATAAAA (SEQ ID NO: 122) |
| | DIVMTQSHKFMSTSVGDRVTITCKASQDVATAVAWYQQKPGQSPKLLIYW<br>ASTRHTGVPDRFTGSGSGTDFTLTISNVQSEDLANYFCQQYSNYPYTFGGG<br>TTLEIK (SEQ ID NO: 123) |
| 27I21-3C7 | GACATCCAGATGACCCAGTCTCCATCCTCCTTATCTGCCTCTCTGGGAGA<br>AAGAGTCAGTCTCACTTGTCGGGCAAGTCAGGACATTGGTAATAGGTTA<br>AACTGGCTTCAGCAGGCACCAGATGGAACTATTAAACGCCTGATCTACG<br>CCACATCCAGTTTAGATTCTGGTGTCCCCAAAAGGTTCAGTGGCAGTCG<br>GTCTGGGTCAGATTATTCTCTCACCATCAGCAGCCTTGAATCTGAAGATT<br>TTGTAGACTATTACTGTCTACAATATGCTAGTTATCCATTCACGTTCGGC<br>ACGGGGACAAAATTGGAAATAAAA (SEQ ID NO: 124) |
| | DIQMTQSPSSLSASLGERVSLTCRASQDIGNRLNWLQQAPDGTIKRLIYATS<br>SLDSGVPKRFSGSRSGSDYSLTISSLESEDFVDYYCLQYASYPFTFGTGTKLE<br>IK (SEQ ID NO: 125) |
| 317H2A6 | GACATTGTGATGACCCAGTCTCAAAAATTTTTGTCCACAACAATAGGAG<br>ACAGGGTCAGCATCACCTGCAAGGCCAGTCAGAATGTGGGTTCTGCTGT<br>AGTCTGGTATCAACAGAAACCAGGCCAACCTCCTAAACTACTGATTACC<br>TCAGCATCCAATCGGTACAGTGGAGTCCCAGATCGCTTCACAGGCAGTG<br>GATCTGGGACAGATTTCACTCTCACCGTTAGCAATGTGCAGTCTGTAGA<br>CCTGGCAGATTATTTCTGTCAACAATATAGCAACTATCCTCTCACGTTCG<br>GTGCTGGGACCAAGCTGGAGCTGAAA (SEQ ID NO: 126) |
| | DIVMTQSQKFLSTTIGDRVSITCKASQNVGSAVVWYQQKPGQPPKLLITSAS<br>NRYSGVPDRFTGSGSGTDFTLTVSNVQSVDLADYFCQQYSNYPLTFGAGTK<br>LELK (SEQ ID NO: 127) |
| 319B8A12 | GACATTGTGATGACCCAGTCTCAAAAATTTGTGTCGACAAGAGTTGGAG<br>ACAGGGTCAGCATCACCTGCAAGGCCAGTCAGAATGTGGGCGCTGCTGT<br>AGTCTGGTATCAACAGAAATCAGGCCAACCTCCTAAACTACTGATTAGG<br>TCAGCATCCAATCGGTACATTGGAGTCCCTGATCGCTTCACAGGCAGTG<br>GGTCTGGGACAGATTTCACTCTCACCGTTAGCGATGTGCAGTCTGGAGA<br>CCTGGCAGATTATTTCTGTCAGCAATATAGCAACTATCCTCTCACGTTCG<br>GTGCTGGGACCAAGCTGGAACTGACACGGGCTGAT<br>(SEQ ID NO: 128) |
| | DIVMTQSQKFVSTRVGDRVSITCKASQNVGAAVVWYQQKSGQPPKLLIRS<br>ASNRYIGVPDRFTGSGSGTDFTLTVSDVQSGDLADYFCQQYSNYPLTFGAG<br>TKLELTRAD (SEQ ID NO: 129) |
| 320F9C5 | GACATTGTGATGACCCAGTCTCAAAAATTCATGTCCACAACAGTAGGAG<br>ACAGGGTCAGCATCACCTGCAAGGCCAGTCAGAATGTGGGTAGTGTTGT<br>AGCCTGGTATCAACAGAGACCAGGACAATCTCCTACACTACTGATTTAC<br>TCAGCATCCAATCGGTACACTGGAGTCCCTGATCGCTTCACTGGCAGTG<br>GATCTGGGACAGATTTCACTCTCACCATTAGCAATATGCAGTCGGAAGA<br>CCTGGCAGATTATTTCTGTCAGCAATATAGCAGCTATCCTCTCACGTTCG<br>GTGCTGGGACCAAGCTGGAGCTGAAA (SEQ ID NO: 130) |
| | DIVMTQSQKFMSTTVGDRVSITCKASQNVGSVVAWYQQRPGQSPTLLIYSA |

TABLE 1-continued

Anti-BAFF Mouse Leads - VK Sequences

| Designation | Sequence |
|---|---|
| | SNRYTGVPDRFTGSGSGTDFTLTISNMQSEDLADYFCQQYSSYPLTFGAGT<br>KLELK (SEQ ID NO: 131) |
| 323E9D1 | GACATTGTGATGACCCAGTCTCAAAAATTTGTGTCGACAAGAGTTGGAG<br>ACAGGGTCAGCATCACCTGCAAGGCCAGTCAGAATGTGGGCGCTGCTGT<br>AGTCTGGTATCAACAGAAATCAGGCCAACCTCCTAAACTACTGATTAGG<br>TCAGCATCCAATCGGTACATTGGAGTCCCTGATCGCTTCACAGGCAGTG<br>GGTCTGGGACAGATTTCACTCTCACCGTTAGCGATGTGCAGTCTGGAGA<br>CCTGGCAGATTATTTCTGTCAGCAATATAGTAACTATCCTCTCACGTTCG<br>GTGCTGGGACCAAGCTGGAACTGACA (SEQ ID NO: 132)<br><br>DIVMTQSQKFVSTRVGDRVSITCKASQNVGAAVVWYQQKSGQPPKLLIRS<br>ASNRYIGVPDRFTGSGSGTDFTLTVSDVQSGDLADYFCQQYSNYPLTFGAG<br>TKLELT (SEQ ID NO: 133) |
| 332C1B12 | GACATTGTGCTGACACAGTCTCCTGCTTCCTTACCTGTTTCTCTGGGGCA<br>GAGGGCCACCATCTCCTGCAGGGCCAGCAAAGGTGTCAGTACATCTAGC<br>TATACTTTTCATTCACTGGTACCAACAGAAACCTGGACAGCCGCCCAAAC<br>TCCTCATCAAGTATGCATCCAACCTAGAATCTGGGGTCCCTGCCAGGTT<br>CAGTGGCAGTGGGTCTGGGACAGACTTCACCCTCAACATCCATCCTGTG<br>GAGGAGGAGGATGTTGCAACATATTACTGTCAGCACAGTAGGGAGTTTC<br>CTCGGACGTTCGGTGGAGGCACCAAGCTGGAAATCAAA<br>(SEQ ID NO: 134)<br><br>DIVLTQSPASLPVSLGQRATISCRASKGVSTSSYTFIHWYQQKPGQPPKLLIK<br>YASNLESGVPARFSGSGSGTDFTLNIHPVEEEDVATYYCQHSREFPRTFGGG<br>TKLEIK (SEQ ID NO: 135) |
| 344B9D9 | GACATCCAGATGACTCAGTCTCCAGCCTCCCTATCTGCATCTGTGGGAG<br>AAACTGTCACCATCACATGTCGAGCAAGTGGGAATATTCACAATTATTT<br>AGCATGGTATCAGCAGAAACAGGGAAAATCTCCTCAGCTCCTGGTCTAT<br>AGTGCAATAACCTTAGCAGATGGTGTGCCATCAAGGTTCAGTGGCAGTG<br>GATCAGAAACACAATTTTCTCTCAAGATCAACAGCCTGCAGCCTGAAGA<br>TTTTGGGATTTATTACTGTCAACATTTTTGGAATACTCCGTACACGTTCG<br>GAGGGGGGACCAAGCTGGAAATAAAA (SEQ ID NO: 136)<br><br>DIQMTQSPASLSASVGETVTITCRASGNIHNYLAWYQQKQGKSPQLLVYSA<br>ITLADGVPSRFSGSGSETQFSLKINSLQPEDFGIYYCQHFWNTPYTFGGGTKL<br>EIK (SEQ ID NO: 137) |
| 348A6C1 | GACATTGTGATGACCCAGTCTCAAAAATTTATGTCCACAACAGTTGGAG<br>ACAGGGTCAGCATCACCTGCAAGGCCAGTCAGAATGTGGGTGCTGCTGT<br>AGCCTGGTATCAACAGAAACCAGGCCAACCTCCTAAACTACTGATTAGG<br>TCAGCATCCAATCGGTACATTGGAGTCCCTGATCGCTTCACAGGCAGTG<br>GGTCTGGGACAGATTTCACTCTCACCGTTAGCGATGTGCAGTCTGTAGA<br>CCTGGCAGATTATTTCTGTCAGCAATATAGCAACTATCCTCTCACGTTCG<br>GTGCTGGGACCAAGCTGGAACTGACACGGGCTGAT<br>(SEQ ID NO: 138)<br><br>DIVMTQSQKFMSTTVGDRVSITCKASQNVGAAVAWYQQKPGQPPKLLIRS<br>ASNRYIGVPDRFTGSGSGTDFTLTVSDVQSVDLADYFCQQYSNYPLTFGAG<br>TKLELTRAD (SEQ ID NO: 139) |
| 352G11A10 | GACATCAAGATGACCCAGTCTCCATCTTCCATATATGCATCTCTAGGAG<br>AGAGAGTCACTATCACTTGCAAGGCGAGTCAGGACATTCATAGCTATTT<br>AAGTTGGTTCCAGCAGAAACCAGGGAAATCTCCTAAGACCCTGATGTAT<br>CGTACAAATAGATTGGTAGATGGGGTCCCATCAAGGTTCAGTGGCAGTG<br>GATCTGGGCAAGATTATTCTCTCACCATCAGGAGCCTGGAATATGAAGA<br>TATGGGAAATTATTATTGTCTACAGTATGATGAATTTCCGTACACGTTCG<br>GCGGGGGGCCAAGTTGGAAGTAAAA (SEQ ID NO: 140)<br><br>DIKMTQSPSSIYASLGERVTITCKASQDIHSYLSWFQQKPGKSPKTLMYRTN<br>RLVDGVPSRFSGSGSGQDYSLTIRSLEYEDMGNYYCLQYDEFPYTFGGGAK<br>LEVK (SEQ ID NO: 141) |
| 363D4A10 | GACATTGTGATGACCCAGTCTCAAAAATTCATGTCCACAACAGTAGGAG<br>ACAGGGTCACCATCACCTGCAAGGCCAGTCAGAATGTGGGTAGTGCTGT<br>AGTCTGGTATCAACAGAAACCAGGACAATCTCCTATATTACTGATTTTCT<br>CAGCATCCAATCGGTACACTGGAGTCCCTGATCGCATCACAGGCAGTGG<br>GTCTGGGGCAGAATTCACTCTCACCATTAGCAGTGTGCAGTCTGAAGAC<br>CTGGCAGAATATTTCTGTCAGCAATATAGCAGCTATCCTCTCACGTTCGG<br>TGCTGGGACCAAGCTGGAGCTGAAA (SEQ ID NO: 142)<br><br>DIVMTQSQKFMSTTVGDRVTITCKASQNVGSAVVWYQQKPGQSPILLIFSA<br>SNRYTGVPDRITGSGSGAEFTLTISSVQSEDLAEYFCQQYSSYPLTFGAGTKL<br>ELK (SEQ ID NO: 143) |

TABLE 1-continued

Anti-BAFF Mouse Leads - Vκ Sequences

Designation Sequence

381A6A9    GACATCAAGATGACCCAGTCTCCATCTTCCATATATGCATCTCTAGGAG
           AGAGAGTCACTATCACTTGCAAGGCGAGTCAGGACATTAATAGCTATTT
           AAGCTGGTTCCAGCAGAAACCAGGGAAATCTCCTAAGACCCTGATGTAT
           CGTGCAAACAGATTGGTAGATGGGGTCCCATCAAGGTTCAGTGGCAGTG
           GATCTGGGCAAGATTATTCTCTCACCATCAGCAGCCTGGAATATGAAGA
           TATGGGAAATTATTATTGTCTACAGTATGATGAGTTTCCGTACACGTTCG
           GAGGGGGGGCCAAGCTGGAAATAAAA (SEQ ID NO: 144)

DIKMTQSPSSIYASLGERVTITCKASQDINSYLSWFQQKPGKSPKTLMYRAN
           RLVDGVPSRFSGSGSGQDYSLTISSLEYEDMGNYYCLQYDEFPYTFGGGAK
           LEIK (SEQ ID NO: 145)

384D5A2    GACATCCAGATGACTCAGTCTCCAGCCTCCCTATCTGTATCTGTGGGAG
           AAACTGTCACCATCACATGTCGATCAAGTGAGAATATTTACAGTAGTTT
           AGCATGGTATCAACAGAAACAGGGAAAATCTCCTCAGCTCCTGGTCTAT
           GCTGCAACAAACTTAGCAAAAGGTGTGCCGTCAAGGTTCAGTGGCAGTG
           GATCAGGCACACAGTATTCCCTCAAGATCAACAGCCTACAGTCTGAAGA
           TTTTGGGAGTTATTTCTGTCAACATTTTTGGGGTAGTCCATTCGCGTTCG
           GCTCGGGGACAAAGTTGGAAATAAAA (SEQ ID NO: 146)

DIQMTQSPASLSVSVGETVTITCRSSENIYSSLAWYQQKQGKSPQLLVYAAT
           NLAKGVPSRFSGSGSGTQYSLKINSLQSEDFGSYFCQHFWGSPFAFGSGTKL
           EIK (SEQ ID NO: 147)

394F5A5    GACATTGTGATGACCCAGTCTCAAAAATTTATGTCCACAACAATAGGAG
           ACAGGGTCAGCATCACCTGCAAGGCCAGTCAGAATGTGGGTTCTGCTGT
           GGCCTGGTATCAACAGAAACCAGGACAACCTCCCAAACTACTGATTTAC
           TCAACATCCAATCGGTACACTGGAGTCCCTGATCGCTTCACAGGCAGTA
           GATCTGGGACAGATTTCACTCTCACCGTTAGCAATATGCAGTCTGAAGA
           CCTGGCAGATTATTTCTGTCAGCAATATGCCAGCTATCCTCTCACATTCG
           GTACTGGGACCAAGCTGGAGCTGAAA (SEQ ID NO: 148)

DIVMTQSQKFMSTTIGDRVSITCKASQNVGSAVAWYQQKPGQPPKLLIYST
           SNRYTGVPDRFTGSRSGTDFTLTVSNMQSEDLADYFCQQYASYPLTFGTGT
           KLELK (SEQ ID NO: 149)

409F12A11  GACATTGTGCTGACACAGTCTCCTGCTTCCTTAGCTTTATCTCTGGGGCA
           GAGGGCCACCATCTCATGCAGGGCCACCAAGGGGTCAGTAAATCTGG
           CTATAGTTATATGCACTGGTACCAACAGAAACAGGGCAGCCACCCAAA
           CTCCTCATCTATCTTGCATCCAACCTAGAATCTGGGGTCCCTGCCAGGTT
           CAGTGGCAGTGGGTCTGGGACAGACTTCACCCTCAATATCCATCCTGTG
           GAGGAGGAGGATGTTGCAACCTATTACTGTCAGCACAGTAGGGAGCTTC
           CGCTCACGTTCGGTGCTGGGACCAAGCTGGAGCTGAAA
           (SEQ ID NO: 150)

DIVLTQSPASLALSLGQRATISCRATKGVSKSGYSYMHWYQQKPGQPPKLL
           IYLASNLESGVPARFSGSGSGTDFTLNIHPVEEEDVATYYCQHSRELPLTFG
           AGTKLELK (SEQ ID NO: 151)

418F6D9    ATTGTGCTGACCCAATCTTCAGCTTCTTTGGCTGTGTCTCTAGGGCAGAG
           GGCCACCATATCCTGCAGAGCCAGTGAAAGTGTTGATAGTTATGGCAAT
           AGTCTTATGCACTGGTACCAGCAGAAACCAGGACAGCCACCCAAACTCC
           TCATCTATATTGCATCCAACCTAGAATCTGGGGTCCCTGCCAGGTTCAGT
           GGCAGTGGGTCTAGGACAGACTTCACCCTCACCATTGATCCTGTGGAGG
           CTGATGATGCTGCAACCTATTACTGTCAGCAAAATAGTGAGGATCCTCG
           GACGTTCGGTGGAGGCACCAAGCTGGAAATCAAA
           (SEQ ID NO: 152)

IVLTQSSASLAVSLGQRATISCRASESVDSYGNSLMHWYQQKPGQPPKLLIY
           IASNLESGVPARFSGSGSRTDFTLTIDPVEADDAATYYCQQNSEDPRTFGGG
           TKLEIK (SEQ ID NO: 153)

431G5A3    AAAATTGTGCTGACCCAATCTTCAGCTTCTTTGGCTGTGTCTCTAGGGCA
           GAGGGCCACCATATCCTGCAGAGCCAGTGAAAGTGTTGATCGTTATGGC
           AATAGTCTTATGCACTGGTACCAGCAGAAACCAGGACAGCCACCCAAA
           CTCCTCATCTATATTGCATCCAACCTAGAATCTGGGGTCCCTGCCAGGTT
           CAGTGGCAGTGGGTCTAGGACAGACTTCACCCTCACCATTGATCCTGTG
           GAGGCTGATGATGCTGCAACCTATTACTGTCAGCAAAATAATGAGGATC
           CTCGGACGTTCGGTGGAGGCACCAAGCTGGAAATCAAA
           (SEQ ID NO: 154)

KIVLTQSSASLAVSLGQRATISCRASESVDRYGNSLMHWYQQKPGQPPKLLI
           YIASNLESGVPARFSGSGSRTDFTLTIDPVEADDAATYYCQQNNEDPRTFGG
           GTKLEIK (SEQ ID NO: 155)

TABLE 1-continued

Anti-BAFF Mouse Leads - Vκ Sequences

Designation Sequence

435A6B3
GACATCAAGATGACCCCGTCTCCTTCTTCCATGTATGCATCTCTCGGAGA
GAGAGTCACTATCACTTGCAAGGCGAGTCAGGACATTAATAGATATTTA
AGCTGGTTCCAGCAGAAACCAGGGAAATCTCCTAAGACCCTGATCTATC
GTGCAAATAGATTGGTAGATGGGGTCCCATCAAGGTTCAGTGGCAGTGG
ATCTGGGCAAGATTACTCTCTCACCATCAGCAGCCTGGAGTATGAAGAT
ATGGGAATTTATTATTGTCTACAGTATGATGAATTTCCTTACACGTTCGG
AGGGGGGACCAAGCTGGAAATAAAA (SEQ ID NO: 156)

DIKMTPSPSSMYASLGERVTITCKASQDINRYLSWFQQKPGKSPKTLIYRAN
RLVDGVPSRFSGSGSGQDYSLTISSLEYEDMGIYYCLQYDEFPYTFGGGTKL
EIK (SEQ ID NO: 157)

436H2C12
AACATTGTGCTGACCCAATCTCCAGCTTCTTTGGCTGTGTCTCTAGGGCA
GAGGGCCACCATATCCTGCAGAGCCAGTGAAAGTGTTGATAATTATGGC
AATAGTTTTATGCACTGGTACCAGCAGAAACCAGGACAGCCACCCAAAC
TCCTCATCTCTCTTGCATCCAACCTAGAATCTGGGGTCCCTGCCAGGTTC
AGTGGCAGTGGGTCTAGGACAGACTTCACCCTCACCATTGATCCTGTGG
AGGCTGATGATGCTGCAACCTATTACTGTCAGCAAAATAATGAGGATCC
TCGGACGTTCGGTGGAGGCACCAAGCTGGAAATCAAA
(SEQ ID NO: 158)

NIVLTQSPASLAVSLGQRATISCRASESVDNYGNSFMHWYQQKPGQPPKLLI
SLASNLESGVPARFSGSGSRTDFTLTIDPVEADDAATYYCQQNNEDPRTFGG
GTKLEIK (SEQ ID NO: 159)

436H6A9
GACATTGTGCTGACACAGTCTCCTGCTTCCTTAGGTGTATCTCTGGGGCA
GAGGGCCACCATCTCTTGCAGGGCCACCAAAGGGGTCACTAAATCTGGC
TATAGTTATATTCACTGGTACCAACAGAAACCAGGACAGCCACCCAAAC
TCCTCATCTATCTTGCATCCAACCTACAATCTGGGGTCCCTGCCAGGTTC
AGTGGCAGTGGGTCTGGGACAGACTTCACCCTCAACATCCATCCGGTGG
AGGAGGAGGATGCTGCAACCTATTACTGTCAGCACAGTAGGGAGCTTCC
GCTCACGTTCGGTGCTGGGACCAAGCTGGAGCTGAAA
(SEQ ID NO: 160)

DIVLTQSPASLGVSLGQRATISCRATKGVTKSGYSYIHWYQQKPGQPPKLLI
YLASNLQSGVPARFSGSGSTDFTLNIHPVEEEDAATYYCQHSRELPLTFGA
GTKLELK (SEQ ID NO: 161)

440E9D12
AACATTGTGCTGACCCAATCTCCAGCTTCTTTGCCTGTGTCTCTAGGGCA
GAGGGCCACCATGTCCTGCAGAGCCAGTAAAAGTGTTGATAGTTATGGC
ACTAGTTTTATGCACTGGTACCAACACAGACCAGGACAGCCACCCAAAC
TCCTCATCTCTCTTGCATCCAACCTAGAATCTGGGGTCCCTGCCAGGTTC
AGTGGCAGTGGGTCTAGGACAGACTTCACCCTCACCATTGATCCTGTGG
AGCCTGATGATGCTGCAACCTATTACTGTCAACAAAATAATGAGGATCC
TCGGACGTTCGGTGGAGGCACCACGCTGGAAATCAAA
(SEQ ID NO: 162)

NIVLTQSPASLPVSLGQRATMSCRASKSVDSYGTSFMHWYQHRPGQPPKLL
ISLASNLESGVPGRFSGSGSRTDFTLTIDPVEPDDAATYYCQQNNEDPRTFG
GGTTLEIK (SEQ ID NO: 163)

441E6F2
AACATTGTGTTGACCCAATCTCCAGCTTCTTTGGCTGTGTCTCTAGGACA
GAGGGCCACCATATCCTGCAGAACCAGTGAAAGTGTTGATAGTTATGGC
AATAGTTTTATGTTCTGGTTCCAGCAGAAACCAGGACAGGCACCCAAAC
TCCTCATCTTTCTTACATCCAACCTCGAATCTGGGGTCCCTGCCAGGTTC
AGTGGCAGTGGGTCTAGGACAGACTTCACCCTCACCATTGATCCTGTGG
AGGCTGATGATGCTGCAACCTATTACTGTCAGCAAAGTAATGAGGATCC
TCGGACGTTCGGTGGAGGCACCAAGCTGGAAATCAAA
(SEQ ID NO: 164)

NIVLTQSPASLAVSLGQRATISCRTSESVDSYGNSFMFWFQQKPGQAPKLLI
FLTSNLESGVPARFSGSGSRTDFTLTIDPVEADDAATYYCQQSNEDPRTFGG
GTKLEIK (SEQ ID NO: 165)

443C11A12
GACATCAAGATGACCCCGTCTCCTTCTTCCATGTATGCATCTCTCGGAGA
GAGAGTCACTATCACTTGCAAGGCGAGTCAGGACATTAATAGCTATTTA
AGTTGGTTCCAGCAGAAACCAGGGAAATCTCCTAAGACCCTGATCTATC
GTGCAAATAGATTGGTAGATGGGGTCCCATCAAGGTTCAGTGGCAGTGG
ATCTGGCCAAGATTACTCTCTCACCATCAGCAGCCTGGAATATGAAGAT
ATGGGAATTTATTATTGTCTACAGTATGATGAATTTCCTTACACGTTCCGG
AGGGGGGACCAAGCTGGAAATAAAG (SEQ ID NO: 166)

DIKMTPSPSSMYASLGERVTITCKASQDINSYLSWFQQKPGKSPKTLIYRAN
RLVDGVPSRFSGSGSGQDYSLTISSLEYEDMGIYYCLQYDEFPYTSGGGTKL
EIK (SEQ ID NO: 167)

TABLE 1-continued

Anti-BAFF Mouse Leads - Vκ Sequences

| Designation | Sequence |
|---|---|
| 444G1A10 | AACATTGTGTTGACCCAATCTCCAGCTTCTTTGGCTGTGTCTCTAGGACA<br>GAGGGCCACCATATCCTGCAGAGCCAGTGAAAGTGTTGATAGTTATGGC<br>AATAGTTTTATGTTCTGGTTCCAGCAGAAACCAGGACAGGCACCCAAAC<br>TCCTCATCTTTCTTACATCCAACCTCGAATCTGGGGTCCCTGCCAGGTTC<br>AGTGGCAGTGGGTCTAGGACAGACTTCACCCTCACCATTGATCGTGTGG<br>AGGCTGATGATGCTGCAACCTATTACTGTCAGCAAAGTAATGAGGATCC<br>TCGGACGTTCGGTGGAGGCACCAAGCTGGAAATCAAA<br>(SEQ ID NO: 168)<br><br>NIVLTQSPASLAVSLGQRATISCRASESVDSYGNSFMFWFQQKPGQAPKLLI<br>FLTSNLESGVPARFSGSGSRTDFTLTIDRVEADDAATYYCQQSNEDPRTFGG<br>GTKLEIK (SEQ ID NO: 169) |
| 450A2A7 | ATTGTGCTGACCCAATCTTCAGCTTCTTTGGCTGTGTCTCTAGGGCAGAG<br>GGCCACCATATCCTGCAGAGCCAGTGAAAGTGTTGATCGTTATGGCAAT<br>AGTCTTATGCACTGGTACCAGCAGAAACCAGGACAGCCACCCAAACTCC<br>TCATCTATATTGCATCCAACCTAGAATCTGGGGTCCCTGCCAGGTTCAGT<br>GGCAGTGGGTCTAGGACAGACTTCACCCTCACCATTGATCCTGTGGAGG<br>CTGATGATGCTGCAACCTATTACTGTCAGCAAAATAATGAGGATCCTCG<br>GACGTTCGGTGGAGGCACCAAGCTGGAAATCAAA<br>(SEQ ID NO: 170)<br><br>IVLTQSSASLAVSLGQRATISCRASESVDRYGNSLMHWYQQKPGQPPKLLIY<br>IASNLESGVPARFSGSGSRTDFTLTIDPVEADDAATYYCQQNNEDPRTFGGG<br>TKLEIK (SEQ ID NO: 171) |
| 456H11B7 | AACATTGTGCTGACCCAATCTCCAGCTTCTTTGCCTGTGTCTCTAGGGCA<br>GAGGGCCACCATGTCCTGCAGAGCCAGTAAAAGTGTTGATAGTTATGGC<br>ACTAGTTTTATGCACTGGTACCAACACAGACCAGGACAGCCACCCAAAC<br>TCCTCATCTCTCTTGCATCCAACCTAGAATCTGGGGTCCCTGGCAGGTTC<br>AGTGGCAGTGGGTCTAGGACAGACTTCACCCTCACCATTGATCCTGTGG<br>AGCCTGATGATGCTGCAACCTATTACTGTCAACAAAATAATGAGGATCC<br>TCGGACGTTCGGTGGAGGCACCACGCTGGAAATCAAA<br>(SEQ ID NO: 172)<br><br>NIVLTQSPASLPVSLGQRATMSCRASKSVDSYGTSFMHWYQHRPGQPPKLL<br>ISLASNLESGVPGRFSGSGSRTDFTLTIDPVEPDDAATYYCQQNNEDPRTFG<br>GGTTLEIK (SEQ ID NO: 173) |
| 537G7A6 | GACATTGTGCTGACACAGTCTCCTGCTTCTTTGGCTGTGTCTGTAGGGCA<br>GAGGGCCACCGTATCCTGCAGAGTCAGTGAAAGTGTTGATAGATATGGC<br>GATAGTTTTATGCACTGGTACCAGCAGAAACCAGGACAGCCACCCAAAC<br>TCCTCATCTATCTTGCATCCAACCTAGAATCTGGGGTCCCTGCCAGGTTC<br>AGTGGCAGTGGGTCTAGGACAGACTTCACCCTCACCATTGATCCTGTGG<br>AGGCTGATGATGCTGCAACCTATTACTGTCAGCAAAATAAAGAGGATCC<br>GTACACGTTCGGAGGGGGGACCAAGCTGGAACTTAAA<br>(SEQ ID NO: 174)<br><br>DIVLTQSPASLAVSVGQRATVSCRVSESVDRYADSFMHWYQQKPGQPPKL<br>LIYLASNLESGVPARFSGSGSRTDFTLTIDPVEADDAATYYCQQNKEDPYTF<br>GGGTKLELK (SEQ ID NO: 175) |
| 551H4D6 | GACATTGTGCTGACCCAATCTCCAGCTTCTTTGGCTGTGTCTCTAGGGCA<br>GAGGGCCACCATGTCCTGCAGAGCCAGTGAAAGTGTTGATAGTTATGGC<br>AATAGTTTTATACACTGGTACCAGCAGAAACCAGGACAGCCACCCAGAC<br>TCCTCATCTATCGTGCATCCAACCTAAATTCTGGGATCCCTGCCAGGTTC<br>AGTGGCAGTGGGTCTAGGACAGACTTCACCCTCACCATTAGTTCTGTGG<br>AGGCTGATGATGTTGCAACCTATTACTGTCACCAAAATAATGAGGATCC<br>TCGGACGTTCGGTGGAGGCACCAAGCTGGAAATCAAA<br>(SEQ ID NO: 176)<br><br>DIVLTQSPASLAVSLGQRATMSCRASESVDSYGNSFIHWYQQKPGQPPRLLI<br>YRASNLNSGIPARFSGSGSRTDFTLTISSVEADDVATYYCHQNNEDPRTFGG<br>GTKLEIK (SEQ ID NO: 177) |
| 560H2A7 | GACATTGTGCTGACCCAATCTCCAGCTTCTTTGGCTGTGTCTCTAGGGCA<br>GAGGGCCACCATCTCCTGCAGAGCCAGCGAAAGTATTGATAATTATGCC<br>CTTATTTTTATGAGCTGGTTCCAACAGAAACCAGGACAGCCACCCAAAC<br>TCCTCATCTATGCTGCATCCAACCGAGGATCCGGGGTCCCTGCCAGGTTT<br>AGTGGCAGTGGGTCTGGGACAGACTTCAGCCTCAACATCCATCCTATGG<br>AGGAGGATGATACTGCAATGTATTTCTGTCAGCAAAGTAAGGAGGTTCC<br>GTGGACGTTCGGTGGAGGCACCAAGCTGGAAGTCAAA<br>(SEQ ID NO: 178) |

TABLE 1-continued

Anti-BAFF Mouse Leads - Vκ Sequences

| Designation | Sequence |
|---|---|
| | DIVLTQSPASLAVSLGQRATISCRASESIDNYGLIFMSWFQQKPGQPPKLLIY<br>AASNRGSGVPARFSGSGSGTDFSLNIHPMEEDDTAMYFCQQSKEVPWTFGG<br>GTKLEVK (SEQ ID NO: 179) |
| 606H7F8 | GACATCCAGATGACTCAGTCTCCAGCCTCCCTATCTGCATCTGTGGGAG<br>AAACTGTCACCATCACATGTCGAGCAAGTGGGAATATTCACAATTATTT<br>AGCATGGTATCAGCAGAAACAGGGAAAATCTCCTCAGCTCCTGGTCTAT<br>AATGCAAAAACCTTAGCAGATGGTGTGCCATCAAGGTTCAGTGGCAGTG<br>GATCAGGAACACAATTTTCTCTCAAGATCAACAGCCTGCAGCCTGAAGA<br>TTTTGGGAGTTATTACTGTCAACATTTTTGGAGTACTCCGTACACGTTCG<br>GAGGGGGGACCAAGCTGGAAATAAAA (SEQ ID NO: 180) |
| | DIQMTQSPASLSASVGETVTITCRASGNIHNYLAWYQQKQGKSPQLLVYNA<br>KTLADGVPSRFSGSGSGTQFSLKINSLQPEDFGSYYCQHFWSTPYTFGGGTK<br>LEIK (SEQ ID NO: 181) |

TABLE 2

Anti-BAFF Mouse Leads - VH Sequences

| Designation | Sequence |
|---|---|
| 206G9A10 | CAGGTCCAACTGCAGCAGCCTGGGGCTGAGCTTGTGAAGCCTGGGGCT<br>TCAGTGAAGCTGTCCTGCAAGGCTTCTGGCTACACCTTCAGTATCTTCT<br>GTATACACTGGGTGCAACAGAGGCCTGGACGAGGCCTTGAGTGGATTG<br>GAAGGATTGATCCTAGTAGTGGTGGTACTAAGTACAATGAGAAGTTCG<br>AGAGCAAGGCCACACTGACTGTAGACAAATCCTCCAGCACAGCCTACA<br>TGCAGCTCAGCAGCCTGACATCTGAGGACTCTGCGGTCTATTATTGTGC<br>AAGAGGGGAGGATTTATTAGTACGGACGGATGCTATGGACTACTGGGG<br>TCAAGGAACCTCAGTCACCGTCTCCTCA (SEQ ID NO: 58) |
| | QVQLQQPGAELVKPGASVKLSCKASGYTFSIFCIHWVQQRPGRGLEWIGRI<br>DPSSGGTKYNEKFESKATLTVDKSSTAYMQLSSLTSEDSAVYYCARGEDL<br>LVRTDAMDYWGQGTSVTVSS (SEQ ID NO: 59) |
| 227D5A7 | CAGGTCCAACTGCAGCAGCCTGGGGCTGAACTTGTGAAGCCTGGGGCT<br>TCAGTGAAGCTGTCCTGCAAGGCTTCTGGCTACACCTTCAGTATTTTCTG<br>TGTACACTGGGTGCAACAGAGGCCTGGACGAGGCCTTGAGTGGATTGG<br>AAGGATTGATCCTAGTAGTGGTGGTACTAAGTACAATGAGAAGTTCGA<br>GAGCAAGGCCACACTGACTGTAGACAAATCGTCCAGCACAGCCTACAT<br>GCAGCTCAGCAGCCTGACACCTGAGGACTCTGCGGTCTATTATTGTGCA<br>AGAGGGGAGGATTTATTAGTACGGACGGATGCTCTGGACTACTGGGGT<br>CAAGGATCCTCAGTCACCGTCTCCTCA (SEQ ID NO: 60) |
| | QVQLQQPGAELVKPGASVKLSCKASGYTFSIFCVHWVQQRPGRGLEWIGR<br>IDPSSGGTKYNEKFESKATLTVDKSSTAYMQLSSLTPEDSAVYYCARGED<br>LLVRTDALDYWGQGSSVTVSS (SEQ ID NO: 61) |
| 250E5A11 | CAGGTCCAACTGCAGCAGCCTGGGACTGAGCTTGTGAAGCCTGGGGCT<br>TCAGTGAAGCTGTCCTGCAAGGCTTCTGGCTACACCTTCAGTATCTTCT<br>GTATACACTGGGTGCAACAGAGGCCTGGACGAGGCCTTGAGTGGATTG<br>GAAGGATTGATCCTAGTAGTGGTGGCACTAAATATAATGAGAGGTTCG<br>AAAACAAGGCCACACTGACTGTAGACAAATCCTCCAGCACAGCCTACA<br>TGCAGCTCAGCAGTCTGACATTTGAGGACTCTGCGGTCTATTATTGTGC<br>AAGAGGGGAGGATTTATTAGTACGGACGGATGCTATGGACTACTGGGG<br>TCAAGGAACCTCAGTCACCGTCTCCTCA (SEQ ID NO: 62) |
| | QVQLQQPGTELVKPGASVKLSCKASGYTFSIFCIHWVQQRPGRGLEWIGRI<br>DPSSGGTKYNERFENKATLTVDKSSTAYMQLSSLTFEDSAVYYCARGED<br>LLVRTDAMDYWGQGTSVTVSS (SEQ ID NO: 63) |
| 227D3B11 | CAGGTCCAACTGCAGCAGCCTGGGGCTGAGCTTGTGAAGCCTGGGGCT<br>TCAGTGAAGCTGTCCTGTAAGGCTTCTGGCTACTCCTTCAGCACCTTCTT<br>TATACACTGGATACAGCAGAGGCCTGGGCGAGGCCTTGAGTGGATTGG<br>AAGGATTGATCCTAATAGTGGTGGTACTAAGTACAATGAGAAGTTCGA<br>GAGTAAGGCCACACTGACTGTTGACAAACCCTCCAGTACAGCCTACAT<br>GCACCTCAGCAGCCTGACATCTGAGGACTCTGCGGTCTATTATTGTGCA<br>AGAGGGGAGGATTTATTGATACGGACGGATGCTATGGACTACTGGGGT<br>CAAGGAACCTCAGTCACCGTCTCCTCA (SEQ ID NO: 64) |

TABLE 2-continued

Anti-BAFF Mouse Leads - VH Sequences

| Designation | Sequence |
|---|---|
| | QVQLQQPGAELVKPGASVKLSCKASGYSFSTFFIHWIQQRPGRGLEWIGRI<br>DPNSGGTKYNEKFESKATLTVDKPSSTAYMHLSSLTSEDSAVYYCARGED<br>LLIRTDAMDYWGQGTSVTVSS (SEQ ID NO: 65) |
| 235F5B9 | CAGGTCCAACTGCAGCAGCCTGGGGCTGAGCTTGTGAAGCCTGGGGCT<br>TCAGTGAAGCTGTCCTGCAAGGCTTCTGGCTACTCCTTCAGTACCTTCTT<br>TATACACTGGATACAGCAGAGGCCTGGGCGAGGCCTTGAGTGGATTGG<br>AAGGATTGATCCTAATAGTGGTGCTACTAAATACAATGAGAAGTTCGA<br>GAGTAAGGCCACACTGACTGTTGACAAACCCTCCAGTACAGCCTACAT<br>GCACCTCAGCAGCCTGACATCTGAGGACTCTGCGGTCTATTATTGTGCA<br>AGAGGGGAGGATTTATTGATTCGGACGGATGCTCTGGACTACTGGGGT<br>CAAGGAACCTCAGTCACCGTCTCCTCA (SEQ ID NO: 66) |
| | QVQLQQPGAELVKPGASVKLSCKASGYSFSTFFIHWIQQRPGRGLEWIGRI<br>DPNSGATKYNEKFESKATLTVDKPSSTAYMHLSSLTSEDSAVYYCARGED<br>LLIRTDALDYWGQGTSVTVSS (SEQ ID NO: 67) |
| 217H12A7 | CAGGTCCAACTGCAGCAGCCTGGGGCTGAGCTTGTGAAGCCTGGGGCT<br>TCAGTGAAGCTGTCCTGCAAGGCTTCTGGCTACACCTTCAGTACCTTCTT<br>AATACACTGGGTGCAGCAGAGGCCTGGACGAGGCCTTGAGTGGATTGG<br>AAGGATTGATCCTAATAGTGGTGGTACTAAGTACAATGAGAAGTTCGA<br>GAGGAAGGCCACACTGACTGTAGACAAACCCTCCAGCACAGCCTACAT<br>GCAGCTCAGCAGCCTGACATCTGAGGACTCTGCGGTCTATTATTGTGCA<br>AGAGGGGAGGATTTATTACTACGGACGGATGCTATGGACTACTGGGGT<br>CAAGGAACCTCAGTCACCGTCTCCTCA (SEQ ID NO: 68) |
| | QVQLQQPGAELVKPGASVKLSCKASGYTFSTFLIHWVQQRPGRGLEWIGRI<br>DPNSGGTKYNEKFERKVTLTVDKPSSTAYMQLSSLTSEDSAVYYCARGED<br>LLLRTDAMDYWGQGTSVTVSS (SEQ ID NO: 69) |
| 210D9B8 | CAGGTCCAACTGCAGCAGCCTGGGACTGAATTTGTGAAGCCTGGGGCTT<br>CAGTGAAGCTGTCCTGCGAGGCTTCTGGCTACACCTTCATCACCTACTG<br>GATGCACTGGGTGAAGCAGAGGCCTGGACGAGGCCTTGAGTGGATTGG<br>AGGGATTGATCCTAATAGTGGTGTTATTAAGTACAATGAGAAGTTCAAG<br>AGTAAGGCCACACTGACTGTAGACAAACCCTCCAGCACAGCCTACATG<br>CAGCTCAGCAGCCTGACATCTGAGGACTCTGCGGTCTACTATTGTGCAA<br>GAGGGGAGGATTTATTAATACGGACGGATGCTATGGACTACTGGGGTC<br>AAGGAACCTCAGTCACCGTCTCCTCA (SEQ ID NO: 70) |
| | QVQLQQPGTEFVKPGASVKLSCEASGYTFITYWMHWVKQRPGRGLEWIG<br>GIDPNSGVIKYNEKFKSKATLTVDKPSSTAYMQLSSLTSEDSAVYYCARGE<br>DLLIRTDAMDYWGQGTSVTVSS (SEQ ID NO: 71) |
| 214G4B7 | CAGGTCCAACTGCAGCAGCCTGGGGCTGAGTTTGTGAAGCCTGGGGCTT<br>CAGTGAAGCTGTCCTGCAAGGCTTCTGGCTACTCCTTCAGTACCTTCTGT<br>ATACACTGGGTGCAGCAGAGGCCTGGGCGAGGCCTTGAGTGGATTGGA<br>AGGATTGATCCTAATAGTGGTGGTACTAAATACAATGAGAAGTTCGAG<br>AGTAAGGCCACACTGACTATAGACAAACCCTCCAGTACAGCCTACGTG<br>CACCTCAGCAGCCTGACATCTGAGGACTCTGCGGTCTATTATTGTGCAA<br>GAGGGGAGGATTTATTGATACGGACGGATGCTATGGACTACTGGGGTC<br>AAGGAACCTCAGTCACCGTCTCCTCA (SEQ ID NO: 72) |
| | QVQLQQPGAEFVKPGASVKLSCKASGYSFSTFCIHWVQQRPGRGLEWIGRI<br>DPNSGGTKYNEKFESKATLTIDKPSSTAYVHLSSLTSEDSAVYYCARGEDL<br>LIRTDAMDYWGQGTSVTVSS (SEQ ID NO: 73) |
| 13J018-1A4 | CAGGTTCAGCTGCAGCAGTCTGGACCTGAGGTGGTGAGGCCTGGGGCT<br>TCAGTGAAGATATCCTGCAAGGCTCCTGACCATATTTTCAGTATCCACT<br>GGATGCAGTGGGTAAGCAGAGGCCTGGACCGGGCCTTGAGTGGATTG<br>GAGAGATTTTTCCTGGAAGTGGTACTACTGATTATAATGAGAAATTCAA<br>GGGCAAGGCCACAGTGACGGTAGATAGAGGCTCCAGGTCAGCCTACAT<br>GCAGTTCAACAGCCTGACATCTGAGGACTCTGCGGTCTATTTCTGTGCA<br>AGCGGAGCCTTTGACTACTGGGGCCAAGGCACCACTCTCACAGTCTCTT<br>CA (SEQ ID NO: 74) |
| | QVQLQQSGPEVVRPGASVKISCKAPDHIFSIHWMQWVRQRPGPGLEWIGEI<br>FPGSGTTDYNEKFKGKATVTVDRGSRSAYMQFNSLTSEDSAVYFCASGAF<br>DYWGQGTTLTVSS (SEQ ID NO: 75) |
| 1002E8A6 | GAGGTCCAGCTGCAGCAGTCTGGACCTGAGCTGGTAAAGCCTGGGGCT<br>TCAGTGAAGATGTCCTGCAAGGCTTCTGGATACACAATCACTAGTTATG<br>TTATGCACTGGGTGAAGCAGAAGCCTGGGCAGGGCCTTGAGTGGATTG<br>GATATATTAATCCTAACAATGATGGCACTAAGTACAATGAGAAGTTCA<br>AAGGCAAGGCCACACTGACTTCAGACAAATCCTCCAACACAGCCTACA<br>TGGAGCTCAGCAGCCTGACCTCTGAGGACTCTGCGGTCTATTATTGTGC |

TABLE 2-continued

Anti-BAFF Mouse Leads - VH Sequences

| Designation | Sequence |
|---|---|
| | AAGAGGGGACTATAGTAACTACTTCTACTGGTACTTCGATGTCTGGGGC<br>GCAGGGACCACGGTCACCGTCTCCTCA (SEQ ID NO: 182)<br><br>EVQLQQSGPELVKPGASVKMSCKASGYTITSYVMHWVKQKPGQGLEWIG<br>YINPNNDGTKYNEKFKGKATLTSDKSSNTAYMELSSLTSEDSAVYYCARG<br>DYSNYFYWYFDVWGAGTTVTVSS (SEQ ID NO: 183) |
| 1070A6B7 | CAGGTCCCGCTGCAGCAGCCTGGGGCTGAGATGGTGAGGCCTGGGGCT<br>TCAATGAGGTTGTCCTGTAAGGCTTCTGGCTACACCTTCCCCGGCTACT<br>GGATGCACTGGGTGAAGCAGAGGCCTAGACAAGGCCTTGAGTGGATTG<br>CTAAGATTGATCCCTCTGATAGTGAAACTCACTACAATCAAAACTTCAA<br>GGACAAGGCCACATTGACTGTAGACAAATATTCCAACACAGTCTACAT<br>GCAGCTCAACAGCCTGACATCTGAAGACTCTGCGGTCTATTACTGTGCA<br>AACGAGGGTTGGGACAGCCTTACGAAAGTCTGGTTTGGTTGGTGGGGC<br>CAAGGGACTCTGGTCACTGTCTCTGCA (SEQ ID NO: 184)<br><br>QVPLQQPGAEMVRPGASMRLSCKASGYTFPGYWMHWVKQRPRQGLEWI<br>AKIDPSDSETHYNQNFKDKATLTVDKYSNTVYMQLNSLTSEDSAVYYCAN<br>EGWDSLTKVWFGWWGQGTLVTVSA (SEQ ID NO: 185) |
| 1094C4E6 | GAGGTTCAGCTGCAGCAGTCTGGGGCTGAGCTTGTGAGGCCAGGGGCC<br>TCAGTCAAGTTGTCCTGCACAGCTTCTGGCTTTAACATTAAAGACGACT<br>ATATGCACTGGGTGAAGCAGACGCCTGAACAGGGCCTGGAGTGGATTG<br>GAAGGATTGATCCTGCGTATGGTAATGGTAAGTATGTCCCGAAGTTCCA<br>GGACAAGGCCACTATAACTGCAGACACATCCTCCAACACAGCCTACCT<br>GCAGCTCAGCAGCCTGACATCTGAGGACACTGCCGTCTATTACTGTGCT<br>AGACGGTACTACGCTGTTAGTTCCGTAGACTATGCTCTGGACTACTGGG<br>GTCAAGGAACCTCAGTCACCGTCTCCTCA (SEQ ID NO: 186)<br><br>EVQLQQSGAELVRPGASVKLSCTASGFNIKDDYMHWVKQTPEQGLEWIGR<br>IDPAYGNGKYVPKFQDKATITADTSSNTAYLQLSSLTSEDTAVYYCARRYY<br>AVSSVDYALDYWGQGTSVTVSS (SEQ ID NO: 187) |
| 27I21-3C7 | CAGGTTCAGCTGCAGCAGTCTGGACCTGAGCTGGTGAGGCCTGGGACTT<br>CAGTGAAGATATCCTGCAAGGCTCCTGGCTATATCTTCACCAGCCACTG<br>GATGCAGTGGGTAAGACAGAGGCCTGGACAGGGCCTTGAGTGGATTGG<br>AGACATTTTTCCTGGAAGCGGTACTACTGATTATAATGAGAAGTTCAAG<br>GACAAGGCCACAGTGACGGTAGACAGATCCTCCAGTTCAGCCTACATG<br>CAGTTCAACAGCCTGACATCTGAGGACTCTGCGGTCTATTTCTGTGCAA<br>GCGGAGCCTTTGACTACTGGGGCCAAGGCACCACTCTCACAGTCTCCTC<br>A (SEQ ID NO: 188)<br><br>QVQLQQSGPELVRPGTSVKISCKAPGYIFTSHWMQWVRQRPGQGLEWIGD<br>IFPGSGTTDYNEKFKDKATVTVDRSSSSAYMQFNSLTSEDSAVYFCASGAF<br>DYWGQGTTLTVSS (SEQ ID NO: 189) |
| 317H2A6 | CAGGTTACTCTGAAAGAGTCTGGCCCTGGGATATTGCAGCCCTCCCAGA<br>CCCTCAGTCTGACTTGTTCCTTCTCTGGGTTTTCACTGAGGACTTTTGGC<br>ATGGGTGTAGGCTGGATTCGTCAGCCTTCAGGGAAGGGTCTGGAGTGG<br>CTGGCACACATTTGGTGGAATGGTGATAAATACTATGACCCAGCCCTGA<br>AGAGTCGGCTCACAATTTCCAAGGATACCTCCGAAAACCGGGTATTCCT<br>CAATATCGCCAATGTGGACACTACAGATACTGCCCCATACTACTGTGTT<br>CGAATTGGTCCTTCTATTACTACGGTAGCAGAGGGATTGCTTACTGGG<br>GCCAAGGGACTCTGGTCACTGTCTCTGCA (SEQ ID NO: 190)<br><br>QVTLKESGPGILQPSQTLSLTCSFSGFSLRTFGMGVGWIRQPSGKGLEWLA<br>HIWWNGDKYYDPALKSRLTISKDTSENRVFLNIANVDTTDTAPYYCVRIGP<br>SITTVAEGFAYWGQGTLVTVSA (SEQ ID NO: 191) |
| 319B8A12 | AAGGTTACTCTGAAAGAGTCTGGCCCTGGGATATTGCAGCCCTCCCAGA<br>CCCTCAGTCTGACTTGTTCCTTCTCTGGATTTTCACTGAGGACTTTTGGT<br>ATGGGTGTAGGCTGGATTCGTCAGCCTTCAGGGAAGGGTCTGGAGTGG<br>CTGGCACACATTTGGTGGAATGATGAGAAATACTATAATCCAGACCTG<br>AAGAGTCGGCTCACAGTTTCCAAGGATTCCTCCAAAAACCAGGTATTCC<br>TCACGATCGCCAATGTGGACACTTCAGATACTGCCCCATACTACTGTAC<br>TCGAGTTGGTCCTTCTATTTCTACGGTTGCAGAGGGATTTCCTTACTGGG<br>GCCAAGGGACTCTGGTCACTGTCTCTGCA (SEQ ID NO: 192)<br><br>KVTLKESGPGILQPSQTLSLTCSFSGFSLRTFGMGVGWIRQPSGKGLEWLA<br>HIWWNDEKYYNPDLKSRLTVSKDSSKNQVFLTIANVDTSDTAPYYCTRVG<br>PSISTVAEGFPYWGQGTLVTVSA (SEQ ID NO: 193) |
| 320F9C5 | CAGGTTACTCTGAAAGAGTCTGGCCCTGGGATATTGCAGTCCTCCCAGA<br>CCCTCAGTCTGACTTGTTCTTTCTCTGGGTTTTCACTGAGGACCTTTGGT<br>ATGGGTGTAGGCTGGATTCGTCAACCTTCAGGGAAGGGTCTGGAATGG<br>CTGGCACACATTTGGTGGAATGATGATAAGTCCTCTCACCCAGCCCTGA |

TABLE 2-continued

Anti-BAFF Mouse Leads - VH Sequences

| Designation | Sequence |
|---|---|
| | AGAGTCGTCTCACAATCTCCAAGGATACCTCCAAAAACCAGGTATTCCT<br>CAAGATCGCCAATGTGGACACTGCAGAAACTGCCACATATTATTGTGTT<br>CGAATAGGTCCTTCAATTACTACGGTTGCAGAGGGGTTTGCTTACTGGG<br>GCCAAGGGACTCTGGTCACTGTCTCTGCA (SEQ ID NO: 194)<br><br>QVTLKESGPGILQSSQTLSLTCSFSGFSLRTFGMGVGWIRQPSGKGLEWLA<br>HIWWNDDKSSHPALKSRLTISKDTSKNQVFLKIANVDTAETATYYCVRIGP<br>SITTVAEGFAYWGQGTLVTVSA (SEQ ID NO: 195) |
| 323E9D1 | CAGGTTACTCTGAAAGAGTCTGGCCCTGGGATATTGCAGCCCTCCCAGA<br>CCCTCAGTCTGACTTGTTCCTTCTCTGGATTTTCAATGAGGACTTTTGGT<br>ATGGGTGTAGGCTGGATTCGTCAGCCTTCAGGGAAGGGTCTGGAGTGG<br>CTGGCACACATTTGGTGGAATGATGAGAAATACTATAATCCAGACCTG<br>AAGAGTCGGCTCACAGTTTCCAAGGATTCCTCAAAAACCAGGTATTCC<br>TCACGATCGCCAATGTGGACACTTCAGATACTGCCCCATACTACTGTAC<br>TCGAGTTGGTCCTTCTATTTCTACGATTGCAGAGGGATTTCCTTACTGGG<br>GCCAAGGGACTCTGGTCACTGTCTCTGCA (SEQ ID NO: 196)<br><br>QVTLKESGPGILQPSQTLSLTCSFSGFSMRTFGMGVGWIRQPSGKGLEWLA<br>HIWWNDEKYYNPDLKSRLTVSKDSSKNQVFLTIANVDTSDTAPYYCTRVG<br>PSISTIAEGFPYWGQGTLVTVSA (SEQ ID NO: 197) |
| 332C1B12 | CAGGTCCAACTGCAGCAGCCTGGGGCTGAATTGGTGAAGCCTGGGGCT<br>TCAGTGAAGCTGTCCTGCAAGGCTTCTGGCTACACTTTCACCAACGACA<br>ATTACTGGATGAACTGGATGAAACAGAGGCCTGGACGAGGCCTCGAGT<br>GGATTGGAAGGATTCGTCCTTCTGATAGTGAAACTCACTACAATCAAAA<br>ATTCACGAACAAGGCCACACTGACTGTAGACAAATCCTCCAGCACAGC<br>CTACATCCAACTCAGCAGCCTGACATCTGTGGACTCTGCGGTCTATTAT<br>TGTGCAAGATCTTGGGAAGATTATTACTACGATCGATGGAGGACTACT<br>TTGACTACTGGGGCCAAGGCACCACTCTCACAGTCTCCTCA<br>(SEQ ID NO: 198)<br><br>QVQLQQPGAELVKPGASVKLSCKASGYTFTNDNYWMNWMKQRPGRGLE<br>WIGRIRPSDSETHYNQKFTNKATLTVDKSSSTAYIQLSSLTSVDSAVYYCAR<br>SWEDLLLRSMEDYFDYWGQGTTLTVSS (SEQ ID NO: 199) |
| 344B9D9 | GAGTTCCAACTGCAGCAGTCTGGACCTGAGCTGGGGGAGCCTGGCGCT<br>TCAGTGAAAATCTCCTGCAAGGCTTCTGGTTTCTCATTCAGTGACTACA<br>ACATAAATTGGGTGAAGCAGAGCAATGGAAAGAGTCTTGAGTGGATTG<br>GAAAAGTTCATCCTAAGGATGGTACTGCTACCTACAATCAGAAGTTCCA<br>GGACAAGGCCACATTGACTCTAGACCAGTCTTCCAGCACAGCCTACATG<br>CAACTCAGCAGCCTGACATCGGAGGACTCTGCAGTCTATTACTGTCTCC<br>CGCTCTACTATGATTCCCTGACAAAAATTTTGTTTGCTTATTGGGGCCAA<br>GGGACTCTGGTCACTGTCTCTGCA (SEQ ID NO: 200)<br><br>EFQLQQSGPELGEPGASVKISCKASGFSFSDYNINWVKQSNGKSLEWIGKV<br>HPKDGTATYNQKFQDKATLTLDQSSSTAYMQLSSLTSEDSAVYYCLPLYY<br>DSLTKILFAYWGQGTLVTVSA (SEQ ID NO: 201) |
| 348A6C1 | CAGGTTACTCTGAGAGAGTCTGGGCCTGGGATATTGCAGCCCTCCCAGA<br>CCCTCAGTCTGACTTGTTCCTTCTCTGGGTTTTCACTGAGGACCTTTGGT<br>ATGGGTGTAGGCTGGATTCGTCAGCCTTCAGGGAAGGGTCTGGAGTGG<br>CTGGCACACATCTGGTGGAATGATGAGAAATATTATAACCCAGCCCTG<br>AAGAGTCGGCTCACAGTTTCCAAGGATTCCTCCGAAAACCAGGTATTCC<br>TCAAGATCGCCAATGTGGACACTACAGATACTGCCCCATACTACTGTGC<br>TCGACTTGGTCCTTCTATTACTACGGTTGCAGAGGGATTTCCGTACTGG<br>GGCCAAGGGACTCTGGTCACTGTCTCTGCA (SEQ ID NO: 202)<br><br>QVTLRESGPGILQPSQTLSLTCSFSGFSLRTFGMGVGWIRQPSGKGLEWLA<br>HIWWNDEKYYNPALKSRLTVSKDSSENQVFLKIANVDTTDTAPYYCARLG<br>PSITTVAEGFPYWGQGTLVTVSA (SEQ ID NO: 203) |
| 352G11A10 | CAGGTCCAGCTGCAGCAGTCTGGACCTGAGCTGGTGAAGCCCGGGGGT<br>TCAGTGAGGATATCCTGCAAGGCTTCTGGTTACAGCCTCATAAGCTACT<br>ATATACACTGGGTGAAACAGAGGCCGGACAGGGCCTGAGTGGATTG<br>GATTGACTTTTCCTGGAAGTGGTAATTCTAAGTTCATTGAGAAGTTCAA<br>GGGCAAGGCCACACTGACGGCAGACACATCCTCCAACACTGCCTACAT<br>ACAGCTCAGCAGTCTAACATCTGAGGACTCTGCGGTCTATTACTGTACA<br>AGGGGGGACTTCGGTAACTACCTTGCCTACTGGTACTTCGATGTCTGGG<br>GCACAGGGACCACGGTCACCGTCTCCTCA (SEQ ID NO: 204)<br><br>QVQLQQSGPELVKPGGSVRISCKASGYSLISYYIHWVKQRPGQGLEWIGLT<br>FPGSGNSKFIEKFKGKATLTADTSSNTAYIQLSSLTSEDSAVYYCTRGDFGN<br>YLAYWYFDVWGTGTTVTVSS (SEQ ID NO: 205) |

TABLE 2-continued

Anti-BAFF Mouse Leads - VH Sequences

Designation Sequence

363D4A10
CAGGTTACTCTGAAAGAGTCTGGCCCTGGGATATTGCAGTCCTCCCAGA
CCCTCAGTCTGACTTGTTCTTTCTCTGGGTTTTCACTGAAGACCTTTGGT
ATGGGTGTGGGCTGGATTCGTCAGCCTTCAGGGAAGGGTCTGGAGTGG
CTGGCACACATTTGGTGGAATGATGATAAATTCTATCACCCAGCCCTGA
AGAGTCGGCTCACAATCTCCAAGGATACCTCCAAAAACCAGGTATTCCT
CAAGATCGCCAATGTGGACACTGCAGAAACTGCCACATACTACTGTGTT
CGAATTGGTCCTTCAATTACTACGGTAGCAGAGGGGTTTGCTTACTGGG
GCCAAGGGACTCTGGTCACTGTCTCTGCA (SEQ ID NO: 206)

QVTLKESGPGILQSSQTLSLTCSFSGFSLKTFGMGVGWIRQPSGKGLEWLA
HIWWNDDKFYHPALKSRLTISKDTSKNQVFLKIANVDTAETATYYCVRIGP
SITTVAEGFAYWGQGTLVTVSA (SEQ ID NO: 207)

381A6A9
CAGGTCCAGCTGCAGCAGTCTGGACCTGAGCTGGTGAAGCCCGGGGGT
TCAGTGAAGATATCCTGCAAGGCTGCTGGCTACAGCCTCACAAGCTACT
ATATACACTGGGTGAAGCAGAGGCCGGGACAGGGACTTGAGTGGATTG
GATTGATTTTTCCTGGAAGTGGTAATTCTAAGTACATTGAGAAGTTCAA
GGGCAAGGCCACACTGACGGCGGACACATCCTCCAACACTGCCTACAT
GCAGCTCAGCAGCCTAACATCTGAGGACTCTGCGGTCTATTATTGTACA
AGGGGGGACTTCGGTAACTACCTTGCCTACTGGTACTTCGATGTCTGGG
GCACAGGGACCACGGTCACCGTCTCCTCA (SEQ ID NO: 208)

QVQLQQSGPELVKPGGSVKISCKAAGYSLTSYYIHWVKQRPGQGLEWIGLI
FPGSGNSKYIEKFKGKATLTADTSSNTAYMQLSSLTSEDSAVYYCTRGDFG
NYLAYWYFDVWGTGTTVTVSS (SEQ ID NO: 209)

384D5A2
CAGGTCACTCTGAAAGAGTCTGGCCCTGGAATATTGCAGCCCTCCCAGA
CCCTCAGTCTGACTTGTTCTTTCTCTGGGTTTTCACTGAACACTTATGGT
ATGGGTGTGGGTTGGATTCGTCAGCCTTCAGGGAAGGGTCTGGAGTGG
CTGGCCAACATTTGGTGGAATGATGATAAGTACTATAACTCAGCCCTGA
AGAGCCGGCTCGCAATCTCCAAAGATGCCTCCAACAGCCAGGTATTCCT
CAAGATCTCCAGTGTGGACACTACAGATACTGCCACATACTACTGTGCT
CAAGTAGCCGCTACTATAGTAACTACGTACGGGGCCTGGTTTGCTTACT
GGGGCCAAGGGACTCTGGTCACTGTCTCTGCA
(SEQ ID NO: 210)

QVTLKESGPGILQPSQTLSLTCSFSGFSLNTYGMGVGWIRQPSGKGLEWLA
NIWWNDDKYYNSALKSRLAISKDASNSQVFLKISSVDTTDTATYYCAQVA
ATIVTTYGAWFAYWGQGTLVTVSA (SEQ ID NO: 211)

394F5A5
GTTACTCTGAAAGAGTCTGGCCCTGGGATATTGCAGCCCTCCCAGACCC
TCAGTCTGACTTGTTCCTTCTCTGGGTTTTCACTGAGGACTTTTGGTATG
GGTGTAGGCTGGATTCGTCAGCCTTCAGGGAAGGGTCTGGAGTGGCTG
GCACACATTTGGTGGAATGATGAGAAATATTATAATCCAACCCTGAAG
AGTCGGCTCACAATTTCCAAGGATACCTCCAAAAACCAGGTATTCCTCA
GGATCGCCAATGTGGACACTGCAGTTACTGCCGCATACTACTGTGCTCG
AATAGGTCCTTCTATTACTACGGTAGTAGAGGGATTTCCTTACTGGGGC
CAAGGGACTCTGGTCACTGTCTCTGCA (SEQ ID NO: 212)

VTLKESGPGILQPSQTLS LTCSFSGFSLRTFGMGVGWIRQPSGKGLEWLAHI
WWNDEKYYNPTLKSRLTISKDTSKNQVFLRIANVDTAVTAAYYCARIGPSI
TTVVEGFPYWGQGTLVTVS A (SEQ ID NO: 213)

409F12A11
ATCCAGCTGCAGCAGTCTGGACCTGAGCTGGTGAAGCCTGGGGCTTCA
ATGAAGATATCGTGCAAGGCTTCTGGCTACACCTTCACTGACAAGTATA
TAAACTGGGTGAAGCAGAGGCCTGGACAGGGACTTGAGTGGATTGGAT
GGATTTATCCTGGAAGCGGTAATACTAAGTACAATGAGAAGTTCAAGG
GCATGGCCACATTGACTGTAGACACATCCTCCAATACAGCCTATATACA
TCTCAGCAGCCTGACCTCTGAGGACTCTGCGGTCTATTTCTGTGCACGA
GGAATTATTTATTACTACGATGGTTCATACCCCTATGCTTTGGACTACTG
GGGTCAAGGAACCTCAGTCACCGTCTCCTCA (SEQ ID NO: 214)

IQLQQSGPELVKPGASMKISCKASGYTFTDKYINWVKQRPGQGLEWIGWIY
PGSGNTKYNEKFKGMATLTVDTSSNTAYIHLSSLTSEDSAVYFCARGIIYY
YDGSYPYALDYWGQGTSVTVSS (SEQ ID NO: 215)

418F6D9
CAGGTCCAGCTGCAGCAGTCTGGACCTGAACTGGTGAAGCCTGGAGCT
TCAGTGAAGTTGTCCTGCAAGGCTTCTGGCTACACCTTCACTGACTATA
GTATACACTGGGTGAAGCAGAGTCCTGGACAGGGACTTGAGTGGATTG
GATGGATTTATCCTGGAAGTGGTAATACTAAGTACAATGACAAGTTCAA
GGGCAAGGCCACAATGACTGCAGACAAATCCTCCAGAACAGTCTACAT
GCAGCTCAGCAGCCTGACGTCTGAGGAGTCTGCGGTCTATTTCTGTGCA
AGAGACTACCGGCGATACTATGCTATAGACTACTGGGGTCAAGGAACC
TCAGTCACCGTCTCCTCA (SEQ ID NO: 216)

TABLE 2-continued

Anti-BAFF Mouse Leads - VH Sequences

| Designation | Sequence |
|---|---|
| | QVQLQQSGPELVKPGASVKLSCKASGYTFTDYSIHWVKQSPGQGLEWIGW IYPGSGNTKYNDKFKGKATMTADKSSRTVYMQLSSLTSEESAVYFCARDY RRYYAIDYWGQGTSVTVSS (SEQ ID NO: 217) |
| 431G5A3 | CAGCTGCAGCAGTCTGGACCTGAGCTGGTGAAGCCTGGAGCTTCAGTG AAGCTGTCCTGCAAGGCTTCTGGCTACACCTTCACTGACTATAGTATAC ACTGGGTGAAACAGAGTCCTGGACAGGGACTTGAGTGGATTGGATGGA TTTATCCTGGAAGTGATAATACTAAGTACAATGACAAGTTCAAGGGCA AGGCCTCAATGACTGCAGACAAATCCTCCAGAACAGTCTACATGCACCT CAGCAGCCTGACGTCTGAGGAATCTGCGGTCTATTTCTGTGCAAGAGAC TACCCGGCGGTACTATGCTATGGACTACTGGGGTCAAGGAACCTCAGTCA CCGTCTCCTCA (SEQ ID NO: 218) |
| | QLQQSGPELVKPGASVKLSCKASGYTFTDYSIHWVKQSPGQGLEWIGWIY PGSDNTKYNDKFKGKASMTADKSSRTVYMHLSSLTSEESAVYFCARDYRR YYAMDYWGQGTSVTVSS (SEQ ID NO: 219) |
| 435A6B3 | GAGGTCCAGCTGCAGCAGTCTGGACCTGAGCTGGTAAAGCCTGGGGCT TCAATGAAGATGTCCTGCAAGGCTTCTGGATACACATTCACTAGCTATG TTATGCACTGGATGAAGCAGAAGCCTGGGCAGGGCCTTGAGTGGATTG GATATCTTAATCCTAACAATGATGGTACTAAGTACAATGAGAAGTTCAA AGGCAAGGCCACACTGACTTCAGACAAATCCTCCAGCACAGCCTACAT GGAGCTCAGCAGCCTGACCTCTGAGGACTCTGCGGTCTATTACTGTGCA AGGGGGGACTATAGTAATTACTTCTACTGGTACTTCGATGTCTGGGGCG CAGGGACCACGGTCTCCGTCTCCTCA (SEQ ID NO: 220) |
| | EVQLQQSGPELVKPGASMKMSCKASGYTFTSYVMHWMKQKPGQGLEWI GYLNPNNDGTKYNEKFKGKATLTSDKSSSTAYMELSSLTSEDSAVYYCAR GDYSNYFYWYFDVWGAGTTVSVSS (SEQ ID NO: 221) |
| 436H2C12 | CAGGTCCAGCTGCAGCAGTCTGGACCTGAGCTGGTGAAGCCTGGAGCT TCAGTGAAGCTGTCCTGCAAGGCTTCTGGCTACACCTTCAGTGACTATA CTATACACTGGGTGAAGCAGAGTCCTGGACAGGGACTTGAGTGGATTG GATGGATTTACCCTGGAAGGGGTAATACTAAGTACAATGACAAGTTCA AGGGCAAGGCCACAATGACTGCTGACAAATCCTCCAGCACAGCCTACA TGCAGCTCAGCAGCCTGACGTCTGAGGAATCTGCGGTCTATTTCTGTGC AAGAGACTACCGGCGGTACTATGCTATGGACTACTGGGGTCAAGGAAC CTCAGTCACCGTCTCCTCA (SEQ ID NO: 222) |
| | QVQLQQSGPELVKPGASVKLSCKASGYTFSDYTIHWVKQSPGQGLEWIGW IYPGRGNTKYNDKFKGKATMTADKSSSTAYMQLSSLTSEESAVYFCARDY RRYYAMDYWGQGTSVTVSS (SEQ ID NO: 223) |
| 436H6A9 | CAGCTGCAGCAGTCTGGACCTGAGCTGGTGAAGCCTGGGGCTTCAGTG AAGATATCCTGCAAGGCTTCTGGCTACACCTTCACTGACAACTTTATAA ACTGGGTGAAACAGAGGCCTGGACAGGGACTTGAGTGGATTGGATGGA TTTTCCTGGAAGCGGTAATACTAAGAACAATGAGAAGTTCAAGGGCA AGGCCACAGTGACTGTAGACACATCCTCCAGCACAGCCTACATGCAGC TCAGCAGCCTGACCTCTGAGGACTCTGCGGTCTATTTCTGTGCACGAGG AATTATTTATTATGATGGTACCTACCCCTATGCTCTGGACTACTGGG GTCAGGGAACCTCAGTCACCGTCTCCTCA (SEQ ID NO: 224) |
| | QLQQSGPELVKPGASVKISCKASGYTFTDNFINWVKQRPGQGLEWIGWISP GSGNTKNNEKFKGKATVTVDTSSSTAYMQLSSLTSEDSAVYFCARGIIYYY DGTYPYALDYWGQGTSVTVSS (SEQ ID NO: 225) |
| 440E9D12 | CAGGTGCGGCTGAGGGAGTCAGGACCTGGCCTGGTGGCGCCCTCCCAG AACCTGTTCATCACATGCACCGTCTCAGGTTTCTCATTAACTGACTATG AAATAAACTGGGTTCGCCAGCCTCCAGGAAAGAATCTGGAGTGGCTGG GAGTGATTTGGACTGGTGGAGGCACAAAATATAATTCAGTTCTCATATC CAGACTGAACATCAGCAAAGACAATTCCAAGAGACAAGTTTTCTTTAA AATGACCAGTCTCCAGACTGATGACACAGCCATATATTACTGTGTAAGA GAGGGGAGGAGATACTATGCTATGGACTACTGGGGTCAAGGAACCTCA GTCACCGTCTCCTCA (SEQ ID NO: 226) |
| | QVRLRESGPGLVAPSQNLFITCTVSGFSLTDYEINWVRQPPGKNLEWLGVI WTGGGTKYNSVLISRLNISKDNSKRQVFFKMTSLQTDDTAIYYCVREGRR YYAMDYWGQGTSVTVSS (SEQ ID NO: 227) |
| 441E6F2 | CGGGTGCAGCTGAAGGAGTCAGGACCTGGCCTGGTGGCGCCCTCACAG AGCCTGTTCATCACATGCACCGTCTCAGGGTTCTCATTAACCACCTATG AAATAAACTGGGTTCGCCAGTCTCCAGGAAAGGGTCTGGAGTGGCTGG GAGTGATATGGACTGGTGGAACCACAAAATATAATTCAGCTTTCATATC CAGACTGAGCATCACCAAAGACAACTCCAAGAGCCTCGTTTTCTTAAAA ATGAGCAGTCTGCAAACTGATGACACAGCCATATATTACTGTGTAAGA |

TABLE 2-continued

Anti-BAFF Mouse Leads - VH Sequences

| Designation | Sequence |
|---|---|
| | GAGGGGAGGAGGTACTATGCTATGGACTACTGGGGTCAAGGAACCTCA<br>GTCACCGTCTCCTCA (SEQ ID NO: 228)<br><br>RVQLKESGPGLVAPSQSLFITCTVSGFSLTTYEINWVRQSPGKGLEWLGVI<br>WTGGTTKYNSAFISRLSITKDNSKSLVFLKMSSLQTDDTAIYYCVREGRRY<br>YAMDYWGQGTSVTVSS (SEQ ID NO: 229) |
| 443C11A12 | GAGGTCCAGCTGCAGCAGTCTGGACCTGAGCTGGTAAAGCCTGGGGCT<br>TCAGTGAAGATGTCCTGCACGGCTTCTGGATACACATTCACTAGCTATG<br>TTATACACTGGATGAAGCAGAAGCCTGGGCAGGGCCTTGAGTGGATTG<br>GATATCTTCATCGTAACAATGATGGTACTAAGTACAATGAGAAGTTCAA<br>AGTCAAGGCCACACTGACTTCAGACGAATCCTCCAACACAGCCTACAT<br>GGAACTCAGCAGCCTGACCTCTGAGGACTCTGCGGTCTATTACTGTGCA<br>AGGGGGGACTATAGTAATTACTTCTACTGGTACTTCGATGTCTGGGGCG<br>CAGGGACTACGGTCTCCGTCTCCTCA (SEQ ID NO: 230)<br><br>EVQLQQSGPELVKPGASVKMSCTASGYTFTSYVIHWMKQKPGQGLEWIG<br>YLHRNNDGTKYNEKFKVKATLTSDESSNTAYMELSSLTSEDSAVYYCARG<br>DYSNYFYWYFDVWGAGTTVSVSS (SEQ ID NO: 231) |
| 444G1A10 | CGGGTGCAGCTGAAGGAGTCAGGACCTGGCCTGGTGGCGCCCTCACAG<br>AGCCTGTTCATCACATGCACCGTCTCAGGGTTTTCATTAACCACCTATG<br>AAATAAACTGGGTTCGCCAGTCTCCAGGAAAGGGTCTGGAGTGGCTGG<br>GAGTGATATGGACTGGTGGAACCACAAAATATAATTCAGCTTTCATATC<br>CAGACTGAGCATCACCAAAGACAACTCCAAGAGCCTCGTTTTCTTAAAA<br>ATGAGCAGTCTGCAAACTGATGACACAGCCATATATTACTGTGTAAGA<br>GAGGGGAGGAGGTACTATGCTATGGACTACTGGGGTCAAGGAACCTCA<br>GTCACCGTCTCCTCA (SEQ ID NO: 232)<br><br>RVQLKESGPGLVAPSQSLFITCTVSGFSLTTYEINWVRQSPGKGLEWLGVI<br>WTGGTTKYNSAFISRLSITKDNSKSLVFLKMSSLQTDDTAIYYCVREGRRY<br>YAMDYWGQGTSVTVSS (SEQ ID NO: 233) |
| 450A2A7 | CAGGTCCAGCTGCAGCAGTCTGGACCTGAGCTGGTGAAGCCTGGAGCT<br>TCAGTGAAGCTGTCCTGCAAGGCTTCTGGCTACACCTTCACTGACTATA<br>GTATACACTGGGTGAAACAGAGTCCTGGACAGGGACTTGAGTGGATTG<br>GATGGATTTATCCTGGAAGTGATAATACTAAGTACAATGACAAGTTCAA<br>GGGCAAGGCCTCAATGACTGCAGACAAATCCTCCAGAACAGTCTACAT<br>GCACCTCAGCAGCCTGACGTCTGAGGAATCTGCGGTCTATTTCTGTGCA<br>AGAGACTACCGGCGGTACTATGCTATGGACTACTGGGGTCAAGGAACC<br>TCAGTCACCGTCTCCTCA (SEQ ID NO: 236)<br><br>QVQLQQSGPELVKPGASVKLSCKASGYTFTDYSIHWVKQSPGQGLEWIGW<br>IYPGSDNTKYNDKFKGKASMTADKSSRTVYMHLSSLTSEESAVYFCARDY<br>RRYYAMDYWGQGTSVTVSS (SEQ ID NO: 235) |
| 456H11B7a | CAGGTGCGGCTGAGGGAGTCAGGACCTGGCCTGGTGGCGCCCTCCCAG<br>AACCTGTTCATCACATGCACCGTCTCAGGTTTTCTCATTAACTGACTATG<br>AAATAAACTGGGTTCGCCAGCCTCCAGGAAAGAATCTGGAGTGGCTGG<br>GAGTGATTTGGACTGGTGGAGGCACAAAATATAATTCAGTTCTCATATC<br>CAGACTGAACATCAGCAAAGACAATTCCAAGAGACAAGTTTTCTTTAA<br>AATGACCAGTCTCCAGACTGATGACACAGCCATATATTACTGTGTAAGA<br>GAGGGGAGGAGATACTATGCTATGGACTACTGGGGTCAAGGAACCTCA<br>GTCACCGTCTCCTCA (SEQ ID NO: 237)<br><br>QVRLRESGPGLVAPSQNLFITCTVSGFSLTDYEINWVRQPPGKNLEWLGVI<br>WTGGGTKYNSVLISRLNISKDNSKRQVFFKMTSLQTDDTAIYYCVREGRR<br>YYAMDYWGQGTSVTVSS (SEQ ID NO: 238) |
| 456H11B7b | CAGGTTACTCTGAAAGAGTCTGGCCCTGGGATATTGCAGCCCTCCCAGA<br>CCCTCAGTCTGACTTGTTCTTTCTCTGGGTTTTCACTGAGCACTTTTGGT<br>ATGGGTGTAGGCTGGATTCGTCAGCCTTCAGGGAAGGGTCTGGAGTGG<br>CTGGCACACATTTGGTGGGATGATGATAAGTACTATAACCCAGCCCTGA<br>AGAGTCGGCTCACAATCTCCAAGGATACCTCCAAAAACCAGGTATTCCT<br>CAAGATCGCCAATGTGGACACTGCAGATACTGCCACATACTACTGTGCT<br>CGAATAGAGGGCCCCTACTACTGGTACTTCGATGTCTGGGGCACAGGG<br>ACCACGGTCACCGTCTCCTCA (SEQ ID NO: 239)<br><br>QVTLKESGPGILQPSQTLSLTCSFSGFSLTFGMGVGWIRQPSGKGLEWLAH<br>IWWDDDKYYNPALKSRLTISKDTSKNQVFLKIANVDTADTATYYCARIEG<br>PYYWYFDVWGTGTTVTVSS (SEQ ID NO: 240) |
| 537G7A6 | CAGGTGCAGCTGAAGGAGTCAGGACCTGGCCTGGTGGCACCCTCACAG<br>AGCCTGTCCATCACATGCACGGTCTCTGGTTTCTCATTATCCAGATATA<br>GTGTACACTGGATTCGTCAGTCTCCAGGAAAGGGTCTGGAGTGGCTGG<br>GAATGATATGGGGGGGTGGAAACACAGACTACAATTCCAGGTCTCAAAT |

TABLE 2-continued

Anti-BAFF Mouse Leads - VH Sequences

| Designation | Sequence |
|---|---|
| | CCAGACTGAGCATCAGCAAGGACAACTCCAAGAGCCAAGTTTTCTTAA<br>AAATGAACAGTCTGGAAAATGATGACACAGCCATGTATTACTGTGCCA<br>GCCCCTCCCTCTATTATTATGATGTTGCCTGGTTTCCTTACTGGGGCCAA<br>GGGACTCTGGTCACTGTCTCTGCA (SEQ ID NO: 241)<br><br>QVQLKESGPGLVAPSQSLSITCTVSGFSLSRYSVHWIRQSPGKGLEWLGMI<br>WGGGNTDYNSGLKSRLSISKDNSKSQVFLKMNSLENDDTAMYYCASPSLY<br>YYDVAWFPYWGQGTLVTVSA (SEQ ID NO: 242) |
| 551H4D6 | GAGGTTCAGCTGCAGCAGTCTGGGGCTGAGCTTGTGAGGCCAGGGGCC<br>TCAGTCGAGTTGTCCTGCACAGCTTCTGGCTTTAATATTAAAAACGACT<br>ATTTGCACTGGGTGAAGCAGAGGCCTGAACAGGGCCTGGAATGGATTG<br>GATGGATTGATTCCGCGAATGATAAGACTAAGTATGCCCCGAAGTTCCA<br>GGACAAGGCCACTATAACTGCAGACCCATCCTCCAACACAGCCTACCT<br>GCAGCTCAGCAGCCTGACATCTGAGGACACTGCCGTCTATTACTGTACT<br>AGAGTTGGGGTTCAGGATGGTTACTACGTTAGGGACTTTGACTACTGGG<br>GCCAGGGCACCACTCTCACAGTCTCCTCA (SEQ ID NO: 243)<br><br>EVQLQQSGAELVRPGASVELSCTASGFNIKNDYLHWVKQRPEQGLEWIGW<br>IDSANDKTKYAPKFQDKATITADPSSNTAYLQLSSLTSEDTAVYYCTRVGV<br>QDGYYVRDFDYWGQGTTLTVSS (SEQ ID NO: 244) |
| 560H2A7 | GAGGTGAAGCTGGTGGAGTCTGGAGGAGGCTTGGTACAGCCTGGGGGT<br>TCTCTGAGTCTCTCCTGTGCAGGTTCTGGATTCACCTTCAGTGATTACTA<br>CATGAGCTGGGTCCGCCAGCCTCCAGGGAAGGCACTTGAGTGGTTGGC<br>TTTGATTAGAAACAAAGCTCCTGGTTACACAACAGAATACAGTGCATCT<br>GTGAAGGGTCGTTTCACCATCTCCAGAGATAATTCCCAAAGCATCCTCT<br>ATCTTCAAATGAATGCCCTGAGACCTGAGGACAGTGCCACTTATTACTG<br>TGCAAGAGTCTTACGACGGGCAGACTGCTTAGACTACTGGGGCCAAGG<br>CACCGCTCTCACAGTCTCCTCA (SEQ ID NO: 245)<br><br>EVKLVESGGGLVQPGGSLSLSCAGSGFTFSDYYMSWVRQPPGKALEWLAL<br>IRNKAPGYTTEYSASVKGRFTISRDNSQSILYLQMNALRPEDSATYYCARV<br>LRRADCLDYWGQGTALTVSS (SEQ ID NO: 246) |
| 606H7F8 | GTGCAGCTGGTGGAGTCTGGGGGAGGCTTAGTGAAGCCTGGAGGGTCC<br>CTGAAACTCTCCTGTGCAGCCTCTGGATTCACTTTCAGTAGTTATGACAT<br>GTCTTGGGTTCGCCAGACTCCAGAGAAGAGGCTGGAGTGGGTCGCAGC<br>CATTAATAGTTATGGTGTTAACACCTACTATCCAGACACTGTGAAGGAC<br>CGATTCACCATCTCCAGAGACAATGCCAAGAACACCCTGTACCTGCAA<br>ATGAGCAGTCTGAGGTCTGAGGACACAGCCTTGTATTACTGTGCAAGAC<br>TTTTAATTGGGCCTTATTACTATGCTATGGACTACTGGGGTCAAGGAAC<br>CTCAGTCACCGTCTCCTCA (SEQ ID NO: 247)<br><br>VQLVESGGGLVKPGGSLKLSCAASGFTFSSYDMSWVRQTPEKRLEWVAAI<br>NSYGVNTYYPDTVKDRFTISRDNAKNTLYLQMSSLRSEDTALYYCARLLIG<br>PYYYAMDYWGQGTSVTVSS (SEQ ID NO: 248) |

TABLE 3

VκCDR Sequences

| Designation | Sequence |
|---|---|
| VLCDR1 9A10 | KASQNAGAAVA (SEQ ID NO: 1) |
| VLCDR2 9A10 | SASNRYT (SEQ ID NO: 2) |
| VLCDR3 9A10 | QQYRSYPRT (SEQ ID NO: 3) |
| VLCDR1 5A7 | KASQNAGAAVA (SEQ ID NO: 1) |
| VLCDR2 5A7 | SASNRYT (SEQ ID NO: 2) |
| VLCDR3 5A7 | QQYRSFPRT (SEQ ID NO: 4) |
| VLCDR1 5A11 | KASQNAGAAVA (SEQ ID NO: 1) |
| VLCDR2 5A11 | SASNRYT (SEQ ID NO: 2) |
| VLCDR3 5A11 | QQYRSFPRT (SEQ ID NO: 4) |
| VLCDR1 3B11 | KASQNAGIDVA (SEQ ID NO: 5) |
| VLCDR2 3B11 | STSNRYT (SEQ ID NO: 6) |
| VLCDR3 3B11 | LQYRSYPRT (SEQ ID NO: 7) |
| VLCDR1 5B9 | KASQNAGIDVA (SEQ ID NO: 5) |
| VLCDR2 5B9 | SKSNRYT (SEQ ID NO: 8) |
| VLCDR3 5B9 | LQYRSYPRT (SEQ ID NO: 9) |
| VLCDR1 12A7 | KASQNAGTAVA (SEQ ID NO: 10) |
| VLCDR2 12A7 | SAFNRYT (SEQ ID NO: 11) |
| VLCDR3 12A7 | QQYRSYPRT (SEQ ID NO: 12) |
| VLCDR1 9B8 | KASQSVGIAVA (SEQ ID NO: 13) |

TABLE 3-continued

VκCDR Sequences

| Designation | Sequence |
|---|---|
| VLCDR2 9B8 | STSNRYT (SEQ ID NO: 6) |
| VLCDR3 9B8 | QQYSRYPRT (SEQ ID NO: 14) |
| VLCDR1 4B7 | KASQNAGTAVA (SEQ ID NO: 10) |
| VLCDR2 4B7 | STSNRYT (SEQ ID NO: 6) |
| VLCDR3 4B7 | LQYRSYPRT (SEQ ID NO: 7) |
| VLCDR1 1A4 | RASQDIGNRLN (SEQ ID NO: 15) |
| VLCDR2 1A4 | ATSSLDS (SEQ ID NO: 16) |
| VLCDR3 1A4 | LQYASSPFT (SEQ ID NO: 17) |
| VLCDR1 c04 | RASQDIGNRLS (SEQ ID NO: 76) |
| VLCDR2 c04 | ATSSLDS (SEQ ID NO: 16) |
| VLCDR3 c04 | LQYASSPFT (SEQ ID NO: 17) |
| VLCDR1 c68 | RASQDIGNRLH (SEQ ID NO: 77) |
| VLCDR2 c68 | ATSSLDS (SEQ ID NO: 16) |
| VLCDR3 c68 | LQYASSPFT (SEQ ID NO: 17) |
| VLCDR1 c44 | RASQDIGNRLP (SEQ ID NO: 78) |
| VLCDR2 c44 | ATSSLDS (SEQ ID NO: 16) |
| VLCDR3 c44 | LQYASSPFT (SEQ ID NO: 17) |
| VLCDR1 c03 | RASQDIGNRLR (SEQ ID NO: 79) |
| VLCDR2 c03 | ATSSLDS (SEQ ID NO: 16) |
| VLCDR3 c03 | LQYASSPFT (SEQ ID NO: 17) |
| VLCDR1 c10 | RASQDIGNRLM (SEQ ID NO: 80) |
| VLCDR2 c10 | ATSSLDS (SEQ ID NO: 16) |
| VLCDR3 c10 | LQYASSPFT (SEQ ID NO: 17) |
| VLCDR1 c10.1 | RASESVDSYGNIFMH (SEQ ID NO: 249) |
| VLCDR2 c10.1 | LASNLES (SEQ ID NO: 276) |
| VLCDR3 c10.1 | QQNNEAPWT (SEQ ID NO: 293) |
| VLCDR1 c10.2 | RASKSVSTSGYSYMH (SEQ ID NO: 250) |
| VLCDR2 c10.2 | LASNLES (SEQ ID NO: 276) |
| VLCDR3 c10.2 | QQNNEAPWT (SEQ ID NO: 293) |
| VLCDR1 8A6 | KASQDINSYLT (SEQ ID NO: 251) |
| VLCDR2 8A6 | RANRLVS (SEQ ID NO: 277) |
| VLCDR3 8A6 | LQYDEFPYT (SEQ ID NO: 294) |
| VLCDR1 6B7 | RCSQSLVHSNGNTYLH (SEQ ID NO: 252) |
| VLCDR2 6B7 | KVSDRFS (SEQ ID NO: 278) |
| VLCDR3 6B7 | SQSTHVPLT (SEQ ID NO: 295) |
| VLCDR1 4E6 | KASQDVATAVA (SEQ ID NO: 253) |
| VLCDR2 4E6 | WASTRHT (SEQ ID NO: 279) |
| VLCDR3 4E6 | QQYSNYPYT (SEQ ID NO: 296) |
| VLCDR1 3C7 | RASQDIGNRLN (SEQ ID NO: 15) |
| VLCDR2 3C7 | ATSSLDS (SEQ ID NO: 16) |
| VLCDR3 3C7 | LQYASYPFT (SEQ ID NO: 297) |
| VLCDR1 2A6 | KASQNVGSAVV (SEQ ID NO: 254) |
| VLCDR2 2A6 | SASNRYS (SEQ ID NO: 280) |
| VLCDR3 2A6 | QQYSNYPLT (SEQ ID NO: 298) |
| VLCDR1 8A12 | KASQNVGAAVV (SEQ ID NO: 255) |
| VLCDR2 8A12 | SASNRYI (SEQ ID NO: 281) |
| VLCDR3 8A12 | QQYSNYPLT (SEQ ID NO: 298) |
| VLCDR1 9C5 | KASQNVGSVVA (SEQ ID NO: 256) |
| VLCDR2 9C5 | SASNRYT (SEQ ID NO: 2) |
| VLCDR3 9C5 | QQYSSYPLT (SEQ ID NO: 299) |
| VLCDR1 1B12 | RASKGVSTSSYTFIH (SEQ ID NO: 257) |
| VLCDR2 1B12 | YASNLES (SEQ ID NO: 282) |
| VLCDR3 1B12 | QHSREFPRT (SEQ ID NO: 300) |
| VLCDR1 9D9 | RASGNIHNYLA (SEQ ID NO: 258) |
| VLCDR2 9D9 | SAITLAD (SEQ ID NO: 283) |
| VLCDR3 9D9 | QHFWNTPYT (SEQ ID NO: 301) |
| VLCDR1 6C1 | KASQNVGAAVA (SEQ ID NO: 259) |
| VLCDR2 6C1 | SASNRYI (SEQ ID NO: 281) |
| VLCDR3 6C1 | QQYSNYPLT (SEQ ID NO: 298) |
| VLCDR1 11A10 | KASQDIHSYLS (SEQ ID NO: 260) |
| VLCDR2 11A10 | RTNRLVD (SEQ ID NO: 284) |
| VLCDR3 11A10 | LQYDEFPYT (SEQ ID NO: 294) |
| VLCDR1 4A10 | KASQNVGSAVV (SEQ ID NO: 254) |
| VLCDR2 4A10 | SASNRYT (SEQ ID NO: 2) |
| VLCDR3 4A10 | QQYSSYPLT (SEQ ID NO: 299) |
| VLCDR1 6A9 | KASQDINSYLS (SEQ ID NO: 261) |
| VLCDR2 6A9 | RANRLVD (SEQ ID NO: 285) |
| VLCDR3 6A9 | LQYDEFPYT (SEQ ID NO: 294) |
| VLCDR1 5A2 | RSSENIYSSLA (SEQ ID NO: 262) |
| VLCDR2 5A2 | AATNLAK (SEQ ID NO: 286) |
| VLCDR3 5A2 | QHFWGSPFA (SEQ ID NO: 302) |
| VLCDR1 5A5 | KASQNVGSAVA (SEQ ID NO: 263) |
| VLCDR2 5A5 | STSNRYT (SEQ ID NO: 6) |
| VLCDR3 5A5 | QQYASYPLT (SEQ ID NO: 303) |
| VLCDR1 12A11 | RATKGVSKSGYSYMH (SEQ ID NO: 264) |
| VLCDR2 12A11 | LASNLES (SEQ ID NO: 276) |

TABLE 3-continued

VκCDR Sequences

| Designation | Sequence |
|---|---|
| VLCDR3 12A11 | QHSRELPLT (SEQ ID NO: 304) |
| VLCDR1 6D9 | RASESVDSYGNSLMH (SEQ ID NO: 265) |
| VLCDR2 6D9 | IASNLES (SEQ ID NO: 287) |
| VLCDR3 6D9 | QQNSEDPRT (SEQ ID NO: 305) |
| VLCDR1 5A3 | RASESVDRYGNSLMH (SEQ ID NO: 266) |
| VLCDR2 5A3 | IASNLES (SEQ ID NO: 287) |
| VLCDR3 5A3 | QQNNEDPRT (SEQ ID NO: 306) |
| VLCDR1 6B3 | KASQDINRYLS (SEQ ID NO: 267) |
| VLCDR2 6B3 | RANRLVD (SEQ ID NO: 285) |
| VLCDR3 6B3 | LQYDEFPYT (SEQ ID NO: 294) |
| VLCDR1 2C12 | RASESVDNYGNSFMH (SEQ ID NO: 268) |
| VLCDR2 2C12 | LASNLES (SEQ ID NO: 276) |
| VLCDR3 2C12 | QQNNEDPRT (SEQ ID NO: 306) |
| VLCDR1 H6A9 | RATKGVTKSGYSYIH (SEQ ID NO: 269) |
| VLCDR2 H6A9 | LASNLQS (SEQ ID NO: 288) |
| VLCDR3 H6A9 | QHSRELPLT (SEQ ID NO: 304) |
| VLCDR1 9D12 | RASKSVDSYGTSFMH (SEQ ID NO: 270) |
| VLCDR2 9D12 | LASNLES (SEQ ID NO: 276) |
| VLCDR3 9D12 | QQNNEDPRT (SEQ ID NO: 306) |
| VLCDR1 6F2 | RTSESVDSYGNSFMF (SEQ ID NO: 271) |
| VLCDR2 6F2 | LTSNLES (SEQ ID NO: 289) |
| VLCDR3 6F2 | QQSNEDPRT (SEQ ID NO: 307) |
| VLCDR1 1A10 | RASESVDSYGNSFMF (SEQ ID NO: 272) |
| VLCDR2 1A10 | LTSNLES (SEQ ID NO: 289) |
| VLCDR3 1A10 | QQSNEDPRT (SEQ ID NO: 307) |
| VLCDR1 2A7 | RASESVDRYGNSLMH (SEQ ID NO: 266) |
| VLCDR2 2A7 | IASNLES (SEQ ID NO: 287) |
| VLCDR3 2A7 | QQNNEDPRT (SEQ ID NO: 306) |
| VLCDR1 11B7_a | RASKSVDSYGTSFMH (SEQ ID NO: 270) |
| VLCDR2 11B7_a | LASNLES (SEQ ID NO: 276) |
| VLCDR3 11B7_a | QQNNEDPRT (SEQ ID NO: 306) |
| VLCDR1 11B7_b | RASKSVDSYGTSFMH (SEQ ID NO: 270) |
| VLCDR2 11B7_b | LASNLES (SEQ ID NO: 276) |
| VLCDR3 11B7_b | QQNNEDPRT (SEQ ID NO: 306) |
| VLCDR1 7A6 | RVSESVDRYADSFMH (SEQ ID NO: 273) |
| VLCDR2 7A6 | LASNLES (SEQ ID NO: 276) |
| VLCDR3 7A6 | QQNKEDPYT (SEQ ID NO: 308) |
| VLCDR1 4D6 | RASESVDSYGNSFIH (SEQ ID NO: 274) |
| VLCDR2 4D6 | RASNLNS (SEQ ID NO: 290) |
| VLCDR3 4D6 | HQNNEDPRT (SEQ ID NO: 309) |
| VLCDR1 H2A7 | RASESIDNYGLIFMS (SEQ ID NO: 275) |
| VLCDR2 H2A7 | AASNRGS (SEQ ID NO: 291) |
| VLCDR3 H2A7 | QQSKEVPWT (SEQ ID NO: 310) |
| VLCDR1 7F8 | RASGNIHNYLA (SEQ ID NO: 258) |
| VLCDR2 7F8 | NAKTLAD (SEQ ID NO: 292) |
| VLCDR3 7F8 | QHFWSTPYT (SEQ ID NO: 311) |

TABLE 4

VH CDR Sequences

| Designation | Sequence |
|---|---|
| VHCDR1 9A10 | GYTFSIFCIH (SEQ ID NO: 18) |
| VHCDR2 9A10 | RIDPSSGGTKYNEKFES (SEQ ID NO: 19) |
| VHCDR3 9A10 | GEDLLVRTDAMDY (SEQ ID NO: 20) |
| VHCDR1 5A7 | GYTFSIFCVH (SEQ ID NO: 21) |
| VHCDR2 5A7 | RIDPSSGGTKYNEKFES (SEQ ID NO: 19) |
| VHCDR3 5A7 | GEDLLVRTDALDY (SEQ ID NO: 22) |
| VHCDR1 5A11 | GYTFSIFCIH (SEQ ID NO: 23) |
| VHCDR2 5A11 | RIDPSSGGTKYNERFEN (SEQ ID NO: 24) |
| VHCDR3 5A11 | GEDLLVRTDAMDY (SEQ ID NO: 20) |
| VHCDR1 3B11 | GYSFSTFFIH (SEQ ID NO: 25) |
| VHCDR2 3B11 | RIDPNSGGTKYNEKFES (SEQ ID NO: 26) |
| VHCDR3 3B11 | GEDLLIRTDAMDY (SEQ ID NO: 27) |
| VHCDR1 5B9 | GYSFSTFFIH (SEQ ID NO: 28) |
| VHCDR2 5B9 | RIDPNSGATKYNEKFES (SEQ ID NO: 29) |
| VHCDR3 5B9 | GEDLLIRTDALDY (SEQ ID NO: 30) |
| VHCDR1 12A7 | GYTFSTFLIH (SEQ ID NO: 31) |
| VHCDR2 12A7 | RIDPNSGGTKYNEKFER (SEQ ID NO: 32) |
| VHCDR3 12A7 | GEDLLLRTDAMDY (SEQ ID NO: 33) |
| VHCDR1 9B8 | GYTFITYWMH (SEQ ID NO: 34) |
| VHCDR2 9B8 | GIDPNSGVIKYNEKFKS (SEQ ID NO: 35) |
| VHCDR3 9B8 | GEDLLIRTDAMDY (SEQ ID NO: 27) |
| VHCDR1 4B7 | GYSFSTFCIH (SEQ ID NO: 36) |
| VHCDR2 4B7 | RIDPNSGGTKYNEKFES (SEQ ID NO: 26) |
| VHCDR3 4B7 | GEDLLIRTDAMDY (SEQ ID NO: 27) |
| VHCDR1 1A4 | DHIFSIHWMQ (SEQ ID NO: 37) |
| VHCDR2 1A4 | EIFPGSGTTDYNEKFKG (SEQ ID NO: 38) |

TABLE 4-continued

VH CDR Sequences

| Designation | Sequence |
|---|---|
| VHCDR3 1A4 | GAFDY (SEQ ID NO: 39) |
| VHCDR1 5B9AS | ASGYSFSTFFIH (SEQ ID NO: 81) |
| VHCDR2 5B9AS | RIDPNSGATKYNEKFES (SEQ ID NO: 29) |
| VHCDR3 5B9AS | GEDLLIRTDALDY (SEQ ID NO: 30) |
| VHCDR1 c04 | DHIFSIHWMQ (SEQ ID NO: 37) |
| VHCDR2 c04 | EIFPGSGTTDYNEKFKG (SEQ ID NO: 38) |
| VHCDR3 c04 | GAFDY (SEQ ID NO: 39) |
| VHCDR1 c68 | DHIFSIHWMQ (SEQ ID NO: 37) |
| VHCDR2 c68 | EIFPGSGTTDYNEKFKG (SEQ ID NO: 38) |
| VHCDR3 c68 | GAFDY (SEQ ID NO: 39) |
| VHCDR1 c44 | DHIFSIHWMQ (SEQ ID NO: 37) |
| VHCDR2 c44 | EIFPGSGTTDYNEKFKG (SEQ ID NO: 38) |
| VHCDR3 c44 | GAFDY (SEQ ID NO: 39) |
| VHCDR1 c03 | DHIFSIHWMQ (SEQ ID NO: 37) |
| VHCDR2 c03 | EIFPGSGTTDYNEKFKG (SEQ ID NO: 38) |
| VHCDR3 c03 | GAFDY (SEQ ID NO: 39) |
| VHCDR1 c10 | DHIFSIHWMQ (SEQ ID NO: 37) |
| VHCDR2 c10 | EIFPGSGTTDYNEKFKG (SEQ ID NO: 38) |
| VHCDR3 c10 | GAFDY (SEQ ID NO: 39) |
| VHCDR1 c10.1 | GYTFTSDDIN (SEQ ID NO: 312) |
| VHCDR2 c10.1 | WIYPRDGRTKYNEKFKG (SEQ ID NO: 337) |
| VHCDR3 c10.1 | SRRVYAMDY (SEQ ID NO: 368) |
| VHCDR1 c10.2 | GYTFTSDDIN (SEQ ID NO: 312) |
| VHCDR2 c10.2 | WIYPRDGRTKYNEKFKG (SEQ ID NO: 337) |
| VHCDR3 c10.2 | SRRVYAMDY (SEQ ID NO: 368) |
| VHCDR1 8A6 | GYTITSYVMH (SEQ ID NO: 313) |
| VHCDR2 8A6 | YINPNNDGTKYNEKFKG (SEQ ID NO: 338) |
| VHCDR3 8A6 | GDYSNYFYWYFDV (SEQ ID NO: 369) |
| VHCDR1 6B7 | GYTFPGYWMH (SEQ ID NO: 314) |
| VHCDR2 6B7 | KIDPSDSETHYNQNFKD (SEQ ID NO: 339) |
| VHCDR3 6B7 | EGWDSLTKVWFGW (SEQ ID NO: 370) |
| VHCDR1 4E6 | GFNIKDDYMH (SEQ ID NO: 315) |
| VHCDR2 4E6 | RIDPAYGNGKYVPKFQD (SEQ ID NO: 340) |
| VHCDR3 4E6 | RYYAVSSVDYALDY (SEQ ID NO: 371) |
| VHCDR1 3C7 | GYIFTSHWMQ (SEQ ID NO: 316) |
| VHCDR2 3C7 | DIFPGSGTTDYNEKFKD (SEQ ID NO: 341) |
| VHCDR3 3C7 | GAFDY (SEQ ID NO: 39) |
| VHCDR1 2A6 | GFSLRTFGMGVG (SEQ ID NO: 317) |

TABLE 4-continued

VH CDR Sequences

| Designation | Sequence |
|---|---|
| VHCDR2 2A6 | HIWWNGDKYYDPALKS (SEQ ID NO: 342) |
| VHCDR3 2A6 | IGPSITTVAEGFAY (SEQ ID NO: 372) |
| VHCDR1 8A12 | GFSLRTFGMGVG (SEQ ID NO: 317) |
| VHCDR2 8A12 | HIWWNDEKYYNPDLKS (SEQ ID NO: 343) |
| VHCDR3 8A12 | VGPSISTVAEGFPY (SEQ ID NO: 373) |
| VHCDR1 9C5 | GFSLRTFGMGVG (SEQ ID NO: 317) |
| VHCDR2 9C5 | HIWWNDDKSSHPALKS (SEQ ID NO: 344) |
| VHCDR3 9C5 | IGPSITTVAEGFAY (SEQ ID NO: 372) |
| VHCDR1 9D1 | GFSMRTFGMGVG (SEQ ID NO: 318) |
| VHCDR2 9D1 | HIWWNDEKYYNPDLKS (SEQ ID NO: 343) |
| VHCDR3 9D1 | VGPSISTIAEGFPY (SEQ ID NO: 374) |
| VHCDR1 1B12 | GYTFTNDNYWMN (SEQ ID NO: 319) |
| VHCDR2 1B12 | RIRPSDSETHYNQKFTN (SEQ ID NO: 345) |
| VHCDR3 1B12 | SWEDLLLRSMEDYFDY (SEQ ID NO: 375) |
| VHCDR1 9D9 | GFSFSDYNIN (SEQ ID NO: 320) |
| VHCDR2 9D9 | KVHPKDGTATYNQKFQD (SEQ ID NO: 346) |
| VHCDR3 9D9 | LYYDSLTKILFAY (SEQ ID NO: 376) |
| VHCDR1 6C1 | GFSLRTFGMGVG (SEQ ID NO: 317) |
| VHCDR2 6C1 | HIWWNDEKYYNPALKS (SEQ ID NO: 347) |
| VHCDR3 6C1 | LGPSITTVAEGFPY (SEQ ID NO: 377) |
| VHCDR1 11A10 | GYSLISYYIH (SEQ ID NO: 321) |
| VHCDR2 11A10 | LTFPGSGNSKFIEKFKG (SEQ ID NO: 348) |
| VHCDR3 11A10 | GDFGNYLAYWYFDV (SEQ ID NO: 378) |
| VHCDR1 4A10 | GFSLKTFGMGVG (SEQ ID NO: 322) |
| VHCDR2 4A10 | HIWWNDDKFYHPALKS (SEQ ID NO: 349) |
| VHCDR3 4A10 | IGPSITTVAEGFAY (SEQ ID NO: 372) |
| VHCDR1 6A9 | GYSLTSYYIH (SEQ ID NO: 323) |
| VHCDR2 6A9 | LIFPGSGNSKYIEKFKG (SEQ ID NO: 350) |
| VHCDR3 6A9 | GDFGNYLAYWYFDV (SEQ ID NO: 378) |
| VHCDR1 5A2 | GFSLNTYGMGVG (SEQ ID NO: 324) |
| VHCDR2 5A2 | NIWWNDDKYYNSALKS (SEQ ID NO: 351) |
| VHCDR3 5A2 | VAATIVTTYGAWFAY (SEQ ID NO: 379) |
| VHCDR1 5A5 | GFSLRTFGMGVG (SEQ ID NO: 317) |
| VHCDR2 5A5 | HIWWNDEKYYNPTLKS (SEQ ID NO: 352) |
| VHCDR3 5A5 | IGPSITTVVEGFPY (SEQ ID NO: 380) |
| VHCDR1 12A11 | GYTFTDKYIN (SEQ ID NO: 325) |
| VHCDR2 12A11 | WIYPGSGNTKYNEKFKG (SEQ ID NO: 353) |
| VHCDR3 12A11 | GIIYYYDGSYPYALDY (SEQ ID NO: 381) |

TABLE 4-continued

VH CDR Sequences

| Designation | Sequence |
|---|---|
| VHCDR1 6D9 | GYTFTDYSIH (SEQ ID NO: 326) |
| VHCDR2 6D9 | WIYPGSGNTKYNDKFKG (SEQ ID NO: 354) |
| VHCDR3 6D9 | DYRRYYAIDY (SEQ ID NO: 382) |
| VHCDR1 5A3 | GYTFTDYSIH (SEQ ID NO: 326) |
| VHCDR2 5A3 | WIYPGSDNTKYNDKFKG (SEQ ID NO: 355) |
| VHCDR3 5A3 | DYRRYYAMDY (SEQ ID NO: 383) |
| VHCDR1 6B3 | GYTFTSYVMH (SEQ ID NO: 327) |
| VHCDR2 6B3 | YLNPNNDGTKYNEKFKG (SEQ ID NO: 356) |
| VHCDR3 6B3 | GDYSNYFYWYFDV (SEQ ID NO: 369) |
| VHCDR1 2C12 | GYTFSDYTIH (SEQ ID NO: 328) |
| VHCDR2 2C12 | WIYPGRGNTKYNDKFKG (SEQ ID NO: 357) |
| VHCDR3 2C12 | DYRRYYAMDY (SEQ ID NO: 383) |
| VHCDR1 H6A9 | GYTFTDNFIN (SEQ ID NO: 329) |
| VHCDR2 H6A9 | WISPGSGNTKNNEKFKG (SEQ ID NO: 358) |
| VHCDR3 H6A9 | GIIYYYDGTYPYALDY (SEQ ID NO: 384) |
| VHCDR1 9D12 | GFSLTDYEIN (SEQ ID NO: 330) |
| VHCDR2 9D12 | VIWTGGGTKYNSVLIS (SEQ ID NO: 359) |
| VHCDR3 9D12 | EGRRYYAMDY (SEQ ID NO: 385) |
| VHCDR1 6F2 | GFSLTTYEIN (SEQ ID NO: 331) |
| VHCDR2 6F2 | VIWTGGTTKYNSAFIS (SEQ ID NO: 360) |
| VHCDR3 6F2 | EGRRYYAMDY (SEQ ID NO: 385) |
| VHCDR1 11A12 | GYTFTSYVIH (SEQ ID NO: 332) |
| VHCDR2 11A12 | YLHRNNDGTKYNEKFKV (SEQ ID NO: 361) |
| VHCDR3 11A12 | GDYSNYFYWYFDV (SEQ ID NO: 386) |
| VHCDR1 1A10 | GFSLTTYEIN (SEQ ID NO: 331) |
| VHCDR2 1A10 | VIWTGGTTKYNSAFIS (SEQ ID NO: 362) |
| VHCDR3 1A10 | EGRRYYAMDY (SEQ ID NO: 385) |
| VHCDR1 2A7 | GYTFTDYSIH (SEQ ID NO: 326) |
| VHCDR2 2A7 | WIYPGSDNTKYNDKFKG (SEQ ID NO: 355) |
| VHCDR3 2A7 | DYRRYYAMDY (SEQ ID NO: 383) |

TABLE 4-continued

VH CDR Sequences

| Designation | Sequence |
|---|---|
| VHCDR1 11B7_a | GFSLTDYEIN (SEQ ID NO: 330) |
| VHCDR2 11B7_a | VIWTGGGTKYNSVLIS (SEQ ID NO: 359) |
| VHCDR3 11B7_a | EGRRYYAMDY (SEQ ID NO: 385) |
| VHCDR1 11B7_b | GFSLSTFGMGVG (SEQ ID NO: 392) |
| VHCDR2 11B7_b | HIWWDDDKYYNPALKS (SEQ ID NO: 363) |
| VHCDR3 11B7_b | IEGPYYWYFDV (SEQ ID NO: 387) |
| VHCDR1 7A6 | GFSLSRYSVH (SEQ ID NO: 333) |
| VHCDR2 7A6 | MIWGGGNTDYNSGLKS (SEQ ID NO: 364) |
| VHCDR3 7A6 | PSLYYYDVAWFPY (SEQ ID NO: 388) |
| VHCDR1 4D6 | GFNIKNDYLH (SEQ ID NO: 334) |
| VHCDR2 4D6 | WIDSANDKTKYAPKFQD (SEQ ID NO: 365) |
| VHCDR3 4D6 | VGVQDGYYVRDFDY (SEQ ID NO: 389) |
| VHCDR1 H2A7 | GFTFSDYYMS (SEQ ID NO: 335) |
| VHCDR2 H2A7 | LIRNKAPGYTTEYSASVKG (SEQ ID NO: 366) |
| VHCDR3 H2A7 | VLRRADCLDY (SEQ ID NO: 390) |
| VHCDR1 H7F8 | GFTFSSYDMS (SEQ ID NO: 336) |
| VHCDR2 H7F8 | AINSYGVNTYYPDTVKD (SEQ ID NO: 367) |
| VHCDR3 H7F8 | LLIGPYYYAMDY (SEQ ID NO: 391) |

The CDRs listed above in Tables 3 and 4 are defined using the Chothia numbering system (Al-Lazikani et al., JMB, 273, 927-948, (1997)) or IGMT numbering system (Lefranc, M.-P. et al., Dev. Comp. Immunol., 27, 55-77 (2003)). The IgAligner IMGT algorithm is from Chemical Computing Group (CCG).

Fabs that showed better or equal binding as compared to the chimeric parent Fab were selected for conversion to IgG. was converted to an IgG1KO format. IgG1KO (knock-out of effector functions) has two mutations in the Fc region, Leu234Ala and Leu235Ala, which reduce effector function such as FcγR and complement binding. The IgG format is described in the literature (see for example Hezareh et al. (2001) Journal of Virology 75: 12161-12168). Example 2 describes the humanization process in further detail. The results of such humanization resulted in humanized antibody sequences. A representative number of humanized light chain and heavy chain variable regions derived from mouse antibodies 5B9 and 1A4 are provided and shown in Tables 5 and 6.

TABLE 5

Humanized 5B9 and 1A4 Vκ Sequences

| Designation | Sequence |
|---|---|
| 148c04VK | DIQMTQSPSSLSASVGDRVTITCRASQDIGNRLSWLQQEPGKAPKRLIYAT SSLDSGVPSRFSGSRSGTEFTLTISSLQPEDFVTYYCLQYASSPFTFGQGTK LEIK (SEQ ID NO: 82)<br><br>GACATCCAGATGACCCAGAGCCCAAGCAGCCTGAGCGCCAGCGTCGG CGACCGCGTGACCATCACCTGCCGCGCCAGCCAGGACATCGGCAACC |

TABLE 5-continued

Humanized 5B9 and 1A4 Vκ Sequences

| Designation | Sequence |
|---|---|
| | GCCTGTCGTGGCTGCAGCAGGAGCCAGGCAAGGCCCCAAAGCGCCTG<br>ATCTACGCCACCAGCAGCCTGGACAGCGGTGTCCCAAGCCGCTTCAGC<br>GGCAGCCGCAGCGGCACCGAGTTCACCCTGACCATCAGCAGCCTGCA<br>ACCAGAGGACTTCGTCACCTACTACTGCCTGCAATACGCCAGCAGCCC<br>ATTCACCTTCGGCCAGGGCACCAAGCTGGAGATCAAG (SEQ ID<br>NO: 234) |
| 148c18VK | DIQMTQSPSSLSASVGDRVTITCRASQDIGNRLNWLQQEPGKAPKRLIYAT<br>SSLDSGVPKRFSSSRSGTEFTLTISSLQPEDFVDYYCLQYASSPFTFGTGTK<br>LEIK (SEQ ID NO: 83) |
| 148c19VK | DIQMTQSPSSLSASVGDRVTITCRASQDIGNRLNWYQQEPGKAPKRLIYAT<br>SSLDSGVPKRFSGSRSGTEFTLTISSLQPEDFVDYYCLQYASSPFTFGTGTK<br>LEIK (SEQ ID NO: 84) |
| 148c68VK | DIQMTQSPSSLSASVGDRVTITCRASQDIGNRLHWYQQKPGKAPKRLIYA<br>TSSLDSGVPKRFSGSRSGTEFTLTISSLQPEDFVTYYCLQYASSPFTFGQGT<br>KLEIK (SEQ ID NO: 85) |
| 148c77VK | DIQMTQSPSSLSASVGDRVTITCRASQDIGNRLNWYQQKPGKAPKRLIYA<br>TSSLDSGVPKRFSGSRSGTEFTLTISSLQPEDFVDYYCLQYASSPFTFGTGT<br>KLEIK (SEQ ID NO: 86) |
| 148c92VK | DIQMTQSPSSLSASVGDRVTITCRASQDIGNRLNWYQQKPGKAPKRLIYA<br>TSSLDSGVPSRFSGSRSGTEFTLTISSLQPEDFVDYYCLQYASSPFTFGTGT<br>KLEIK (SEQ ID NO: 87) |
| 160c16VK | DIQMTQSPSSLSASVGDRVTITCRASQDIGNRLNWYQQKPGKAPKRLIYA<br>TSSLDSGVPSRFSGSRSGTEFTLTISSLQPEDFVTYYCLQYASSPFTFGQGT<br>KLEIK (SEQ ID NO: 88) |
| | GACATCCAGATGACCCAGAGCCCAAGCAGCCTGAGCGCCAGCGTCGG<br>CGACCGCGTGACCATCACCTGCCGCGCCAGCCAGGACATCGGCAACC<br>GCCTGAACTGGTACCAGCAGAAGCCAGGCAAGGCCCCAAAGCGCCTG<br>ATCTACGCCACCAGCAGCCTGGACAGCGGTGTCCCAAGCCGCTTCAGC<br>GGCAGCCGCAGCGGCACCGAGTTCACCCTGACCATCAGCAGCCTGCA<br>ACCAGAGGACTTCGTCACCTACTACTGCCTGCAATACGCCAGCAGCCC<br>ATTCACCTTCGGCCAGGGCACCAAGCTGGAGATCAAG (SEQ ID<br>NO: 393) |
| 148c44VK | DIQMTQSPSSLSASVGDRVTITCRASQDIGNRLPWLQQKPGKAPKRLIYAT<br>SSLDSGVPSRFSGSGSGTEFTLTISSLQPEDFVDYYCLQYASSPFTFGTGTK<br>LEIK (SEQ ID NO: 89) |
| 148c03VK | DIQMTQSPSSLSASVGDRVTITCRASQDIGNRLRWYQQKPGKAPKRLIYA<br>TSSLDSGVPSRFSGSRSGTEFTLTISSLQPEDFATYYCLQYASSPFTFGQGT<br>KLEIK (SEQ ID NO: 90) |
| 148c10VK | DIQMTQSPSSLSASVGDRVTITCRASQDIGNRLMWYQQKPGKAPKRLIYA<br>TSSLDSGVPSRFSGSRSGTEFTLTISSLQPEDFVTYYCLQYASSPFTFGTGTK<br>LEIK (SEQ ID NO: 91) |
| 145c02VK | DIQMTQSPSSLSASVGDRVTITCKASQNAGIDVAWFQQKPGKAPKLLIYS<br>KSNRYTGVPSRFSGSGSGTDFTLTISSLQPEDFATYYCLQYRSYPRTFGQG<br>TKLEIK (SEQ ID NO: 92) |
| 145c08VK | DIQMTQSPSSLSASVGDRVSITCKASQNAGIDVAWFQQKPGKAPKLLIYSK<br>SNRYTGVPSRFSGSGSGTDFTLTISSLQPEDFATYYCLQYRSYPRTFGQGT<br>KLEIK (SEQ ID NO: 93) |
| | GACATCCAGATGACCCAGAGCCCAAGCAGCCTGAGCGCCAGCGTCGG<br>CGACCGCGTGAGCATCACCTGCAAGGCCAGCCAGAACGCCGGCATCG<br>ACGTGGCTTGGTTCCAGCAGAAGCCTGGCAAGGCCCCAAAGCTGCTGA<br>TCTACAGCAAGAGCAACCGCTACACGGCGTGCCAAGCCGCTTCAGCG<br>GCAGCGGCAGCGGCACCGACTTCACCCTGACCATCAGCAGCCTCCAGC<br>CAGAGGACTTCGCCACCTACTACTGCCTCCAGTACCGCAGCTACCCAC<br>GCACCTTCGGCCAGGGCACCAAGCTGGAGATCAAG<br>(SEQ ID NO: 394) |
| 145c15VK | DIQMTQSPSSLSASVGDRVSITCKASQNAGIDVAWFQQKPGKAPKLLIYSK<br>SNRYTGVPSRFSGSGSGTDFTLTISSLQPEDFADYYCLQYRSYPRTFGGGT<br>KLEIK (SEQ ID NO: 94) |
| | GACATCCAGATGACCCAGAGCCCAAGCAGCCTGAGCGCCAGCGTCGG<br>CGACCGCGTGAGCATCACCTGCAAGGCCAGCCAGAACGCCGGCATCG<br>ACGTGGCTTGGTTCCAGCAGAAGCTGGCAAGGCCCCAAAGCTGCTGAT |

TABLE 5-continued

Humanized 5B9 and 1A4 Vκ Sequences

| Designation | Sequence |
|---|---|
| | CTACAGCAAGAGCAACCGCTACACCGGCGTGCCAAGCCGCTTCAGCG<br>GCAGCGGCAGCGGCACCGACTTCACCCTGACCATCAGCAGCCTCCAGC<br>CAGAGGACTTCGCCGACTACTACTGCCTCCAGTACCGCAGCTACCCAC<br>GCACCTTCGGCGGCGGCACCAAGCTGGAGATCAAG<br>(SEQ ID NO: 395) |
| 145c18VK | DIQMTQSPSSLSASVGDRVSITCKASQNAGIDVAWFQQKPGKAPKLLIFSK<br>SNRYTGVPDRFSGSGSGTDFTLTISSLQPEDFADYYCLQYRSYPRTFGQGT<br>KLEIK (SEQ ID NO: 95) |
| 145c28VK | DIQMTQSPSSLSASVGDRVTITCKASQNAGIDVAWFQQKPGKAPKLLIFSK<br>SNRYTGVPSRFSGSGSGTDFTLTISSLQPEDFATYYCLQYRSYPRTFGQGT<br>KLEIK (SEQ ID NO: 96) |
| 145c36VK | DIVMTQSPSSLSASVGDRVSITCKASQNAGIDVAWFQQKPGKAPKLLIYSK<br>SNRYTGVPDRFSGSGSGTDFTLTISSLQPEDFATYYCLQYRSYPRTFGQGT<br>KLEIK (SEQ ID NO: 97) |
| Reference 1 | EIVLTQSPATLSLSPGERATLSCRASQSVSRYLAWYQQKPGQAPRLLIYDA<br>SNRATGIPARFSGSGSGTDSTLTISSLEPEDFAVYYCQQRSNWPRTFGQGT<br>KVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLS<br>SPVTKSFNRGEC (SEQ ID NO: 98) |
| Reference 2 | SSELTQDPAVSVALGQTVRVTCQGDSLRSYYASWYQQKPGQAPVLVIYG<br>KNNRPSGIPDRFSGSSSGNTASLTITGAQAEDEADYYCSSRDSSGNHWVF<br>GGGTELTVLGQPKAAPSVTLFPPSSEELQANKATLVCLISDFYPGAVTVA<br>WKADSSPVKAGVETTTPSKQSNNKYAASSYLSLTPEQWKSHRSYSCQVT<br>HEGSTVEKTVAPTECS (SEQ ID NO: 99) |

TABLE 6

Humanized 5B9 and 1A4 VH Sequences

| Designation | Sequence |
|---|---|
| 148c04VH | QVQLVQSGAEVKKPGSSVKVSCKAPDHIFSIHWMQWVRQRPGQGLEWIG<br>EIFPGSGTTDYNEKFKGKVTITVDKSTSTAYMELSSLRSEDTAVYFCASGA<br>FDYWGQGTTVTVSS (SEQ ID NO: 100) |
| 148c18VH | QVQLVQSGAEVKKPGSSVKVSCKAPDHIFSIHWMQWVRQAPGQGLEWM<br>GEIFPGSGTTDYNEKFKGKVTITVDKSTSTAYMELSSLRSEDTAVYYCASG<br>AFDYWGQGTTVTVSS (SEQ ID NO: 101) |
| | CAGGTGCAGCTGGTGCAGAGCGGCGCCGAGGTGAAGAAGCCAGGCAG<br>CAGCGTGAAGGTCAGCTGCAAGGCCCCCGACCACATCTTCAGCATCCA<br>CTGGATGCAGTGGGTCCGCCAAGCCCCAGGCCAGGGCCTGGAGTGGA<br>TGGGCGAGATTTTCCCAGGCAGCGGCACCACCGACTACAACGAGAAG<br>TTCAAGGGCAAGGTGACCATCACCGTCGACAAGAGCACCAGCACCGC<br>CTACATGGAGCTGAGCAGCCTGCGCAGCGAGGACACCGCCGTCTACTA<br>CTGCGCCAGCGGCGCCTTCGACTACTGGGGCCAGGGCACCACCGTGAC<br>CGTGAGCAGC (SEQ ID NO: 396) |
| 148c19VH | QVQLVQSGAEVKKPGSSVKISCKAPDHIFSIHWMQWVRQRPGQGLEWIG<br>EIFPGSGTTDYNEKFKGKVTVTVDKSTSTAYMELSSLRSEDTAVYYCASG<br>AFDYWGQGTTVTVSS (SEQ ID NO: 102) |
| 148c68VH | QVQLVQSGAEVKKPGSSVKISCKASDHIFSIHWMQWVRQRPGQGLEWIG<br>EIFPGSGTTDYNEKFKGKVTVTVDKSTSTAYMELSSLRSEDTAVYFCARG<br>AFDYWGQGTTVTVSS (SEQ ID NO: 103) |
| 148c75VH | QVQLVQSGAEVKKPGSSVKVSCKAPDHIFSIHWMQWVRQRPGQGLEWM<br>GEIFPGSGTTDYNEKFKGKVTVTADKSTSTAYMELSSLRSEDTAVYFCAS<br>GAFDYWGQGTTVTVSS (SEQ ID NO: 104) |
| 148c77VH | QVQLVQSGAEVKKPGSSVKISCKASDHIFSIHWMQWVRQAPGQGLEWM<br>GEIFPGSGTTDYNEKFKGKVTVTVDKSTSTAYMELSSLRSEDTAVYFCAS<br>GAFDYWGQGTTVTVSS (SEQ ID NO: 105) |
| 148c92VH | QVQLVQSGAEVKKPGSSVKVSCKAPDHIFSIHWMQWVRQAPGQGLEWIG<br>EIFPGSGTTDYNEKFKGKRATVTVDKSTSTAYMELSSLRSEDTAVYFCASG<br>AFDYWGQGTTVTVSS (SEQ ID NO: 106) |

TABLE 6-continued

Humanized 5B9 and 1A4 VH Sequences

| Designation | Sequence |
|---|---|
| 161c01VH | QVQLVQSGAEVKKPGSSVKVSCKASDHIFSIHWMQWVRQAPGQGLEWM<br>GEIFPGSGTTDYNEKFKGRVTITADKSTSTAYMELSSLRSEDTAVYYCAR<br>GAFDYWGQGTTVTVSS (SEQ ID NO: 107) |
| 148c03VH | QVQLVQSGAEVKKPGSSVKISCKAPDHIFSIHWMQWVRQAPGQGLEWIG<br>EIFPGSGTTDYNEKFKGKVTVTVDKSTSTAYMELSSLRSEDTAVYYCASG<br>AFDYWGQGTTVTVSS (SEQ ID NO: 108) |
| 148c10VH | QVQLVQSGAEVKKPGSSVKISCKASDHIFSIHWMQWVRQRPGQGLEWIG<br>EIFPGSGTTDYNEKFKGKVTITADKSTSTAYMELSSLRSEDTAVYYCASGA<br>FDYWGQGTTVTVSS (SEQ ID NO: 109) |
| 145c02VH | QVQLVQSGAEVKKPGASVKVSCKASGYSFSTFFIHWIQQRPGQGLEWMG<br>RIDPNSGATKYNEKFESRVTMTRDTSISTAYMELSRLRSDDTAVYYCARG<br>EDLLIRTDALDYWGQGTLVTVSS (SEQ ID NO: 110) |
| 145c08VH | QVQLVQSGAEVKKPGASVKVSCKASGYSFSTFFIHWIQQRPGQGLEWMG<br>RIDPNSGATKYNEKFESKVTLTVDTSISTAYMELSRLRSDDTAVYYCARG<br>EDLLIRTDALDYWGQGTSVTVSS (SEQ ID NO: 111) |
| 145c15VH | QVQLVQSGAEVKKPGASVKVSCKASGYSFSTFFIHWVRQRPGQGLEWIG<br>RIDPNSGATKYNEKFESKVTLTRDTSISTAYMELSRLRSDDTAVYYCARG<br>EDLLIRTDALDYWGQGTSVTVSS (SEQ ID NO: 112)<br><br>CAGGTGCAGCTGGTGCAGAGCGGCGCTGAGGTGAAGAAGCCAGGCGC<br>CAGCGTGAAGGTGAGCTGCAAGGCCAGCGGCTACAGCTTCAGCACCTT<br>CTTCATCCACTGGGTCCGCCAACGCCCAGGCCAGGGCCTGGAGTGGAT<br>CGGCCGCATCGACCCAAACAGCGGCGCCACCAAGTACAACGAGAAGT<br>TCGAGAGCAAGGTCACCCTGACCCGCGACACCAGCATCAGCACCGCCT<br>ACATGGAGCTGAGCCGCCTGCGCAGCGACGACACCGCCGTCTACTACT<br>GCGCCCGCGGCGAGGACCTGCTGATCCGCACCGACGCCCTGGATTACT<br>GGGGTCAGGGTACTAGCGTGACCGTGAGCAGC<br>(SEQ ID NO: 397) |
| 145c18VH | QVQLVQSGAEVKKPGASVKVSCKASGYSFSTFFIHWVQQRPGQGLEWM<br>GRIDPNSGATKYNEKFESKVTLTRDTSISTAYMELSRLRSDDTAVYYCAR<br>GEDLLIRTDALDYWGQGTLVTVSS (SEQ ID NO: 113) |
| 145c28VH | QVQLVQSGAEVKKPGASVKVSCKASGYSFSTFFIHWVRQAPGQGLEWIG<br>RIDPNSGATKYNEKFESRVTMTRDTSISTAYMELSRLRSDDTAVYYCARG<br>EDLLIRTDALDYWGQGTSVTVSS (SEQ ID NO: 114)<br><br>CAGGTGCAGCTGGTGCAGAGCGGCGCTGAGGTGAAGAAGCCAGGCGC<br>CAGCGTGAAGGTGAGCTGCAAGGCCAGCGGCTACAGCTTCAGCACCTT<br>CTTCATCCACTGGGTCCGCCAAGCCCCAGGCCAGGGCCTGGAGTGGAT<br>CGGCCGCATCGACCCAAACAGCGGCGCCACCAAGTACAACGAGAAGT<br>TCGAGAGCCGCGTCACCATGACCCGCGACACCAGCATCAGCACCGCCT<br>ACATGGAGCTGAGCCGCCTGCGCAGCGACGACACCGCCGTCTACTACT<br>GCGCCCGCGGCGAGGACCTGCTGATCCGCACCGACGCCCTGGATTACT<br>GGGGTCAGGGTACTAGCGTGACCGTGAGCAGC<br>(SEQ ID NO: 398) |
| 145c36VH | QVQLVQSGAEVKKPGASVKVSCKASGYSFSTFFIHWVRQRPGQGLEWM<br>GRIDPNSGATKYNEKFESRATLTVDTSISTAYMELSRLRSDDTAVYYCAR<br>GEDLLIRTDALDYWGQGTSVTVSS (SEQ ID NO: 115) |
| Reference 1 | QVQLQQWGAGLLKPSETLSLTCAVYGGSFSGYYWSWIRQPPGKGLEWIG<br>EINHSGSTNYNPSLKSRVTISVDTSKNQFSLKLSSVTAADTAVYYCARGY<br>YDILTGYYYFDYWGQGTLVTVSSASTKGPSVFPLAPCSRSTSESTAALG<br>CLVKDYFPEPVTVSWNSGALTSGVHTFPAVLQSSGLYSLSSVVTVPSSSLG<br>TKTYTCNVDHKPSNTKVDKRVESKYGPPCPPCPAPEFLGGPSVFLFPPKPK<br>DTLMISRTPEVTCVVVDVSQEDPEVQFNWYVDGVEVHNAKTKPREEQFN<br>STYRVVSVLTVLHQDWLNGKEYKCKVSNKGLPSSIEKTISKAKGQPREPQ<br>VYTLPPSQEEMTKNQVSLTCLVKGFYPSDIAVEWESNGQPENNYKTTPPV<br>LDSDGSFFLYSRLTVDKSRWQEGNVFSCSVMHEALHNHYTQKSLSLSLG<br>K (SEQ ID NO: 116) |
| Reference 2 | QVQLQQSGAEVKKPGSSVRVSCKASGGTFNNNAINWVRQAPGQGLEWM<br>GGIIPMFGTAKYSQNFQGRVAITADESTGTASMELSSLRSEDTAVYYCARS<br>RDLLLFPHHALSPWGRGTMVTVSSASTKGPSVFPLAPSSKSTSGGTAALG<br>CLVKDYFPEPVTVSWNSGALTSGVHTFPAVLQSSGLYSLSSVVTVPSSSLG<br>TQTYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQP |

TABLE 6-continued

Humanized 5B9 and 1A4 VH Sequences

Designation Sequence

REPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLS
LSPG (SEQ ID NO: 117)

The humanized anti-BAFF antibodies optionally include specific amino acid substitutions in the consensus or germline framework regions. The specific substitution of amino acid residues in these framework positions can improve various aspects of antibody performance including binding affinity and/or stability, over that demonstrated in humanized antibodies formed by "direct swap" of CDRs or HVLs into the human germline framework regions.

In some embodiments, the present invention describes other monoclonal antibodies with a light chain variable region having the amino acid sequence set forth in of SEQ ID NO: 41, 43, 45, 47, 49, 51, 53, 55, 57, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179 or 181. In some embodiments, the present invention describes other monoclonal antibodies with a heavy chain variable region having the amino acid sequence set forth in of SEQ ID NO: 59, 61, 63, 65, 67, 69, 71, 73, 75, 183, 185, 187, 189, 191, 193, 195, 197, 199, 201, 203, 205, 207, 209, 211, 213, 215, 217, 219, 221, 223, 225, 227, 229, 231, 233, 235, 238, 240, 242, 244, 246 or 248 (see Tables 1 and 2 above). The CDR sequence of these mouse antibodies are shown in Tables 3 and 4. Placing such CDRs into FRs of the human consensus heavy and light chain variable domains will yield useful humanized antibodies of the present invention.

In particular, the present invention provides monoclonal antibodies with the combinations of light chain variable and heavy chain variable regions of SEQ ID NO: 41/59, 43/61, 45/63, 47/65, 49/67, 51/69, 53/71, 55/73, 57/75, 119/183, 121/185, 123/187, 125/189, 127/191, 129/193, 131/195, 133/197, 135/199, 137/201, 139/203, 141/205, 143/207, 145/209, 147/211, 149/213, 151/215, 153/217, 155/219, 157/221, 159/223, 161/225, 163/227, 165/229, 167/231, 169/233, 171/235, 173/238, 173/240, 175/242, 177/244, 179/246 or 181/248. Such variable regions can be combined with human constant regions.

In some embodiments, the present invention describes other humanized antibodies with light chain variable region sequences having the amino acid sequence set forth in of SEQ ID NO: 82-97. In some embodiments, the present invention describes other humanized antibodies with heavy chain variable region sequences having the amino acid sequence set forth in of SEQ ID NO: 100-115 (see Tables 5 and 6 above). The CDR sequences of these antibodies are shown in Tables 3 and 4. Such variable regions can be combined with human constant regions.

In some specific embodiments, the humanized anti-BAFF antibodies disclosed herein comprise at least a heavy or a light chain variable domain comprising the CDRs or HVLs of the murine monoclonal antibodies or humanized antibodies as shown in Tables 1 through 6 above and the FRs of the human germline heavy and light chain variable domains.

The CDRs of these sequences are shown in Tables 3 and 4. In one embodiment, the invention provides an anti-BAFF antibody molecule comprising a light chain variable domain with a CDR1 selected from the group consisting of SEQ ID NO: 1, SEQ ID NO: 5, SEQ ID NO: 10, SEQ ID NO: 13, SEQ ID NO: 15, SEQ ID NO: 76, SEQ ID NO: 77, SEQ ID NO: 78, SEQ ID NO: 79, SEQ ID NO: 80, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274 and SEQ ID NO: 275; a CDR2 selected from the group consisting of SEQ ID NO: 2, SEQ ID NO: 6, SEQ ID NO: 8, SEQ ID NO: 11, SEQ ID NO: 16, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291 and SEQ ID NO: 292; and a CDR3 selected from the group consisting of SEQ ID NO: 3, SEQ ID NO: 4, SEQ ID NO: 7, SEQ ID NO: 9, SEQ ID NO: 12, SEQ ID NO:14, SEQ ID NO: 17, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310 and SEQ ID NO: 311; and a heavy chain variable domain with a CDR1 selected from the group consisting of SEQ ID NO: 18, SEQ ID NO: 21, SEQ ID NO: 23, SEQ ID NO: 25, SEQ ID NO: 28, SEQ ID NO: 31, SEQ ID NO: 34, SEQ ID NO: 36, SEQ ID NO: 37, SEQ ID NO: 81, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 392, SEQ ID NO: 333, SEQ ID NO: 334, SEQ ID NO: 335 and SEQ ID NO: 336; a CDR2 selected from the group consisting of SEQ ID NO: 19, SEQ ID NO: 24, SEQ ID NO: 26, SEQ ID NO: 29, SEQ ID NO: 32, SEQ ID NO: 35, SEQ ID NO: 38, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 343, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366 and SEQ ID NO: 367; and a CDR3 selected from the group consisting of SEQ ID NO: 20, SEQ ID NO: 22, SEQ ID NO: 27, SEQ ID NO: 30, SEQ ID NO: 33, SEQ ID NO. 39, SEQ ID NO: 368, SEQ ID NO: 369, SEQ ID NO: 370, SEQ ID NO: 371, SEQ ID NO: 372, SEQ ID NO: 373, SEQ ID NO:

374, SEQ ID NO: 375, SEQ ID NO: 376, SEQ ID NO: 377, SEQ ID NO: 378, SEQ ID NO: 378, SEQ ID NO: 379, SEQ ID NO:380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390 and SEQ ID NO: 391.

In another embodiment, the invention provides (a) an anti-BAFF antibody molecule where the light chain variable domain comprises a CDR1 of SEQ ID NO: 1, a CDR2 of SEQ ID NO: 2 and a CDR3 of SEQ ID NO: 3 and a heavy chain variable domain comprises a CDR1 of SEQ ID NO: 18, a CDR2 of SEQ ID NO: 19 and a CDR3 of SEQ ID NO: 20; (b) an anti-BAFF antibody molecule where the light chain variable domain comprises a CDR1 of SEQ ID NO: 1, a CDR2 of SEQ ID NO: 2 and a CDR3 of SEQ ID NO: 4 and a heavy chain variable domain comprises a CDR1 of SEQ ID NO: 21, a CDR2 of SEQ ID NO: 19 and a CDR3 of SEQ ID NO: 22; (c) an anti-BAFF antibody molecule where the light chain variable domain comprises a CDR1 of SEQ ID NO: 1, a CDR2 of SEQ ID NO: 2 and a CDR3 of SEQ ID NO: 4 and a heavy chain variable domain comprises a CDR1 of SEQ ID NO: 23, a CDR2 of SEQ ID NO: 24 and a CDR3 of SEQ ID NO: 20; (d) an anti-BAFF antibody molecule where the light chain variable domain comprises a CDR1 of SEQ ID NO: 5, a CDR2 of SEQ ID NO: 6 and a CDR3 of SEQ ID NO: 7 and a heavy chain variable domain comprises a CDR1 of SEQ ID NO: 25, a CDR2 of SEQ ID NO: 26 and a CDR3 of SEQ ID NO: 27; (e) an anti-BAFF antibody molecule where the light chain variable domain comprises a CDR1 of SEQ ID NO: 5, a CDR2 of SEQ ID NO: 8 and a CDR3 of SEQ ID NO: 9 and a heavy chain variable domain comprises a CDR1 of SEQ ID NO: 28, a CDR2 of SEQ ID NO: 29 and a CDR3 of SEQ ID NO: 30; (f) an anti-BAFF antibody molecule where the light chain variable domain comprises a CDR1 of SEQ ID NO: 10, a CDR2 of SEQ ID NO: 11 and a CDR3 of SEQ ID NO: 12 and a heavy chain variable domain comprises a CDR1 of SEQ ID NO: 31, a CDR2 of SEQ ID NO: 32 and a CDR3 of SEQ ID NO: 33; (g) an anti-BAFF antibody molecule where the light chain variable domain comprises a CDR1 of SEQ ID NO: 13, a CDR2 of SEQ ID NO: 6 and a CDR3 of SEQ ID NO: 14 and a heavy chain variable domain comprises a CDR1 of SEQ ID NO: 34, a CDR2 of SEQ ID NO: 35 and a CDR3 of SEQ ID NO: 27; (h) an anti-BAFF antibody molecule where the light chain variable domain comprises a CDR1 of SEQ ID NO: 10, a CDR2 of SEQ ID NO: 6 and a CDR3 of SEQ ID NO: 7 and a heavy chain variable domain comprises a CDR1 of SEQ ID NO: 36, a CDR2 of SEQ ID NO: 26 and a CDR3 of SEQ ID NO: 27; (i) an anti-BAFF antibody molecule where the light chain variable domain comprises a CDR1 of SEQ ID NO: 15, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (j) an anti-BAFF antibody molecule where the light chain variable domain comprises a CDR1 of SEQ ID NO: 76, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (k) an anti-BAFF antibody molecule where the light chain variable domain comprises a CDR1 of SEQ ID NO: 77, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (l) an anti-BAFF antibody molecule where the light chain variable domain comprises a CDR1 of SEQ ID NO: 78, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (m) an anti-BAFF antibody molecule where the light chain variable domain comprises a CDR1 of SEQ ID NO: 79, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (n) an anti-BAFF antibody molecule where the light chain variable domain comprises a CDR1 of SEQ ID NO: 80, a CDR2 of SEQ ID NO: 16 and a CDR3 of SEQ ID NO: 17 and a heavy chain variable domain comprises a CDR1 of SEQ ID NO: 37, a CDR2 of SEQ ID NO: 38 and a CDR3 of SEQ ID NO: 39; (o) an anti-BAFF antibody molecule where the light chain variable domain comprises a CDR1 of SEQ ID NO: 5, a CDR2 of SEQ ID NO: 8 and a CDR3 of SEQ ID NO: 9 and a heavy chain variable domain comprises a CDR1 of SEQ ID NO: 81, a CDR2 of SEQ ID NO: 29 and a CDR3 of SEQ ID NO: 30; (p) an anti-BAFF antibody molecule where the light chain variable domain comprises a CDR1 of SEQ ID NO: 249, a CDR2 of SEQ ID NO: 276 and a CDR3 of SEQ ID NO: 293 and a heavy chain variable domain comprises a CDR1 of SEQ ID NO: 312, a CDR2 of SEQ ID NO: 337 and a CDR3 of SEQ ID NO: 368; (q) an anti-BAFF antibody molecule where the light chain variable domain comprises a CDR1 of SEQ ID NO: 250, a CDR2 of SEQ ID NO: 276 and a CDR3 of SEQ ID NO: 293 and a heavy chain variable domain comprises a CDR1 of SEQ ID NO: 312, a CDR2 of SEQ ID NO: 337 and a CDR3 of SEQ ID NO: 368; (r) an anti-BAFF antibody molecule where the light chain variable domain comprises a CDR1 of SEQ ID NO: 251, a CDR2 of SEQ ID NO: 277 and a CDR3 of SEQ ID NO: 294 and a heavy chain variable domain comprises a CDR1 of SEQ ID NO: 313, a CDR2 of SEQ ID NO: 338 and a CDR3 of SEQ ID NO: 369; (s) an anti-BAFF antibody molecule where the light chain variable domain comprises a CDR1 of SEQ ID NO: 252, a CDR2 of SEQ ID NO: 278 and a CDR3 of SEQ ID NO: 295 and a heavy chain variable domain comprises a CDR1 of SEQ ID NO: 314, a CDR2 of SEQ ID NO: 339 and a CDR3 of SEQ ID NO: 370; (t) an anti-BAFF antibody molecule where the light chain variable domain comprises a CDR1 of SEQ ID NO: 253, a CDR2 of SEQ ID NO: 279 and a CDR3 of SEQ ID NO: 296 and a heavy chain variable domain comprises a CDR1 of SEQ ID NO: 315, a CDR2 of SEQ ID NO: 340 and a CDR3 of SEQ ID NO: 371; (u) an anti-BAFF antibody molecule where the light chain variable domain comprises a CDR1 of SEQ ID NO: 15, a CDR2 of SEQ ID NO: 16 and a CDR3 of SEQ ID NO: 297 and a heavy chain variable domain comprises a CDR1 of SEQ ID NO: 316, a CDR2 of SEQ ID NO: 341 and a CDR3 of SEQ ID NO: 39; (v) an anti-BAFF antibody molecule where the light chain variable domain comprises a CDR1 of SEQ ID NO: 254, a CDR2 of SEQ ID NO: 280 and a CDR3 of SEQ ID NO: 298 and a heavy chain variable domain comprises a CDR1 of SEQ ID NO: 317, a CDR2 of SEQ ID NO: 342 and a CDR3 of SEQ ID NO: 372; (w) an anti-BAFF antibody molecule where the light chain variable domain comprises a CDR1 of SEQ ID NO: 255, a CDR2 of SEQ ID NO: 281 and a CDR3 of SEQ ID NO: 298 and a heavy chain variable domain comprises a CDR1 of SEQ ID NO: 317, a CDR2 of SEQ ID NO: 343 and a CDR3 of SEQ ID NO: 373; (x) an anti-BAFF antibody molecule where the light chain variable domain comprises a CDR1 of SEQ ID NO: 256, a CDR2 of SEQ ID NO: 2 and a CDR3 of SEQ ID NO: 299 and a heavy chain variable domain comprises a CDR1 of SEQ ID NO: 317, a CDR2 of SEQ ID NO: 344 and a CDR3 of SEQ ID NO: 372; (y) an anti-BAFF antibody molecule where the light chain variable domain comprises a CDR1 of SEQ ID NO: 255, a CDR2 of SEQ ID NO: 281 and a CDR3 of SEQ ID NO: 298 and a heavy chain variable domain comprises a CDR1 of SEQ ID NO: 318, a CDR2 of SEQ ID NO: 343 and a CDR3 of SEQ ID NO: 374; (z) an anti-BAFF antibody molecule where the light chain variable domain comprises a CDR1 of SEQ ID NO: 257, a CDR2 of SEQ ID NO: 282 and a CDR3 of SEQ ID NO: 300 and a heavy chain variable domain comprises a CDR1 of SEQ ID NO: 319, a CDR2 of SEQ ID NO: 345 and a CDR3 of SEQ ID NO: 375; (aa) an anti-BAFF antibody molecule where the light chain variable domain comprises a CDR1 of SEQ ID NO: 258, a CDR2 of SEQ ID NO: 283 and a CDR3 of SEQ ID NO: 301 and a heavy chain variable domain comprises a CDR1 of SEQ ID NO: 320, a CDR2 of SEQ ID NO: 346 and a CDR3 of SEQ ID NO: 376; (bb) an anti-BAFF antibody molecule where the light chain variable domain comprises a CDR1 of SEQ ID NO: 259, a CDR2 of SEQ ID NO: 281 and a CDR3 of SEQ ID NO: 298 and a heavy chain variable domain comprises a CDR1 of SEQ ID NO: 317, a CDR2 of SEQ ID NO: 347 and a CDR3 of SEQ ID NO: 377; (cc) an anti-BAFF antibody molecule where the light chain variable domain comprises a CDR1 of SEQ ID NO: 260, a CDR2 of SEQ ID NO: 284 and a CDR3 of SEQ ID NO: 294 and a heavy chain variable domain comprises a CDR1 of SEQ ID NO: 321, a CDR2 of SEQ ID NO: 348 and a CDR3 of SEQ ID NO: 378; (dd) an anti-BAFF antibody molecule where the light chain variable domain comprises a CDR1 of SEQ ID NO: 254, a CDR2 of SEQ ID NO: 2 and a CDR3 of SEQ ID NO: 299 and a heavy chain variable domain comprises a CDR1 of SEQ ID NO: 322, a CDR2 of SEQ ID NO: 349 and a CDR3 of SEQ ID NO: 372; (ee) an anti-BAFF antibody molecule where the light chain variable domain comprises a CDR1 of SEQ ID NO: 261, a CDR2 of SEQ ID NO: 285 and a CDR3 of SEQ ID NO: 294 and a heavy chain variable domain comprises a CDR1 of SEQ ID NO: 323, a CDR2 of SEQ ID NO: 350 and a CDR3 of SEQ ID NO: 378; (ff) an anti-BAFF antibody molecule where the light chain variable domain comprises a CDR1 of SEQ ID NO: 262, a CDR2 of SEQ ID NO: 286 and a CDR3 of SEQ ID NO: 302 and a heavy chain variable domain comprises a CDR1 of SEQ ID NO: 324, a CDR2 of SEQ ID NO: 351 and a CDR3 of SEQ ID NO: 379; (gg) an anti-BAFF antibody molecule where the light chain variable domain comprises a CDR1 of SEQ ID NO: 263, a CDR2 of SEQ ID NO: 6 and a CDR3 of SEQ ID NO: 303 and a heavy chain variable domain comprises a CDR1 of SEQ ID NO: 317, a CDR2 of SEQ ID NO: 352 and a CDR3 of SEQ ID NO: 380; (hh) an anti-BAFF antibody molecule where the light chain variable domain comprises a CDR1 of SEQ ID NO: 264, a CDR2 of SEQ ID NO: 276 and a CDR3 of SEQ ID NO: 304 and a heavy chain variable domain comprises a CDR1 of SEQ ID NO: 325, a CDR2 of SEQ ID NO: 353 and a CDR3 of SEQ ID NO: 381; (ii) an anti-BAFF antibody molecule where the light chain variable domain comprises a CDR1 of SEQ ID NO: 265, a CDR2 of SEQ ID NO: 287 and a CDR3 of SEQ ID NO: 305 and a heavy chain variable domain comprises a CDR1 of SEQ ID NO: 326, a CDR2 of SEQ ID NO: 354 and a CDR3 of SEQ ID NO: 382; (jj) an anti-BAFF antibody molecule where the light chain variable domain comprises a CDR1 of SEQ ID NO: 266, a CDR2 of SEQ ID NO: 287 and a CDR3 of SEQ ID NO: 306 and a heavy chain variable domain comprises a CDR1 of SEQ ID NO: 326, a CDR2 of SEQ ID NO: 355 and a CDR3 of SEQ ID NO: 383; (kk) an anti-BAFF antibody molecule where the light chain variable domain comprises a CDR1 of SEQ ID NO: 267, a CDR2 of SEQ ID NO: 285 and a CDR3 of SEQ ID NO: 294 and a heavy chain variable domain comprises a CDR1 of SEQ ID NO: 327, a CDR2 of SEQ ID NO: 356 and a CDR3 of SEQ ID NO: 369; (ll) an anti-BAFF antibody molecule where the light chain variable domain comprises a CDR1 of SEQ ID NO: 268, a CDR2 of SEQ ID NO: 276 and a CDR3 of SEQ ID NO: 306 and a heavy chain variable domain comprises a CDR1 of SEQ ID NO: 328, a CDR2 of SEQ ID NO: 357 and a CDR3 of SEQ ID NO: 383; (mm) an anti-BAFF antibody molecule where the light chain variable domain comprises a CDR1 of SEQ ID NO: 269, a CDR2 of SEQ ID NO: 288 and a CDR3 of SEQ ID NO: 304 and a heavy chain variable domain comprises a CDR1 of SEQ ID NO: 329, a CDR2 of SEQ ID NO: 358 and a CDR3 of SEQ ID NO: 384; (nn) an anti-BAFF antibody molecule where the light chain variable domain comprises a CDR1 of SEQ ID NO: 270, a CDR2 of SEQ ID NO: 276 and a CDR3 of SEQ ID NO: 306 and a heavy chain variable domain comprises a CDR1 of SEQ ID NO: 330, a CDR2 of SEQ ID NO: 359 and a CDR3 of SEQ ID NO: 385; (oo) an anti-BAFF antibody molecule where the light chain variable domain comprises a CDR1 of SEQ ID NO: 271, a CDR2 of SEQ ID NO: 289 and a CDR3 of SEQ ID NO: 307 and a heavy chain variable domain comprises a CDR1 of SEQ ID NO: 331, a CDR2 of SEQ ID NO: 360 and a CDR3 of SEQ ID NO: 385; (pp) an anti-BAFF antibody molecule where the light chain variable domain comprises a CDR1 of SEQ ID NO: 261, a CDR2 of SEQ ID NO: 285 and a CDR3 of SEQ ID NO: 294 and a heavy chain variable domain comprises a CDR1 of SEQ ID NO: 332, a CDR2 of SEQ ID NO: 361 and a CDR3 of SEQ ID NO: 386; (qq) an anti-BAFF antibody molecule where the light chain variable domain comprises a CDR1 of SEQ ID NO: 272, a CDR2 of SEQ ID NO: 289 and a CDR3 of SEQ ID NO: 307 and a heavy chain variable domain comprises a CDR1 of SEQ ID NO: 331, a CDR2 of SEQ ID NO: 362 and a CDR3 of SEQ ID NO: 385; (rr) an anti-BAFF antibody molecule where the light chain variable domain comprises a CDR1 of SEQ ID NO: 266, a CDR2 of SEQ ID NO: 287 and a CDR3 of SEQ ID NO: 306 and a heavy chain variable domain comprises a CDR1 of SEQ ID NO: 326, a CDR2 of SEQ ID NO: 355 and a CDR3 of SEQ ID NO: 383; (ss) an anti-BAFF antibody molecule where the light chain variable domain comprises a CDR1 of SEQ ID NO: 270, a CDR2 of SEQ ID NO: 276 and a CDR3 of SEQ ID NO: 306 and a heavy chain variable domain comprises a CDR1 of SEQ ID NO: 330, a CDR2 of SEQ ID NO: 359 and a CDR3 of SEQ ID NO: 285; (tt) an anti-BAFF antibody molecule where the light chain variable domain comprises a CDR1 of SEQ ID NO: 270, a CDR2 of SEQ ID NO: 276 and a CDR3 of SEQ ID NO: 306 and a heavy chain variable domain comprises a CDR1 of SEQ ID NO: 392, a CDR2 of SEQ ID NO: 363 and a CDR3 of SEQ ID NO: 387; (uu) an anti-BAFF antibody molecule where the light chain variable domain comprises a CDR1 of SEQ ID NO: 273, a CDR2 of SEQ ID NO: 276 and a CDR3 of SEQ ID NO: 308 and a heavy chain variable domain comprises a CDR1 of SEQ ID NO: 333, a CDR2 of SEQ ID NO: 364 and a CDR3 of SEQ ID NO: 388; (vv) an anti-BAFF antibody molecule where the light chain variable domain comprises a CDR1 of SEQ ID NO: 274, a CDR2 of SEQ ID NO: 290 and a CDR3 of SEQ ID NO: 309 and a heavy chain variable domain comprises a CDR1 of SEQ ID NO: 334, a CDR2 of SEQ ID NO: 365 and a CDR3 of SEQ ID NO: 389; (ww) an anti-BAFF antibody molecule where the light chain variable domain comprises a CDR1 of SEQ ID NO: 275, a CDR2 of SEQ ID NO: 291 and a CDR3 of SEQ ID NO: 310 and a heavy chain variable domain comprises a CDR1 of SEQ ID NO: 335, a CDR2 of SEQ ID NO: 366 and a CDR3 of SEQ ID NO: 390; and (xx) an anti-BAFF antibody molecule where the light chain variable domain comprises a CDR1 of SEQ ID NO: 258, a CDR2 of SEQ ID NO: 292 and a CDR3 of SEQ ID NO: 311 and a heavy chain variable domain comprises a CDR1 of SEQ ID NO: 336, a CDR2 of SEQ ID NO: 367 and a CDR3 of SEQ ID NO: 391.

In another embodiment of the present invention, the anti-BAFF antibody molecule comprises a light chain variable region of any one of SEQ ID NOS: 82-97, and a heavy chain variable region of any one of SEQ ID NOS: 100-115. In a preferred embodiment, the present invention provides monoclonal antibodies with the combinations of light chain variable and heavy chain variable regions of SEQ ID NO: 82/101, 88/101, 94/112 or 93/114. Such variable regions can be combined with human constant regions.

In an additional embodiment of the present invention, the anti-BAFF antibody molecule neutralizes all three forms of human BAFF, the forms of which include membrane bound (mbBAFF), soluble trimeric BAFF, and soluble 60-mer BAFF. In particular, the anti-BAFF antibody molecules of the present invention neutralize human soluble 60-mer BAFF. Furthermore, the anti-BAFF antibody molecules of the present invention neutralize human soluble trimeric BAFF. Finally, the anti-BAFF antibody molecules of the present invention neutralize human membrane-bound BAFF.

In a further embodiment, the present invention relates to an anti-BAFF antibody molecule comprising a humanized light chain variable domain comprising the CDRs of SEQ ID NO: 76, 16 and 17 and framework regions having an amino acid sequence at least 90% identical, at least 93% identical or at least 95% identical to the amino acid sequence of the framework regions of the variable domain light chain amino acid sequence of SEQ ID NO: 82 and a humanized heavy chain variable domain comprising the CDRs of SEQ ID NO: 37, 38 and 39 and framework regions having an amino acid sequence at least 90% identical, at least 93% identical or at least 95% identical to the amino acid sequence of the framework regions of the variable domain heavy chain amino acid sequence of SEQ ID NO: 101. In one embodiment, the anti-BAFF antibody molecule is a humanized monoclonal antibody.

In a further embodiment, the present invention relates to an anti-BAFF antibody molecule comprising a humanized light chain variable domain comprising the CDRs of SEQ ID NO: 15, 16 and 17 and framework regions having an amino acid sequence at least 90% identical, at least 93% identical or at least 95% identical to the amino acid sequence of the framework regions of the variable domain light chain amino acid sequence of SEQ ID NO: 88 and a humanized heavy chain variable domain comprising the CDRs of SEQ ID NO: 37, 38 and 39 and framework regions having an amino acid sequence at least 90% identical, at least 93% identical or at least 95% identical to the amino acid sequence of the framework regions of the variable domain heavy chain amino acid sequence of SEQ ID NO: 101. In one embodiment, the anti-BAFF antibody molecule is a humanized monoclonal antibody.

In a further embodiment, the present invention relates to an anti-BAFF antibody molecule comprising a humanized light chain variable domain comprising the CDRs of SEQ ID NO:5, 8 and 9 and framework regions having an amino acid sequence at least 90% identical, at least 93% identical or at least 95% identical to the amino acid sequence of the framework regions of the variable domain light chain amino acid sequence of SEQ ID NO: 94 and a humanized heavy chain variable domain comprising the CDRs of SEQ ID NO: 81, 29 and 30 and framework regions having an amino acid sequence at least 90% identical, at least 93% identical or at least 95% identical to the amino acid sequence of the framework regions of the variable domain heavy chain amino acid sequence of SEQ ID NO: 112. In one embodiment, the anti-BAFF antibody molecule is a humanized monoclonal antibody.

In a further embodiment, the present invention relates to an anti-BAFF antibody molecule comprising a humanized light chain variable domain comprising the CDRs of SEQ ID NO: 5, 8 and 9 and framework regions having an amino acid sequence at least 90% identical, at least 93% identical or at least 95% identical to the amino acid sequence of the framework regions of the variable domain light chain amino acid sequence of SEQ ID NO: 93 and a humanized heavy chain variable domain comprising the CDRs of SEQ ID NO: 81, 29 and 30 and framework regions having an amino acid sequence at least 90% identical, at least 93% identical or at least 95% identical to the amino acid sequence of the framework regions of the variable domain heavy chain amino acid sequence of SEQ ID NO: 114. In one embodiment, the anti-BAFF antibody molecule is a humanized monoclonal antibody.

In specific embodiments, it is contemplated that chimeric antibodies with switched CDR regions (i.e., for example switching one or two CDRs of one of the mouse antibodies or humanized antibody derived therefrom with the analogous CDR from another mouse antibody or humanized antibody derived therefrom) between these exemplary immunoglobulins may yield useful antibodies.

In certain embodiments, the humanized anti-BAFF antibody is an antibody fragment. Various antibody fragments have been generally discussed above and there are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')$_2$ fragments (see, e.g., Carter et al., 1992, Bio/Technology 10:163-167). By another approach, F(ab')$_2$ fragments can be isolated directly from recombinant host cell culture. Other techniques for the production of antibody fragments will be apparent to the skilled practitioner. Accordingly, in one aspect, the present invention provides antibody fragments comprising the CDRs described herein, in particular one of the combinations of L-CDR1, L-CDR2, L-CDR3, H-CDR1, H-CDR2 and H-CDR3 described herein. In a further aspect, the present invention provides antibody fragments comprising the variable regions described herein, for example one of the combinations of light chain variable regions and heavy chain variable regions described herein.

In some embodiments, the antibody or antibody fragment includes a constant region that mediates effector function. The constant region can provide antibody-dependent cellular cytotoxicity (ADCC), antibody-dependent cellular phagocytosis (ADCP) and/or complement-dependent cytotoxicity (CDC) responses against a BAFF expressing target cell. The effector domain(s) can be, for example, an Fc region of an Ig molecule.

The effector domain of an antibody can be from any suitable vertebrate animal species and isotypes. The isotypes from different animal species differ in the abilities to mediate effector functions. For example, the ability of human immunoglobulin to mediate CDC and ADCC/ADCP is generally in the order of IgM≈IgG$_1$≈IgG$_3$>IgG$_2$>IgG$_4$ and IgG$_1$≈IgG$_3$>IgG$_2$/IgM/IgG$_4$, respectively. Murine immunoglobulins mediate CDC and ADCC/ADCP generally in the order of murine IgM≈IgG$_3$>>IgG$_{2b}$>IgG$_{2a}$>>IgG$_1$ and IgG$_{2b}$>IgG$_{2a}$>IgG$_1$>>IgG$_3$, respectively. In another example, murine IgG$_{2a}$ mediates ADCC while both murine IgG$_{2a}$ and IgM mediate CDC.

Antibody Modifications

The humanized anti-BAFF antibodies and agents can include modifications of the humanized anti-BAFF antibody or antigen-binding fragment thereof. For example, it may be desirable to modify the antibody with respect to effector function, so as to enhance the effectiveness of the antibody in treating cancer. One such modification is the introduction of cysteine residue(s) into the Fc region, thereby allowing interchain disulfide bond formation in this region. The homodimeric antibody thus generated can have improved internalization capability and/or increased complement-mediated cell killing and/or antibody-dependent cellular cytotoxicity (ADCC). See, for example, Caron et al., 1992, J. Exp Med. 176:1191-1195; and Shopes, 1992, J. Immunol. 148:2918-2922. Homodimeric antibodies having enhanced anti-tumor activity can also be prepared using heterobifunctional cross-linkers as described in Wolff et al., 1993, Cancer Research 53: 2560-2565. Alternatively, an antibody can be engineered to contain dual Fc regions, enhancing complement lysis and ADCC capabilities of the antibody. See Stevenson et al., 1989, Anti-Cancer Drug Design 3: 219-230.

Antibodies with improved ability to support ADCC have been generated by modifying the glycosylation pattern of their Fc region. This is possible since antibody glycosylation at the asparagine residue, N297, in the $C_{H2}$ domain is involved in the interaction between IgG and Fcγ receptors prerequisite to ADCC. Host cell lines have been engineered to express antibodies with altered glycosylation, such as increased bisecting N-acetylglucosamine or reduced fucose. Fucose reduction provides greater enhancement to ADCC activity than does increasing the presence of bisecting N-acetylglucosamine. Moreover, enhancement of ADCC by low fucose antibodies is independent of the FcγRIIIa V/F polymorphism.

Modifying the amino acid sequence of the Fc region of antibodies is an alternative to glycosylation engineering to enhance ADCC. The binding site on human IgG$_1$ for Fcγ receptors has been determined by extensive mutational analysis. This led to the generation of humanized IgG$_1$ antibodies with Fc mutations that increase the binding affinity for FcγRIIIa and enhance ADCC in vitro. Additionally, Fc variants have been obtained with many different permutations of binding properties, e.g., improved binding to specific FcγR receptors with unchanged or diminished binding to other FcγR receptors.

Another aspect includes immunoconjugates comprising the humanized antibody or fragments thereof conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used to form useful immunoconjugates include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, the tricothecenes, and the like. A variety of radionuclides are available for the production of radioconjugated humanized anti-BAFF antibodies. Examples include $^{212}$Bi, $^{131}$I, $^{131}$In, $^{90}$Y and $^{186}$Re.

Conjugates of the humanized anti-BAFF antibody and cytotoxic or chemotherapeutic agent can be made by known methods, using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., 1987, Science 238:1098. Carbon-14-labeled 1-isothiocyanatobenzyl-3-methyldiethylene triaminepentaacetic acid (MX-DTPA) is an exemplary chelating agent for conjugation of radionucleotide to the antibody. Conjugates also can be formed with a cleavable linker.

The humanized anti-BAFF antibodies disclosed herein can also be formulated as immunoliposomes. Liposomes containing the antibody are prepared by methods known in the art, such as described in Epstein et al., 1985, Proc. Natl. Acad. Sci. USA 82:3688; Hwang et al., 1980, Proc. Natl. Acad. Sci. USA 77:4030; and U.S. Pat. Nos. 4,485,045 and 4,544,545. Liposomes having enhanced circulation time are disclosed, for example, in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody disclosed herein can be conjugated to the liposomes as described in Martin et al., 1982, J. Biol. Chem. 257:286-288 via a disulfide interchange reaction. A chemotherapeutic agent (such as doxorubicin) is optionally contained within the liposome. See, e.g., Gabizon et al., 1989, J. National Cancer Inst. 81(19):1484.

The antibodies described and disclosed herein can also be used in ADEPT (Antibody-Directed Enzyme Prodrug Therapy) procedures by conjugating the antibody to a prodrug-activating enzyme that converts a prodrug (e.g., a peptidyl chemotherapeutic agent), to an active anti-cancer drug. See, for example, WO 81/01145, WO 88/07378, and U.S. Pat. No. 4,975,278. The enzyme component of the immunoconjugate useful for ADEPT is an enzyme capable of acting on a prodrug in such a way so as to convert it into its more active, cytotoxic form. Specific enzymes that are useful in ADEPT include, but are not limited to, alkaline phosphatase for converting phosphate-containing prodrugs into free drugs; arylsulfatase for converting sulfate-containing prodrugs into free drugs; cytosine deaminase for converting non-toxic 5-fluorocytosine into the anti-cancer drug, 5-fluorouracil; proteases, such as serratia protease, thermolysin, subtilisin, carboxypeptidases, and cathepsins (such as cathepsins B and L), for converting peptide-containing prodrugs into free drugs; D-alanylcarboxypeptidases, for converting prodrugs containing D-amino acid substituents;

carbohydrate-cleaving enzymes such as β-galactosidase and neuraminidase for converting glycosylated prodrugs into free drugs; β-lactamase for converting drugs derivatized with β-lactams into free drugs; and penicillin amidases, such as penicillin V amidase or penicillin G amidase, for converting drugs derivatized at their amine nitrogens with phenoxyacetyl or phenylacetyl groups, respectively, into free drugs. Alternatively, antibodies having enzymatic activity ("abzymes") can be used to convert the prodrugs into free active drugs (see, for example, Massey, 1987, Nature 328: 457-458). Antibody-abzyme conjugates can be prepared by known methods for delivery of the abzyme to a tumor cell population, for example, by covalently binding the enzyme to the humanized anti-BAFF antibody/heterobifunctional crosslinking reagents discussed above. Alternatively, fusion proteins comprising at least the antigen binding region of an antibody disclosed herein linked to at least a functionally active portion of an enzyme as described above can be constructed using recombinant DNA techniques (see, e.g., Neuberger et al., 1984, Nature 312:604-608).

In certain embodiments, it may be desirable to use a humanized anti-BAFF antibody fragment, rather than an intact antibody, to increase tissue penetration, for example. It may be desirable to modify the antibody fragment in order to increase its serum half-life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, covalent modifications of the humanized anti-BAFF antibody are also included. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670, 417, 4,791,192 and 4,179,337.

Humanization and Amino Acid Sequence Variants

Amino acid sequence variants of the anti-BAFF antibody can be prepared by introducing appropriate nucleotide changes into the anti-BAFF antibody DNA, or by peptide synthesis. Such variants include, for example, deletions from, and/or insertions into and/or substitutions of, residues within the amino acid sequences of the anti-BAFF antibodies of the examples herein. Any combination of deletions, insertions, and substitutions is made to arrive at the final construct, provided that the final construct possesses the desired characteristics. The amino acid changes also may alter post-translational processes of the humanized or variant anti-BAFF antibody, such as changing the number or position of glycosylation sites.

A useful method for identification of certain residues or regions of the anti-BAFF antibody that are preferred locations for mutagenesis is called "alanine scanning mutagenesis," as described by Cunningham and Wells (Science, 244:1081-1085 (1989)). Here, a residue or group of target residues are identified (e.g., charged residues such as arg, asp, his, lys, and glu) and replaced by a neutral or negatively charged amino acid (typically alanine) to affect the interaction of the amino acids with BAFF antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-BAFF antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-BAFF antibody fused to an epitope tag. Other insertional variants of the anti-BAFF antibody molecule include a fusion to the N- or C-terminus of the anti-BAFF antibody of an enzyme or a polypeptide which increases the serum half-life of the antibody.

Another type of variant is an amino acid substitution variant. These variants have at least one amino acid residue in the anti-BAFF antibody molecule removed and a different residue inserted in its place. The sites of greatest interest for substitutional mutagenesis include the hypervariable regions, but FR alterations are also contemplated. Conservative substitutions are shown below under the heading of "preferred substitutions". If such substitutions result in a change in biological activity, then more substantial changes, denominated "exemplary substitutions", or as further described below in reference to amino acid classes, may be introduced and the products screened.

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |

| Original Residue | Exemplary Substitutions | Preferred Substitutions |
|---|---|---|
| Pro (P) | ala | ala |
| Ser (S) | thr | thr |
| Thr (T) | ser | ser |
| Trp (W) | tyr; phe | tyr |
| Tyr (Y) | phe; trp; thr; ser | phe |
| Val (V) | leu; ile; met; phe ala; norleucine; | leu |

In protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant anti-BAFF antibody also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody to improve its stability (particularly where the antibody is an antibody fragment such as an Fv fragment).

A type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human BAFF. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By "altering" is meant deleting one or more carbohydrate moieties found in the antibody, and/or adding one or more glycosylation sites that are not present in the antibody. In some embodiments, it may be desirable to modify the antibodies of the invention to add glycosylations sites. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Thus, in order to glycosylate a given protein, e.g., an antibody, the amino acid sequence of the protein is engineered to contain one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-BAFF antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-BAFF antibody.

Polynucleotides, Vectors, Host Cells, and Recombinant Methods

Other embodiments encompass isolated polynucleotides that comprise a sequence encoding a humanized anti-BAFF antibody, vectors, and host cells comprising the polynucleotides, and recombinant techniques for production of the humanized antibody. The isolated polynucleotides can encode any desired form of the anti-BAFF antibody including, for example, full length monoclonal antibodies, Fab, Fab', F(ab')$_2$, and Fv fragments, diabodies, linear antibodies, single-chain antibody molecules, and multispecific antibodies formed from antibody fragments.

In one embodiment, the present invention provides isolated polynucleotides comprising combinations of light chain variable and heavy chain variable regions of SEQ ID NO: 40/58, 42/60, 44/62, 46/64, 48/66, 50/68, 52/70, 54/72, 56/74, 118/182, 120/184, 122/186, 124/188, 126/190, 128/192, 130/194, 132/196, 134/198, 136/200, 138/202, 140/204, 142/206, 144/208, 146/210, 148/212, 150/214, 152/216, 154/218, 156/220, 158/222, 160/224, 162/226, 164/228, 166/230, 168/232, 170/236, 172/237, 172/239, 174/241, 176/243, 178/245 or 180/247.

Some embodiments include isolated polynucleotides comprising sequences that encode the light chain variable region of an antibody or antibody fragment having the amino acid sequence of any of SEQ ID NOs: 82, 83, 84, 85, 86, 87, 88, 89, 90, 91, 92, 93, 94, 95, 96, or 97. Exemplary polynucleotide sequences encoding such amino acid sequences are SEQ ID NOs: 234, 392, 393 and 394. Other embodiments include isolated polynucleotides comprising sequences that encode the heavy chain variable region of an antibody or antibody fragment having the amino acid sequence of any of the SEQ ID NOs: 100, 101, 102, 103, 104, 105, 106, 107, 108, 109, 110, 111, 112, 113, 114 or 115. Exemplary polynucleotide sequences encoding such amino acid sequences are SEQ ID NOs: 395, 396 and 397.

In one embodiment, the isolated polynucleotide comprises a light chain variable region is SEQ ID NO: 234 and the heavy chain variable region is SEQ ID NO: 396, the light chain variable region is SEQ ID NO: 393 and the heavy chain variable region is SEQ ID NO: 396, the light chain variable region is SEQ ID NO: 395 and the heavy chain variable region is SEQ ID NO: 397 or the light chain variable region is SEQ ID NO: 394 and the heavy chain variable region is SEQ ID NO: 398.

The polynucleotide(s) that comprise a sequence encoding a humanized anti-BAFF antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The humanized anti-BAFF antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the humanized anti-BAFF antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-BAFF antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-BAFF antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-BAFF antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-BAFF antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-BAFF antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Humanized anti-BAFF antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the Rous sarcoma virus long terminal repeat can be used as the promoter.

Another useful element that can be used in a recombinant expression vector is an enhancer sequence, which is used to increase the transcription of a DNA encoding a humanized anti-BAFF antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the humanized anti-BAFF antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-BAFF antibody. One useful transcription termination component is the bovine growth hormone polyadenylation region. See WO94/11026 and the expression vector disclosed therein. In some embodiments, humanized anti-BAFF antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for humanized anti-BAFFantibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated humanized anti-BAFF antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa*

*californica* NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

In another aspect, expression of humanized anti-BAFF is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/−DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for humanized anti-BAFF antibody production and cultured in conventional nutrient media modified as appropriate for inducing promoters, selecting transformants, or amplifying the genes encoding the desired sequences.

The host cells used to produce a humanized anti-BAFF antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657,866, 4,927,762, 4,560,655, 5,122, 469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an antibody or antibody fragment of the present invention. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-BAFF polypeptide (e.g., a heavy chain or light chain variable region), or its complement. Hybridizing nucleic acids of the type described herein can be used, for example, as a cloning probe, a primer, e.g., a PCR primer, or a diagnostic probe.

Some embodiments include isolated polynucleotides including sequences that encode an antibody or antibody fragment having the amino acid sequence of any one of 82, 83, 84, 85, 86, 87, 88, 89, 90, 91, 92, 93, 94, 95, 96, 97, 100, 101, 102, 103, 104, 105, 106, 107, 108, 109, 110, 111, 112, 113, 114 or 115 and that is at least 80%, at least 90%, at least 95%, at least 98%, or at least 99% identical to the polynucleotide sequences of SEQ ID NO: 234, 393, 394, 395, 396, 397 or 398.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the BAFF protein (or fragment thereof) to be purified, and thereafter the support is washed with a suitable solvent that will remove substantially all the material in the sample except the BAFF protein, which is bound to the immobilized antibody. Finally, the support is washed with another suitable solvent that will release the BAFF protein from the antibody.

Anti-BAFF antibodies, for example humanized anti-BAFF antibodies, are also useful in diagnostic assays to detect and/or quantify BAFF protein, for example, detecting BAFF expression in specific cells, tissues, or serum. The anti-BAFF antibodies can be used diagnostically to, for example, monitor the development or progression of a disease as part of a clinical testing procedure to, e.g., determine the efficacy of a given treatment and/or prevention regimen. Detection can be facilitated by coupling the anti-BAFF antibody. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention.

The anti-BAFF antibodies can be used in methods for diagnosing a BAFF-associated disorder (e.g., a disorder characterized by abnormal expression of BAFF) or to determine if a subject has an increased risk of developing a BAFF-associated disorder. Such methods include contacting a biological sample from a subject with a BAFF antibody and detecting binding of the antibody to BAFF. By "biological sample" is intended any biological sample obtained from an individual, cell line, tissue culture, or other source of cells potentially expressing BAFF. Methods for obtaining tissue biopsies and body fluids from mammals are well known in the art.

In some embodiments, the method can further comprise comparing the level of BAFF in a patient sample to a control sample (e.g., a subject that does not have a BAFF-associated disorder) to determine if the patient has a BAFF-associated disorder or is at risk of developing a BAFF-associated disorder.

It will be advantageous in some embodiments, for example, for diagnostic purposes to label the antibody with a detectable moiety. Numerous detectable labels are available, including radioisotopes, fluorescent labels, enzyme substrate labels and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Exemplary radioisotopes labels include $^{35}S$, $^{14}C$, $^{125}I$, $^{3}H$, and $^{131}I$. The antibody can be labeled with the radioisotope, using the techniques described in, for example, Current Protocols in Immunology, Volumes 1 and 2, 1991, Coligen et al., Ed. Wiley-Interscience, New York, N.Y., Pubs. Radioactivity can be measured, for example, by scintillation counting.

Exemplary fluorescent labels include labels derived from rare earth chelates (europium chelates) or fluorescein and its derivatives, rhodamine and its derivatives, dansyl, Lissamine, phycoerythrin, and Texas Red are available. The fluorescent labels can be conjugated to the antibody via known techniques, such as those disclosed in Current Protocols in Immunology, for example. Fluorescence can be quantified using a fluorimeter.

There are various well-characterized enzyme-substrate labels known in the art (see, e.g., U.S. Pat. No. 4,275,149). The enzyme generally catalyzes a chemical alteration of the chromogenic substrate that can be measured using various techniques. For example, alteration may be a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor.

Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (such as glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N.Y., 73: 147-166.

Examples of enzyme-substrate combinations include, for example: Horseradish peroxidase (HRPO) with hydrogen peroxidase as a substrate, wherein the hydrogen peroxidase oxidizes a dye precursor such as orthophenylene diamine (OPD) or 3,3',5,5'-tetramethyl benzidine hydrochloride (TMB); alkaline phosphatase (AP) with para-Nitrophenyl phosphate as chromogenic substrate; and β-D-galactosidase (β-D-Gal) with a chromogenic substrate such as p-nitrophenyl-β-D-galactosidase or fluorogenic substrate 4-methyl-umbelliferyl-β-D-galactosidase.

Numerous other enzyme-substrate combinations are available to those skilled in the art. For a general review of these, see U.S. Pat. No. 4,275,149 and U.S. Pat. No. 4,318,980.

In another embodiment, the humanized anti-BAFF antibody is used unlabeled and detected with a labeled antibody that binds the humanized anti-BAFF antibody.

The antibodies described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

The anti-BAFF antibody or antigen binding fragment thereof can be used to inhibit the binding of BAFF to one of the BAFF receptors. Such methods comprise administering an anti-BAFF antibody or antigen binding fragment thereof to a cell (e.g., a mammalian cell) or cellular environment, whereby signaling mediated by the BAFF receptor is inhibited. These methods can be performed in vitro or in vivo. By "cellular environment" is intended the tissue, medium, or extracellular matrix surrounding a cell. The anti-BAFF antibody or antigen binding fragment thereof is administered to the cellular environment of a cell in such a manner that the antibody or fragment is capable of binding to BAFF molecules outside of and surrounding the cell, therefore, preventing the binding of BAFF to its receptor.

Diagnostic kits

An anti-BAFF antibody can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Therapeutic Uses

In another embodiment, a humanized anti-BAFF antibody disclosed herein is useful in the treatment of various disorders associated with the expression of BAFF as described herein. Methods for treating a BAFF associated disorder comprise administering a therapeutically effective amount of a humanized anti-BAFF antibody to a subject in need thereof.

The humanized anti-BAFF antibody or agent is administered by any suitable means, including parenteral, subcutaneous, intraperitoneal, intrapulmonary, and intranasal, and, if desired for local immunosuppressive treatment, intralesional administration (including perfusing or otherwise contacting the graft with the antibody before transplantation). The humanized anti-BAFF antibody or agent can be administered, for example, as an infusion or as a bolus. Parenteral infusions include intramuscular, intravenous, intraarterial, intraperitoneal, or subcutaneous administration. In addition, the humanized anti-BAFF antibody is suitably administered by pulse infusion, particularly with declining doses of the antibody. In one aspect, the dosing is given by injections, most preferably intravenous or subcutaneous injections, depending in part on whether the administration is brief or chronic.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 20 mg/kg (e.g., 0.1-15 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is that disclosed in WO 94/04188.

The term "suppression" is used herein in the same context as "amelioration" and "alleviation" to mean a lessening of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the disorder associated with BAFF expression.

The antibody need not be, but is optionally, formulated with one or more agents currently used to prevent or treat the disorder in question. The effective amount of such other agents depends on the amount of humanized anti-BAFF antibody present in the formulation, the type of disorder or treatment, and other factors discussed above. These are generally used in the same dosages and with administration routes as used hereinbefore or about from 1 to 99% of the heretofore employed dosages.

BAFF-Associated Disorders

The anti-BAFF antibodies or agents are useful for treating or preventing an immunological disorder characterized by abnormal expression of BAFF. The anti-BAFF antibodies or antigen binding fragments thereof also find use in the treatment or prevention of respiratory disorders, metabolic disorders, for example diabetes mellitus, and certain cancers. Treatment or prevention of the immunological disorder, respiratory disorder, metabolic disorder or cancer, according to the methods described herein, is achieved by administering to a subject in need of such treatment or prevention an effective amount of the anti-BAFF antibody or agent, whereby the antibody decreases the activity of BAFF associated with the disease state.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., Fundamental Immunology (William E. Paul ed., Raven Press, N.Y., 3rd ed. 1993).) Immunological diseases include inflammatory diseases and autoimmune diseases.

Specific examples of such immunological diseases include the following: rheumatoid arthritis, autoimmune demyelinative diseases (e.g., multiple sclerosis, allergic encephalomyelitis), endocrine opthalmopathy, uveoretinitis, systemic lupus erythematosus, myasthenia gravis, Grave's disease, glomerulonephritis, autoimmune hepatological disorder, inflammatory bowel disease (e.g., Crohn's disease or ulcerative colitis), anaphylaxis, allergic reaction, Sjogren's syndrome, type I diabetes mellitus, primary biliary cirrhosis, Wegener's granulomatosis, fibromyalgia, polymyositis, dermatomyositis, inflammatory myositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, psoriatic arthritis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, anti-neutrophil cytoplasmic antibodies (ANCA)-associated vasculitis, transplantation rejection, cardiomyopathy, Eaton-Lambert syndrome, relapsing polychondritis, cryoglobulinemia, Waldenstrom's macroglobulemia, Evan's syndrome, acute respiratory distress syndrome, pulmonary inflammation, osteoporosis, delayed type hypersensitivity and autoimmune gonadal failure.

In another aspect, the anti-BAFF antibodies and agents as described herein are also useful for treating cancers, in which BAFF is abnormally expressed.

BAFF-expressing cancers that can be treated by the methods described herein include, for example, leukemia, such as acute leukemia, acute lymphocytic leukemia, acute myelocytic leukemia (e.g., myeloblastic, promyelocytic, myelomonocytic, monocytic, or erythroleukemia), chronic leukemia, chronic myelocytic (granulocytic) leukemia, or chronic lymphocytic leukemia; Polycythemia vera; Lymphoma (e.g., Hodgkin's disease or Non-Hodgkin's disease); multiple myeloma, Waldenstrom's macroglobulinemia; heavy chain disease; solid tumors such sarcomas and carcinomas (e.g., fibrosarcoma, myxosarcoma, liposarcoma, chondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, or esophageal carcinoma).

Pharmaceutical Compositions and Administration Thereof

A composition comprising a BAFF binding agent (e.g., an anti-BAFF antibody) can be administered to a subject having or at risk of having an immunological disorder, respiratory disorder or a cancer. The invention further provides for the use of a BAFF binding agent (e.g., an anti-BAFF antibody) in the manufacture of a medicament for prevention or treatment of a cancer, respiratory disorder or immunological disorder. The term "subject" as used herein means any mammalian patient to which a BAFF binding agent can be administered, including, e.g., humans and non-human mammals, such as primates, rodents, and dogs. Subjects specifically intended for treatment using the methods described herein include humans. The antibodies or agents can be administered either alone or in combination with other compositions in the prevention or treatment of the immunological disorder, respiratory disorder or cancer. Such compositions which can be administered in combination with the antibodies or agents include methotrexate (MTX) and immunomodulators, e.g. antibodies or small molecules.

Examples of antibodies for use in such pharmaceutical compositions are those that comprise a humanized antibody or antibody fragment having the light chain variable region amino acid sequence of any of SEQ ID NO: 82, 83, 84, 85, 86, 87, 88, 89, 90, 91, 92, 93, 94, 95, 96, or 97. Examples of antibodies for use in such pharmaceutical compositions are also those that comprise a humanized antibody or antibody fragment having the heavy chain variable region amino acid sequence of any of SEQ ID NO: 100, 101, 102, 103, 104, 105, 106, 107, 108, 109, 110, 111, 112, 113, 114 or 115.

Various delivery systems are known and can be used to administer the BAFF binding agent. Methods of introduction include but are not limited to intradermal, intramuscular, intraperitoneal, intravenous, subcutaneous, intranasal, epidural, and oral routes. The BAFF binding agent can be administered, for example by infusion, bolus or injection, and can be administered together with other biologically active agents such as chemotherapeutic agents. Administration can be systemic or local. In preferred embodiments, the administration is by subcutaneous injection. Formulations for such injections may be prepared in for example prefilled syringes that may be administered once every other week.

In specific embodiments, the BAFF binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-BAFF antibody or agent does not absorb are used.

In other embodiments, the anti-BAFF antibody or agent is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

An BAFF binding agent (e.g., an anti-BAFF antibody) can be administered as pharmaceutical compositions comprising a therapeutically effective amount of the binding agent and one or more pharmaceutically compatible ingredients.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a BAFF binding agent (e.g., an anti-BAFF antibody) in lyophilized form and (b) a second container containing a pharmaceutically acceptable diluent (e.g., sterile water) for injection. The pharmaceutically acceptable diluent can be used for reconstitution or dilution of the lyophilized anti-BAFF antibody or agent. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the BAFF binding agent (e.g., anti-BAFF antibody) that is effective in the treatment or prevention of an immunological disorder or cancer can be determined by standard clinical techniques. In addition, in vitro assays may optionally be employed to help identify optimal dosage ranges. The precise dose to be employed in the formulation will also depend on the route of administration, and the stage of immunological disorder or cancer, and should be decided according to the judgment of the practitioner and each patient's circumstances. Effective doses may be extrapolated from dose-response curves derived from in vitro or animal model test systems.

Generally, the dosage of an anti-BAFF antibody or BAFF binding agent administered to a patient with an immunological disorder is typically about 0.1 mg/kg to about 100 mg/kg of the subject's body weight. The dosage administered to a subject is about 0.1 mg/kg to about 50 mg/kg, about 1 mg/kg to about 30 mg/kg, about 1 mg/kg to about 20 mg/kg, about 1 mg/kg to about 15 mg/kg, or about 1 mg/kg to about 10 mg/kg of the subject's body weight.

Exemplary doses include, but are not limited to, from 1 mg/kg to 100 mg/kg. In some embodiments, a dose is about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg or about 16 mg/kg. The dose can be administered, for example, daily, once per week (weekly), twice per week, thrice per week, four times per week, five times per week, six times per week, biweekly or monthly, every two months, or every three months. In specific embodiments, the dose is about 0.5 mg/kg/week, about 1 mg/kg/week, about 2 mg/kg/week, about 3 mg/kg/week, about 4 mg/kg/week, about 5 mg/kg/week, about 6 mg/kg/week, about 7 mg/kg/week, about 8 mg/kg/week, about 9 mg/kg/week, about 10 mg/kg/week, about 11 mg/kg/week, about 12 mg/kg/week, about 13 mg/kg/week, about 14 mg/kg/week, about 15 mg/kg/week or about 16 mg/kg/week. In some embodiments, the dose ranges from about 1 mg/kg/week to about 15 mg/kg/week.

In some embodiments, the pharmaceutical compositions comprising the BAFF binding agent can further comprise a therapeutic agent, either conjugated or unconjugated to the binding agent. The anti-BAFF antibody or BAFF binding agent can be co-administered in combination with one or more therapeutic agents for the treatment or prevention of immunological disorders or cancers.

Such combination therapy administration can have an additive or synergistic effect on disease parameters (e.g., severity of a symptom, the number of symptoms, or frequency of relapse). With respect to therapeutic regimens for combinatorial administration, in a specific embodiment, an anti-BAFF antibody or BAFF binding agent is administered concurrently with a therapeutic agent. In another specific embodiment, the therapeutic agent is administered prior or subsequent to administration of the anti-BAFF antibody or BAFF binding agent, by at least an hour and up to several months, for example at least an hour, five hours, 12 hours, a day, a week, a month, or three months, prior or subsequent to administration of the anti-BAFF antibody or BAFF binding agent.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the humanized anti-BAFF antibody. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

Example 1

Generation of Mouse Antibodies

The lead mouse antibodies of the present invention were derived from mouse hybridomas. Various strains of mice were immunized multiple times for up to 6 months. Immunization of mice was carried out using suitable techniques contained in the art. For example, to obtain a specific immunogenic response, various versions of recombinant soluble human BAFF protein (amino acids 72-285) were used, including human BAFF fusion protein antigen immunizations. In addition, some mice were immunized with a mouse cell line transfected to express human BAFF on the cell surface. Preparation of immunogenic antigens including adjuvants and immunization routes can also be performed using suitable techniques known in the art. Serum binding titers of sufficient requirements were met, and mouse lymphocytes were fused to mouse myeloma cells using various methods of the established art. Screening of hybridomas was performed to obtained high affinity, and specific antibodies.

Example 2

Generation of Humanized Anti-BAFF Fabs

Mouse lead antibodies 13J018 and 235F5 were converted to a chimeric antibody consisting of the mouse variable domains of 1A4 and 5B9, respectively, and a human constant IgG1KO domain. Mouse antibodies 1A4 and 5B9 are shown in Tables 3 and 4 above. The IgG1KO (knock out) has two replacement mutations (Leu234Ala and Leu235Ala) that eliminate ADCC and CDC activity by reducing effector functions such as FcγR and complement binding. The variable domains of the mouse and chimeric antibodies are identical. Chimeric antibodies are generated to confirm the function of the antibody and to ensure the correct sequences have been obtained. Once correct sequences were identified, the mouse variable domains were used to generate chimeric Fab wherein mouse Vk and Vh residues were in frame with human Ck and Ch1 residues respectively. These chimeric Fabs were used as benchmark molecules to screen the humanized Fabs during the screening process. Next, the mouse variable regions (Vk and Vh) were then humanized through a design and screening process. A library was made where human and mouse residues were varied in such a way that in any given position there could be either a human or mouse residue. Such a library was made for those amino acids that were different between human germline and mouse antibody. Only the clones that retain the function of the parent mouse antibody were selected using the chimeric Fab. Representative humanized variable regions for antibodies 1A4(13 J018) and 5B9(235F5) are shown in Tables 5 and 6.

Example 3

Generation of Recombinant Soluble Trimeric Human BAFF Protein

Human BAFF(72-285) with an N-terminal His-tag (SEQ ID: 398) was expressed transiently in HEK293-6E cells through standard lipid-based transfection. 96-hours post transfection, cells were pelleted and expression of protein in the supernatant was verified via an anti 6×His western blot ("6×His" disclosed as SEQ ID NO: 407). Supernatant purification was completed using Ni-Sepharose Affinity Chromatography. Purified His-BAFF was cleaved with His-tagged furin protease to produce C-terminal fragment (amino acids 134-285. SEQ ID: 399). To remove furin and cleaved N-terminal fragment species from the sample, the total protein sample was passed through an Ni/NTA drip column and the flow through was collected. The furin cleaved-huBAFF was polished by Size Exclusion Chromatography. Trimeric status was confirmed by Analytical Ultracentrifuge analysis.

```
Sequence for His-tagged human BAFF (72-285):
                                             (SEQ ID NO: 399)
HHHHHHENLYFQGLQGDLASLRAELQGHHAEKLPAGAGAPKAGLEEAPAV

TAGLKIFEPPAPGEGNSSQNSRNKRAVQGPEETVTQDCLQLIADSETPTI

QKGSYTFVPWLLSFKRGSALEEKENKILVKETGYFFIYGQVLYTDKTYAM

GHLIQRKKVHVFGDELSLVTLFRCIQNMPETLPNNSCYSAGIAKLEEGDE

LQLAIPRENAQISLDGDVTFFGALKLL

Sequence for furin-cleaved human BAFF
(134-285):
                                             (SEQ ID NO: 400)
AVQGPEETVTQDCLQLIADSETPTIQKGSYTFVPWLLSFKRGSALEEKEN

KILVKETGYFFIYGVLYTDKTYAMGHLIQRKKVHVFGDELSLVTLFRCIQ

NMPETLPNNSCYSAGIAKLEEGDELQLAIPRENAQISLDGDVTFFGALKL

L
```

Example 4

Binding and Affinity Data for Anti-BAFF Antibodies (Refers to Tables 7 and 8)

Apparent binding affinities were evaluated using surface plasmon resonance where the antibodies were captured at different surface densities on a Protein A/G surface. Soluble trimeric BAFF at different concentrations were flowed over the captured antibody. The kinetic values are obtained from a global fit of all surface densities using a 1:1 Langmuir model and reported in Tables 7 and 8. Clinical reference antibodies (Reference 1 comprising SEQ ID NOS: 98 and 116) and Reference 2 comprising SEQ ID NOS: 99 and 117) were used as comparators.

TABLE 7

Functional Inhibition and Affinity Determination of Anti-BAFF Antibodies.

| Designation | Soluble trimeric huBAFF (52 pM) Neutralization IC90 (pM) n = 2 | Soluble 60-mer huBAFF (4.2 pM) Neutralization IC90 (pM) n = 2 | mbBAFF Neutralization IC90 (pM) n = 1 | Apparent Affinity $K_D$ (pM)** |
|---|---|---|---|---|
| Reference 1 | 290.0 | 21.0 | 1052 | <10 |
| Reference 2 | 1000.0 | 93% @ 67 nM | 151000 | 22.2 |
| 206G9A10 | 35.1 | 0.2 | ND* | <10 |
| 227D5A7 | 56.8 | 0.8 | ND | <10 |
| 250E5A11 | 97.5 | 0.3 | ND | <10 |
| 235F5B9 | 107.4 | 2.2 | 1050 | <10 |
| 227D3B11 | 127.7 | 1.6 | ND | <10 |
| 217H12A7 | 129.4 | 13.4 | ND | <10 |
| 210D9B8 | 155.6 | 14.0 | ND | <10 |
| 214G4B7 | 296.1 | 3.0 | ND | <10 |
| 13J018-1A4 | 304.8 | 23.0 | 4650 | <10 |
| 218H1C10.1 | 370 | 41 | ND | ND |
| 218H1C10.2 | 370 | ND | ND | ND |

*ND: not determined
**at detection limit

TABLE 8

Functional Inhibition and Affinity Determination of Anti-BAFF Antibodies.

| Designation | Soluble trimeric huBAFF (50 pM) Neutralization | | Soluble 60-mer huBAFF (4 pM) Neutralization | | Potent mbBAFF Neutralization | |
|---|---|---|---|---|---|---|
| | IC90 (pM) | IC50 (pM) | IC90 (pM) | IC50 (pM) | IC90 (pM) | IC50 (pM) |
| Reference 1 | 290 | | 102 | 40 | 1052 | 177 |
| Reference 2 | 1000 | | 197985 | 38298 | 151000 | 2180 |
| 1002E8A6 | 824 | 107 | 79 | 29 | 2087 | 141 |
| 1070A6B7 | 677 | 43 | 56 | 20 | 1065 | 147 |

TABLE 8-continued

Functional Inhibition and Affinity Determination of Anti-BAFF Antibodies.

| Designation | Soluble trimeric huBAFF (50 pM) Neutralization | | Soluble 60-mer huBAFF (4 pM) Neutralization | | Potent mbBAFF Neutralization | |
|---|---|---|---|---|---|---|
| | IC90 (pM) | IC50 (pM) | IC90 (pM) | IC50 (pM) | IC90 (pM) | IC50 (pM) |
| 1094C4E6 | 1099 | 384 | 20925 | 4048 | 175030 | 2561 |
| 27121-3C7 | 326 | 55 | 33 | 11 | ND* | ND |
| 317H2A6 | 327 | 97 | 13 | 4 | ND | ND |
| 319B8A12 | 331 | 91 | 24 | 8 | ND | ND |
| 320F9C5 | 3107 | 110 | 24 | 10 | ND | ND |
| 323E9D1 | 312 | 148 | 23 | 6 | ND | ND |
| 332C1B12 | 457 | 99 | 40 | 12 | ND | ND |
| 344B9D9 | 352 | 102 | 32 | 11 | ND | ND |
| 348A6C1 | 329 | 110 | 29 | 9 | ND | ND |
| 352G11A10 | 444 | 99 | 90 | 21 | ND | ND |
| 363D4A10 | 473 | 21 | 23 | 9 | ND | ND |
| 381A6A9 | 240 | 44 | 42 | 17 | ND | ND |
| 384D5A2 | 765 | 42 | 44 | 15 | ND | ND |
| 394F5A5 | 433 | 16 | 29 | 7 | ND | ND |
| 409F12A11 | 390 | 31 | 44 | 16 | ND | ND |
| 418F6D9 | 491 | 38 | 154 | 27 | ND | ND |
| 431G5A3 | 336 | 28 | 100 | 21 | ND | ND |
| 435A6B3 | 294 | 23 | 26 | 10 | ND | ND |
| 436H2C12 | 408 | 27 | 37 | 15 | ND | ND |
| 436H6A9 | 266 | 26 | 27 | 10 | ND | ND |
| 440E9D12 | 259 | 31 | 31 | 11 | ND | ND |
| 441E6F2 | 293 | 43 | 37 | 16 | ND | ND |
| 443C11A12 | 309 | 33 | 30 | 13 | ND | ND |
| 444G1A10 | 284 | 25 | 35 | 12 | ND | ND |
| 450A2A7 | 602 | 36 | 130 | 24 | ND | ND |
| 456H11B7 | 299 | 32 | 37 | 12 | ND | ND |
| 537G7A6 | 329 | 28 | 39 | 13 | ND | ND |
| 551H4D6 | 257 | 110 | 1979 | 234 | ND | ND |
| 560H2A7 | 324 | 35 | 30 | 13 | ND | ND |
| 606H7F8 | 378 | 29 | 44 | 12 | ND | ND |

*ND: not determined

Example 5

Functional Inhibition of Antibodies to Soluble Trimeric Human BAFF (Refers to Tables 7 and 8, and FIG. 1)

Antibodies were assessed for the ability to neutralize soluble trimeric human BAFF activation of the human BAFF receptor (BAFFR). A fixed concentration of the trimeric (52 pM) BAFF was mixed in assay medium with CHO cells expressing recombinant human BAFFR and a luciferase reporter system and stimulated for 24 hours in an incubator at 37° C., 5% CO2 in the presence of varying doses of anti-BAFF antibodies. Luciferase expression was assessed at the end of the incubation to quantify the level of neutralization achieved. IC50 and IC90 values were determined from the plots of the antibody dose titration luciferase inhibition results. Clinical reference antibodies (Reference 1 and Reference 2) were used as comparators.

Example 6

Generation of Recombinant Soluble 60-mer Human BAFF Protein

Stable HEK293F cells expressing human BAFF(134-285) with an N-terminal His-tag (SEQ ID: 401) was produced using lentivirus based technologies from Clontech (pLVX-IRES-ZsGreen). The lentivirus line was generated using Clontech's standard protocols, and high-expressing cells were enriched by sorting for cells expressing green fluorescent protein. BAFF(134-285) expressing HEK293F cells were incubated for 96 hours before cells were pelleted and expression of the supernatant was verified with an anti 6×His western blot ("6×His" disclosed as SEQ ID NO: 407). Supernatant purification was completed using Ni-Sepharose Affinity Chromatography as first step. Affinity purified BAFF(134-285) was polished by Size Exclusion Chromatography using Sephacryl S-400 resin. 60-mer BAFF eluted as major peak that was separated from both larger aggregates and small molecular weight species. The molecular weight of 60-mer BAFF was confirmed by Analytical Ultracentrifugation and SEC-multi angle laser light scattering detector system.

```
Sequence for His-HuBAFF (134-285):
                                         (SEQ ID NO: 401)
HHHHHHENLYFQGAVQGPEETVTQDCLQLIADSETPTIQKGSYTFVPWLL

SFKRGSALEEKENKILVKETGYFFIYGVLYTDKTYAMGHLIQRKKVHVFG

DELSLVTLFRCIQNMPETLPNNSCYSAGIAKLEEGDELQLAIPRENAQIS

LDGDVTFFGALKLL
```

Example 7

Functional Inhibition of Antibodies to Soluble 60-Mer Human BAFF (Refers to Tables 7 and 8)

Antibodies were assessed for the ability to neutralize soluble 60-mer human BAFF activation of the human BAFF receptor (BAFFR). A fixed concentration of the 60-mer (4.2 pM) BAFF was mixed in assay medium with CHO cells expressing recombinant human BAFFR and a luciferase reporter system and stimulated for 24 hours in an incubator at 37° C., 5% CO2 in the presence of varying doses of anti-BAFF antibodies. Luciferase expression was assessed at the end of the incubation to quantify the level of neutralization achieved. IC50 and IC90 values were determined from the plots of the antibody dose titration luciferase inhibition results. Clinical reference antibodies (Reference 1 and Reference 2) were used as comparators.

Example 8

Figure 2:
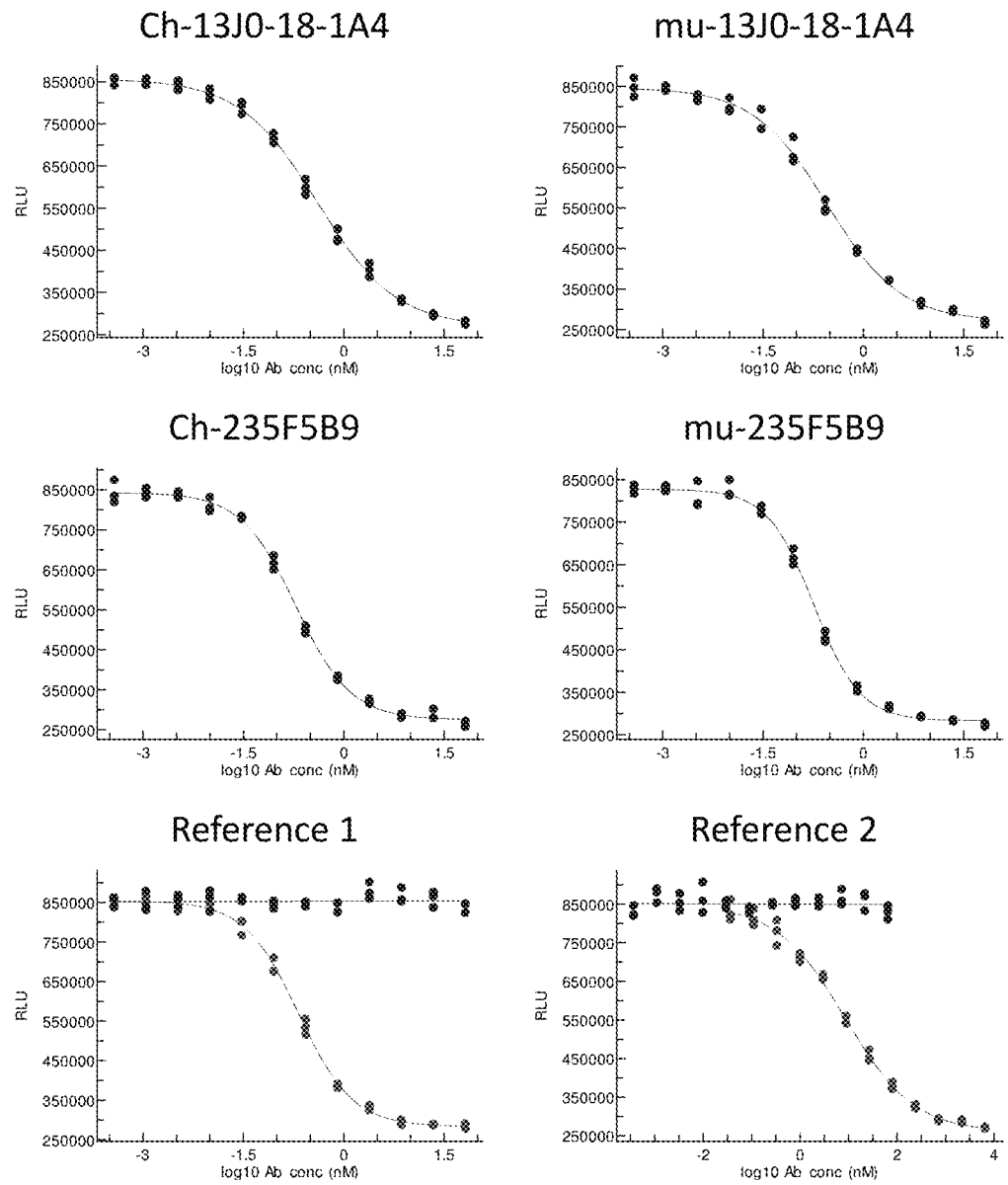
FIG. 2: Anti-BAFF monoclonal antibody against mbBAFF: chimeric HuIgG1 KO vs. parental mouse monoclonal antibodies.

Functional Inhibition of Antibodies to mbBAFF
(Refers to Tables 7 and 8, and FIG. 2)

Antibodies were assessed for the ability to neutralize human membrane-bound BAFF (mbBAFF) activation of the human BAFF receptor (BAFFR). In brief, Chinese hamster ovary (CHO) cells overexpressing recombinant human full-length BAFF sequences were produced and used as a source of cell associated (mbBAFF) BAFF. The mbBAFF-CHO were fixed in paraformaldehyde at room temperature for 1 hour with intermittent mixing. The fixed cells were washed and resuspended in complete medium for incubation at 37C and 5% $CO_2$ overnight. The next day, the fixed mbBAFF cells were mixed in assay medium at a of 1:3 ratio with CHO cells expressing recombinant human BAFFR and a luciferase reporter system and stimulated for 24 hours in an incubator at 37° C., 5% CO2 in the presence of varying doses of anti-BAFF antibodies. Luciferase expression was assessed at the end of the incubation to quantify the level of neutralization achieved. IC50 and IC90 values were determined from the plots of the antibody dose titration luciferase inhibition results. Clinical reference antibodies (Reference 1 and Reference 2) were used as comparators.

BAFF can exist in three forms: membrane bound (mbBAFF), soluble trimeric BAFF, and soluble 60-mer BAFF. The relative importance of the various forms of BAFF in normal and disease physiology is not well understood. In previous studies, soluble BAFF was treated as a single entity (Manetta et al., Journal of Inflammation Research, 2014:7, 121-131). In the present invention, soluble trimeric and 60-mer human BAFF proteins, as well as human mbBAFF, were explicitly generated, and their polymeric status confirmed. In functional assays, novel anti-BAFF antibodies described herein showed profiles that were different from the two reference antibodies (Reference 1 and Reference 2) in their ability to neutralize soluble trimeric human BAFF, soluble 60-mer human BAFF and membrane-bound human BAFF activation of the human BAFF receptor (BAFFR).

Example 9

Epitope Mapping of Antibodies

Hydrogen/Deuterium Exchange Mass Spectrometry (HXMS) was employed to map the epitope of IgG antibodies comprising mouse variable regions (Tables 1 and 2) binding to human BAFF (subsequence amino acid positions 134-285, tumor necrosis actor ligand superfamily member 13b, soluble form). This method determined the susceptibility of the amide backbone hydrogens of BAFF to exchange with $D_2O$. The experiment was conducted with BAFF alone and BAFF with added antibodies (with deuterium). Regions of the BAFF sequence showing significant protection from exchange due to binding of antibodies were thus identified. Resolution of the method is determined by the peptides produced by digestion with pepsin. These BAFF derived peptides were identified by additional control experiments with unexchanged samples employing standard accurate mass and HPLC MS/MS technologies.

Recombinant human BAFF was used (SEQ ID NO: 401). For each protein+antibody sample, an equimolar amount of BAFF (0.48 mg/mL) and antibody was incubated for 15 minutes at room temperature. A LEAP HDX-PAL system was used for all sample handling. Using the LEAP robot system (exchange plate kept at 25 degrees C., sample/quench plate kept at 4 degrees C.), 8 µL of sample was added to 80 µL of exchange buffer (10 mM NaH2PO4 in D2O, pH=7.4 or 10 mM NaH2PO4 in H2O, pH=7.4), mixed, and allowed to exchange for various times (60, 120, and 240 seconds). 80 µL of this solution was then transferred to 80 µL of quench buffer (4M Guanidine-HCL, 0.5M TCEP-HCl), mixed, and kept at 4 degrees C. for 60 seconds. 60 µL of this solution was then injected and flowed over a pepsin column (2.1 mm×30 mm, Applied Biosystems), and flowed onto a Michrom C18 trap cartridge. The cartridge was washed with H2O+0.1% formic acid for 2 minutes at 100 µL/min. A valve was then switched and the cartridge eluted onto a Phenomenex Jupiter C5 column, 1.0×50 mm, 5um, 300A. Mobile Phase A was water/acetonitrile/formic acid (99/1/0.1) and Mobile Phase B was acetonitrile/water/formic acid (95/5/0.1). Flow rate was 100 ul/min. Gradient was: 0 minutes (0% B), 6 minutes (40% B), 7 minutes (40% B), 8 minutes (90% B), 10 minutes (90% B), 11 minutes (0% B). The LEAP system precools the mobile phase to ~4 degrees C. Mass Spectrometry is performed on a Thermo Orbitrap Velos (0900865). For the MS experiments (used to quantitate exchange with the D2O buffer), a single scan method from 300-2000 for 14 minutes was used at resolution 60,000. For the MS/MS experiments (used to ID peptides with the H2O exchange buffer), a method with 7 scans was used for 14 minutes. The first scan was a full range scan from 300-2000 at 60,000 resolution. Subsequent scans were CID scans of the 6 most intense ions from scan #1. Isolation width was 1.5 amu, collision energy was 35V, and activation time was 30 msec.

MS/MS data was analyzed with the program Proteome Discoverer 1.3 (Thermo Scientific). Briefly, the program uses the accurate molecular weight of the precursor ion and the fragmentation data for the product ions to match regions of the protein sequence. From this analysis, peptides produced from pepsin were identified. MS data was analyzed with the in-house program BI-SHAFT. Briefly, the list of peptic peptides, as well as their charge state and retention time, and the protein sequence were entered. The program then searches for data meeting the accurate mass criteria and calculates the average molecular weight of the isotopic distribution. The data is inspected to identify errors, and where errors occur, manual calculations are done using Microsoft Excel when necessary. Areas of protection are identified by comparing the control data (protein alone) to the experimental data (protein with antibody). Regions of protection are indicative of binding.

The regions of the BAFF sequence showing significant protection from exchange due to binding of antibodies (light/heavy chains comprising SEQ ID NOS: 49/67, 57/75, 41/58, 43/61, 45/63, 47/65, 51/69 and 53/71) were identified as amino acid residues 17 to 31 (SEQ ID NO: 403), 68 to 90

(SEQ ID NO: 404), 126 to 137 (SEQ ID NO: 405) and 137 to 145 (SEQ ID NO: 406).

TABLE 9

Epitope Mapping Sequences.

| Name | Amino Acid Sequence |
|---|---|
| Recombinant Human BAFF | MAVQGPEETVTQDCLQLIADSETPTIQKGSYTFVPWLLSF KRGSALEEKENKIVKETGYFFIYGQVLYTDKTYAMGHLI QRKKVHVFGDELSLVTLFRCIQNMPETLPNNSCYSAGIAK LEEGDELQLAIPRENAQISLDGDVTFFGALKLL (SEQ ID NO: 402) |
| Amino acid position 17-31* | IADSETPTIQKGSYT (SEQ ID NO: 403) |

TABLE 9-continued

Epitope Mapping Sequences.

| Name | Amino Acid Sequence |
|---|---|
| Amino acid position 68-90* | YTDKTYAMGHLIQRKKVHVFGDE (SEQ ID NO: 404) |
| Amino Acid position 126-137* | LQLAIPRENAQI (SEQ ID NO: 405) |
| Amino acid position 137-145* | ISLDGDVTF (SEQ ID NO: 406) |

*'N' methionine of recombinant human BAFF not counted towards position number.

The invention claimed is:

1. An anti-B-cell activating factor (BAFF) antibody molecule comprising a light chain variable domain with a CDR1 selected from the group consisting of any one of SEQ ID NO: 1, 5, 10, 13, 15, 76, 77, 78, 79, 80, 249, 250, 251, 252, 253, 254, 255, 256, 257, 258, 259, 260, 261, 262, 263, 264, 265, 266, 267, 268, 269, 270, 271, 272, 273, 274 and 275, a CDR2 selected from the group consisting of any one of SEQ ID NO: 2, 6, 8, 11, 16, 276, 277, 278, 279, 280, 281, 282, 283, 284, 285, 286, 287, 288, 289, 290, 291 and 292, and a CDR3 selected from the group consisting of any one of SEQ ID NO: 3, 4, 7, 9, 12, 14, 17, 293, 294, 295, 296, 297, 298, 299, 300, 301, 302, 303, 304, 305, 306, 307, 308, 309, 310 and 311; and a heavy chain variable domain with a CDR1 selected from the group consisting of any one of SEQ ID NO: 18, 21, 23, 25, 28, 31, 34, 36, 37, 81, 312, 313, 314, 315, 316, 317, 318, 319, 320, 321, 322, 323, 324, 325, 326, 327, 328, 329, 330, 331, 332, 392, 333, 334, 335 and 336, a CDR2 selected from the group consisting of any one of SEQ ID NO: 19, 24, 26, 29, 32, 35, 38, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366 and 367, and a CDR3 selected from the group consisting of any one of SEQ ID NO: 20, 22, 27, 30, 33, 39, 368, 369, 370, 371, 372, 373, 374, 375, 376, 377, 378, 379, 380, 381, 382, 383, 384, 385, 386, 387, 388, 389, 390 and 391.

2. An anti-BAFF antibody molecule according to claim 1, wherein the antibody is a monoclonal antibody.

3. The anti-BAFF antibody molecule according to claim 2, wherein the monoclonal antibody is a humanized monoclonal antibody.

4. A pharmaceutical composition comprising an anti-BAFF antibody molecule according to claim 1 and a pharmaceutically acceptable carrier.

5. An anti-B-cell activating factor (BAFF) antibody molecule comprising:
   (a) a light chain variable domain comprising a CDR1 of SEQ ID NO: 1, a CDR2 of SEQ ID NO: 2 and a CDR3 of SEQ ID NO: 3, and a heavy chain variable domain comprising a CDR1 of SEQ ID NO: 18, a CDR2 of SEQ ID NO: 19 and a CDR3 of SEQ ID NO: 20; or
   (b) a light chain variable domain comprising a CDR1 of SEQ ID NO: 1, a CDR2 of SEQ ID NO: 2 and a CDR3 of SEQ ID NO: 4, and a heavy chain variable domain comprising a CDR1 of SEQ ID NO: 21, a CDR2 of SEQ ID NO: 19 and a CDR3 of SEQ ID NO: 22; or
   (c) a light chain variable domain comprising a CDR1 of SEQ ID NO: 1, a CDR2 of SEQ ID NO: 2 and a CDR3 of SEQ ID NO: 4 and a heavy chain variable domain comprising a CDR1 of SEQ ID NO: 23, a CDR2 of SEQ ID NO: 24 and a CDR3 of SEQ ID NO: 20; or
   (d) a light chain variable domain comprising a CDR1 of SEQ ID NO: 5, a CDR2 of SEQ ID NO: 6 and a CDR3 of SEQ ID NO: 7 and a heavy chain variable domain comprising a CDR1 of SEQ ID NO: 25, a CDR2 of SEQ ID NO: 26 and a CDR3 of SEQ ID NO: 27; or
   (e) a light chain variable domain comprising a CDR1 of SEQ ID NO: 5, a CDR2 of SEQ ID NO: 8 and a CDR3 of SEQ ID NO: 9 and a heavy chain variable domain comprising a CDR1 of SEQ ID NO: 28, a CDR2 of SEQ ID NO: 29 and a CDR3 of SEQ ID NO: 30; or
   (f) a light chain variable domain comprising a CDR1 of SEQ ID NO: 10, a CDR2 of SEQ ID NO: 11 and a CDR3 of SEQ ID NO: 12 and a heavy chain variable domain comprising a CDR1 of SEQ ID NO: 31, a CDR2 of SEQ ID NO: 32 and a CDR3 of SEQ ID NO: 33; or
   (g) a light chain variable domain comprising a CDR1 of SEQ ID NO: 13, a CDR2 of SEQ ID NO: 6 and a CDR3 of SEQ ID NO: 14 and a heavy chain variable domain comprising a CDR1 of SEQ ID NO: 34, a CDR2 of SEQ ID NO: 35 and a CDR3 of SEQ ID NO: 27; or
   (h) a light chain variable domain comprising a CDR1 of SEQ ID NO: 10, a CDR2 of SEQ ID NO: 6 and a CDR3 of SEQ ID NO: 7 and a heavy chain variable domain comprising a CDR1 of SEQ ID NO: 36, a CDR2 of SEQ ID NO: 26 and a CDR3 of SEQ ID NO: 27; or
   (i) a light chain variable domain comprising a CDR1 of SEQ ID NO: 15, a CDR2 of SEQ ID NO: 16 and a CDR3 of SEQ ID NO: 17 and a heavy chain variable domain comprising a CDR1 of SEQ ID NO: 37, a CDR2 of SEQ ID NO: 38 and a CDR3 of SEQ ID NO: 39; or
   (j) a light chain variable domain comprising a CDR1 of SEQ ID NO: 76, a CDR2 of SEQ ID NO: 16 and a CDR3 of SEQ ID NO: 17 and a heavy chain variable domain comprising a CDR1 of SEQ ID NO: 37, a CDR2 of SEQ ID NO: 38 and a CDR3 of SEQ ID NO: 39; or
   (k) a light chain variable domain comprising a CDR1 of SEQ ID NO: 77, a CDR2 of SEQ ID NO: 16 and a CDR3 of SEQ ID NO: 17 and a heavy chain variable domain comprising a CDR1 of SEQ ID NO: 37, a CDR2 of SEQ ID NO: 38 and a CDR3 of SEQ ID NO: 39; or
   (l) a light chain variable domain comprising a CDR1 of SEQ ID NO: 78, a CDR2 of SEQ ID NO: 16 and a CDR3 of SEQ ID NO: 17 and a heavy chain variable domain comprising a CDR1 of SEQ ID NO: 37, a CDR2 of SEQ ID NO: 38 and a CDR3 of SEQ ID NO: 39; or
   (m) a light chain variable domain comprising a CDR1 of SEQ ID NO: 79, a CDR2 of SEQ ID NO: 16 and a CDR3 of SEQ ID NO: 17 and a heavy chain variable domain comprising a CDR1 of SEQ ID NO: 37, a CDR2 of SEQ ID NO: 38 and a CDR3 of SEQ ID NO: 39; or
(n) a light chain variable domain comprising a CDR1 of SEQ ID NO: 80, a CDR2 of SEQ ID NO: 16 and a CDR3 of SEQ ID NO: 17 and a heavy chain variable domain comprising a CDR1 of SEQ ID NO: 37, a CDR2 of SEQ ID NO: 38 and a CDR3 of SEQ ID NO: 39; or
(o) a light chain variable domain comprising a CDR1 of SEQ ID NO: 5, a CDR2 of SEQ ID NO: 8 and a CDR3 of SEQ ID NO: 9 and a heavy chain variable domain comprising a CDR1 of SEQ ID NO: 81, a CDR2 of SEQ ID NO: 29 and a CDR3 of SEQ ID NO: 30; or
(p) a light chain variable domain comprising a CDR1 of SEQ ID NO: 249, a CDR2 of SEQ ID NO: 276 and a CDR3 of SEQ ID NO: 293 and a heavy chain variable domain comprising a CDR1 of SEQ ID NO: 312, a CDR2 of SEQ ID NO: 337 and a CDR3 of SEQ ID NO: 368; or
(q) a light chain variable domain comprising a CDR1 of SEQ ID NO: 250, a CDR2 of SEQ ID NO: 276 and a CDR3 of SEQ ID NO: 293 and a heavy chain variable domain comprising a CDR1 of SEQ ID NO: 312, a CDR2 of SEQ ID NO: 337 and a CDR3 of SEQ ID NO: 368; or
(r) a light chain variable domain comprising a CDR1 of SEQ ID NO: 251, a CDR2 of SEQ ID NO: 277 and a CDR3 of SEQ ID NO: 294 and a heavy chain variable domain comprising a CDR1 of SEQ ID NO: 313, a CDR2 of SEQ ID NO: 338 and a CDR3 of SEQ ID NO: 369; or
(s) a light chain variable domain comprising a CDR1 of SEQ ID NO: 252, a CDR2 of SEQ ID NO: 278 and a CDR3 of SEQ ID NO: 295 and a heavy chain variable domain comprising a CDR1 of SEQ ID NO: 314, a CDR2 of SEQ ID NO: 339 and a CDR3 of SEQ ID NO: 370; or
(t) a light chain variable domain comprising a CDR1 of SEQ ID NO: 253, a CDR2 of SEQ ID NO: 279 and a CDR3 of SEQ ID NO: 296 and a heavy chain variable domain comprising a CDR1 of SEQ ID NO: 315, a CDR2 of SEQ ID NO: 340 and a CDR3 of SEQ ID NO: 371; or
(u) a light chain variable domain comprising a CDR1 of SEQ ID NO: 15, a CDR2 of SEQ ID NO: 16 and a CDR3 of SEQ ID NO: 297 and a heavy chain variable domain comprising a CDR1 of SEQ ID NO: 316, a CDR2 of SEQ ID NO: 341 and a CDR3 of SEQ ID NO: 39; or
(v) a light chain variable domain comprising a CDR1 of SEQ ID NO: 254, a CDR2 of SEQ ID NO: 280 and a CDR3 of SEQ ID NO: 298 and a heavy chain variable domain comprising a CDR1 of SEQ ID NO: 317, a CDR2 of SEQ ID NO: 342 and a CDR3 of SEQ ID NO: 372; or
(w) a light chain variable domain comprising a CDR1 of SEQ ID NO: 255, a CDR2 of SEQ ID NO: 281 and a CDR3 of SEQ ID NO: 298 and a heavy chain variable domain comprising a CDR1 of SEQ ID NO: 317, a CDR2 of SEQ ID NO: 343 and a CDR3 of SEQ ID NO: 373; or
(x) a light chain variable domain comprising a CDR1 of SEQ ID NO: 256, a CDR2 of SEQ ID NO: 2 and a CDR3 of SEQ ID NO: 299 and a heavy chain variable domain comprising a CDR1 of SEQ ID NO: 317, a CDR2 of SEQ ID NO: 344 and a CDR3 of SEQ ID NO: 372; or
(y) a light chain variable domain comprising a CDR1 of SEQ ID NO: 255, a CDR2 of SEQ ID NO: 281 and a CDR3 of SEQ ID NO: 298 and a heavy chain variable domain comprising a CDR1 of SEQ ID NO: 318, a CDR2 of SEQ ID NO: 343 and a CDR3 of SEQ ID NO: 374; or
(z) a light chain variable domain comprising a CDR1 of SEQ ID NO: 257, a CDR2 of SEQ ID NO: 282 and a CDR3 of SEQ ID NO: 300 and a heavy chain variable domain comprising a CDR1 of SEQ ID NO: 319, a CDR2 of SEQ ID NO: 345 and a CDR3 of SEQ ID NO: 375; or
(aa) a light chain variable domain comprising a CDR1 of SEQ ID NO: 258, a CDR2 of SEQ ID NO: 283 and a CDR3 of SEQ ID NO: 301 and a heavy chain variable domain comprising a CDR1 of SEQ ID NO: 320, a CDR2 of SEQ ID NO: 346 and a CDR3 of SEQ ID NO: 376; or
(bb) a light chain variable domain comprising a CDR1 of SEQ ID NO: 259, a CDR2 of SEQ ID NO: 281 and a CDR3 of SEQ ID NO: 298 and a heavy chain variable domain comprising a CDR1 of SEQ ID NO: 317, a CDR2 of SEQ ID NO: 347 and a CDR3 of SEQ ID NO: 377; or
(cc) a light chain variable domain comprising a CDR1 of SEQ ID NO: 260, a CDR2 of SEQ ID NO: 284 and a CDR3 of SEQ ID NO: 294 and a heavy chain variable domain comprising a CDR1 of SEQ ID NO: 321, a CDR2 of SEQ ID NO: 348 and a CDR3 of SEQ ID NO: 378; or
(dd) a light chain variable domain comprising a CDR1 of SEQ ID NO: 254, a CDR2 of SEQ ID NO: 2 and a CDR3 of SEQ ID NO: 299 and a heavy chain variable domain comprising a CDR1 of SEQ ID NO: 322, a CDR2 of SEQ ID NO: 349 and a CDR3 of SEQ ID NO: 372; or
(ee) a light chain variable domain comprising a CDR1 of SEQ ID NO: 261, a CDR2 of SEQ ID NO: 285 and a CDR3 of SEQ ID NO: 294 and a heavy chain variable domain comprising a CDR1 of SEQ ID NO: 323, a CDR2 of SEQ ID NO: 350 and a CDR3 of SEQ ID NO: 378; or
(ff) a light chain variable domain comprising a CDR1 of SEQ ID NO: 262, a CDR2 of SEQ ID NO: 286 and a CDR3 of SEQ ID NO: 302 and a heavy chain variable domain comprising a CDR1 of SEQ ID NO: 324, a CDR2 of SEQ ID NO: 351 and a CDR3 of SEQ ID NO: 379; or
(gg) a light chain variable domain comprising a CDR1 of SEQ ID NO: 263, a CDR2 of SEQ ID NO: 6 and a CDR3 of SEQ ID NO: 303 and a heavy chain variable domain comprising a CDR1 of SEQ ID NO: 317, a CDR2 of SEQ ID NO: 352 and a CDR3 of SEQ ID NO: 380; or
(hh) a light chain variable domain comprising a CDR1 of SEQ ID NO: 264, a CDR2 of SEQ ID NO: 276 and a CDR3 of SEQ ID NO: 304 and a heavy chain variable domain comprising a CDR1 of SEQ ID NO: 325, a CDR2 of SEQ ID NO: 353 and a CDR3 of SEQ ID NO: 381; or
(ii) a light chain variable domain comprising a CDR1 of SEQ ID NO: 265, a CDR2 of SEQ ID NO: 287 and a CDR3 of SEQ ID NO: 305 and a heavy chain variable domain comprising a CDR1 of SEQ ID NO: 326, a CDR2 of SEQ ID NO: 354 and a CDR3 of SEQ ID NO: 382; or (jj) a light chain variable domain comprising a CDR1 of SEQ ID NO: 266, a CDR2 of SEQ ID NO: 287 and a CDR3 of SEQ ID NO: 306 and a heavy chain variable domain comprising a CDR1 of SEQ ID NO: 326, a CDR2 of SEQ ID NO: 355 and a CDR3 of SEQ ID NO: 383; or (kk) a light chain variable domain comprising a CDR1 of SEQ ID NO: 267, a CDR2 of SEQ ID NO: 285 and a CDR3 of SEQ ID NO: 294 and a heavy chain variable domain comprising a CDR1 of SEQ ID NO: 327, a CDR2 of SEQ ID NO: 356 and a CDR3 of SEQ ID NO: 369; or (ll) a light chain variable domain comprising a CDR1 of SEQ ID NO: 268, a CDR2 of SEQ ID NO: 276 and a CDR3 of SEQ ID NO: 306 and a heavy chain variable domain comprising a CDR1 of SEQ ID NO: 328, a CDR2 of SEQ ID NO: 357 and a CDR3 of SEQ ID NO: 383; or (mm) a light chain variable domain comprising a CDR1 of SEQ ID NO: 269, a CDR2 of SEQ ID NO: 288 and a CDR3 of SEQ ID NO: 304 and a heavy chain variable domain comprising a CDR1 of SEQ ID NO: 329, a CDR2 of SEQ ID NO: 358 and a CDR3 of SEQ ID NO: 384; or (nn) a light chain variable domain comprising a CDR1 of SEQ ID NO: 270, a CDR2 of SEQ ID NO: 276 and a CDR3 of SEQ ID NO: 306 and a heavy chain variable domain comprising a CDR1 of SEQ ID NO: 330, a CDR2 of SEQ ID NO: 359 and a CDR3 of SEQ ID NO: 385; or (oo) a light chain variable domain comprising a CDR1 of SEQ ID NO: 371, a CDR2 of SEQ ID NO: 289 and a CDR3 of SEQ ID NO: 307 and a heavy chain variable domain comprising a CDR1 of SEQ ID NO: 331, a CDR2 of SEQ ID NO: 360 and a CDR3 of SEQ ID NO: 385; or (pp) a light chain variable domain comprising a CDR1 of SEQ ID NO: 261, a CDR2 of SEQ ID NO: 285 and a CDR3 of SEQ ID NO: 294 and a heavy chain variable domain comprising a CDR1 of SEQ ID NO: 332, a CDR2 of SEQ ID NO: 361 and a CDR3 of SEQ ID NO: 386; or (qq) a light chain variable domain comprising a CDR1 of SEQ ID NO: 272, a CDR2 of SEQ ID NO: 289 and a CDR3 of SEQ ID NO: 307 and a heavy chain variable domain comprising a CDR1 of SEQ ID NO: 331, a CDR2 of SEQ ID NO: 362 and a CDR3 of SEQ ID NO: 385; or (rr) a light chain variable domain comprising a CDR1 of SEQ ID NO: 266, a CDR2 of SEQ ID NO: 287 and a CDR3 of SEQ ID NO: 306 and a heavy chain variable domain comprising a CDR1 of SEQ ID NO: 326, a CDR2 of SEQ ID NO: 355 and a CDR3 of SEQ ID NO: 383; or (ss) a light chain variable domain comprising a CDR1 of SEQ ID NO: 270, a CDR2 of SEQ ID NO: 276 and a CDR3 of SEQ ID NO: 306 and a heavy chain variable domain comprising a CDR1 of SEQ ID NO: 330, a CDR2 of SEQ ID NO: 359 and a CDR3 of SEQ ID NO: 385; or (tt) a light chain variable domain comprising a CDR1 of SEQ ID NO: 270, a CDR2 of SEQ ID NO: 276 and a CDR3 of SEQ ID NO: 306 and a heavy chain variable domain comprising a CDR1 of SEQ ID NO: 392, a CDR2 of SEQ ID NO: 363 and a CDR3 of SEQ ID NO: 387; or (uu) a light chain variable domain comprising a CDR1 of SEQ ID NO: 273, a CDR2 of SEQ ID NO: 276 and a CDR3 of SEQ ID NO: 308 and a heavy chain variable domain comprising a CDR1 of SEQ ID NO: 333, a CDR2 of SEQ ID NO: 364 and a CDR3 of SEQ ID NO: 388; or (vv) a light chain variable domain comprising a CDR1 of SEQ ID NO: 274, a CDR2 of SEQ ID NO: 290 and a CDR3 of SEQ ID NO: 309 and a heavy chain variable domain comprising a CDR1 of SEQ ID NO: 334, a CDR2 of SEQ ID NO: 365 and a CDR3 of SEQ ID NO: 389; or (ww) a light chain variable domain comprising a CDR1 of SEQ ID NO: 275, a CDR2 of SEQ ID NO: 291 and a CDR3 of SEQ ID NO: 310 and a heavy chain variable domain comprising a CDR1 of SEQ ID NO: 335, a CDR2 of SEQ ID NO: 366 and a CDR3 of SEQ ID NO: 390; or (xx) a light chain variable domain comprising a CDR1 of SEQ ID NO: 258, a CDR2 of SEQ ID NO: 292 and a CDR3 of SEQ ID NO: 311 and a heavy chain variable domain comprising a CDR1 of SEQ ID NO: 336, a CDR2 of SEQ ID NO: 367 and a CDR3 of SEQ ID NO: 391.

6. The anti-BAFF antibody molecule of claim 5, wherein the anti-BAFF antibody molecule neutralizes a BAFF molecule comprising a human membrane bound BAFF (mb-BAFF), a human soluable trimeric BAFF, or a human soluable 60-mer BAFF.

7. The anti-BAFF antibody molecule of claim 5, wherein the anti-BAFF antibody molecule neutralizes human soluble trimeric BAFF.

8. The anti-BAFF antibody molecule of claim 5, wherein the anti-BAFF antibody molecule neutralizes human membrane bound BAFF.

9. The anti-BAFF antibody molecule of claim 5, wherein the anti-BAFF antibody molecule neutralizes human soluble 60-mer BAFF.

10. An anti-B-cell activating factor (BAFF) antibody molecule comprising a light chain variable domain of any one of SEQ ID NOs: 82-97, and a heavy chain variable domain of any one of SEQ ID NOs: 100-115.

11. The anti-BAFF antibody molecule of claim 10, wherein a combination of light chain variable domain and heavy chain variable domain comprises SEQ ID NOs: 82/101, 88/101, 94/112 or 93/114.

12. An anti-B-cell activating factor (BAFF) antibody molecule comprising:
a) a humanized light chain variable domain comprising the CDRs of SEQ ID NO: 76, 16 and 17 and framework regions having an amino acid sequence at least 90% identical to the amino acid sequence of the framework regions of the variable domain light chain amino acid sequence of SEQ ID NO: 82; and
b) a humanized heavy chain variable domain comprising the CDRs of SEQ ID NO:37, 38 and 39 and framework regions having an amino acid sequence at least 90% identical to the amino acid sequence of the framework regions of the variable domain heavy chain amino acid sequence of SEQ ID NO: 101.

13. An anti-B-cell activating factor (BAFF) antibody molecule comprising:
a) a humanized light chain variable domain comprising the CDRs of SEQ ID NO: 15, 16 and 17 and framework regions having an amino acid sequence at least 90% identical to the amino acid sequence of the framework regions of the variable domain light chain amino acid sequence of SEQ ID NO: 88; and
b) a humanized heavy chain variable domain comprising the CDRs of SEQ ID NO:37, 38 and 39 and framework regions having an amino acid sequence at least 90% identical to the amino acid sequence of the framework regions of the variable domain heavy chain amino acid sequence of SEQ ID NO: 101.

14. An anti-B-cell activating factor (BAFF) antibody molecule comprising:
a) a humanized light chain variable domain comprising the CDRs of SEQ ID NO: 5, 8 and 9 and framework regions having an amino acid sequence at least 90% identical to the amino acid sequence of the framework regions of the variable domain light chain amino acid sequence of SEQ ID NO: 94; and
b) a humanized heavy chain variable domain comprising the CDRs of SEQ ID NO: 81, 29 and 30 and framework regions having an amino acid sequence at least 90% identical to the amino acid sequence of the framework regions of the variable domain heavy chain amino acid sequence of SEQ ID NO: 112.

15. An anti-B-cell activating factor (BAFF) antibody molecule comprising:
a) a humanized light chain variable domain comprising the CDRs of SEQ ID NO: 5, 8 and 9 and framework regions having an amino acid sequence at least 90% identical to the amino acid sequence of the framework regions of the variable domain light chain amino acid sequence of SEQ ID NO: 93; and
b) a humanized heavy chain variable domain comprising the CDRs of SEQ ID NO: 81, 29 and 30 and framework regions having an amino acid sequence at least 90% identical to the amino acid sequence of the framework regions of the variable domain heavy chain amino acid sequence of SEQ ID NO: 114.

* * * * *

UNITED STATES PATENT AND TRADEMARK OFFICE
CERTIFICATE OF CORRECTION

PATENT NO. : 9,840,543 B2  
APPLICATION NO. : 14/609756  
DATED : December 12, 2017  
INVENTOR(S) : Scott Ronald Brodeur et al.

Page 1 of 1

It is certified that error appears in the above-identified patent and that said Letters Patent is hereby corrected as shown below:

On the Title Page

Left column, item (72) Inventors, Line 3, please change "MIchael" to --Michael--

Signed and Sealed this  
Fifth Day of June, 2018

Andrei Iancu  
*Director of the United States Patent and Trademark Office*

SEQUENCE LISTING

```
<160> NUMBER OF SEQ ID NOS: 407

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ala Ser Gln Asn Ala Gly Ala Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Asn Arg Tyr Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Tyr Arg Ser Tyr Pro Arg Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gln Tyr Arg Ser Phe Pro Arg Thr
1               5
```

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Ala Ser Gln Asn Ala Gly Ile Asp Val Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Thr Ser Asn Arg Tyr Thr
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Gln Tyr Arg Ser Tyr Pro Arg Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Lys Ser Asn Arg Tyr Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Gln Tyr Arg Ser Tyr Pro Arg Thr
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 10

Lys Ala Ser Gln Asn Ala Gly Thr Ala Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Ala Phe Asn Arg Tyr Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Tyr Arg Ser Tyr Pro Arg Thr
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ala Ser Gln Ser Val Gly Ile Ala Val Ala
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Tyr Ser Arg Tyr Pro Arg Thr
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ala Ser Gln Asp Ile Gly Asn Arg Leu Asn
1               5                   10

<210> SEQ ID NO 16
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Thr Ser Ser Leu Asp Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Gln Tyr Ala Ser Ser Pro Phe Thr
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Tyr Thr Phe Ser Ile Phe Cys Ile His
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ile Asp Pro Ser Ser Gly Gly Thr Lys Tyr Asn Glu Lys Phe Glu
1               5                   10                  15

Ser

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Glu Asp Leu Leu Val Arg Thr Asp Ala Met Asp Tyr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21
```

Gly Tyr Thr Phe Ser Ile Phe Cys Val His
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Glu Asp Leu Leu Val Arg Thr Asp Ala Leu Asp Tyr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Tyr Thr Phe Ser Ile Phe Cys Ile His
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ile Asp Pro Ser Ser Gly Gly Thr Lys Tyr Asn Glu Arg Phe Glu
1               5                   10                  15

Asn

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Tyr Ser Phe Ser Thr Phe Phe Ile His
1               5                   10

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ile Asp Pro Asn Ser Gly Gly Thr Lys Tyr Asn Glu Lys Phe Glu
1               5                   10                  15

Ser

```
<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Glu Asp Leu Leu Ile Arg Thr Asp Ala Met Asp Tyr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Ser Phe Ser Thr Phe Phe Ile His
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ile Asp Pro Asn Ser Gly Ala Thr Lys Tyr Asn Glu Lys Phe Glu
1               5                   10                  15

Ser

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Glu Asp Leu Leu Ile Arg Thr Asp Ala Leu Asp Tyr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Tyr Thr Phe Ser Thr Phe Leu Ile His
1               5                   10

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 32

Arg Ile Asp Pro Asn Ser Gly Gly Thr Lys Tyr Asn Glu Lys Phe Glu
1               5                   10                  15
Arg

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Glu Asp Leu Leu Leu Arg Thr Asp Ala Met Asp Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Tyr Thr Phe Ile Thr Tyr Trp Met His
1               5                   10

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ile Asp Pro Asn Ser Gly Val Ile Lys Tyr Asn Glu Lys Phe Lys
1               5                   10                  15
Ser

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Tyr Ser Phe Ser Thr Phe Cys Ile His
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp His Ile Phe Ser Ile His Trp Met Gln
1               5                   10
```

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Glu Ile Phe Pro Gly Ser Gly Thr Thr Asp Tyr Asn Glu Lys Phe Lys
1               5                   10                  15

Gly

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gly Ala Phe Asp Tyr
1               5

<210> SEQ ID NO 40
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40
gacattgtga tgacccagtc tcaaaaattc atgtccacaa cagtaggaga cagggtcagc    60
atcacctgca aggccagtca gaatgcgggt gctgctgtag cctggtttca acagaaacca   120
ggacaatctc ctaaactact gatttactca gcatccaatc ggtatactgg agtccctgat   180
cgcttcacag gcagtggatc ggggacagat ttcactctca ccattagcaa tgtgcagtct   240
gaggacctgg cagattatat ctgtcaacaa tacagaagct atcctcggac gttcggagga   300
ggcaccaagc tggaaatcaa a                                             321

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Ala Gly Ala Ala
                20                  25                  30

Val Ala Trp Phe Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Ile Cys Gln Gln Tyr Arg Ser Tyr Pro Arg
            85                  90                  95

Thr Phe Gly Gly Gly Thr Lys Leu Glu Ile Lys
            100                 105

<210> SEQ ID NO 42
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gacattgtga tgacccagtc tcaaaaattc atgtccacaa cagtaggaga cagggtcagc    60
atcacctgca aggccagtca gaatgcgggt gctgctgtag cctggtttca acagaaaccg   120
ggacaatctc ctaaattact gatttactca gcatccaatc ggtatactgg agtccctgat   180
cgcttcacag gcagtggatc ggggacagat ttcactctca ccattagcaa tgtgcagtct   240
gaggacctgg cagattatat ctgtcaacaa tacagaagct ttcctcggac gttcggagga   300
ggcaccaagc tggaaatcaa a                                             321

<210> SEQ ID NO 43
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Ala Gly Ala Ala
            20                  25                  30

Val Ala Trp Phe Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Ile Cys Gln Gln Tyr Arg Ser Phe Pro Arg
            85                  90                  95

Thr Phe Gly Gly Gly Thr Lys Leu Glu Ile Lys
            100                 105

<210> SEQ ID NO 44
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gacattgtga tgacccagtc tcaaaaattc atgtccacaa cagtaggaga cagggtcagc    60
atcacctgca aggccagtca gaatgcgggt gctgctgtag cctggtttca acagaaacca   120
ggacaatctc ctaaactact gatttactca gcatccaatc ggtatactgg agtccctgat   180

```
cgcttcacag gcagtggatc ggggacagat tcactctca ccattaccaa tgtgcagtct    240
gaggacctgg cagattatat ctgtcaacaa tacagaagct ttcctcggac gttcggagga    300
ggcactaagc tggaaatcaa a                                              321
```

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Ala Gly Ala Ala
            20                  25                  30

Val Ala Trp Phe Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Ile Cys Gln Gln Tyr Arg Ser Ser Phe Pro Arg
                85                  90                  95

Thr Phe Gly Gly Gly Thr Lys Leu Glu Ile Lys
            100                 105
```

<210> SEQ ID NO 46
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
gacattgtga tgacccagtc tcaaaaaatc atgtccacaa cagtgggaga cagggtcagc    60
atcacctgca aggccagtca gaatgcgggt attgatgtag cctggtttca acagaaacca    120
agacaatctc ctaaactact gattttctca acatccaatc gatatactgg agtcccagat    180
cgcttcgcag gcagtggatc ggggacagat tcactctca ccatttacaa tgtgcagtct    240
gaagacctgg cagattattt ctgtctgcaa tatagaagtt atcctcggac gttcggaggg    300
gggaccaagc tggaaataaa a                                              321
```

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Arg Gln Ser Pro Lys Leu Leu Ile
```

35                  40                  45

Phe Ser Thr Ser Asn Arg Tyr Thr Gly Val Pro Asp Arg Phe Ala Gly
         50                  55                  60

Ser Gly Ser Gly Thr Asp Phe Thr Leu Thr Ile Tyr Asn Val Gln Ser
 65                  70                  75                  80

Glu Asp Leu Ala Asp Tyr Phe Cys Leu Gln Tyr Arg Ser Tyr Pro Arg
                 85                  90                  95

Thr Phe Gly Gly Gly Thr Lys Leu Glu Ile Lys
            100                 105

<210> SEQ ID NO 48
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gacattgtga tgacccagtc tcaaaaaatc atgtccacaa cagtgggaga cagggtcagc      60
atcacctgca aggccagtca gaatgcgggt attgatgtag cctggtttca acagaaacca     120
agacaatctc ctaaactact gattttctca aaatccaatc gatatactgg agtcccagat     180
cgcttcgcag gcagtggatc ggggacagat ttcactctca ccatttacaa tgtgcagtct     240
gaagacctgg cagattattt ctgtctgcaa tatagaagtt atcctcggac gttcggagga     300
ggcaccaagc tggaaatcaa a                                               321

<210> SEQ ID NO 49
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Val Met Thr Gln Ser Gln Lys Ile Met Ser Thr Thr Val Gly
 1               5                  10                  15

Asp Arg Val Ser Ile Thr Cys Lys Ala Ser Gln Asn Ala Gly Ile Asp
             20                  25                  30

Val Ala Trp Phe Gln Gln Lys Pro Arg Gln Ser Pro Lys Leu Leu Ile
         35                  40                  45

Phe Ser Lys Ser Asn Arg Tyr Thr Gly Val Pro Asp Arg Phe Ala Gly
     50                  55                  60

Ser Gly Ser Gly Thr Asp Phe Thr Leu Thr Ile Tyr Asn Val Gln Ser
 65                  70                  75                  80

Glu Asp Leu Ala Asp Tyr Phe Cys Leu Gln Tyr Arg Ser Tyr Pro Arg
                 85                  90                  95

Thr Phe Gly Gly Gly Thr Lys Leu Glu Ile Lys
            100                 105

<210> SEQ ID NO 50
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
gacattgtga tgacccagtc tcaaaaattc atgtccacaa cagtaggaga cagggtcagc    60
atcacctgca aggccagtca gaatgcgggt actgctgtag cctggtttca acagaaacca   120
ggacaatctc ctaaactact gatttactca gcatttaatc ggtatactgg agtccctgat   180
cgcttcacag gcagtggatc ggggacagat ttcactctca ccattagcaa tatgcagtct   240
gaagacctgg cagattatat ctgtcaacaa tatagaagct atcctcggac gttcggagga   300
ggcaccaagc tggaaatcaa a                                             321
```

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Ala Gly Thr Ala
            20                  25                  30

Val Ala Trp Phe Gln Gln Lys Pro Gly Gln Ser Pro Lys Leu Leu Ile
        35                  40                  45

Tyr Ser Ala Phe Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Ile Cys Gln Gln Tyr Arg Ser Tyr Pro Arg
                85                  90                  95

Thr Phe Gly Gly Gly Thr Lys Leu Glu Ile Lys
            100                 105
```

<210> SEQ ID NO 52
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
gacattgtga tgacccagtc tcaaaaattc gtgtccacaa cactagggga cagggtcagc    60
atcacctgca aggccagtca gagtgtgggt attgctgtag cctggtatca acagaaacca   120
ggacattctc ctaacctact gattttctca acatccaatc gctacactgg agtccctgat   180
cgcttcacag gcagcggatc tgggacagat ttcactctca ccattagcga tgtgcagtct   240
gaagacctgg cagattattt ctgtcagcaa tatagcaggt atcctcggac gttcggtgga   300
ggcaccaagc tggagatcaa a                                             321
```

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Val Met Thr Gln Ser Gln Lys Phe Val Ser Thr Thr Leu Gly
1               5                   10                  15

Asp Arg Val Ser Ile Thr Cys Lys Ala Ser Gln Ser Val Gly Ile Ala
            20                  25                  30

Val Ala Trp Tyr Gln Gln Lys Pro Gly His Ser Pro Asn Leu Leu Ile
        35                  40                  45

Phe Ser Thr Ser Asn Arg Tyr Thr Gly Val Pro Asp Arg Phe Thr Gly
    50                  55                  60

Ser Gly Ser Gly Thr Asp Phe Thr Leu Thr Ile Ser Asp Val Gln Ser
65                  70                  75                  80

Glu Asp Leu Ala Asp Tyr Phe Cys Gln Gln Tyr Ser Arg Tyr Pro Arg
                85                  90                  95

Thr Phe Gly Gly Gly Thr Lys Leu Glu Ile Lys
            100                 105

<210> SEQ ID NO 54
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gacattgtga tgacccagtc tcaaaaattc atgtccacaa cagtaggaga cagggtcagc    60
atcacctgca aggccagtca gaatgcgggt actgctgtag cctggtttca acagaaacca   120
ggacaatctc ctaaactact gattttctca acatccaatc ggtatactgg agtccctgat   180
cgcttcacag gcagtggatc ggggacagat ttcactctca ccattagcaa tatgcagtct   240
gaagacctgg cagattattt ctgtctgcaa tatagaagct atcctcggac gttcggagga   300
ggcaccaagc tggaaatcaa a                                             321

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Ala Gly Thr Ala
            20                  25                  30

Val Ala Trp Phe Gln Gln Lys Pro Gly Gln Ser Pro Lys Leu Leu Ile
        35                  40                  45

Phe Ser Thr Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Leu Gln Tyr Arg Ser Tyr Pro Arg
                85                  90                  95

Thr Phe Gly Gly Gly Thr Lys Leu Glu Ile Lys
            100                 105

<210> SEQ ID NO 56
<211> LENGTH: 321

<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 56

```
gacatccaga tgacccagtc tccatcctca ttatctgcct ctctgggaga aagagtcagt      60
ctcacttgtc gggcaagtca agacattggt aataggttaa actggcttca gcaggaacca     120
gatggaacta ttaaacgcct gatctacgcc acatccagtt tagattctgg tgtccccaaa     180
aggttcagtg gcagtaggtc tgggtcggat tattctctca ccatcagcag ccttgagtct     240
gaagattttg tagactatta ctgtctacaa tatgctagtt ctccattcac gttcggcacg     300
gggacaaaat tggaaataaa a                                               321
```

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 57

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Asn Arg
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Phe
                85                  90                  95

Thr Phe Gly Thr Gly Thr Lys Leu Glu Ile Lys
            100                 105

<210> SEQ ID NO 58
<211> LENGTH: 366
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 58

```
caggtccaac tgcagcagcc tggggctgag cttgtgaagc ctggggcttc agtgaagctg      60
tcctgcaagg cttctggcta caccttcagt atcttctgta cactgggt gcaacagagg       120
cctggacgag gccttgagtg gattggaagg attgatccta gtagtggtgg tactaagtac     180
aatgagaagt tcgagagcaa ggccacactg actgtagaca atcctccag cacagcctac      240
atgcagctca gcagcctgac atctgaggac tctgcggtct attattgtgc aagaggggag     300
gatttattag tacggacgga tgctatggac tactggggtc aaggaacctc agtcaccgtc     360
tcctca                                                                366
```

<210> SEQ ID NO 59

```
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ile Phe
            20                  25                  30

Cys Ile His Trp Val Gln Gln Arg Pro Gly Arg Gly Leu Glu Trp Ile
        35                  40                  45

Gly Arg Ile Asp Pro Ser Ser Gly Gly Thr Lys Tyr Asn Glu Lys Phe
    50                  55                  60

Glu Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Glu Asp Leu Leu Val Arg Thr Asp Ala Met Asp Tyr Trp
            100                 105                 110

Gly Gln Gly Thr Ser Val Thr Val Ser Ser
        115                 120

<210> SEQ ID NO 60
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
caggtccaac tgcagcagcc tggggctgaa cttgtgaagc ctggggcttc agtgaagctg      60
tcctgcaagg cttctggcta caccttcagt attttctgtg tacactgggt gcaacagagg     120
cctggacgag gccttgagtg gattggaagg attgatccta gtagtggtgg tactaagtac     180
aatgagaagt tcgagagcaa ggccacactg actgtagaca atcgtccag cacagcctac      240 atgcagctca gcagcctgac acctgaggac tctgcggtct attattgtgc aagaggggag     300
gatttattag tacggacgga tgctctggac tactggggtc aaggatcctc agtcaccgtc     360
tcctca                                                                366

<210> SEQ ID NO 61
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ile Phe
            20                  25                  30

Cys Val His Trp Val Gln Gln Arg Pro Gly Arg Gly Leu Glu Trp Ile
        35                  40                  45

Gly Arg Ile Asp Pro Ser Ser Gly Gly Thr Lys Tyr Asn Glu Lys Phe
```

```
                 50                  55                  60

Glu Ser Lys Ala Thr Leu Thr Val Asp Lys Ser Ser Thr Ala Tyr
 65                  70                  75                  80

Met Gln Leu Ser Ser Leu Thr Pro Glu Asp Ser Ala Val Tyr Tyr Cys
                 85                  90                  95

Ala Arg Gly Glu Asp Leu Leu Val Arg Thr Asp Ala Leu Asp Tyr Trp
                100                 105                 110

Gly Gln Gly Ser Ser Val Thr Val Ser Ser
            115                 120

<210> SEQ ID NO 62
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
caggtccaac tgcagcagcc tggggactgag cttgtgaagc ctggggcttc agtgaagctg    60
tcctgcaagg cttctggcta caccttcagt atcttctgta cactgggt gcaacagagg      120 cctggacgag gccttgagtg gattggaagg attgatccta gtagtggtgg cactaaatat    180
aatgagaggt tcgaaaacaa ggccacactg actgtagaca atcctccag cacagcctac    240 atgcagctca gcagtctgac atttgaggac tctgcggtct attattgtgc aagaggggag    300
gatttattag tacggacgga tgctatggac tactggggtc aaggaacctc agtcaccgtc    360
tcctca                                                              366

<210> SEQ ID NO 63
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Gln Gln Pro Gly Thr Glu Leu Val Lys Pro Gly Ala
  1               5                  10                  15

Ser Val Lys Leu Ser Cys Lys Ala Ser Gly Tyr Thr Phe Ser Ile Phe
                 20                  25                  30

Cys Ile His Trp Val Gln Gln Arg Pro Gly Arg Gly Leu Glu Trp Ile
                 35                  40                  45

Gly Arg Ile Asp Pro Ser Ser Gly Gly Thr Lys Tyr Asn Glu Arg Phe
     50                  55                  60

Glu Asn Lys Ala Thr Leu Thr Val Asp Lys Ser Ser Thr Ala Tyr
 65                  70                  75                  80

Met Gln Leu Ser Ser Leu Thr Phe Glu Asp Ser Ala Val Tyr Tyr Cys
                 85                  90                  95

Ala Arg Gly Glu Asp Leu Leu Val Arg Thr Asp Ala Met Asp Tyr Trp
                100                 105                 110

Gly Gln Gly Thr Ser Val Thr Val Ser Ser
            115                 120

<210> SEQ ID NO 64
<211> LENGTH: 366
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 64

```
caggtccaac tgcagcagcc tggggctgag cttgtgaagc ctggggcttc agtgaagctg      60
tcctgtaagg cttctggcta ctccttcagc accttcttta tacactggat acagcagagg    120
cctgggcgag gccttgagtg gattggaagg attgatccta atagtggtgg tactaagtac    180
aatgagaagt tcgagagtaa ggccacactg actgttgaca aaccctccag tacagcctac    240
atgcacctca gcagcctgac atctgaggac tctgcggtct attattgtgc aagaggggag    300
gatttattga tacggacgga tgctatggac tactggggtc aaggaacctc agtcaccgtc    360
tcctca                                                               366
```

<210> SEQ ID NO 65
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Ser Thr Phe
            20                  25                  30

Phe Ile His Trp Ile Gln Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Glu Ser Lys Ala Thr Leu Thr Val Asp Lys Pro Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Gly Glu Asp Leu Leu Ile Arg Thr Asp Ala Met Asp Tyr Trp
            100                 105                 110

Gly Gln Gly Thr Ser Val Thr Val Ser Ser
        115                 120
```

<210> SEQ ID NO 66
<211> LENGTH: 366
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 66

```
caggtccaac tgcagcagcc tggggctgag cttgtgaagc ctggggcttc agtgaagctg      60
tcctgcaagg cttctggcta ctccttcagt accttcttta tacactggat acagcagagg    120
cctgggcgag gccttgagtg gattggaagg attgatccta atagtggtgc tactaaatac    180
aatgagaagt tcgagagtaa ggccacactg actgttgaca aaccctccag tacagcctac    240
atgcacctca gcagcctgac atctgaggac tctgcggtct attattgtgc aagaggggag    300
gatttattga ttcggacgga tgctctggac tactggggtc aaggaacctc agtcaccgtc    360
tcctca                                                               366
```

<210> SEQ ID NO 67
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Ser Thr Phe
            20                  25                  30

Phe Ile His Trp Ile Gln Gln Arg Pro Gly Arg Gly Leu Glu Trp Ile
        35                  40                  45

Gly Arg Ile Asp Pro Asn Ser Gly Ala Thr Lys Tyr Asn Glu Lys Phe
    50                  55                  60

Glu Ser Lys Ala Thr Leu Thr Val Asp Lys Pro Ser Thr Ala Tyr
65                  70                  75                  80

Met His Leu Ser Ser Leu Thr Ser Glu Asp Ser Ala Val Tyr Tyr Cys
                85                  90                  95

Ala Arg Gly Glu Asp Leu Leu Ile Arg Thr Asp Ala Leu Asp Tyr Trp
            100                 105                 110

Gly Gln Gly Thr Ser Val Thr Val Ser Ser
        115                 120

<210> SEQ ID NO 68
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
caggtccaac tgcagcagcc tggggctgag cttgtgaagc ctggggcttc agtgaagctg      60
tcctgcaagg cttctggcta caccttcagt accttcttaa tacactgggt gcagcagagg     120
cctggacgag gccttgagtg gattggaagg attgatccta atagtggtgg tactaagtac     180
aatgagaagt tcgagaggaa ggccacactg actgtagaca accctccag cacagcctac      240 atgcagctca gcagcctgac atctgaggac tctgcggtct attattgtgc aagaggggag     300
gatttattac tacggacgga tgctatggac tactggggtc aaggaacctc agtcaccgtc     360
tcctca                                                                366

<210> SEQ ID NO 69
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Thr Phe
            20                  25                  30

Leu Ile His Trp Val Gln Gln Arg Pro Gly Arg Gly Leu Glu Trp Ile

```
                    35                  40                  45
Gly Arg Ile Asp Pro Asn Ser Gly Gly Thr Lys Tyr Asn Glu Lys Phe
        50                  55                  60

Glu Arg Lys Val Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Glu Asp Leu Leu Leu Arg Thr Asp Ala Met Asp Tyr Trp
            100                 105                 110

Gly Gln Gly Thr Ser Val Thr Val Ser Ser
            115                 120

<210> SEQ ID NO 70
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
caggtccaac tgcagcagcc tgggactgaa tttgtgaagc ctggggcttc agtgaagctg      60
tcctgcgagg cttctggcta caccttcatc acctactgga tgcactgggt gaagcagagg    120
cctggacgag gccttgagtg gattggaggg attgatccta atagtggtgt tattaagtac    180
aatgagaagt tcaagagtaa ggccacactg actgtagaca aacctccag cacagcctac     240 atgcagctca gcagcctgac atctgaggac tctgcggtct actattgtgc aagaggggag    300
gatttattaa tacggacgga tgctatggac tactggggtc aaggaacctc agtcaccgtc    360
tcctca                                                              366

<210> SEQ ID NO 71
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Gln Gln Pro Gly Thr Glu Phe Val Lys Pro Gly Ala
1               5                   10                  15

Ser Val Lys Leu Ser Cys Glu Ala Ser Gly Tyr Thr Phe Ile Thr Tyr
            20                  25                  30

Trp Met His Trp Val Lys Gln Arg Pro Gly Arg Gly Leu Glu Trp Ile
        35                  40                  45

Gly Gly Ile Asp Pro Asn Ser Gly Val Ile Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Glu Asp Leu Leu Ile Arg Thr Asp Ala Met Asp Tyr Trp
            100                 105                 110

Gly Gln Gly Thr Ser Val Thr Val Ser Ser
            115                 120

<210> SEQ ID NO 72
```

```
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
caggtccaac tgcagcagcc tggggctgag tttgtgaagc ctggggcttc agtgaagctg    60
tcctgcaagg cttctggcta ctccttcagt accttctgta tacactgggt gcagcagagg   120
cctgggcgag gccttgagtg gattggaagg attgatccta atagtggtgg tactaaatac   180
aatgagaagt tcgagagtaa ggccacactg actatagaca aaccctccag tacagcctac   240
gtgcacctca gcagcctgac atctgaggac tctgcggtct attattgtgc aagaggggag   300
gatttattga tacggacgga tgctatggac tactggggtc aaggaacctc agtcaccgtc   360
tcctca                                                              366

<210> SEQ ID NO 73
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Gln Pro Gly Ala Glu Phe Val Lys Pro Gly Ala
1               5                   10                  15

Ser Val Lys Leu Ser Cys Lys Ala Ser Gly Tyr Ser Phe Ser Thr Phe
            20                  25                  30

Cys Ile His Trp Val Gln Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Glu Ser Lys Ala Thr Leu Thr Ile Asp Lys Pro Ser Ser Thr Ala Tyr
65                  70                  75                  80

Val His Leu Ser Ser Leu Thr Ser Glu Asp Ser Ala Val Tyr Tyr Cys
                85                  90                  95

Ala Arg Gly Glu Asp Leu Leu Ile Arg Thr Asp Ala Met Asp Tyr Trp
            100                 105                 110

Gly Gln Gly Thr Ser Val Thr Val Ser Ser
        115                 120

<210> SEQ ID NO 74
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
caggttcagc tgcagcagtc tggacctgag gtggtgaggc ctggggcttc agtgaagata    60
tcctgcaagg ctcctgacca tattttcagt atccactgga tgcagtgggt aagacagagg   120
cctggaccgg gccttgagtg gattggagag atttttcctg gaagtggtac tactgattat   180
aatgagaaat tcaagggcaa ggccacagtg acggtagata gaggctccag gtcagcctac   240
atgcagttca acagcctgac atctgaggac tctgcggtct atttctgtgc aagcggagcc   300
```
tttgactact ggggccaagg caccactctc acagtctctt ca     342

<210> SEQ ID NO 75
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Gln Gln Ser Gly Pro Glu Val Val Arg Pro Gly Ala
1               5                   10                  15

Ser Val Lys Ile Ser Cys Lys Ala Pro Asp His Ile Phe Ser Ile His
            20                  25                  30

Trp Met Gln Trp Val Arg Gln Arg Pro Gly Pro Gly Leu Glu Trp Ile
        35                  40                  45

Gly Glu Ile Phe Pro Gly Ser Gly Thr Thr Asp Tyr Asn Glu Lys Phe
    50                  55                  60

Lys Gly Lys Ala Thr Val Thr Val Asp Arg Gly Ser Arg Ser Ala Tyr
65                  70                  75                  80

Met Gln Phe Asn Ser Leu Thr Ser Glu Asp Ser Ala Val Tyr Phe Cys
                85                  90                  95

Ala Ser Gly Ala Phe Asp Tyr Trp Gly Gln Gly Thr Thr Leu Thr Val
            100                 105                 110

Ser Ser

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ala Ser Gln Asp Ile Gly Asn Arg Leu Ser
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Ala Ser Gln Asp Ile Gly Asn Arg Leu His
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Ala Ser Gln Asp Ile Gly Asn Arg Leu Pro
1               5                   10

-continued

```
<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ala Ser Gln Asp Ile Gly Asn Arg Leu Arg
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ala Ser Gln Asp Ile Gly Asn Arg Leu Met
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Ser Gly Tyr Ser Phe Ser Thr Phe Phe Ile His
1               5                   10

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Ser Trp Leu Gln Gln Glu Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys
            100                 105

<210> SEQ ID NO 83
<211> LENGTH: 107
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 83

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asn Arg
             20                  25                  30

Leu Asn Trp Leu Gln Gln Glu Pro Gly Lys Ala Pro Lys Arg Leu Ile
         35                  40                  45

Tyr Ala Thr Ser Ser Leu Asp Ser Gly Val Pro Lys Arg Phe Ser Ser
     50                  55                  60

Ser Arg Ser Gly Thr Glu Phe Thr Leu Thr Ile Ser Ser Leu Gln Pro
 65                  70                  75                  80

Glu Asp Phe Val Asp Tyr Tyr Cys Leu Gln Tyr Ala Ser Ser Pro Phe
                 85                  90                  95

Thr Phe Gly Thr Gly Thr Lys Leu Glu Ile Lys
            100                 105

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asn Arg
             20                  25                  30

Leu Asn Trp Tyr Gln Gln Glu Pro Gly Lys Ala Pro Lys Arg Leu Ile
         35                  40                  45

Tyr Ala Thr Ser Ser Leu Asp Ser Gly Val Pro Lys Arg Phe Ser Gly
     50                  55                  60

Ser Arg Ser Gly Thr Glu Phe Thr Leu Thr Ile Ser Ser Leu Gln Pro
 65                  70                  75                  80

Glu Asp Phe Val Asp Tyr Tyr Cys Leu Gln Tyr Ala Ser Ser Pro Phe
                 85                  90                  95

Thr Phe Gly Thr Gly Thr Lys Leu Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asn Arg
             20                  25                  30

Leu His Trp Tyr Gln Gln Lys Pro Gly Lys Ala Pro Lys Arg Leu Ile
         35                  40                  45

Tyr Ala Thr Ser Ser Leu Asp Ser Gly Val Pro Lys Arg Phe Ser Gly
```

```
                50                  55                  60
Ser Arg Ser Gly Thr Glu Phe Thr Leu Thr Ile Ser Ser Leu Gln Pro
 65                  70                  75                  80

Glu Asp Phe Val Thr Tyr Tyr Cys Leu Gln Tyr Ala Ser Ser Pro Phe
                 85                  90                  95

Thr Phe Gly Gln Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asn Arg
             20                  25                  30

Leu Asn Trp Tyr Gln Gln Lys Pro Gly Lys Ala Pro Lys Arg Leu Ile
         35                  40                  45

Tyr Ala Thr Ser Ser Leu Asp Ser Gly Val Pro Lys Arg Phe Ser Gly
     50                  55                  60

Ser Arg Ser Gly Thr Glu Phe Thr Leu Thr Ile Ser Ser Leu Gln Pro
 65                  70                  75                  80

Glu Asp Phe Val Asp Tyr Tyr Cys Leu Gln Tyr Ala Ser Ser Pro Phe
                 85                  90                  95

Thr Phe Gly Thr Gly Thr Lys Leu Glu Ile Lys
            100                 105

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asn Arg
             20                  25                  30

Leu Asn Trp Tyr Gln Gln Lys Pro Gly Lys Ala Pro Lys Arg Leu Ile
         35                  40                  45

Tyr Ala Thr Ser Ser Leu Asp Ser Gly Val Pro Ser Arg Phe Ser Gly
     50                  55                  60

Ser Arg Ser Gly Thr Glu Phe Thr Leu Thr Ile Ser Ser Leu Gln Pro
 65                  70                  75                  80

Glu Asp Phe Val Asp Tyr Tyr Cys Leu Gln Tyr Ala Ser Ser Pro Phe
                 85                  90                  95

Thr Phe Gly Thr Gly Thr Lys Leu Glu Ile Lys
            100                 105

<210> SEQ ID NO 88
<211> LENGTH: 107
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Pro Trp Leu Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Val Asp Tyr Tyr Cys Leu Gln Tyr Ala Ser Ser Pro Phe
                85                  90                  95

Thr Phe Gly Thr Gly Thr Lys Leu Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Arg Trp Tyr Gln Gln Lys Pro Gly Lys Ala Pro Lys Arg Leu Ile
        35                  40                  45

```
Tyr Ala Thr Ser Ser Leu Asp Ser Gly Val Pro Ser Arg Phe Ser Gly
            50                  55                  60

Ser Arg Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Ala Ser Ser Pro Phe
                 85                  90                  95

Thr Phe Gly Gln Gly Thr Lys Leu Glu Ile Lys
                100                 105

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asn Arg
            20                  25                  30

Leu Met Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
 65                  70                  75                  80

Glu Asp Phe Val Thr Tyr Tyr Cys Leu Gln Tyr Ala Ser Ser Pro Phe
                 85                  90                  95

Thr Phe Gly Thr Gly Thr Lys Leu Glu Ile Lys
                100                 105

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Arg Ser Tyr Pro Arg
                 85                  90                  95

Thr Phe Gly Gln Gly Thr Lys Leu Glu Ile Lys
                100                 105

<210> SEQ ID NO 93
```

<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Arg Ser Tyr Pro Arg
                85                  90                  95

Thr Phe Gly Gln Gly Thr Lys Leu Glu Ile Lys
            100                 105

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Leu Gln Tyr Arg Ser Tyr Pro Arg
                85                  90                  95

Thr Phe Gly Gly Gly Thr Lys Leu Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
            35                  40                  45

Phe Ser Lys Ser Asn Arg Tyr Thr Gly Val Pro Asp Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Asp Tyr Tyr Cys Leu Gln Tyr Arg Ser Tyr Pro Arg
                 85                  90                  95

Thr Phe Gly Gln Gly Thr Lys Leu Glu Ile Lys
                100                 105

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Ala Gly Ile Asp
                 20                  25                  30

Val Ala Trp Phe Gln Gln Lys Pro Gly Lys Ala Pro Lys Leu Leu Ile
            35                  40                  45

Phe Ser Lys Ser Asn Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Arg Ser Tyr Pro Arg
                 85                  90                  95

Thr Phe Gly Gln Gly Thr Lys Leu Glu Ile Lys
                100                 105

<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Val Met Thr Gln Ser Pro Ser Ser Leu Ser Ala Ser Val Gly
 1               5                  10                  15

Asp Arg Val Ser Ile Thr Cys Lys Ala Ser Gln Asn Ala Gly Ile Asp
                 20                  25                  30

Val Ala Trp Phe Gln Gln Lys Pro Gly Lys Ala Pro Lys Leu Leu Ile
            35                  40                  45

Tyr Ser Lys Ser Asn Arg Tyr Thr Gly Val Pro Asp Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Arg Ser Tyr Pro Arg
                 85                  90                  95

Thr Phe Gly Gln Gly Thr Lys Leu Glu Ile Lys
                100                 105

<210> SEQ ID NO 98
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Ser Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 99
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

```
Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80
```

```
Asp Glu Ala Asp Tyr Tyr Cys Ser Ser Arg Asp Ser Ser Gly Asn His
            85                  90                  95

Trp Val Phe Gly Gly Gly Thr Glu Leu Thr Val Leu Gly Gln Pro Lys
        100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
        210

<210> SEQ ID NO 100
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Val Gln Ser Gly Ala Glu Val Lys Lys Pro Gly Ser
1               5                   10                  15

Ser Val Lys Val Ser Cys Lys Ala Pro Asp His Ile Phe Ser Ile His
            20                  25                  30

Trp Met Gln Trp Val Arg Gln Arg Pro Gly Gln Gly Leu Glu Trp Ile
        35                  40                  45

Gly Glu Ile Phe Pro Gly Ser Gly Thr Thr Asp Tyr Asn Glu Lys Phe
    50                  55                  60

Lys Gly Lys Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Ser Gly Ala Phe Asp Tyr Trp Gly Gln Gly Thr Thr Val Thr Val
            100                 105                 110

Ser Ser

<210> SEQ ID NO 101
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Pro Asp His Ile Phe Ser Ile His
            20                  25                  30

Trp Met Gln Trp Val Arg Gln Ala Pro Gly Gln Gly Leu Glu Trp Met
```

```
                    35                  40                  45

Gly Glu Ile Phe Pro Gly Ser Gly Thr Thr Asp Tyr Asn Glu Lys Phe
             50                  55                  60

Lys Gly Lys Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Gly Ala Phe Asp Tyr Trp Gly Gln Gly Thr Thr Val Thr Val
            100                 105                 110

Ser Ser

<210> SEQ ID NO 102
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Val Gln Ser Gly Ala Glu Val Lys Lys Pro Gly Ser
 1               5                  10                  15

Ser Val Lys Ile Ser Cys Lys Ala Pro Asp His Ile Phe Ser Ile His
                20                  25                  30

Trp Met Gln Trp Val Arg Gln Arg Pro Gly Gln Gly Leu Glu Trp Ile
            35                  40                  45

Gly Glu Ile Phe Pro Gly Ser Gly Thr Thr Asp Tyr Asn Glu Lys Phe
         50                  55                  60

Lys Gly Lys Val Thr Val Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Gly Ala Phe Asp Tyr Trp Gly Gln Gly Thr Thr Val Thr Val
            100                 105                 110

Ser Ser

<210> SEQ ID NO 103
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Val Gln Ser Gly Ala Glu Val Lys Lys Pro Gly Ser
 1               5                  10                  15

Ser Val Lys Ile Ser Cys Lys Ala Ser Asp His Ile Phe Ser Ile His
                20                  25                  30

Trp Met Gln Trp Val Arg Gln Arg Pro Gly Gln Gly Leu Glu Trp Ile
            35                  40                  45

Gly Glu Ile Phe Pro Gly Ser Gly Thr Thr Asp Tyr Asn Glu Lys Phe
         50                  55                  60

Lys Gly Lys Val Thr Val Thr Val Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95
```

Ala Arg Gly Ala Phe Asp Tyr Trp Gly Gln Gly Thr Thr Val Thr Val
            100                 105                 110

Ser Ser

<210> SEQ ID NO 104
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Val Gln Ser Gly Ala Glu Val Lys Lys Pro Gly Ser
1               5                   10                  15

Ser Val Lys Val Ser Cys Lys Ala Pro Asp His Ile Phe Ser Ile His
            20                  25                  30

Trp Met Gln Trp Val Arg Gln Arg Pro Gly Gln Gly Leu Glu Trp Met
        35                  40                  45

Gly Glu Ile Phe Pro Gly Ser Gly Thr Thr Asp Tyr Asn Glu Lys Phe
    50                  55                  60

Lys Gly Lys Val Thr Val Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Ser Gly Ala Phe Asp Tyr Trp Gly Gln Gly Thr Thr Val Thr Val
            100                 105                 110

Ser Ser

<210> SEQ ID NO 105
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Val Gln Leu Val Gln Ser Gly Ala Glu Val Lys Lys Pro Gly Ser
1               5                   10                  15

Ser Val Lys Ile Ser Cys Lys Ala Ser Asp His Ile Phe Ser Ile His
            20                  25                  30

Trp Met Gln Trp Val Arg Gln Ala Pro Gly Gln Gly Leu Glu Trp Met
        35                  40                  45

Gly Glu Ile Phe Pro Gly Ser Gly Thr Thr Asp Tyr Asn Glu Lys Phe
    50                  55                  60

Lys Gly Lys Val Thr Val Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Ser Gly Ala Phe Asp Tyr Trp Gly Gln Gly Thr Thr Val Thr Val
            100                 105                 110

Ser Ser

<210> SEQ ID NO 106
<211> LENGTH: 114
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 106

Gln Val Gln Leu Val Gln Ser Gly Ala Glu Val Lys Lys Pro Gly Ser
1               5                   10                  15

Ser Val Lys Val Ser Cys Lys Ala Pro Asp His Ile Phe Ser Ile His
            20                  25                  30

Trp Met Gln Trp Val Arg Gln Ala Pro Gly Gln Gly Leu Glu Trp Ile
        35                  40                  45

Gly Glu Ile Phe Pro Gly Ser Gly Thr Thr Asp Tyr Asn Glu Lys Phe
    50                  55                  60

Lys Gly Arg Ala Thr Val Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Ser Gly Ala Phe Asp Tyr Trp Gly Gln Gly Thr Thr Val Thr Val
            100                 105                 110

Ser Ser

<210> SEQ ID NO 107
<211> LENGTH: 114
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Asp His Ile Phe Ser Ile His
            20                  25                  30

Trp Met Gln Trp Val Arg Gln Ala Pro Gly Gln Gly Leu Glu Trp Met
        35                  40                  45

Gly Glu Ile Phe Pro Gly Ser Gly Thr Thr Asp Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Phe Asp Tyr Trp Gly Gln Gly Thr Thr Val Thr Val
            100                 105                 110

Ser Ser

<210> SEQ ID NO 108
<211> LENGTH: 114
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 108

Gln Val Gln Leu Val Gln Ser Gly Ala Glu Val Lys Lys Pro Gly Ser
1               5                   10                  15

Ser Val Lys Ile Ser Cys Lys Ala Pro Asp His Ile Phe Ser Ile His
            20                  25                  30

```
Trp Met Gln Trp Val Arg Gln Ala Pro Gly Gln Gly Leu Glu Trp Ile
        35                  40                  45

Gly Glu Ile Phe Pro Gly Ser Gly Thr Thr Asp Tyr Asn Glu Lys Phe
 50                  55                  60

Lys Gly Lys Val Thr Val Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Gly Ala Phe Asp Tyr Trp Gly Gln Gly Thr Thr Val Thr Val
                100                 105                 110

Ser Ser

<210> SEQ ID NO 109
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Val Gln Ser Gly Ala Glu Val Lys Lys Pro Gly Ser
 1               5                  10                  15

Ser Val Lys Ile Ser Cys Lys Ala Ser Asp His Ile Phe Ser Ile His
                 20                  25                  30

Trp Met Gln Trp Val Arg Gln Arg Pro Gly Gln Gly Leu Glu Trp Ile
        35                  40                  45

Gly Glu Ile Phe Pro Gly Ser Gly Thr Thr Asp Tyr Asn Glu Lys Phe
 50                  55                  60

Lys Gly Lys Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Gly Ala Phe Asp Tyr Trp Gly Gln Gly Thr Thr Val Thr Val
                100                 105                 110

Ser Ser

<210> SEQ ID NO 110
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Ser Thr Phe
                 20                  25                  30

Phe Ile His Trp Ile Gln Gln Arg Pro Gly Gln Gly Leu Glu Trp Met
        35                  40                  45

Gly Arg Ile Asp Pro Asn Ser Gly Ala Thr Lys Tyr Asn Glu Lys Phe
 50                  55                  60

Glu Ser Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95
```

```
Ala Arg Gly Glu Asp Leu Leu Ile Arg Thr Asp Ala Leu Asp Tyr Trp
            100                 105                 110

Gly Gln Gly Thr Leu Val Thr Val Ser Ser
        115                 120

<210> SEQ ID NO 111
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Thr Phe
            20                  25                  30

Phe Ile His Trp Ile Gln Gln Arg Pro Gly Gln Gly Leu Glu Trp Met
        35                  40                  45

Gly Arg Ile Asp Pro Asn Ser Gly Ala Thr Lys Tyr Asn Glu Lys Phe
    50                  55                  60

Glu Ser Lys Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Asp Leu Leu Ile Arg Thr Asp Ala Leu Asp Tyr Trp
            100                 105                 110

Gly Gln Gly Thr Ser Val Thr Val Ser Ser
        115                 120

<210> SEQ ID NO 112
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Thr Phe
            20                  25                  30

Phe Ile His Trp Val Arg Gln Arg Pro Gly Gln Gly Leu Glu Trp Ile
        35                  40                  45

Gly Arg Ile Asp Pro Asn Ser Gly Ala Thr Lys Tyr Asn Glu Lys Phe
    50                  55                  60

Glu Ser Lys Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Asp Leu Leu Ile Arg Thr Asp Ala Leu Asp Tyr Trp
            100                 105                 110

Gly Gln Gly Thr Ser Val Thr Val Ser Ser
        115                 120

<210> SEQ ID NO 113
```

<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Thr Phe
            20                  25                  30

Phe Ile His Trp Val Gln Gln Arg Pro Gly Gln Gly Leu Glu Trp Met
        35                  40                  45

Gly Arg Ile Asp Pro Asn Ser Gly Ala Thr Lys Tyr Asn Glu Lys Phe
    50                  55                  60

Glu Ser Lys Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Asp Leu Leu Ile Arg Thr Asp Ala Leu Asp Tyr Trp
            100                 105                 110

Gly Gln Gly Thr Leu Val Thr Val Ser Ser
        115                 120

<210> SEQ ID NO 114
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Thr Phe
            20                  25                  30

Phe Ile His Trp Val Arg Gln Ala Pro Gly Gln Gly Leu Glu Trp Ile
        35                  40                  45

Gly Arg Ile Asp Pro Asn Ser Gly Ala Thr Lys Tyr Asn Glu Lys Phe
    50                  55                  60

Glu Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Asp Leu Leu Ile Arg Thr Asp Ala Leu Asp Tyr Trp
            100                 105                 110

Gly Gln Gly Thr Ser Val Thr Val Ser Ser
        115                 120

<210> SEQ ID NO 115
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Thr Phe
            20                  25                  30

Phe Ile His Trp Val Arg Gln Arg Pro Gly Gln Gly Leu Glu Trp Met
        35                  40                  45

Gly Arg Ile Asp Pro Asn Ser Gly Ala Thr Lys Tyr Asn Glu Lys Phe
    50                  55                  60

Glu Ser Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Asp Leu Leu Ile Arg Thr Asp Ala Leu Asp Tyr Trp
            100                 105                 110

Gly Gln Gly Thr Ser Val Thr Val Ser Ser
            115                 120

<210> SEQ ID NO 116
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Asp Ile Leu Thr Gly Tyr Tyr Tyr Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Phe Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser Gln Glu
        260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 117
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Gln Gln Ser Gly Ala Glu Val Lys Lys Pro Gly Ser
1               5                   10                  15

Ser Val Arg Val Ser Cys Lys Ala Ser Gly Gly Thr Phe Asn Asn Asn
            20                  25                  30

Ala Ile Asn Trp Val Arg Gln Ala Pro Gly Gln Gly Leu Glu Trp Met
        35                  40                  45

Gly Gly Ile Ile Pro Met Phe Gly Thr Ala Lys Tyr Ser Gln Asn Phe
    50                  55                  60

Gln Gly Arg Val Ala Ile Thr Ala Asp Glu Ser Thr Gly Thr Ala Ser
65                  70                  75                  80

Met Glu Leu Ser Ser Leu Arg Ser Glu Asp Thr Ala Val Tyr Tyr Cys
                85                  90                  95

Ala Arg Ser Arg Asp Leu Leu Leu Phe Pro His His Ala Leu Ser Pro
            100                 105                 110

Trp Gly Arg Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
```

130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
450

<210> SEQ ID NO 118
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
gacatcaaaa tgacccagtc tccatcttcc atgtatgcat ctctaggaga gagagtcact    60
atcacttgca aggcgagtca ggacattaat agctatttaa cctggttcca gcagaaacca   120
gggaaatctc ctgagaccct gatctatcgt gcaaacagat tggtatctgg ggtcccatca   180

```
aggttcagtg gcagtggatc tgggcaagat tattctctca ccatcagcag cctggaatat    240
gaagatatgg gaatttattc ttgtctacag tatgatgagt ttccgtacac gttcggaggg    300
gggaccaagc tggaaataaa a                                              321
```

<210> SEQ ID NO 119
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Glu Thr Leu Ile
        35                  40                  45

Tyr Arg Ala Asn Arg Leu Val Ser Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Ser Cys Leu Gln Tyr Asp Glu Phe Pro Tyr
                85                  90                  95

Thr Phe Gly Gly Gly Thr Lys Leu Glu Ile Lys
            100                 105
```

<210> SEQ ID NO 120
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
gatgttgtga tgacccaaac tccactctcc ctgcctgtca gtcttggaga tcaagcctcc    60
atctcttgca gatgtagtca gagccttgta cacagtaatg gaaacacgta tttacattgg   120
tacctgcaga agccaggcca gtctccaaag ctcctgatct acaaagtttc cgaccgattt   180
tctggggtcc cagacaggtt cagtggcagt ggatcaggga cagatttcac actcaggatc   240
agcagagtgg aggctgacga tctgggagtt tatttctgct ctcaaagtac acatgttccg   300
ctcacgttcg gtgctgggac caagctggag ctgaaa                             336
```

<210> SEQ ID NO 121
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Asp Val Val Met Thr Gln Thr Pro Leu Ser Leu Pro Val Ser Leu Gly
1               5                   10                  15

Asp Gln Ala Ser Ile Ser Cys Arg Cys Ser Gln Ser Leu Val His Ser
            20                  25                  30

Asn Gly Asn Thr Tyr Leu His Trp Tyr Leu Gln Lys Pro Gly Gln Ser
```

```
                35                  40                  45
Pro Lys Leu Leu Ile Tyr Lys Val Ser Asp Arg Phe Ser Gly Val Pro
             50                  55                  60

Asp Arg Phe Ser Gly Ser Gly Ser Gly Thr Asp Phe Thr Leu Arg Ile
 65                  70                  75                  80

Ser Arg Val Glu Ala Asp Asp Leu Gly Val Tyr Phe Cys Ser Gln Ser
                 85                  90                  95

Thr His Val Pro Leu Thr Phe Gly Ala Gly Thr Lys Leu Glu Leu Lys
            100                 105                 110
```

<210> SEQ ID NO 122
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
gacattgtga tgacccagtc tcacaaattc atgtccacat cagtaggaga cagggtcacc     60
atcacctgca aggccagtca ggatgtggct actgctgtag cctggtatca acagaaacca    120
gggcaatctc ctaaactact aatttactgg gcatccaccc ggcacactgg agtccctgat    180
cgcttcacag gcagtggatc tgggacagat ttcactctca ccattagcaa tgtgcagtct    240
gaagacttgg caaattattt ctgtcagcaa tatagcaact atccgtacac gttcggaggg    300
gggaccacgc tggaaataaa a                                              321
```

<210> SEQ ID NO 123
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Asp Ile Val Met Thr Gln Ser His Lys Phe Met Ser Thr Ser Val Gly
 1               5                  10                  15

Asp Arg Val Thr Ile Thr Cys Lys Ala Ser Gln Asp Val Ala Thr Ala
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
     50                  55                  60

Ser Gly Ser Gly Thr Asp Phe Thr Leu Thr Ile Ser Asn Val Gln Ser
 65                  70                  75                  80

Glu Asp Leu Ala Asn Tyr Phe Cys Gln Gln Tyr Ser Asn Tyr Pro Tyr
                 85                  90                  95

Thr Phe Gly Gly Gly Thr Thr Leu Glu Ile Lys
            100                 105
```

<210> SEQ ID NO 124
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

```
gacatccaga tgacccagtc tccatcctcc ttatctgcct ctctgggaga aagagtcagt    60
ctcacttgtc gggcaagtca ggacattggt aataggttaa actggcttca gcaggcacca   120
gatggaacta ttaaacgcct gatctacgcc acatccagtt tagattctgg tgtccccaaa   180
aggttcagtg gcagtcggtc tgggtcagat tattctctca ccatcagcag ccttgaatct   240
gaagattttg tagactatta ctgtctacaa tatgctagtt atccattcac gttcggcacg   300
gggacaaaat tggaaataaa a                                             321
```

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Asn Arg
            20                  25                  30

Leu Asn Trp Leu Gln Gln Ala Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Tyr Pro Phe
                85                  90                  95

Thr Phe Gly Thr Gly Thr Lys Leu Glu Ile Lys
            100                 105
```

<210> SEQ ID NO 126
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

```
gacattgtga tgacccagtc tcaaaaattt ttgtccacaa caataggaga cagggtcagc    60
atcacctgca aggccagtca gaatgtgggt tctgctgtag tctggtatca acagaaacca   120
ggccaacctc ctaaactact gattacctca gcatccaatc ggtacagtgg agtcccagat   180
cgcttcacag gcagtggatc tgggacagat ttcactctca ccgttagcaa tgtgcagtct   240
gtagacctgg cagattattt ctgtcaacaa tatagcaact atcctctcac gttcggtgct   300
gggaccaagc tggagctgaa a                                             321
```

<210> SEQ ID NO 127
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Asp Ile Val Met Thr Gln Ser Gln Lys Phe Leu Ser Thr Thr Ile Gly
1               5                   10                  15

Asp Arg Val Ser Ile Thr Cys Lys Ala Ser Gln Asn Val Gly Ser Ala
                20                  25                  30

Val Val Trp Tyr Gln Gln Lys Pro Gly Gln Pro Pro Lys Leu Leu Ile
            35                  40                  45

Thr Ser Ala Ser Asn Arg Tyr Ser Gly Val Pro Asp Arg Phe Thr Gly
        50                  55                  60

Ser Gly Ser Gly Thr Asp Phe Thr Leu Thr Val Ser Asn Val Gln Ser
65                  70                  75                  80

Val Asp Leu Ala Asp Tyr Phe Cys Gln Gln Tyr Ser Asn Tyr Pro Leu
                85                  90                  95

Thr Phe Gly Ala Gly Thr Lys Leu Glu Leu Lys
            100                 105
```

<210> SEQ ID NO 128
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
gacattgtga tgacccagtc tcaaaaattt gtgtcgacaa gagttggaga cagggtcagc      60
atcacctgca aggccagtca gaatgtgggc gctgctgtag tctggtatca acagaaatca     120
ggccaacctc ctaaaactac tgattaggtc gcatccaatc ggtacattgg agtccctgat     180
cgcttcacag gcagtgggtc tgggacagat ttcactctca ccgttagcga tgtgcagtct     240
ggagacctgg cagattattt ctgtcagcaa tatagcaact atcctctcac gttcggtgct     300
gggaccaagc tggaactgac acgggctgat                                      330
```

<210> SEQ ID NO 129
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Asp Ile Val Met Thr Gln Ser Gln Lys Phe Val Ser Thr Arg Val Gly
1               5                   10                  15

Asp Arg Val Ser Ile Thr Cys Lys Ala Ser Gln Asn Val Gly Ala Ala
                20                  25                  30

Val Val Trp Tyr Gln Gln Lys Ser Gly Gln Pro Pro Lys Leu Leu Ile
            35                  40                  45

Arg Ser Ala Ser Asn Arg Tyr Ile Gly Val Pro Asp Arg Phe Thr Gly
        50                  55                  60

Ser Gly Ser Gly Thr Asp Phe Thr Leu Thr Val Ser Asp Val Gln Ser
65                  70                  75                  80

Gly Asp Leu Ala Asp Tyr Phe Cys Gln Gln Tyr Ser Asn Tyr Pro Leu
                85                  90                  95

Thr Phe Gly Ala Gly Thr Lys Leu Glu Leu Thr Arg Ala Asp
            100                 105                 110
```

<210> SEQ ID NO 130
<211> LENGTH: 321

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130

```
gacattgtga tgacccagtc tcaaaaattc atgtccacaa cagtaggaga cagggtcagc    60
atcacctgca aggccagtca gaatgtgggt agtgttgtag cctggtatca acagagacca   120
ggacaatctc ctacactact gatttactca gcatccaatc ggtacactgg agtccctgat   180
cgcttcactg gcagtggatc tgggacagat ttcactctca ccattagcaa tatgcagtcg   240
gaagacctgg cagattattt ctgtcagcaa tatagcagct atcctctcac gttcggtgct   300
gggaccaagc tggagctgaa a                                             321
```

<210> SEQ ID NO 131
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

```
Asp Ile Val Met Thr Gln Ser Gln Lys Phe Met Ser Thr Thr Val Gly
1               5                   10                  15
Asp Arg Val Ser Ile Thr Cys Lys Ala Ser Gln Asn Val Gly Ser Val
            20                  25                  30
Val Ala Trp Tyr Gln Gln Arg Pro Gly Gln Ser Pro Thr Leu Leu Ile
        35                  40                  45
Tyr Ser Ala Ser Asn Arg Tyr Thr Gly Val Pro Asp Arg Phe Thr Gly
    50                  55                  60
Ser Gly Ser Gly Thr Asp Phe Thr Leu Thr Ile Ser Asn Met Gln Ser
65                  70                  75                  80
Glu Asp Leu Ala Asp Tyr Phe Cys Gln Gln Tyr Ser Ser Tyr Pro Leu
                85                  90                  95
Thr Phe Gly Ala Gly Thr Lys Leu Glu Leu Lys
            100                 105
```

<210> SEQ ID NO 132
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
gacattgtga tgacccagtc tcaaaaattt gtgtcgacaa gagttggaga cagggtcagc    60
atcacctgca aggccagtca gaatgtgggc gctgctgtag tctggtatca acagaaatca   120
ggccaacctc ctaaactact gattaggtca gcatccaatc ggtacattgg agtccctgat   180
cgcttcacag gcagtgggtc tgggacagat ttcactctca ccgttagcga tgtgcagtct   240
ggagacctgg cagattattt ctgtcagcaa tatagtaact atcctctcac gttcggtgct   300
gggaccaagc tggaactgac a                                             321
```

<210> SEQ ID NO 133
<211> LENGTH: 107
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Val Met Thr Gln Ser Gln Lys Phe Val Ser Thr Arg Val Gly
1               5                   10                  15

Asp Arg Val Ser Ile Thr Cys Lys Ala Ser Gln Asn Val Gly Ala Ala
            20                  25                  30

Val Val Trp Tyr Gln Gln Lys Ser Gly Gln Pro Pro Lys Leu Leu Ile
        35                  40                  45

Arg Ser Ala Ser Asn Arg Tyr Ile Gly Val Pro Asp Arg Phe Thr Gly
    50                  55                  60

Ser Gly Ser Gly Thr Asp Phe Thr Leu Thr Val Ser Asp Val Gln Ser
65                  70                  75                  80

Gly Asp Leu Ala Asp Tyr Phe Cys Gln Gln Tyr Ser Asn Tyr Pro Leu
                85                  90                  95

Thr Phe Gly Ala Gly Thr Lys Leu Glu Leu Thr
            100                 105

<210> SEQ ID NO 134
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
gacattgtgc tgacacagtc tcctgcttcc ttacctgttt ctctggggca gagggccacc    60
atctcctgca gggccagcaa aggtgtcagt acatctagct atactttcat tcactggtac   120
caacagaaac tggacagcc gcccaaactc ctcatcaagt atgcatccaa cctagaatct   180
ggggtccctg ccaggttcag tggcagtggg tctgggacag acttcaccct caacatccat   240
cctgtggagg aggaggatgt tgcaacatat tactgtcagc acagtaggga gtttcctcgg   300
acgttcggtg gaggcaccaa gctggaaatc aaa                                333

<210> SEQ ID NO 135
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Ile Val Leu Thr Gln Ser Pro Ala Ser Leu Pro Val Ser Leu Gly
1               5                   10                  15

Gln Arg Ala Thr Ile Ser Cys Arg Ala Ser Lys Gly Val Ser Thr Ser
            20                  25                  30

Ser Tyr Thr Phe Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln His Ser Arg
                85                  90                  95
```

Glu Phe Pro Arg Thr Phe Gly Gly Gly Thr Lys Leu Glu Ile Lys
            100                 105                 110

<210> SEQ ID NO 136
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
gacatccaga tgactcagtc tccagcctcc ctatctgcat ctgtgggaga aactgtcacc    60
atcacatgtc gagcaagtgg gaatattcac aattatttag catggtatca gcagaaacag   120
ggaaaatctc ctcagctcct ggtctatagt gcaataacct tagcagatgg tgtgccatca   180
aggttcagtg gcagtggatc agaaacacaa tttctctca agatcaacag cctgcagcct   240
gaagattttg ggatttatta ctgtcaacat ttttggaata ctccgtacac gttcggaggg   300
gggaccaagc tggaaataaa a                                             321

<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Ser Ala Ile Thr Leu Ala Asp Gly Val Pro Ser Arg Phe Ser Gly
    50                  55                  60

Ser Gly Ser Glu Thr Gln Phe Ser Leu Lys Ile Asn Ser Leu Gln Pro
65                  70                  75                  80

Glu Asp Phe Gly Ile Tyr Tyr Cys Gln His Phe Trp Asn Thr Pro Tyr
                85                  90                  95

Thr Phe Gly Gly Gly Thr Lys Leu Glu Ile Lys
            100                 105

<210> SEQ ID NO 138
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gacattgtga tgacccagtc tcaaaaattt atgtccacaa cagttggaga cagggtcagc    60
atcacctgca aggccagtca gaatgtgggt gctgctgtag cctggtatca acagaaacca   120
ggccaacctc ctaaactact gattaggtca gcatccaatc ggtacattgg agtccctgat   180
cgcttcacag gcagtgggtc tgggacagat ttcactctca ccgttagcga tgtgcagtct   240
gtagacctgg cagattattt ctgtcagcaa tatagcaact atcctctcac gttcggtgct   300
gggaccaagc tggaactgac acgggctgat                                              330

<210> SEQ ID NO 139
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Ala Ala
            20                  25                  30

Val Ala Trp Tyr Gln Gln Lys Pro Gly Gln Pro Pro Lys Leu Leu Ile
        35                  40                  45

Arg Ser Ala Ser Asn Arg Tyr Ile Gly Val Pro Asp Arg Phe Thr Gly
    50                  55                  60

Ser Gly Ser Gly Thr Asp Phe Thr Leu Thr Val Ser Asp Val Gln Ser
65                  70                  75                  80

Val Asp Leu Ala Asp Tyr Phe Cys Gln Gln Tyr Ser Asn Tyr Pro Leu
                85                  90                  95

Thr Phe Gly Ala Gly Thr Lys Leu Glu Leu Thr Arg Ala Asp
            100                 105                 110

<210> SEQ ID NO 140
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
gacatcaaga tgacccagtc tccatcttcc atatatgcat ctctaggaga gagagtcact    60
atcacttgca aggcgagtca ggacattcat agctatttaa gttggttcca gcagaaacca   120
gggaaatctc ctaagaccct gatgtatcgt acaaatagat tggtagatgg ggtcccatca   180
aggttcagtg gcagtggatc tgggcaagat tattctctca ccatcaggag cctggaatat   240
gaagatatgg gaattatta ttgtctacag tatgatgaat ttccgtacac gttcggcggg    300
ggggccaagt tggaagtaaa a                                             321

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Lys Met Thr Gln Ser Pro Ser Ser Ile Tyr Ala Ser Leu Gly
1               5                   10                  15

Glu Arg Val Thr Ile Thr Cys Lys Ala Ser Gln Asp Ile His Ser Tyr
            20                  25                  30

Leu Ser Trp Phe Gln Gln Lys Pro Gly Lys Ser Pro Lys Thr Leu Met
        35                  40                  45

Tyr Arg Thr Asn Arg Leu Val Asp Gly Val Pro Ser Arg Phe Ser Gly

```
                    50                  55                  60

Ser Gly Ser Gly Gln Asp Tyr Ser Leu Thr Ile Arg Ser Leu Glu Tyr
 65                  70                  75                  80

Glu Asp Met Gly Asn Tyr Tyr Cys Leu Gln Tyr Asp Glu Phe Pro Tyr
                 85                  90                  95

Thr Phe Gly Gly Gly Ala Lys Leu Glu Val Lys
            100                 105

<210> SEQ ID NO 142
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
gacattgtga tgacccagtc tcaaaaattc atgtccacaa cagtaggaga cagggtcacc        60
atcacctgca aggccagtca gaatgtgggt agtgctgtag tctggtatca acagaaacca      120
ggacaatctc ctatattact gatttttctca gcatccaatc ggtacactgg agtccctgat     180
cgcatcacag gcagtgggtc tggggcagaa ttcactctca ccattagcag tgtgcagtct      240
gaagacctgg cagaatattt ctgtcagcaa tatagcagct atcctctcac gttcggtgct      300
gggaccaagc tggagctgaa a                                                 321

<210> SEQ ID NO 143
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Val Met Thr Gln Ser Gln Lys Phe Met Ser Thr Thr Val Gly
  1               5                  10                  15

Asp Arg Val Thr Ile Thr Cys Lys Ala Ser Gln Asn Val Gly Ser Ala
                 20                  25                  30

Val Val Trp Tyr Gln Gln Lys Pro Gly Gln Ser Pro Ile Leu Leu Ile
             35                  40                  45

Phe Ser Ala Ser Asn Arg Tyr Thr Gly Val Pro Asp Arg Ile Thr Gly
     50                  55                  60

Ser Gly Ser Gly Ala Glu Phe Thr Leu Thr Ile Ser Ser Val Gln Ser
 65                  70                  75                  80

Glu Asp Leu Ala Glu Tyr Phe Cys Gln Gln Tyr Ser Ser Tyr Pro Leu
                 85                  90                  95

Thr Phe Gly Ala Gly Thr Lys Leu Glu Leu Lys
            100                 105

<210> SEQ ID NO 144
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
gacatcaaga tgacccagtc tccatcttcc atatatgcat ctctaggaga gagagtcact        60
```

```
atcacttgca aggcgagtca ggacattaat agctatttaa gctggttcca gcagaaacca    120
gggaaatctc ctaagaccct gatgtatcgt gcaaacagat tggtagatgg ggtcccatca    180
aggttcagtg gcagtggatc tgggcaagat tattctctca ccatcagcag cctggaatat    240
gaagatatgg gaaattatta ttgtctacag tatgatgagt ttccgtacac gttcggaggg    300
ggggccaagc tggaaataaa a                                              321
```

<210> SEQ ID NO 145
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

```
Asp Ile Lys Met Thr Gln Ser Pro Ser Ser Ile Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Met
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Asn Tyr Tyr Cys Leu Gln Tyr Asp Glu Phe Pro Tyr
                85                  90                  95

Thr Phe Gly Gly Gly Ala Lys Leu Glu Ile Lys
            100                 105
```

<210> SEQ ID NO 146
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146

```
gacatccaga tgactcagtc tccagcctcc ctatctgtat ctgtgggaga aactgtcacc     60
atcacatgtc gatcaagtga gaatatttac agtagtttag catggtatca acagaaacag    120
ggaaaatctc ctcagctcct ggtctatgct gcaacaaact agcaaaagg tgtgccgtca     180 aggttcagtg gcagtggatc aggcacacag tattccctca agatcaacag cctacagtct    240
gaagattttg ggagttattt ctgtcaacat ttttggggta gtccattcgc gttcggctcg    300
gggacaaagt tggaaataaa a                                              321
```

<210> SEQ ID NO 147
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Asp Ile Gln Met Thr Gln Ser Pro Ala Ser Leu Ser Val Ser Val Gly
1               5                   10                  15
```

```
Glu Thr Val Thr Ile Thr Cys Arg Ser Ser Glu Asn Ile Tyr Ser Ser
                20                  25                  30

Leu Ala Trp Tyr Gln Gln Lys Gln Gly Lys Ser Pro Gln Leu Leu Val
        35                  40                  45

Tyr Ala Ala Thr Asn Leu Ala Lys Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Phe Cys Gln His Phe Trp Gly Ser Pro Phe
                85                  90                  95

Ala Phe Gly Ser Gly Thr Lys Leu Glu Ile Lys
            100                 105

<210> SEQ ID NO 148
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
gacattgtga tgacccagtc tcaaaaattt atgtccacaa caataggaga cagggtcagc      60
atcacctgca aggccagtca gaatgtgggt tctgctgtgg cctggtatca acagaaacca    120
ggacaacctc ccaaactact gatttactca acatccaatc ggtacactgg agtccctgat    180
cgcttcacag gcagtagatc tgggacagat ttcactctca ccgttagcaa tatgcagtct    240
gaagacctgg cagattattt ctgtcagcaa tatgccagct atcctctcac attcggtact    300
gggaccaagc tggagctgaa a                                              321

<210> SEQ ID NO 149
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Val Met Thr Gln Ser Gln Lys Phe Met Ser Thr Thr Ile Gly
1               5                   10                  15

Asp Arg Val Ser Ile Thr Cys Lys Ala Ser Gln Asn Val Gly Ser Ala
                20                  25                  30

Val Ala Trp Tyr Gln Gln Lys Pro Gly Gln Pro Pro Lys Leu Leu Ile
        35                  40                  45

Tyr Ser Thr Ser Asn Arg Tyr Thr Gly Val Pro Asp Arg Phe Thr Gly
    50                  55                  60

Ser Arg Ser Gly Thr Asp Phe Thr Leu Thr Val Ser Asn Met Gln Ser
65                  70                  75                  80

Glu Asp Leu Ala Asp Tyr Phe Cys Gln Gln Tyr Ala Ser Tyr Pro Leu
                85                  90                  95

Thr Phe Gly Thr Gly Thr Lys Leu Glu Leu Lys
            100                 105

<210> SEQ ID NO 150
<211> LENGTH: 333
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 150
gacattgtgc tgacacagtc tcctgcttcc ttagctttat ctctggggca gagggccacc      60
atctcatgca gggccaccaa aggggtcagt aaatctggct atagttatat gcactggtac     120
caacagaaac cagggcagcc acccaaactc ctcatctatc ttgcatccaa cctagaatct     180
ggggtccctg ccaggttcag tggcagtggg tctgggacag acttcaccct caatatccat     240
cctgtggagg aggaggatgt tgcaacctat tactgtcagc acagtaggga gcttccgctc     300
acgttcggtg ctgggaccaa gctggagctg aaa                                  333

<210> SEQ ID NO 151
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asp Ile Val Leu Thr Gln Ser Pro Ala Ser Leu Ala Leu Ser Leu Gly
1               5                   10                  15

Gln Arg Ala Thr Ile Ser Cys Arg Ala Thr Lys Gly Val Ser Lys Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 152
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
attgtgctga cccaatcttc agcttctttg gctgtgtctc tagggcagag ggccaccata      60
tcctgcagag ccagtgaaag tgttgatagt tatggcaata gtcttatgca ctggtaccag     120
cagaaaccag gacagccacc caaactcctc atctatattg catccaacct agaatctggg     180
gtccctgcca ggttcagtgg cagtgggtct aggacagact tcaccctcac cattgatcct     240
gtggaggctg atgatgctgc aacctattac tgtcagcaaa atagtgagga tcctcggacg     300
ttcggtggag gcaccaagct ggaaatcaaa                                      330

<210> SEQ ID NO 153
<211> LENGTH: 110
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 153

| Ile | Val | Leu | Thr | Gln | Ser | Ser | Ala | Ser | Leu | Ala | Val | Ser | Leu | Gly | Gln |
|---|---|---|---|---|---|---|---|---|---|---|---|---|---|---|---|
| 1 | | | | 5 | | | | | 10 | | | | | 15 | |

| Arg | Ala | Thr | Ile | Ser | Cys | Arg | Ala | Ser | Glu | Ser | Val | Asp | Ser | Tyr | Gly |
|---|---|---|---|---|---|---|---|---|---|---|---|---|---|---|---|
| | | | 20 | | | | | 25 | | | | | 30 | | |

| Asn | Ser | Leu | Met | His | Trp | Tyr | Gln | Gln | Lys | Pro | Gly | Gln | Pro | Pro | Lys |
|---|---|---|---|---|---|---|---|---|---|---|---|---|---|---|---|
| | | 35 | | | | | 40 | | | | | 45 | | | |

| Leu | Leu | Ile | Tyr | Ile | Ala | Ser | Asn | Leu | Glu | Ser | Gly | Val | Pro | Ala | Arg |
|---|---|---|---|---|---|---|---|---|---|---|---|---|---|---|---|
| | 50 | | | | | 55 | | | | | 60 | | | | |

| Phe | Ser | Gly | Ser | Gly | Ser | Arg | Thr | Asp | Phe | Thr | Leu | Thr | Ile | Asp | Pro |
|---|---|---|---|---|---|---|---|---|---|---|---|---|---|---|---|
| 65 | | | | | 70 | | | | | 75 | | | | | 80 |

| Val | Glu | Ala | Asp | Asp | Ala | Ala | Thr | Tyr | Tyr | Cys | Gln | Gln | Asn | Ser | Glu |
|---|---|---|---|---|---|---|---|---|---|---|---|---|---|---|---|
| | | | | 85 | | | | | 90 | | | | | 95 | |

| Asp | Pro | Arg | Thr | Phe | Gly | Gly | Gly | Thr | Lys | Leu | Glu | Ile | Lys |
|---|---|---|---|---|---|---|---|---|---|---|---|---|---|
| | | | 100 | | | | | 105 | | | | | 110 |

<210> SEQ ID NO 154
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154

```
aaaattgtgc tgacccaatc ttcagcttct ttggctgtgt ctctagggca gagggccacc      60
atatcctgca gagccagtga agtgttgat cgttatggca atagtcttat gcactggtac     120
cagcagaaac caggacagcc acccaaactc ctcatctata ttgcatccaa cctagaatct     180
ggggtccctg ccaggttcag tggcagtggg tctaggacag acttcaccct caccattgat     240
cctgtggagg ctgatgatgc tgcaacctat tactgtcagc aaaataatga ggatcctcgg     300
acgttcggtg gaggcaccaa gctggaaatc aaa                                  333
```

<210> SEQ ID NO 155
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

| Lys | Ile | Val | Leu | Thr | Gln | Ser | Ser | Ala | Ser | Leu | Ala | Val | Ser | Leu | Gly |
|---|---|---|---|---|---|---|---|---|---|---|---|---|---|---|---|
| 1 | | | | 5 | | | | | 10 | | | | | 15 | |

| Gln | Arg | Ala | Thr | Ile | Ser | Cys | Arg | Ala | Ser | Glu | Ser | Val | Asp | Arg | Tyr |
|---|---|---|---|---|---|---|---|---|---|---|---|---|---|---|---|
| | | | 20 | | | | | 25 | | | | | 30 | | |

| Gly | Asn | Ser | Leu | Met | His | Trp | Tyr | Gln | Gln | Lys | Pro | Gly | Gln | Pro | Pro |
|---|---|---|---|---|---|---|---|---|---|---|---|---|---|---|---|
| | | 35 | | | | | 40 | | | | | 45 | | | |

| Lys | Leu | Leu | Ile | Tyr | Ile | Ala | Ser | Asn | Leu | Glu | Ser | Gly | Val | Pro | Ala |
|---|---|---|---|---|---|---|---|---|---|---|---|---|---|---|---|
| | 50 | | | | | 55 | | | | | 60 | | | | |

| Arg | Phe | Ser | Gly | Ser | Gly | Ser | Arg | Thr | Asp | Phe | Thr | Leu | Thr | Ile | Asp |
|---|---|---|---|---|---|---|---|---|---|---|---|---|---|---|---|
| 65 | | | | | 70 | | | | | 75 | | | | | 80 |

| Pro | Val | Glu | Ala | Asp | Asp | Ala | Ala | Thr | Tyr | Tyr | Cys | Gln | Gln | Asn | Asn |
|---|---|---|---|---|---|---|---|---|---|---|---|---|---|---|---|
| | | | | 85 | | | | | 90 | | | | | 95 | |

| Glu | Asp | Pro | Arg | Thr | Phe | Gly | Gly | Gly | Thr | Lys | Leu | Glu | Ile | Lys |
|---|---|---|---|---|---|---|---|---|---|---|---|---|---|---|
| | | | 100 | | | | | 105 | | | | | 110 | |

<210> SEQ ID NO 156
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156

```
gacatcaaga tgaccccgtc tccttcttcc atgtatgcat ctctcggaga gagagtcact    60
atcacttgca aggcgagtca ggacattaat agatatttaa gctggttcca gcagaaacca   120
gggaaatctc ctaagaccct gatctatcgt gcaaatagat tggtagatgg ggtcccatca   180
aggttcagtg gcagtggatc tgggcaagat tactctctca ccatcagcag cctggagtat   240
gaagatatgg gaatttatta ttgtctacag tatgatgaat tccttacac gttcggaggg   300
gggaccaagc tggaaataaa a                                             321
```

<210> SEQ ID NO 157
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

```
Asp Ile Lys Met Thr Pro Ser Pro Ser Ser Met Tyr Ala Ser Leu Gly
1               5                  10                  15
Glu Arg Val Thr Ile Thr Cys Lys Ala Ser Gln Asp Ile Asn Arg Tyr
            20                  25                  30
Leu Ser Trp Phe Gln Gln Lys Pro Gly Lys Ser Pro Lys Thr Leu Ile
        35                  40                  45
Tyr Arg Ala Asn Arg Leu Val Asp Gly Val Pro Ser Arg Phe Ser Gly
    50                  55                  60
Ser Gly Ser Gly Gln Asp Tyr Ser Leu Thr Ile Ser Ser Leu Glu Tyr
65                  70                  75                  80
Glu Asp Met Gly Ile Tyr Tyr Cys Leu Gln Tyr Asp Glu Phe Pro Tyr
                85                  90                  95
Thr Phe Gly Gly Gly Thr Lys Leu Glu Ile Lys
            100                 105
```

<210> SEQ ID NO 158
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 158

```
aacattgtgc tgacccaatc tccagcttct ttggctgtgt ctctagggca gagggccacc    60
atatcctgca gagccagtga aagtgttgat aattatggca atagttttat gcactggtac   120
cagcagaaac aggacagcc acccaaactc ctcatctctc ttgcatccaa ctagaatct    180
ggggtccctg ccaggttcag tggcagtggg tctaggacag acttcaccct caccattgat   240
cctgtggagg ctgatgatgc tgcaacctat tactgtcagc aaaataatga ggatcctcgg   300
acgttcggtg gaggcaccaa gctggaaatc aaa                                333
```

<210> SEQ ID NO 159
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Ser Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Arg Thr Phe Gly Gly Gly Thr Lys Leu Glu Ile Lys
            100                 105                 110

<210> SEQ ID NO 160
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
gacattgtgc tgacacagtc tcctgcttcc ttaggtgtat ctctggggca gagggccacc    60
atctcttgca gggccaccaa aggggtcact aaatctggct atagttatat tcactggtac   120
caacagaaac caggacagcc acccaaactc ctcatctatc ttgcatccaa cctacaatct   180
ggggtccctg ccaggttcag tggcagtggg tctgggacag acttcaccct caacatccat   240
ccggtggagg aggaggatgc tgcaacctat tactgtcagc acagtaggga gcttccgctc   300
acgttcggtg ctgggaccaa gctggagctg aaa                                333

<210> SEQ ID NO 161
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Ile Val Leu Thr Gln Ser Pro Ala Ser Leu Gly Val Ser Leu Gly
1               5                   10                  15

Gln Arg Ala Thr Ile Ser Cys Arg Ala Thr Lys Gly Val Thr Lys Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asn Leu Gln Ser Gly Val Pro Ala
    50                  55                  60

Arg Phe Ser Gly Ser Gly Ser Gly Thr Asp Phe Thr Leu Asn Ile His

```
                65                  70                  75                  80
Pro Val Glu Glu Glu Asp Ala Ala Thr Tyr Tyr Cys Gln His Ser Arg
                    85                  90                  95

Glu Leu Pro Leu Thr Phe Gly Ala Gly Thr Lys Leu Glu Leu Lys
            100                 105                 110
```

<210> SEQ ID NO 162
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162

```
aacattgtgc tgacccaatc tccagcttct ttgcctgtgt ctctagggca gagggccacc    60
atgtcctgca gagccagtaa aagtgttgat agttatggca ctagttttat gcactggtac   120
caacacagac caggacagcc acccaaactc ctcatctctc ttgcatccaa cctagaatct   180
ggggtccctg gcaggttcag tggcagtggg tctaggacag acttcaccct caccattgat   240
cctgtggagc ctgatgatgc tgcaacctat tactgtcaac aaaataatga ggatcctcgg   300
acgttcggtg gaggcaccac gctggaaatc aaa                                333
```

<210> SEQ ID NO 163
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Asn Ile Val Leu Thr Gln Ser Pro Ala Ser Leu Pro Val Ser Leu Gly
1               5                   10                  15

Gln Arg Ala Thr Met Ser Cys Arg Ala Ser Lys Ser Val Asp Ser Tyr
            20                  25                  30

Gly Thr Ser Phe Met His Trp Tyr Gln His Arg Pro Gly Gln Pro Pro
        35                  40                  45

Lys Leu Leu Ile Ser Leu Ala Ser Asn Leu Glu Ser Gly Val Pro Gly
    50                  55                  60

Arg Phe Ser Gly Ser Gly Ser Arg Thr Asp Phe Thr Leu Thr Ile Asp
65                  70                  75                  80

Pro Val Glu Pro Asp Asp Ala Ala Thr Tyr Tyr Cys Gln Gln Asn Asn
                85                  90                  95

Glu Asp Pro Arg Thr Phe Gly Gly Gly Thr Thr Leu Glu Ile Lys
            100                 105                 110
```

<210> SEQ ID NO 164
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164

```
aacattgtgt tgacccaatc tccagcttct ttggctgtgt ctctaggaca gagggccacc    60
atatcctgca gaaccagtga aagtgttgat agttatggca atagtttat gttctggttc   120
cagcagaaac caggacaggc acccaaactc ctcatctttc ttacatccaa cctcgaatct   180
```

```
ggggtccctg ccaggttcag tggcagtggg tctaggacag acttcaccct caccattgat      240
cctgtggagg ctgatgatgc tgcaacctat tactgtcagc aaagtaatga ggatcctcgg      300
acgttcggtg gaggcaccaa gctggaaatc aaa                                   333
```

```
<210> SEQ ID NO 165
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165
```

```
Asn Ile Val Leu Thr Gln Ser Pro Ala Ser Leu Ala Val Ser Leu Gly
1               5                   10                  15

Gln Arg Ala Thr Ile Ser Cys Arg Thr Ser Glu Ser Val Asp Ser Tyr
            20                  25                  30

Gly Asn Ser Phe Met Phe Trp Phe Gln Gln Lys Pro Gly Gln Ala Pro
        35                  40                  45

Lys Leu Leu Ile Phe Leu Thr Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Ser Asn
                85                  90                  95

Glu Asp Pro Arg Thr Phe Gly Gly Gly Thr Lys Leu Glu Ile Lys
            100                 105                 110
```

```
<210> SEQ ID NO 166
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166
```

```
gacatcaaga tgaccccgtc tccttcttcc atgtatgcat ctctcggaga gagagtcact      60
atcacttgca aggcgagtca ggacattaat agctatttaa gttggttcca gcagaaacca      120
gggaaatctc ctaagaccct gatctatcgt gcaaatagat tggtagatgg ggtcccatca      180
aggttcagtg gcagtggatc tggccaagat tactctctca ccatcagcag cctggaatat      240
gaagatatgg gaatttatta ttgtctacag tatgatgaat tccttacac gtccggaggg       300 gggaccaagc tggaaataaa g                                                321
```

```
<210> SEQ ID NO 167
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167
```

```
Asp Ile Lys Met Thr Pro Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30
```

```
Leu Ser Trp Phe Gln Gln Lys Pro Gly Lys Ser Pro Lys Thr Leu Ile
         35                  40                  45

Tyr Arg Ala Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Phe Pro Tyr
                 85                  90                  95

Thr Ser Gly Gly Gly Thr Lys Leu Glu Ile Lys
            100                 105
```

<210> SEQ ID NO 168
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168

```
aacattgtgt tgacccaatc tccagcttct ttggctgtgt ctctaggaca gagggccacc    60
atatcctgca gagccagtga aagtgttgat agttatggca atagttttat gttctggttc   120
cagcagaaac caggacaggc acccaaactc ctcatctttc ttacatccaa cctcgaatct   180
ggggtccctg ccaggttcag tggcagtggg tctaggacag acttcaccct caccattgat   240
cgtgtggagg ctgatgatgc tgcaacctat tactgtcagc aaagtaatga ggatcctcgg   300
acgttcggtg gaggcaccaa gctggaaatc aaa                                333
```

<210> SEQ ID NO 169
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

```
Asn Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Gly Asn Ser Phe Met Phe Trp Phe Gln Gln Lys Pro Gly Gln Ala Pro
         35                  40                  45

Lys Leu Leu Ile Phe Leu Thr Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Arg Val Glu Ala Asp Asp Ala Ala Thr Tyr Tyr Cys Gln Gln Ser Asn
                 85                  90                  95

Glu Asp Pro Arg Thr Phe Gly Gly Gly Thr Lys Leu Glu Ile Lys
            100                 105                 110
```

<210> SEQ ID NO 170
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170

```
attgtgctga cccaatcttc agcttctttg gctgtgtctc tagggcagag ggccaccata    60
tcctgcagag ccagtgaaag tgttgatcgt tatggcaata gtcttatgca ctggtaccag   120
cagaaaccag acagccacc caaactcctc atctatattg catccaacct agaatctggg   180
gtccctgcca ggttcagtgg cagtgggtct aggacagact tcaccctcac cattgatcct   240
gtggaggctg atgatgctgc aacctattac tgtcagcaaa ataatgagga tcctcggacg   300
ttcggtggag gcaccaagct ggaaatcaaa                                    330
```

<210> SEQ ID NO 171
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Ile Val Leu Thr Gln Ser Ser Ala Ser Leu Ala Val Ser Leu Gly Gln
1               5                   10                  15
Arg Ala Thr Ile Ser Cys Arg Ala Ser Glu Ser Val Asp Arg Tyr Gly
                20                  25                  30
Asn Ser Leu Met His Trp Tyr Gln Gln Lys Pro Gly Gln Pro Pro Lys
            35                  40                  45
Leu Leu Ile Tyr Ile Ala Ser Asn Leu Glu Ser Gly Val Pro Ala Arg
        50                  55                  60
Phe Ser Gly Ser Gly Ser Arg Thr Asp Phe Thr Leu Thr Ile Asp Pro
65                  70                  75                  80
Val Glu Ala Asp Asp Ala Ala Thr Tyr Tyr Cys Gln Gln Asn Asn Glu
                85                  90                  95
Asp Pro Arg Thr Phe Gly Gly Gly Thr Lys Leu Glu Ile Lys
            100                 105                 110
```

<210> SEQ ID NO 172
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172

```
aacattgtgc tgacccaatc tccagcttct ttgcctgtgt ctctagggca gagggccacc    60
atgtcctgca gagccagtaa agtgttgat agttatggca ctagttttat gcactggtac   120
caacacagac caggacagcc acccaaactc ctcatctctc ttgcatccaa cctagaatct   180
ggggtccctg caggttcagt ggcagtggg tctaggacag acttcaccct caccattgat   240
cctgtggagc tgatgatgc tgcaacctat tactgtcaac aaaataatga ggatcctcgg   300
acgttcggtg gaggcaccac gctggaaatc aaa                                333
```

<210> SEQ ID NO 173
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asn Ile Val Leu Thr Gln Ser Pro Ala Ser Leu Pro Val Ser Leu Gly
1               5                   10                  15

Gln Arg Ala Thr Met Ser Cys Arg Ala Ser Lys Ser Val Asp Ser Tyr
            20                  25                  30

Gly Thr Ser Phe Met His Trp Tyr Gln His Arg Pro Gly Gln Pro Pro
        35                  40                  45

Lys Leu Leu Ile Ser Leu Ala Ser Asn Leu Glu Ser Gly Val Pro Gly
    50                  55                  60

Arg Phe Ser Gly Ser Gly Ser Arg Thr Asp Phe Thr Leu Thr Ile Asp
65                  70                  75                  80

Pro Val Glu Pro Asp Asp Ala Ala Thr Tyr Tyr Cys Gln Gln Asn Asn
                85                  90                  95

Glu Asp Pro Arg Thr Phe Gly Gly Gly Thr Leu Glu Ile Lys
            100                 105                 110

<210> SEQ ID NO 174
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174
gacattgtgc tgacacagtc tcctgcttct ttggctgtgt ctgtagggca gagggccacc     60
gtatcctgca gagtcagtga aagtgttgat agatatgccg atagttttat gcactggtac    120
cagcagaaac aggacagcc acccaaactc ctcatctatc ttgcatccaa cctagaatct    180
ggggtccctg ccaggttcag tggcagtggg tctaggacag acttcaccct caccattgat    240
cctgtggagg ctgatgatgc tgcaacctat tactgtcagc aaaataaaga ggatccgtac    300
acgttcggag gggggaccaa gctggaactt aaa                                 333

<210> SEQ ID NO 175
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Asp Ile Val Leu Thr Gln Ser Pro Ala Ser Leu Ala Val Ser Val Gly
1               5                   10                  15

Gln Arg Ala Thr Val Ser Cys Arg Val Ser Glu Ser Val Asp Arg Tyr
            20                  25                  30

Ala Asp Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Lys
                85                  90                  95

Glu Asp Pro Tyr Thr Phe Gly Gly Gly Thr Lys Leu Glu Leu Lys
            100                 105                 110

<210> SEQ ID NO 176

<210> SEQ ID NO 176
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176

```
gacattgtgc tgacccaatc tccagcttct ttggctgtgt ctctagggca gagggccacc    60
atgtcctgca gagccagtga aagtgttgat agttatggca atagtttat acactggtac    120
cagcagaaac caggacagcc acccagactc ctcatctatc gtgcatccaa cctaaattct    180
gggatccctg ccaggttcag tggcagtggg tctaggacag acttcaccct caccattagt    240
tctgtggagg ctgatgatgt tgcaacctat tactgtcacc aaaataatga ggatcctcgg    300
acgttcggtg gaggcaccaa gctggaaatc aaa                                333
```

<210> SEQ ID NO 177
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Asp Ile Val Leu Thr Gln Ser Pro Ala Ser Leu Ala Val Ser Leu Gly
1               5                   10                  15
Gln Arg Ala Thr Met Ser Cys Arg Ala Ser Glu Ser Val Asp Ser Tyr
            20                  25                  30
Gly Asn Ser Phe Ile His Trp Tyr Gln Gln Lys Pro Gly Gln Pro Pro
        35                  40                  45
Arg Leu Leu Ile Tyr Arg Ala Ser Asn Leu Asn Ser Gly Ile Pro Ala
    50                  55                  60
Arg Phe Ser Gly Ser Gly Ser Arg Thr Asp Phe Thr Leu Thr Ile Ser
65                  70                  75                  80
Ser Val Glu Ala Asp Asp Val Ala Thr Tyr Tyr Cys His Gln Asn Asn
                85                  90                  95
Glu Asp Pro Arg Thr Phe Gly Gly Gly Thr Lys Leu Glu Ile Lys
            100                 105                 110
```

<210> SEQ ID NO 178
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178

```
gacattgtgc tgacccaatc tccagcttct ttggctgtgt ctctagggca gagggccacc    60
atctcctgca gagccagcga aagtattgat aattatggcc ttatttttat gagctggttc    120
caacagaaac caggacagcc acccaaactc ctcatctatg ctgcatccaa ccgaggatcc    180
ggggtccctg ccaggtttag tggcagtggg tctgggacag acttcagcct caacatccat    240
cctatggagg aggatgatac tgcaatgtat ttctgtcagc aaagtaagga ggttccgtgg    300
acgttcggtg gaggcaccaa gctggaagtc aaa                                333
```

<210> SEQ ID NO 179
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Ile Asp Asn Tyr
            20                  25                  30

Gly Leu Ile Phe Met Ser Trp Phe Gln Gln Lys Pro Gly Gln Pro Pro
        35                  40                  45

Lys Leu Leu Ile Tyr Ala Ala Ser Asn Arg Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Val Lys
            100                 105                 110

<210> SEQ ID NO 180
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
gacatccaga tgactcagtc tccagcctcc ctatctgcat ctgtgggaga aactgtcacc      60
atcacatgtc gagcaagtgg gaatattcac aattatttag catggtatca gcagaaacag     120
ggaaaatctc ctcagctcct ggtctataat gcaaaaacct tagcagatgg tgtgccatca     180
aggttcagtg gcagtggatc aggaacacaa ttttctctca agatcaacag cctgcagcct     240
gaagattttg ggagttatta ctgtcaacat ttttggagta ctccgtacac gttcggaggg     300
gggaccaagc tggaaataaa a                                                321

<210> SEQ ID NO 181
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Trp Ser Thr Pro Tyr
```

Thr Phe Gly Gly Gly Thr Lys Leu Glu Ile Lys
                    100                 105

<210> SEQ ID NO 182
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182

```
gaggtccagc tgcagcagtc tggacctgag ctggtaaagc ctggggcttc agtgaagatg    60
tcctgcaagg cttctggata cacaatcact agttatgtta tgcactgggt gaagcagaag   120
cctgggcagg gccttgagtg gattggatat attaatccta acaatgatgg cactaagtac   180
aatgagaagt tcaaaggcaa ggccacactg acttcagaca atcctccaa cacagcctac   240
atggagctca gcagcctgac ctctgaggac tctgcggtct attattgtgc aagagggac   300
tatagtaact acttctactg gtacttcgat gtctggggcg cagggaccac ggtcaccgtc   360
tcctca                                                              366
```

<210> SEQ ID NO 183
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Ile Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Asn Asn Asp Gly Thr Lys Tyr Asn Glu Lys Phe
    50                  55                  60

Lys Gly Lys Ala Thr Leu Thr Ser Asp Lys Ser Ser Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Asp Tyr Ser Asn Tyr Phe Tyr Trp Tyr Phe Asp Val Trp
            100                 105                 110

Gly Ala Gly Thr Thr Val Thr Val Ser Ser
        115                 120

<210> SEQ ID NO 184
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 184

```
caggtccccgc tgcagcagcc tggggctgag atggtgaggc ctggggcttc aatgaggttg    60
tcctgtaagg cttctggcta caccttcccc ggctactgga tgcactgggt gaagcagagg   120
```

```
cctagacaag gccttgagtg gattgctaag attgatccct ctgatagtga aactcactac    180
aatcaaaact tcaaggacaa ggccacattg actgtagaca atattccaa cacagtctac     240 atgcagctca acagcctgac atctgaagac tctgcggtct attactgtgc aaacgagggt    300
tgggacagcc ttacgaaagt ctggtttggt tggtggggcc aagggactct ggtcactgtc    360
tctgca                                                                366
```

<210> SEQ ID NO 185
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

```
Gln Val Pro Leu Gln Gln Pro Gly Ala Glu Met Val Arg Pro Gly Ala
1               5                   10                  15

Ser Met Arg Leu Ser Cys Lys Ala Ser Gly Tyr Thr Phe Pro Gly Tyr
            20                  25                  30

Trp Met His Trp Val Lys Gln Arg Pro Arg Gln Gly Leu Glu Trp Ile
        35                  40                  45

Ala Lys Ile Asp Pro Ser Asp Ser Glu Thr His Tyr Asn Gln Asn Phe
    50                  55                  60

Lys Asp Lys Ala Thr Leu Thr Val Asp Lys Tyr Ser Asn Thr Val Tyr
65                  70                  75                  80

Met Gln Leu Asn Ser Leu Thr Ser Glu Asp Ser Ala Val Tyr Tyr Cys
                85                  90                  95

Ala Asn Glu Gly Trp Asp Ser Leu Thr Lys Val Trp Phe Gly Trp Trp
            100                 105                 110

Gly Gln Gly Thr Leu Val Thr Val Ser Ala
        115                 120
```

<210> SEQ ID NO 186
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 186

```
gaggttcagc tgcagcagtc tggggctgag cttgtgaggc caggggcctc agtcaagttg     60
tcctgcacag cttctggctt taacattaaa gacgactata tgcactgggt gaagcagacg    120
cctgaacagg gctggagtg gattggaagg attgatcctg cgtatggtaa tggtaagtat     180
gtcccgaagt tccaggacaa ggccactata actgcagaca catcctccaa cacagcctac    240
ctgcagctca gcagcctgac atctgaggac actgccgtct attactgtgc tagacggtac    300
tacgctgtta gttccgtaga ctatgctctg gactactggg gtcaaggaac ctcagtcacc    360
gtctcctca                                                             369
```

<210> SEQ ID NO 187
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Thr Pro Glu Gln Gly Leu Glu Trp Ile
        35                  40                  45

Gly Arg Ile Asp Pro Ala Tyr Gly Asn Gly Lys Tyr Val Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Tyr Tyr Ala Val Ser Ser Val Asp Tyr Ala Leu Asp Tyr
            100                 105                 110

Trp Gly Gln Gly Thr Ser Val Thr Val Ser Ser
        115                 120

<210> SEQ ID NO 188
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
caggttcagc tgcagcagtc tggacctgag ctggtgaggc ctgggacttc agtgaagata      60
tcctgcaagg ctcctggcta tatcttcacc agccactgga tgcagtgggt aagacagagg     120
cctggacagg gccttgagtg gattggagac atttttcctg gaagcggtac tactgattat     180
aatgagaagt tcaaggacaa ggccacagtg acggtagaca gatcctccag ttcagcctac     240
atgcagttca acagcctgac atctgaggac tctgcggtct atttctgtgc aagcggagcc     300
tttgactact ggggccaagg caccactctc acagtctcct ca                        342

<210> SEQ ID NO 189
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Val Gln Leu Gln Gln Ser Gly Pro Glu Leu Val Arg Pro Gly Thr
1               5                   10                  15

Ser Val Lys Ile Ser Cys Lys Ala Pro Gly Tyr Ile Phe Thr Ser His
            20                  25                  30

Trp Met Gln Trp Val Arg Gln Arg Pro Gly Gln Gly Leu Glu Trp Ile
        35                  40                  45

Gly Asp Ile Phe Pro Gly Ser Gly Thr Thr Asp Tyr Asn Glu Lys Phe
    50                  55                  60

Lys Asp Lys Ala Thr Val Thr Val Asp Arg Ser Ser Ser Ser Ala Tyr
65                  70                  75                  80

Met Gln Phe Asn Ser Leu Thr Ser Glu Asp Ser Ala Val Tyr Phe Cys
                85                  90                  95

Ala Ser Gly Ala Phe Asp Tyr Trp Gly Gln Gly Thr Thr Leu Thr Val
            100                 105                 110

Ser Ser

<210> SEQ ID NO 190
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
caggttactc tgaaagagtc tggccctggg atattgcagc cctcccagac cctcagtctg     60
acttgttcct tctctgggtt ttcactgagg acttttggca tgggtgtagg ctggattcgt    120
cagccttcag ggaagggtct ggagtggctg gcacacattt ggtggaatgg tgataaatac    180
tatgacccag ccctgaagag tcggctcaca atttccaagg atacctccga aaaccgggta    240
ttcctcaata tcgccaatgt ggacactaca gatactgccc catactactg tgttcgaatt    300
ggtccttcta ttactacggt agcagaggga tttgcttact ggggccaagg gactctggtc    360
actgtctctg ca                                                        372

<210> SEQ ID NO 191
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asn Gly Asp Lys Tyr Tyr Asp Pro Ala
    50                  55                  60

Leu Lys Ser Arg Leu Thr Ile Ser Lys Asp Thr Ser Glu Asn Arg Val
65                  70                  75                  80

Phe Leu Asn Ile Ala Asn Val Asp Thr Thr Asp Thr Ala Pro Tyr Tyr
                85                  90                  95

Cys Val Arg Ile Gly Pro Ser Ile Thr Thr Val Ala Glu Gly Phe Ala
            100                 105                 110

Tyr Trp Gly Gln Gly Thr Leu Val Thr Val Ser Ala
        115                 120

<210> SEQ ID NO 192
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
aaggttactc tgaaagagtc tggccctggg atattgcagc cctcccagac cctcagtctg     60
acttgttcct tctctggatt ttcactgagg acttttggta tgggtgtagg ctggattcgt    120

```
cagccttcag ggaagggtct ggagtggctg gcacacattt ggtggaatga tgagaaatac    180
tataatccag acctgaagag tcggctcaca gtttccaagg attcctccaa aaaccaggta    240
ttcctcacga tcgccaatgt ggacacttca gatactgccc catactactg tactcgagtt    300
ggtccttcta tttctacggt tgcagaggga tttccttact ggggccaagg gactctggtc    360
actgtctctg ca                                                       372
```

```
<210> SEQ ID NO 193
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Lys Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asn Asp Glu Lys Tyr Tyr Asn Pro Asp
    50                  55                  60

Leu Lys Ser Arg Leu Thr Val Ser Lys Asp Ser Ser Lys Asn Gln Val
65                  70                  75                  80

Phe Leu Thr Ile Ala Asn Val Asp Thr Ser Asp Thr Ala Pro Tyr Tyr
                85                  90                  95

Cys Thr Arg Val Gly Pro Ser Ile Ser Thr Val Ala Glu Gly Phe Pro
            100                 105                 110

Tyr Trp Gly Gln Gly Thr Leu Val Thr Val Ser Ala
        115                 120
```

```
<210> SEQ ID NO 194
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
caggttactc tgaaagagtc tggccctggg atattgcagt cctcccagac cctcagtctg    60
acttgttctt tctctgggtt ttcactgagg acctttggta tgggtgtagg ctggattcgt   120
caaccttcag ggaagggtct ggaatggctg cacacattt ggtggaatga tgataagtcc    180
tctcacccag ccctgaagag tcgtctcaca atctccaagg ataccctccaa aaaccaggta   240 ttcctcaaga tcgccaatgt ggacactgca gaaactgcca catattattg tgttcgaata    300
ggtccttcaa ttactacggt tgcagagggg tttgcttact ggggccaagg gactctggtc    360
actgtctctg ca                                                       372
```

```
<210> SEQ ID NO 195
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 195

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Arg Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asn Asp Lys Ser Ser His Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Glu Thr Ala Thr Tyr Tyr
                85                  90                  95

Cys Val Arg Ile Gly Pro Ser Ile Thr Thr Val Ala Glu Gly Phe Ala
                100                 105                 110

Tyr Trp Gly Gln Gly Thr Leu Val Thr Val Ser Ala
            115                 120

<210> SEQ ID NO 196
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
caggttactc tgaaagagtc tggccctggg atattgcagc cctcccagac cctcagtctg      60
acttgttcct tctctggatt ttcaatgagg acttttggta tgggtgtagg ctggattcgt     120
cagccttcag ggaagggtct ggagtggctg gcacacattt ggtggaatga tgagaaatac     180
tataatccag acctgaagag tcggctcaca gtttccaagg attcctccaa aaaccaggta     240
ttcctcacga tcgccaatgt ggacacttca gatactgccc catactactg tactcgagtt     300
ggtccttcta tttctacgat tgcagaggga tttccttact ggggccaagg gactctggtc     360
actgtctctg ca                                                         372

<210> SEQ ID NO 197
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Met Arg Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asn Asp Glu Lys Tyr Tyr Asn Pro Asp
    50                  55                  60

Leu Lys Ser Arg Leu Thr Val Ser Lys Asp Ser Ser Lys Asn Gln Val
65                  70                  75                  80

Phe Leu Thr Ile Ala Asn Val Asp Thr Ser Asp Thr Ala Pro Tyr Tyr

```
                    85                  90                  95
Cys Thr Arg Val Gly Pro Ser Ile Ser Thr Ile Ala Glu Gly Phe Pro
                100                 105                 110

Tyr Trp Gly Gln Gly Thr Leu Val Thr Val Ser Ala
        115                 120
```

<210> SEQ ID NO 198
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198

```
caggtccaac tgcagcagcc tggggctgaa ttggtgaagc ctggggcttc agtgaagctg      60
tcctgcaagg cttctggcta cactttcacc aacgacaatt actggatgaa ctggatgaaa     120
cagaggcctg gacgaggcct cgagtggatt ggaaggattc gtccttctga tagtgaaact     180
cactacaatc aaaaattcac gaacaaggcc acactgactg tagacaaatc ctccagcaca     240
gcctacatcc aactcagcag cctgacatct gtggactctg cggtctatta ttgtgcaaga     300
tcttgggaag atttattact acgatcgatg gaggactact ttgactactg gggccaaggc     360
accactctca cagtctcctc a                                                381
```

<210> SEQ ID NO 199
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Asp
            20                  25                  30

Asn Tyr Trp Met Asn Trp Met Lys Gln Arg Pro Gly Arg Gly Leu Glu
        35                  40                  45

Trp Ile Gly Arg Ile Arg Pro Ser Asp Ser Glu Thr His Tyr Asn Gln
    50                  55                  60

Lys Phe Thr Asn Lys Ala Thr Leu Thr Val Asp Lys Ser Ser Ser Thr
65                  70                  75                  80

Ala Tyr Ile Gln Leu Ser Ser Leu Thr Ser Val Asp Ser Ala Val Tyr
                85                  90                  95

Tyr Cys Ala Arg Ser Trp Glu Asp Leu Leu Leu Arg Ser Met Glu Asp
                100                 105                 110

Tyr Phe Asp Tyr Trp Gly Gln Gly Thr Thr Leu Thr Val Ser Ser
            115                 120                 125
```

<210> SEQ ID NO 200
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200

```
gagttccaac tgcagcagtc tggacctgag ctggggagc ctggcgcttc agtgaaaatc      60
tcctgcaagg cttctggttt ctcattcagt gactacaaca taaattgggt gaagcagagc    120
aatggaaaga gtcttgagtg gattggaaaa gttcatccta aggatggtac tgctacctac    180
aatcagaagt tccaggacaa ggccacattg actctagacc agtcttccag cacagcctac    240
atgcaactca gcagcctgac atcggaggac tctgcagtct attactgtct cccgctctac    300
tatgattccc tgacaaaaat tttgtttgct tattggggcc aagggactct ggtcactgtc    360
tctgca                                                               366

<210> SEQ ID NO 201
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Phe Gln Leu Gln Gln Ser Gly Pro Glu Leu Gly Glu Pro Gly Ala
1               5                   10                  15

Ser Val Lys Ile Ser Cys Lys Ala Ser Gly Phe Ser Phe Ser Asp Tyr
            20                  25                  30

Asn Ile Asn Trp Val Lys Gln Ser Asn Gly Lys Ser Leu Glu Trp Ile
        35                  40                  45

Gly Lys Val His Pro Lys Asp Gly Thr Ala Thr Tyr Asn Gln Lys Phe
    50                  55                  60

Gln Asp Lys Ala Thr Leu Thr Leu Asp Gln Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Leu Pro Leu Tyr Tyr Asp Ser Leu Thr Lys Ile Leu Phe Ala Tyr Trp
            100                 105                 110

Gly Gln Gly Thr Leu Val Thr Val Ser Ala
        115                 120

<210> SEQ ID NO 202
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
caggttactc tgagagagtc tgggcctggg atattgcagc cctcccagac cctcagtctg     60
acttgttcct tctctggggtt tcactgagg acctttggta tgggtgtagg ctggattcgt    120
cagccttcag ggaagggtct ggagtggctg cacacatct ggtggaatga tgagaaatat     180
tataacccag ccctgaagag tcggctcaca gtttccaagg attcctccga aaaccaggta    240
ttcctcaaga tcgccaatgt ggacactaca gatactgccc catactactg tgctcgactt    300
ggtccttcta ttactacggt tgcagaggga tttccgtact ggggccaagg gactctggtc    360
actgtctctg ca                                                       372

<210> SEQ ID NO 203
<211> LENGTH: 124
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 203

Gln Val Thr Leu Arg Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asn Asp Glu Lys Tyr Tyr Asn Pro Ala
    50                  55                  60

Leu Lys Ser Arg Leu Thr Val Ser Lys Asp Ser Ser Glu Asn Gln Val
65                  70                  75                  80

Phe Leu Lys Ile Ala Asn Val Asp Thr Thr Asp Thr Ala Pro Tyr Tyr
                85                  90                  95

Cys Ala Arg Leu Gly Pro Ser Ile Thr Thr Val Ala Glu Gly Phe Pro
            100                 105                 110

Tyr Trp Gly Gln Gly Thr Leu Val Thr Val Ser Ala
        115                 120

<210> SEQ ID NO 204
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
caggtccagc tgcagcagtc tggacctgag ctggtgaagc cggggggttc agtgaggata      60
tcctgcaagg cttctggtta cagcctcata agctactata tacactgggt gaaacagagg     120
ccgggacagg gccttgagtg gattggattg acttttcctg gaagtggtaa ttctaagttc     180
attgagaagt tcaagggcaa ggccacactg acggcagaca catcctccaa cactgcctac     240
atacagctca gcagtctaac atctgaggac tctgcggtct attactgtac aagggggggac    300 ttcggtaact accttgccta ctggtacttc gatgtctggg gcacagggac cacggtcacc     360
gtctcctca                                                             369

<210> SEQ ID NO 205
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gln Val Gln Leu Gln Gln Ser Gly Pro Glu Leu Val Lys Pro Gly Gly
1               5                   10                  15

Ser Val Arg Ile Ser Cys Lys Ala Ser Gly Tyr Ser Leu Ile Ser Tyr
            20                  25                  30

Tyr Ile His Trp Val Lys Gln Arg Pro Gly Gln Gly Leu Glu Trp Ile
        35                  40                  45

Gly Leu Thr Phe Pro Gly Ser Gly Asn Ser Lys Phe Ile Glu Lys Phe
    50                  55                  60

Lys Gly Lys Ala Thr Leu Thr Ala Asp Thr Ser Ser Asn Thr Ala Tyr
```

```
                65                  70                  75                  80
Ile Gln Leu Ser Ser Leu Thr Ser Glu Asp Ser Ala Val Tyr Tyr Cys
                    85                  90                  95

Thr Arg Gly Asp Phe Gly Asn Tyr Leu Ala Tyr Trp Tyr Phe Asp Val
                    100                 105                 110

Trp Gly Thr Gly Thr Thr Val Thr Val Ser Ser
            115                 120

<210> SEQ ID NO 206
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
caggttactc tgaaagagtc tggccctggg atattgcagt cctcccagac cctcagtctg      60
acttgttctt tctctgggtt tcactgaag accttggta tgggtgtggg ctggattcgt      120
cagccttcag ggaagggtct ggagtggctg gcacacattt ggtggaatga tgataaattc      180
tatcacccag ccctgaagag tcggctcaca atctccaagg atacctccaa aaaccaggta      240
ttcctcaaga tcgccaatgt ggacactgca gaaactgcca catactactg tgttcgaatt      300
ggtccttcaa ttactacggt agcagagggg tttgcttact ggggccaagg gactctggtc      360
actgtctctg ca                                                         372

<210> SEQ ID NO 207
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gln Val Thr Leu Lys Glu Ser Gly Pro Gly Ile Leu Gln Ser Gln
1               5                   10                  15

Thr Leu Ser Leu Thr Cys Ser Phe Ser Gly Phe Ser Leu Lys Thr Phe
                20                  25                  30

Gly Met Gly Val Gly Trp Ile Arg Gln Pro Ser Gly Lys Gly Leu Glu
            35                  40                  45

Trp Leu Ala His Ile Trp Trp Asn Asp Asp Lys Phe Tyr His Pro Ala
        50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Glu Thr Ala Thr Tyr Tyr
                85                  90                  95

Cys Val Arg Ile Gly Pro Ser Ile Thr Thr Val Ala Glu Gly Phe Ala
                100                 105                 110

Tyr Trp Gly Gln Gly Thr Leu Val Thr Val Ser Ala
            115                 120

<210> SEQ ID NO 208
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 208

```
caggtccagc tgcagcagtc tggacctgag ctggtgaagc cggggggttc agtgaagata      60
tcctgcaagg ctgctggcta cagcctcaca agctactata tacactgggt gaagcagagg     120
ccgggacagg gacttgagtg gattggattg attttcctg gaagtggtaa ttctaagtac     180
attgagaagt tcaagggcaa ggccacactg acggcggaca catcctccaa cactgcctac     240
atgcagctca gcagcctaac atctgaggac tctgcggtct attattgtac aaggggggac     300
ttcggtaact accttgccta ctggtacttc gatgtctggg gcacagggac cacggtcacc     360
gtctcctca                                                              369
```

<210> SEQ ID NO 209
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 209

```
Gln Val Gln Leu Gln Gln Ser Gly Pro Glu Leu Val Lys Pro Gly Gly
1               5                   10                  15
Ser Val Lys Ile Ser Cys Lys Ala Ala Gly Tyr Ser Leu Thr Ser Tyr
            20                  25                  30
Tyr Ile His Trp Val Lys Gln Arg Pro Gly Gln Gly Leu Glu Trp Ile
        35                  40                  45
Gly Leu Ile Phe Pro Gly Ser Gly Asn Ser Lys Tyr Ile Glu Lys Phe
    50                  55                  60
Lys Gly Lys Ala Thr Leu Thr Ala Asp Thr Ser Ser Asn Thr Ala Tyr
65                  70                  75                  80
Met Gln Leu Ser Ser Leu Thr Ser Glu Asp Ser Ala Val Tyr Tyr Cys
                85                  90                  95
Thr Arg Gly Asp Phe Gly Asn Tyr Leu Ala Tyr Trp Tyr Phe Asp Val
            100                 105                 110
Trp Gly Thr Gly Thr Thr Val Thr Val Ser Ser
        115                 120
```

<210> SEQ ID NO 210
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 210

```
caggtcactc tgaaagagtc tggccctgga atattgcagc cctcccagac cctcagtctg      60
acttgttctt tctctgggtt ttcactgaac acttatggta tgggtgtggg ttggattcgt     120
cagccttcag ggaagggtct ggagtggctg gccaacattt ggtggaatga tgataagtac     180
tataactcag ccctgaagag ccggctcgca atctccaaag atgcctccaa cagccaggta     240
ttcctcaaga tctccagtgt ggacactaca gatactgcca catactactg tgctcaagta     300
gccgctacta tagtaactac gtacggggcc tggtttgctt actggggcca agggactctg     360
gtcactgtct ctgca                                                       375
```

<210> SEQ ID NO 211

<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 211

| | | | | | | | | | | | | | | |
|---|---|---|---|---|---|---|---|---|---|---|---|---|---|---|
| Gln | Val | Thr | Leu | Lys | Glu | Ser | Gly | Pro | Gly | Ile | Leu | Gln | Pro | Ser | Gln |
| 1 | | | | 5 | | | | | 10 | | | | | 15 | |
| Thr | Leu | Ser | Leu | Thr | Cys | Ser | Phe | Ser | Gly | Phe | Ser | Leu | Asn | Thr | Tyr |
| | | | 20 | | | | | 25 | | | | | 30 | | |
| Gly | Met | Gly | Val | Gly | Trp | Ile | Arg | Gln | Pro | Ser | Gly | Lys | Gly | Leu | Glu |
| | | 35 | | | | | 40 | | | | | 45 | | | |
| Trp | Leu | Ala | Asn | Ile | Trp | Trp | Asn | Asp | Asp | Lys | Tyr | Tyr | Asn | Ser | Ala |
| | 50 | | | | | 55 | | | | | 60 | | | | |
| Leu | Lys | Ser | Arg | Leu | Ala | Ile | Ser | Lys | Asp | Ala | Ser | Asn | Ser | Gln | Val |
| 65 | | | | | 70 | | | | | 75 | | | | | 80 |
| Phe | Leu | Lys | Ile | Ser | Ser | Val | Asp | Thr | Thr | Asp | Thr | Ala | Thr | Tyr | Tyr |
| | | | | 85 | | | | | 90 | | | | | 95 | |
| Cys | Ala | Gln | Val | Ala | Ala | Thr | Ile | Val | Thr | Thr | Tyr | Gly | Ala | Trp | Phe |
| | | | 100 | | | | | 105 | | | | | 110 | | |
| Ala | Tyr | Trp | Gly | Gln | Gly | Thr | Leu | Val | Thr | Val | Ser | Ala | | | |
| | | 115 | | | | | 120 | | | | | 125 | | | |

<210> SEQ ID NO 212
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 212

```
gttactctga aagagtctgg ccctgggata ttgcagccct cccagaccct cagtctgact      60
tgttccttct ctgggttttc actgaggact tttggtatgg gtgtaggctg gattcgtcag     120
ccttcaggga agggtctgga gtggctggca cacatttggt ggaatgatga gaaatattat     180
aatccaaccc tgaagagtcg gctcacaatt tccaaggata cctccaaaaa ccaggtattc     240
ctcaggatcg ccaatgtgga cactgcagtt actgccgcat actactgtgc tcgaataggt     300
ccttctatta ctacggtagt agagggattt ccttactggg gccaagggac tctggtcact     360
gtctctgca                                                              369
```

<210> SEQ ID NO 213
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 213

| | | | | | | | | | | | | | | |
|---|---|---|---|---|---|---|---|---|---|---|---|---|---|---|
| Val | Thr | Leu | Lys | Glu | Ser | Gly | Pro | Gly | Ile | Leu | Gln | Pro | Ser | Gln | Thr |
| 1 | | | | 5 | | | | | 10 | | | | | 15 | |
| Leu | Ser | Leu | Thr | Cys | Ser | Phe | Ser | Gly | Phe | Ser | Leu | Arg | Thr | Phe | Gly |
| | | | 20 | | | | | 25 | | | | | 30 | | |
| Met | Gly | Val | Gly | Trp | Ile | Arg | Gln | Pro | Ser | Gly | Lys | Gly | Leu | Glu | Trp |
| | | 35 | | | | | 40 | | | | | 45 | | | |
| Leu | Ala | His | Ile | Trp | Trp | Asn | Asp | Glu | Lys | Tyr | Tyr | Asn | Pro | Thr | Leu |

Lys Ser Arg Leu Thr Ile Ser Lys Asp Thr Ser Lys Asn Gln Val Phe
65                  70                  75                  80

Leu Arg Ile Ala Asn Val Asp Thr Ala Val Thr Ala Ala Tyr Tyr Cys
                85                  90                  95

Ala Arg Ile Gly Pro Ser Ile Thr Thr Val Val Glu Gly Phe Pro Tyr
            100                 105                 110

Trp Gly Gln Gly Thr Leu Val Thr Val Ser Ala
        115                 120

<210> SEQ ID NO 214
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
atccagctgc agcagtctgg acctgagctg gtgaagcctg gggcttcaat gaagatatcg      60
tgcaaggctt ctggctacac cttcactgac aagtatataa actgggtgaa gcagaggcct     120
ggacagggac ttgagtggat tggatggatt tatcctggaa gcggtaatac taagtacaat     180
gagaagttca aggcatggc cacattgact gtagacacat cctccaatac agcctatata      240
catctcagca gcctgacctc tgaggactct gcggtctatt tctgtgcacg aggaattatt     300
tattactacg atggttcata ccctatgct ttggactact ggggtcaagg aacctcagtc      360
accgtctcct ca                                                         372

<210> SEQ ID NO 215
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Ile Gln Leu Gln Gln Ser Gly Pro Glu Leu Val Lys Pro Gly Ala Ser
1               5                   10                  15

Met Lys Ile Ser Cys Lys Ala Ser Gly Tyr Thr Phe Thr Asp Lys Tyr
            20                  25                  30

Ile Asn Trp Val Lys Gln Arg Pro Gly Gln Gly Leu Glu Trp Ile Gly
        35                  40                  45

Trp Ile Tyr Pro Gly Ser Gly Asn Thr Lys Tyr Asn Glu Lys Phe Lys
    50                  55                  60

Gly Met Ala Thr Leu Thr Val Asp Thr Ser Ser Asn Thr Ala Tyr Ile
65                  70                  75                  80

His Leu Ser Ser Leu Thr Ser Glu Asp Ser Ala Val Tyr Phe Cys Ala
                85                  90                  95

Arg Gly Ile Ile Tyr Tyr Tyr Asp Gly Ser Tyr Pro Tyr Ala Leu Asp
            100                 105                 110

Tyr Trp Gly Gln Gly Thr Ser Val Thr Val Ser Ser
        115                 120

<210> SEQ ID NO 216
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 216
caggtccagc tgcagcagtc tggacctgaa ctggtgaagc ctggagcttc agtgaagttg    60
tcctgcaagg cttctggcta caccttcact gactatagta tacactgggt gaagcagagt   120
cctggacagg gacttgagtg gattggatgg atttatcctg aagtggtaa tactaagtac    180 aatgacaagt tcaagggcaa ggccacaatg actgcagaca atcctccag aacagtctac    240 atgcagctca gcagcctgac gtctgaggag tctgcggtct atttctgtgc aagagactac   300
cggcgatact atgctataga ctactgggt caaggaacct cagtcaccgt ctcctca       357

<210> SEQ ID NO 217
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Ser Ile His Trp Val Lys Gln Ser Pro Gly Gln Gly Leu Glu Trp Ile
        35                  40                  45

Gly Trp Ile Tyr Pro Gly Ser Gly Asn Thr Lys Tyr Asn Asp Lys Phe
    50                  55                  60

Lys Gly Lys Ala Thr Met Thr Ala Asp Lys Ser Ser Arg Thr Val Tyr
65                  70                  75                  80

Met Gln Leu Ser Ser Leu Thr Ser Glu Glu Ser Ala Val Tyr Phe Cys
                85                  90                  95

Ala Arg Asp Tyr Arg Arg Tyr Tyr Ala Ile Asp Tyr Trp Gly Gln Gly
            100                 105                 110

Thr Ser Val Thr Val Ser Ser
        115

<210> SEQ ID NO 218
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218
cagctgcagc agtctggacc tgagctggtg aagcctggag cttcagtgaa gctgtcctgc    60
aaggcttctg gctacacctt cactgactat agtatacact gggtgaaaca gagtcctgga   120
cagggacttg agtggattgg atggatttat cctggaagtg ataatactaa gtacaatgac   180
aagttcaagg gcaaggcctc aatgactgca gacaaatcct ccagaacagt ctacatgcac   240
ctcagcagcc tgacgtctga ggaatctgcg gtctatttct gtgcaagaga ctaccggcgg   300
tactatgcta tggactactg gggtcaagga acctcagtca ccgtctcctc a            351

<210> SEQ ID NO 219
<211> LENGTH: 117

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gln Leu Gln Gln Ser Gly Pro Glu Leu Val Lys Pro Gly Ala Ser Val
1               5                   10                  15

Lys Leu Ser Cys Lys Ala Ser Gly Tyr Thr Phe Thr Asp Tyr Ser Ile
            20                  25                  30

His Trp Val Lys Gln Ser Pro Gly Gln Gly Leu Glu Trp Ile Gly Trp
        35                  40                  45

Ile Tyr Pro Gly Ser Asp Asn Thr Lys Tyr Asn Asp Lys Phe Lys Gly
    50                  55                  60

Lys Ala Ser Met Thr Ala Asp Lys Ser Ser Arg Thr Val Tyr Met His
65                  70                  75                  80

Leu Ser Ser Leu Thr Ser Glu Glu Ser Ala Val Tyr Phe Cys Ala Arg
                85                  90                  95

Asp Tyr Arg Arg Tyr Tyr Ala Met Asp Tyr Trp Gly Gln Gly Thr Ser
            100                 105                 110

Val Thr Val Ser Ser
        115

<210> SEQ ID NO 220
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220
gaggtccagc tgcagcagtc tggacctgag ctggtaaagc ctggggcttc aatgaagatg      60
tcctgcaagg cttctggata cacattcact agctatgtta tgcactggat gaagcagaag    120
cctgggcagg gccttgagtg gattggatat cttaatccta acaatgatgg tactaagtac    180
aatgagaagt tcaaaggcaa ggccacactg acttcagaca atcctccag cacagcctac     240 atggagctca gcagcctgac ctctgaggac tctgcggtct attactgtgc aaggggggac    300
tatagtaatt acttctactg gtacttcgat gtctggggcg cagggaccac ggtctccgtc    360
tcctca                                                                366

<210> SEQ ID NO 221
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Glu Val Gln Leu Gln Gln Ser Gly Pro Glu Leu Val Lys Pro Gly Ala
1               5                   10                  15

Ser Met Lys Met Ser Cys Lys Ala Ser Gly Tyr Thr Phe Thr Ser Tyr
            20                  25                  30

Val Met His Trp Met Lys Gln Lys Pro Gly Gln Gly Leu Glu Trp Ile
        35                  40                  45

Gly Tyr Leu Asn Pro Asn Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Asp Tyr Ser Asn Tyr Phe Tyr Trp Tyr Phe Asp Val Trp
            100                 105                 110

Gly Ala Gly Thr Thr Val Ser Val Ser Ser
        115                 120

<210> SEQ ID NO 222
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
caggtccagc tgcagcagtc tggacctgag ctggtgaagc ctggagcttc agtgaagctg      60
tcctgcaagg cttctggcta caccttcagt gactatacta tacactgggt gaagcagagt    120
cctggacagg gacttgagtg gattggatgg atttaccctg aaggggtaa tactaagtac     180 aatgacaagt tcaagggcaa ggccacaatg actgctgaca atcctccag cacagcctac     240 atgcagctca gcagcctgac gtctgaggaa tctgcggtct atttctgtgc aagagactac    300
cggcggtact atgctatgga ctactggggt caaggaacct cagtcaccgt ctcctca       357

<210> SEQ ID NO 223
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Ser Asp Tyr
            20                  25                  30

Thr Ile His Trp Val Lys Gln Ser Pro Gly Gln Gly Leu Glu Trp Ile
        35                  40                  45

Gly Trp Ile Tyr Pro Gly Arg Gly Asn Thr Lys Tyr Asn Asp Lys Phe
    50                  55                  60

Lys Gly Lys Ala Thr Met Thr Ala Asp Lys Ser Ser Ser Thr Ala Tyr
65                  70                  75                  80

Met Gln Leu Ser Ser Leu Thr Ser Glu Glu Ser Ala Val Tyr Phe Cys
                85                  90                  95

Ala Arg Asp Tyr Arg Arg Tyr Tyr Ala Met Asp Tyr Trp Gly Gln Gly
            100                 105                 110

Thr Ser Val Thr Val Ser Ser
        115

<210> SEQ ID NO 224
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224

```
cagctgcagc agtctggacc tgagctggtg aagcctgggg cttcagtgaa gatatcctgc     60
aaggcttctg gctacacctt cactgacaac tttataaact gggtgaaaca gaggcctgga    120
cagggacttg agtggattgg atggatttct cctggaagcg gtaatactaa gaacaatgag    180
aagttcaagg gcaaggccac agtgactgta gacacatcct ccagcacagc ctacatgcag    240
ctcagcagcc tgacctctga ggactctgcg gtctatttct gtgcacgagg aattatttat    300
tattatgatg gtacctaccc ctatgctctg gactactggg gtcagggaac ctcagtcacc    360
gtctcctca                                                            369
```

<210> SEQ ID NO 225
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 225

```
Gln Leu Gln Gln Ser Gly Pro Glu Leu Val Lys Pro Gly Ala Ser Val
1               5                   10                  15
Lys Ile Ser Cys Lys Ala Ser Gly Tyr Thr Phe Thr Asp Asn Phe Ile
            20                  25                  30
Asn Trp Val Lys Gln Arg Pro Gly Gln Gly Leu Glu Trp Ile Gly Trp
        35                  40                  45
Ile Ser Pro Gly Ser Gly Asn Thr Lys Asn Asn Glu Lys Phe Lys Gly
    50                  55                  60
Lys Ala Thr Val Thr Val Asp Thr Ser Ser Thr Ala Tyr Met Gln
65                  70                  75                  80
Leu Ser Ser Leu Thr Ser Glu Asp Ser Ala Val Tyr Phe Cys Ala Arg
                85                  90                  95
Gly Ile Ile Tyr Tyr Tyr Asp Gly Thr Tyr Pro Tyr Ala Leu Asp Tyr
            100                 105                 110
Trp Gly Gln Gly Thr Ser Val Thr Val Ser Ser
        115                 120
```

<210> SEQ ID NO 226
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 226

```
caggtgcggc tgagggagtc aggacctggc ctggtggcgc cctcccagaa cctgttcatc     60
acatgcaccg tctcaggttt ctcattaact gactatgaaa taaactgggt tcgccagcct    120
ccaggaaaga atctggagtg gctgggagtg atttggactg gtggaggcac aaaatataat    180
tcagttctca tatccagact gaacatcagc aaagacaatt ccaagagaca gttttctttt    240
aaaatgacca gtctccagac tgatgacaca gccatatatt actgtgtaag agaggggagg    300
agatactatg ctatggacta ctggggtcaa ggaacctcag tcaccgtctc ctca          354
```

<210> SEQ ID NO 227
<211> LENGTH: 118
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 227

```
Gln Val Arg Leu Arg Glu Ser Gly Pro Gly Leu Val Ala Pro Ser Gln
1               5                   10                  15

Asn Leu Phe Ile Thr Cys Thr Val Ser Gly Phe Ser Leu Thr Asp Tyr
            20                  25                  30

Glu Ile Asn Trp Val Arg Gln Pro Pro Gly Lys Asn Leu Glu Trp Leu
        35                  40                  45

Gly Val Ile Trp Thr Gly Gly Thr Lys Tyr Asn Ser Val Leu Ile
    50                  55                  60

Ser Arg Leu Asn Ile Ser Lys Asp Asn Ser Lys Arg Gln Val Phe Phe
65                  70                  75                  80

Lys Met Thr Ser Leu Gln Thr Asp Asp Thr Ala Ile Tyr Tyr Cys Val
                85                  90                  95

Arg Glu Gly Arg Arg Tyr Tyr Ala Met Asp Tyr Trp Gly Gln Gly Thr
            100                 105                 110

Ser Val Thr Val Ser Ser
        115
```

<210> SEQ ID NO 228
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 228

```
cgggtgcagc tgaaggagtc aggacctggc ctggtggcgc cctcacagag cctgttcatc    60
acatgcaccg tctcagggtt ctcattaacc acctatgaaa taaactgggt tcgccagtct   120
ccaggaaagg gtctggagtg gctgggagtg atatggactg gtggaaccac aaaatataat   180
tcagctttca tatccagact gagcatcacc aaagacaact ccaagagcct cgttttctta   240
aaaatgagca gtctgcaaac tgatgacaca gccatatatt actgtgtaag agaggggagg   300
aggtactatg ctatggacta ctggggtcaa ggaacctcag tcaccgtctc ctca         354
```

<210> SEQ ID NO 229
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 229

```
Arg Val Gln Leu Lys Glu Ser Gly Pro Gly Leu Val Ala Pro Ser Gln
1               5                   10                  15

Ser Leu Phe Ile Thr Cys Thr Val Ser Gly Phe Ser Leu Thr Thr Tyr
            20                  25                  30

Glu Ile Asn Trp Val Arg Gln Ser Pro Gly Lys Gly Leu Glu Trp Leu
        35                  40                  45

Gly Val Ile Trp Thr Gly Gly Thr Thr Lys Tyr Asn Ser Ala Phe Ile
    50                  55                  60

Ser Arg Leu Ser Ile Thr Lys Asp Asn Ser Lys Ser Leu Val Phe Leu
65                  70                  75                  80
```

-continued

```
Lys Met Ser Ser Leu Gln Thr Asp Asp Thr Ala Ile Tyr Tyr Cys Val
                85                  90                  95

Arg Glu Gly Arg Arg Tyr Tyr Ala Met Asp Tyr Trp Gly Gln Gly Thr
            100                 105                 110

Ser Val Thr Val Ser Ser
        115
```

<210> SEQ ID NO 230
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230

```
gaggtccagc tgcagcagtc tggacctgag ctggtaaagc ctggggcttc agtgaagatg    60
tcctgcacgg cttctggata cacattcact agctatgtta tacactggat gaagcagaag   120
cctgggcagg gccttgagtg gattggatat cttcatcgta acaatgatgg tactaagtac   180
aatgagaagt tcaaagtcaa ggccacactg acttcagacg aatcctccaa cacagcctac   240
atggaactca gcagcctgac ctctgaggac tctgcggtct attactgtgc aagggggac    300 tatagtaatt acttctactg gtacttcgat gtctggggcg cagggactac ggtctccgtc   360
tcctca                                                              366
```

<210> SEQ ID NO 231
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

```
Glu Val Gln Leu Gln Gln Ser Gly Pro Glu Leu Val Lys Pro Gly Ala
1               5                   10                  15

Ser Val Lys Met Ser Cys Thr Ala Ser Gly Tyr Thr Phe Thr Ser Tyr
            20                  25                  30

Val Ile His Trp Met Lys Gln Lys Pro Gly Gln Gly Leu Glu Trp Ile
        35                  40                  45

Gly Tyr Leu His Arg Asn Asn Asp Gly Thr Lys Tyr Asn Glu Lys Phe
    50                  55                  60

Lys Val Lys Ala Thr Leu Thr Ser Asp Glu Ser Ser Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Asp Tyr Ser Asn Tyr Phe Tyr Trp Tyr Phe Asp Val Trp
            100                 105                 110

Gly Ala Gly Thr Thr Val Ser Val Ser Ser
        115                 120
```

<210> SEQ ID NO 232
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232

```
cgggtgcagc tgaaggagtc aggacctggc ctggtggcgc cctcacagag cctgttcatc      60
acatgcaccg tctcagggtt ttcattaacc acctatgaaa taaactgggt tcgccagtct     120
ccaggaaagg gtctggagtg gctgggagtg atatggactg gtggaaccac aaaatataat     180
tcagctttca tatccagact gagcatcacc aaagacaact ccaagagcct cgttttctta     240
aaaatgagca gtctgcaaac tgatgacaca gccatatatt actgtgtaag agaggggagg     300
aggtactatg ctatggacta ctggggtcaa ggaacctcag tcaccgtctc ctca           354
```

<210> SEQ ID NO 233
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 233

```
Arg Val Gln Leu Lys Glu Ser Gly Pro Gly Leu Val Ala Pro Ser Gln
 1               5                  10                  15

Ser Leu Phe Ile Thr Cys Thr Val Ser Gly Phe Ser Leu Thr Thr Tyr
            20                  25                  30

Glu Ile Asn Trp Val Arg Gln Ser Pro Gly Lys Gly Leu Glu Trp Leu
        35                  40                  45

Gly Val Ile Trp Thr Gly Gly Thr Thr Lys Tyr Asn Ser Ala Phe Ile
    50                  55                  60

Ser Arg Leu Ser Ile Thr Lys Asp Asn Ser Lys Ser Leu Val Phe Leu
65                  70                  75                  80

Lys Met Ser Ser Leu Gln Thr Asp Asp Thr Ala Ile Tyr Tyr Cys Val
                85                  90                  95

Arg Glu Gly Arg Arg Tyr Tyr Ala Met Asp Tyr Trp Gly Gln Gly Thr
            100                 105                 110

Ser Val Thr Val Ser Ser
        115
```

<210> SEQ ID NO 234
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 234

```
gacatccaga tgacccagag cccaagcagc ctgagcgcca cgtcggcga ccgcgtgacc       60
atcacctgcc gcgccagcca ggacatcggc aaccgcctgt cgtggctgca gcaggagcca     120
ggcaaggccc caaagcgcct gatctacgcc accagcagcc tggacagcgg tgtcccaagc     180
cgcttcagcg gcagccgcag cggcaccgag ttcaccctga ccatcagcag cctgcaacca     240
gaggacttcg tcacctacta ctgcctgcaa tacgccagca gcccattcac cttcggccag     300
ggcaccaagc tggagatcaa g                                               321
```

<210> SEQ ID NO 235
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 235

```
Gln Val Gln Leu Gln Gln Ser Gly Pro Glu Leu Val Lys Pro Gly Ala
1               5                   10                  15
Ser Val Lys Leu Ser Cys Lys Ala Ser Gly Tyr Thr Phe Thr Asp Tyr
            20                  25                  30
Ser Ile His Trp Val Lys Gln Ser Pro Gly Gln Gly Leu Glu Trp Ile
        35                  40                  45
Gly Trp Ile Tyr Pro Gly Ser Asp Asn Thr Lys Tyr Asn Asp Lys Phe
    50                  55                  60
Lys Gly Lys Ala Ser Met Thr Ala Asp Lys Ser Ser Arg Thr Val Tyr
65                  70                  75                  80
Met His Leu Ser Ser Leu Thr Ser Glu Glu Ser Ala Val Tyr Phe Cys
                85                  90                  95
Ala Arg Asp Tyr Arg Arg Tyr Tyr Ala Met Asp Tyr Trp Gly Gln Gly
            100                 105                 110
Thr Ser Val Thr Val Ser Ser
        115
```

<210> SEQ ID NO 236
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 236

```
caggtccagc tgcagcagtc tggacctgag ctggtgaagc ctggagcttc agtgaagctg     60
tcctgcaagg cttctggcta caccttcact gactatagta tacactgggt gaaacagagt    120
cctggacagg gacttgagtg gattggatgg atttatcctg gaagtgataa tactaagtac    180
aatgacaagt tcaagggcaa ggcctcaatg actgcagaca atcctccag aacagtctac     240
atgcacctca gcagcctgac gtctgaggaa tctgcggtct atttctgtgc aagagactac    300
cggcggtact atgctatgga ctactggggt caaggaacct cagtcaccgt ctcctca       357
```

<210> SEQ ID NO 237
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 237

```
caggtgcggc tgagggagtc aggacctggc ctggtggcgc cctcccagaa cctgttcatc     60
acatgcaccg tctcaggttt ctcattaact gactatgaaa taaactgggt tcgccagcct    120
ccaggaaaga atctggagtg gctgggagtg attggactg gtggaggcac aaaatataat     180
tcagttctca tatccagact gaacatcagc aaagacaatt ccaagagaca gttttctttt    240
aaaatgacca gtctccagac tgatgacaca gccatatatt actgtgtaag agaggggagg    300
agatactatg ctatggacta ctggggtcaa ggaacctcag tcaccgtctc ctca          354
```

<210> SEQ ID NO 238
<211> LENGTH: 118
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 238

Gln Val Arg Leu Arg Glu Ser Gly Pro Gly Leu Val Ala Pro Ser Gln
1               5                   10                  15

Asn Leu Phe Ile Thr Cys Thr Val Ser Gly Phe Ser Leu Thr Asp Tyr
            20                  25                  30

Glu Ile Asn Trp Val Arg Gln Pro Pro Gly Lys Asn Leu Glu Trp Leu
        35                  40                  45

Gly Val Ile Trp Thr Gly Gly Gly Thr Lys Tyr Asn Ser Val Leu Ile
    50                  55                  60

Ser Arg Leu Asn Ile Ser Lys Asp Asn Ser Lys Arg Gln Val Phe Phe
65                  70                  75                  80

Lys Met Thr Ser Leu Gln Thr Asp Asp Thr Ala Ile Tyr Tyr Cys Val
                85                  90                  95

Arg Glu Gly Arg Arg Tyr Tyr Ala Met Asp Tyr Trp Gly Gln Gly Thr
            100                 105                 110

Ser Val Thr Val Ser Ser
        115

<210> SEQ ID NO 239
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239
caggttactc tgaaagagtc tggccctggg atattgcagc cctcccagac cctcagtctg     60
acttgttctt tctctgggtt ttcactgagc acttttggta tgggtgtagg ctggattcgt    120
cagccttcag ggaagggtct ggagtggctg gcacacattt ggtgggatga tgataagtac    180
tataacccag ccctgaagag tcggctcaca atctccaagg atacctccaa aaaccaggta    240
ttcctcaaga tcgccaatgt ggacactgca gatactgcca catactactg tgctcgaata    300
gagggcccct actactggta cttcgatgtc tggggcacag ggaccacggt caccgtctcc    360
tca                                                                  363

<210> SEQ ID NO 240
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
```

```
                65                  70                  75                  80
Phe Leu Lys Ile Ala Asn Val Asp Thr Ala Asp Thr Ala Thr Tyr Tyr
                    85                  90                  95

Cys Ala Arg Ile Glu Gly Pro Tyr Tyr Trp Tyr Phe Asp Val Trp Gly
                    100                 105                 110

Thr Gly Thr Thr Val Thr Val Ser Ser
                115                 120
```

<210> SEQ ID NO 241
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241

```
caggtgcagc tgaaggagtc aggacctggc ctggtggcac cctcacagag cctgtccatc      60
acatgcacgg tctctggttt ctcattatcc agatatagtg tacactggat tcgtcagtct     120
ccaggaaagg gtctggagtg gctgggaatg atatggggggg gtggaaacac agactacaat     180
tcaggtctca aatccagact gagcatcagc aaggacaact ccaagagcca agttttctta     240
aaaatgaaca gtctggaaaa tgatgacaca gccatgtatt actgtgccag ccccctccctc     300 tattattatg atgttgcctg gtttccttac tggggccaag ggactctggt cactgtctct     360
gca                                                                    363
```

<210> SEQ ID NO 242
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
                20                  25                  30

Ser Val His Trp Ile Arg Gln Ser Pro Gly Lys Gly Leu Glu Trp Leu
            35                  40                  45

Gly Met Ile Trp Gly Gly Gly Asn Thr Asp Tyr Asn Ser Gly Leu Lys
        50                  55                  60

Ser Arg Leu Ser Ile Ser Lys Asp Asn Ser Lys Ser Gln Val Phe Leu
65                  70                  75                  80

Lys Met Asn Ser Leu Glu Asn Asp Asp Thr Ala Met Tyr Tyr Cys Ala
                85                  90                  95

Ser Pro Ser Leu Tyr Tyr Tyr Asp Val Ala Trp Phe Pro Tyr Trp Gly
                100                 105                 110

Gln Gly Thr Leu Val Thr Val Ser Ala
                115                 120
```

<210> SEQ ID NO 243
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 243

```
gaggttcagc tgcagcagtc tggggctgag cttgtgaggc caggggcctc agtcgagttg      60
tcctgcacag cttctggctt taatattaaa aacgactatt tgcactgggt gaagcagagg     120
cctgaacagg gcctggaatg gattggatgg attgattccg cgaatgataa gactaagtat     180
gccccgaagt tccaggacaa ggccactata actgcagacc catcctccaa cacagcctac     240
ctgcagctca gcagcctgac atctgaggac actgccgtct attactgtac tagagttggg     300
gttcaggatg ttactacgt tagggacttt gactactggg gccagggcac cactctcaca     360
gtctcctca                                                              369
```

<210> SEQ ID NO 244
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 244

```
Glu Val Gln Leu Gln Gln Ser Gly Ala Glu Leu Val Arg Pro Gly Ala
1               5                   10                  15
Ser Val Glu Leu Ser Cys Thr Ala Ser Gly Phe Asn Ile Lys Asn Asp
            20                  25                  30
Tyr Leu His Trp Val Lys Gln Arg Pro Glu Gln Gly Leu Glu Trp Ile
        35                  40                  45
Gly Trp Ile Asp Ser Ala Asn Asp Lys Thr Lys Tyr Ala Pro Lys Phe
    50                  55                  60
Gln Asp Lys Ala Thr Ile Thr Ala Asp Pro Ser Ser Asn Thr Ala Tyr
65                  70                  75                  80
Leu Gln Leu Ser Ser Leu Thr Ser Glu Asp Thr Ala Val Tyr Tyr Cys
                85                  90                  95
Thr Arg Val Gly Val Gln Asp Gly Tyr Tyr Val Arg Asp Phe Asp Tyr
            100                 105                 110
Trp Gly Gln Gly Thr Thr Leu Thr Val Ser Ser
        115                 120
```

<210> SEQ ID NO 245
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 245

```
gaggtgaagc tggtggagtc tggaggaggc ttggtacagc ctgggggttc tctgagtctc      60
tcctgtgcag gttctggatt caccttcagt gattactaca tgagctgggt ccgccagcct     120
ccagggaagg cacttgagtg gttggctttg attagaaaca agctcctggg ttacacaaca     180
gaatacagtg catctgtgaa gggtcgtttc accatctcca gagataattc ccaaagcatc     240
ctctatcttc aaatgaatgc cctgagacct gaggacagtg ccacttatta ctgtgcaaga     300
gtcttacgac gggcagactg cttagactac tggggccaag caccgctct cacagtctcc     360
tca                                                                    363
```

<210> SEQ ID NO 246

```
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Glu Val Lys Leu Val Glu Ser Gly Gly Gly Leu Val Gln Pro Gly Gly
1               5                   10                  15

Ser Leu Ser Leu Ser Cys Ala Gly Ser Gly Phe Thr Phe Ser Asp Tyr
            20                  25                  30

Tyr Met Ser Trp Val Arg Gln Pro Pro Gly Lys Ala Leu Glu Trp Leu
        35                  40                  45

Ala Leu Ile Arg Asn Lys Ala Pro Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Ala Leu Arg Pro Glu Asp Ser Ala Thr Tyr
                85                  90                  95

Tyr Cys Ala Arg Val Leu Arg Arg Ala Asp Cys Leu Asp Tyr Trp Gly
            100                 105                 110

Gln Gly Thr Ala Leu Thr Val Ser Ser
        115                 120

<210> SEQ ID NO 247
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
gtgcagctgg tggagtctgg gggaggctta gtgaagcctg agggtccct gaaactctcc      60 tgtgcagcct ctggattcac tttcagtagt tatgacatgt cttgggttcg ccagactcca     120
gagaagaggc tggagtgggt cgcagccatt aatagttatg gtgttaacac ctactatcca     180
gacactgtga aggaccgatt caccatctcc agagacaatg ccaagaacac cctgtacctg     240
caaatgagca gtctgaggtc tgaggacaca gccttgtatt actgtgcaag acttttaatt     300
gggccttatt actatgctat ggactactgg ggtcaaggaa cctcagtcac cgtctcctca     360

<210> SEQ ID NO 248
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Val Gln Leu Val Glu Ser Gly Gly Gly Leu Val Lys Pro Gly Gly Ser
1               5                   10                  15

Leu Lys Leu Ser Cys Ala Ala Ser Gly Phe Thr Phe Ser Ser Tyr Asp
            20                  25                  30

Met Ser Trp Val Arg Gln Thr Pro Glu Lys Arg Leu Glu Trp Val Ala
        35                  40                  45

Ala Ile Asn Ser Tyr Gly Val Asn Thr Tyr Tyr Pro Asp Thr Val Lys
    50                  55                  60
```

Asp Arg Phe Thr Ile Ser Arg Asp Asn Ala Lys Asn Thr Leu Tyr Leu
65                  70                  75                  80

Gln Met Ser Ser Leu Arg Ser Glu Asp Thr Ala Leu Tyr Tyr Cys Ala
                85                  90                  95

Arg Leu Leu Ile Gly Pro Tyr Tyr Ala Met Asp Tyr Trp Gly Gln
            100                 105                 110

Gly Thr Ser Val Thr Val Ser Ser
        115                 120

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Arg Ala Ser Glu Ser Val Asp Ser Tyr Gly Asn Ile Phe Met His
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Arg Ala Ser Lys Ser Val Ser Thr Ser Gly Tyr Ser Tyr Met His
1               5                   10                  15

<210> SEQ ID NO 251
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Lys Ala Ser Gln Asp Ile Asn Ser Tyr Leu Thr
1               5                   10

<210> SEQ ID NO 252
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Arg Cys Ser Gln Ser Leu Val His Ser Asn Gly Asn Thr Tyr Leu His
1               5                   10                  15

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

```
Lys Ala Ser Gln Asp Val Ala Thr Ala Val Ala
1               5                   10

<210> SEQ ID NO 254
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Lys Ala Ser Gln Asn Val Gly Ser Ala Val Val
1               5                   10

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Lys Ala Ser Gln Asn Val Gly Ala Ala Val Val
1               5                   10

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Lys Ala Ser Gln Asn Val Gly Ser Val Val Ala
1               5                   10

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Ala Ser Lys Gly Val Ser Thr Ser Ser Tyr Thr Phe Ile His
1               5                   10                  15

<210> SEQ ID NO 258
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Arg Ala Ser Gly Asn Ile His Asn Tyr Leu Ala
1               5                   10

<210> SEQ ID NO 259
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 259

Lys Ala Ser Gln Asn Val Gly Ala Ala Val Ala
1               5                   10

<210> SEQ ID NO 260
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Lys Ala Ser Gln Asp Ile His Ser Tyr Leu Ser
1               5                   10

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Lys Ala Ser Gln Asp Ile Asn Ser Tyr Leu Ser
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Arg Ser Ser Glu Asn Ile Tyr Ser Ser Leu Ala
1               5                   10

<210> SEQ ID NO 263
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Lys Ala Ser Gln Asn Val Gly Ser Ala Val Ala
1               5                   10

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Arg Ala Thr Lys Gly Val Ser Lys Ser Gly Tyr Ser Tyr Met His
1               5                   10                  15
```

```
<210> SEQ ID NO 265
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Arg Ala Ser Glu Ser Val Asp Ser Tyr Gly Asn Ser Leu Met His
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Arg Ala Ser Glu Ser Val Asp Arg Tyr Gly Asn Ser Leu Met His
1               5                   10                  15

<210> SEQ ID NO 267
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Lys Ala Ser Gln Asp Ile Asn Arg Tyr Leu Ser
1               5                   10

<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Arg Ala Ser Glu Ser Val Asp Asn Tyr Gly Asn Ser Phe Met His
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Arg Ala Thr Lys Gly Val Thr Lys Ser Gly Tyr Ser Tyr Ile His
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270
```

Arg Ala Ser Lys Ser Val Asp Ser Tyr Gly Thr Ser Phe Met His
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Arg Thr Ser Glu Ser Val Asp Ser Tyr Gly Asn Ser Phe Met Phe
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Arg Ala Ser Glu Ser Val Asp Ser Tyr Gly Asn Ser Phe Met Phe
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Arg Val Ser Glu Ser Val Asp Arg Tyr Ala Asp Ser Phe Met His
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Arg Ala Ser Glu Ser Val Asp Ser Tyr Gly Asn Ser Phe Ile His
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Arg Ala Ser Glu Ser Ile Asp Asn Tyr Gly Leu Ile Phe Met Ser
1               5                   10                  15

<210> SEQ ID NO 276
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 276

Leu Ala Ser Asn Leu Glu Ser
1               5

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Arg Ala Asn Arg Leu Val Ser
1               5

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Lys Val Ser Asp Arg Phe Ser
1               5

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Trp Ala Ser Thr Arg His Thr
1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ser Ala Ser Asn Arg Tyr Ser
1               5

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ser Ala Ser Asn Arg Tyr Ile
1               5
```

<210> SEQ ID NO 282
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Tyr Ala Ser Asn Leu Glu Ser
1               5

<210> SEQ ID NO 283
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ser Ala Ile Thr Leu Ala Asp
1               5

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Thr Asn Arg Leu Val Asp
1               5

<210> SEQ ID NO 285
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Arg Ala Asn Arg Leu Val Asp
1               5

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ala Ala Thr Asn Leu Ala Lys
1               5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 287

Ile Ala Ser Asn Leu Glu Ser
1               5

<210> SEQ ID NO 288
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Leu Ala Ser Asn Leu Gln Ser
1               5

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Leu Thr Ser Asn Leu Glu Ser
1               5

<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Arg Ala Ser Asn Leu Asn Ser
1               5

<210> SEQ ID NO 291
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Ala Ser Asn Arg Gly Ser
1               5

<210> SEQ ID NO 292
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Asn Ala Lys Thr Leu Ala Asp
1               5

<210> SEQ ID NO 293
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 293

Gln Gln Asn Asn Glu Ala Pro Trp Thr
1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Leu Gln Tyr Asp Glu Phe Pro Tyr Thr
1               5

<210> SEQ ID NO 295
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ser Gln Ser Thr His Val Pro Leu Thr
1               5

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gln Gln Tyr Ser Asn Tyr Pro Tyr Thr
1               5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Leu Gln Tyr Ala Ser Tyr Pro Phe Thr
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gln Gln Tyr Ser Asn Tyr Pro Leu Thr
1               5
```

```
<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gln Gln Tyr Ser Ser Tyr Pro Leu Thr
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gln His Ser Arg Glu Phe Pro Arg Thr
1               5

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gln His Phe Trp Asn Thr Pro Tyr Thr
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gln His Phe Trp Gly Ser Pro Phe Ala
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gln Gln Tyr Ala Ser Tyr Pro Leu Thr
1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 304

Gln His Ser Arg Glu Leu Pro Leu Thr
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gln Gln Asn Ser Glu Asp Pro Arg Thr
1               5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gln Gln Asn Asn Glu Asp Pro Arg Thr
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gln Gln Ser Asn Glu Asp Pro Arg Thr
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gln Gln Asn Lys Glu Asp Pro Tyr Thr
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

His Gln Asn Asn Glu Asp Pro Arg Thr
1               5

<210> SEQ ID NO 310
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gln Gln Ser Lys Glu Val Pro Trp Thr
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gln His Phe Trp Ser Thr Pro Tyr Thr
1               5

<210> SEQ ID NO 312
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Tyr Thr Phe Thr Ser Asp Asp Ile Asn
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gly Tyr Thr Ile Thr Ser Tyr Val Met His
1               5                   10

<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Tyr Thr Phe Pro Gly Tyr Trp Met His
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gly Phe Asn Ile Lys Asp Asp Tyr Met His
```

```
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gly Tyr Ile Phe Thr Ser His Trp Met Gln
1               5                   10

<210> SEQ ID NO 317
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gly Phe Ser Leu Arg Thr Phe Gly Met Gly Val Gly
1               5                   10

<210> SEQ ID NO 318
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Gly Phe Ser Met Arg Thr Phe Gly Met Gly Val Gly
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gly Tyr Thr Phe Thr Asn Asp Asn Tyr Trp Met Asn
1               5                   10

<210> SEQ ID NO 320
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gly Phe Ser Phe Ser Asp Tyr Asn Ile Asn
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 321

Gly Tyr Ser Leu Ile Ser Tyr Tyr Ile His
1               5                   10

<210> SEQ ID NO 322
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gly Phe Ser Leu Lys Thr Phe Gly Met Gly Val Gly
1               5                   10

<210> SEQ ID NO 323
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Gly Tyr Ser Leu Thr Ser Tyr Tyr Ile His
1               5                   10

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Gly Phe Ser Leu Asn Thr Tyr Gly Met Gly Val Gly
1               5                   10

<210> SEQ ID NO 325
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Gly Tyr Thr Phe Thr Asp Lys Tyr Ile Asn
1               5                   10

<210> SEQ ID NO 326
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Tyr Thr Phe Thr Asp Tyr Ser Ile His
1               5                   10

<210> SEQ ID NO 327

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gly Tyr Thr Phe Thr Ser Tyr Val Met His
1               5                   10

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gly Tyr Thr Phe Ser Asp Tyr Thr Ile His
1               5                   10

<210> SEQ ID NO 329
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Tyr Thr Phe Thr Asp Asn Phe Ile Asn
1               5                   10

<210> SEQ ID NO 330
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gly Phe Ser Leu Thr Asp Tyr Glu Ile Asn
1               5                   10

<210> SEQ ID NO 331
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gly Phe Ser Leu Thr Thr Tyr Glu Ile Asn
1               5                   10

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332
```

Gly Tyr Thr Phe Thr Ser Tyr Val Ile His
1               5                   10

<210> SEQ ID NO 333
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gly Phe Ser Leu Ser Arg Tyr Ser Val His
1               5                   10

<210> SEQ ID NO 334
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gly Phe Asn Ile Lys Asn Asp Tyr Leu His
1               5                   10

<210> SEQ ID NO 335
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gly Phe Thr Phe Ser Asp Tyr Tyr Met Ser
1               5                   10

<210> SEQ ID NO 336
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gly Phe Thr Phe Ser Ser Tyr Asp Met Ser
1               5                   10

<210> SEQ ID NO 337
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Trp Ile Tyr Pro Arg Asp Gly Arg Thr Lys Tyr Asn Glu Lys Phe Lys
1               5                   10                  15

Gly

<210> SEQ ID NO 338
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 338

Tyr Ile Asn Pro Asn Asn Asp Gly Thr Lys Tyr Asn Glu Lys Phe Lys
1               5                   10                  15

Gly

<210> SEQ ID NO 339
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Lys Ile Asp Pro Ser Asp Ser Glu Thr His Tyr Asn Gln Asn Phe Lys
1               5                   10                  15

Asp

<210> SEQ ID NO 340
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Arg Ile Asp Pro Ala Tyr Gly Asn Gly Lys Tyr Val Pro Lys Phe Gln
1               5                   10                  15

Asp

<210> SEQ ID NO 341
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Asp Ile Phe Pro Gly Ser Gly Thr Thr Asp Tyr Asn Glu Lys Phe Lys
1               5                   10                  15

Asp

<210> SEQ ID NO 342
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

His Ile Trp Trp Asn Gly Asp Lys Tyr Tyr Asp Pro Ala Leu Lys Ser
1               5                   10                  15

<210> SEQ ID NO 343
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 343

His Ile Trp Trp Asn Asp Glu Lys Tyr Tyr Asn Pro Asp Leu Lys Ser
1               5                   10                  15

<210> SEQ ID NO 344
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

His Ile Trp Trp Asn Asp Lys Ser Ser His Pro Ala Leu Lys Ser
1               5                   10                  15

<210> SEQ ID NO 345
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Arg Ile Arg Pro Ser Asp Ser Glu Thr His Tyr Asn Gln Lys Phe Thr
1               5                   10                  15

Asn

<210> SEQ ID NO 346
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Lys Val His Pro Lys Asp Gly Thr Ala Thr Tyr Asn Gln Lys Phe Gln
1               5                   10                  15

Asp

<210> SEQ ID NO 347
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

His Ile Trp Trp Asn Asp Glu Lys Tyr Tyr Asn Pro Ala Leu Lys Ser
1               5                   10                  15

<210> SEQ ID NO 348
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348
```

```
Leu Thr Phe Pro Gly Ser Gly Asn Ser Lys Phe Ile Glu Lys Phe Lys
 1               5                  10                  15

Gly

<210> SEQ ID NO 349
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

His Ile Trp Trp Asn Asp Asp Lys Phe Tyr His Pro Ala Leu Lys Ser
 1               5                  10                  15

<210> SEQ ID NO 350
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Leu Ile Phe Pro Gly Ser Gly Asn Ser Lys Tyr Ile Glu Lys Phe Lys
 1               5                  10                  15

Gly

<210> SEQ ID NO 351
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asn Ile Trp Trp Asn Asp Asp Lys Tyr Tyr Asn Ser Ala Leu Lys Ser
 1               5                  10                  15

<210> SEQ ID NO 352
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

His Ile Trp Trp Asn Asp Glu Lys Tyr Tyr Asn Pro Thr Leu Lys Ser
 1               5                  10                  15

<210> SEQ ID NO 353
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Trp Ile Tyr Pro Gly Ser Gly Asn Thr Lys Tyr Asn Glu Lys Phe Lys
 1               5                  10                  15

Gly
```

```
<210> SEQ ID NO 354
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Trp Ile Tyr Pro Gly Ser Gly Asn Thr Lys Tyr Asn Asp Lys Phe Lys
1               5                   10                  15

Gly

<210> SEQ ID NO 355
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Trp Ile Tyr Pro Gly Ser Asp Asn Thr Lys Tyr Asn Asp Lys Phe Lys
1               5                   10                  15

Gly

<210> SEQ ID NO 356
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Tyr Leu Asn Pro Asn Asn Asp Gly Thr Lys Tyr Asn Glu Lys Phe Lys
1               5                   10                  15

Gly

<210> SEQ ID NO 357
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Trp Ile Tyr Pro Gly Arg Gly Asn Thr Lys Tyr Asn Asp Lys Phe Lys
1               5                   10                  15

Gly

<210> SEQ ID NO 358
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Trp Ile Ser Pro Gly Ser Gly Asn Thr Lys Asn Asn Glu Lys Phe Lys
1               5                   10                  15
```

Gly

<210> SEQ ID NO 359
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Val Ile Trp Thr Gly Gly Thr Lys Tyr Asn Ser Val Leu Ile Ser
1               5                   10                  15

<210> SEQ ID NO 360
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Val Ile Trp Thr Gly Gly Thr Thr Lys Tyr Asn Ser Ala Phe Ile Ser
1               5                   10                  15

<210> SEQ ID NO 361
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Tyr Leu His Arg Asn Asn Asp Gly Thr Lys Tyr Asn Glu Lys Phe Lys
1               5                   10                  15
Val

<210> SEQ ID NO 362
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Val Ile Trp Thr Gly Gly Thr Thr Lys Tyr Asn Ser Ala Phe Ile Ser
1               5                   10                  15

<210> SEQ ID NO 363
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

His Ile Trp Trp Asp Asp Asp Lys Tyr Tyr Asn Pro Ala Leu Lys Ser
1               5                   10                  15

<210> SEQ ID NO 364
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Met Ile Trp Gly Gly Gly Asn Thr Asp Tyr Asn Ser Gly Leu Lys Ser
1               5                   10                  15

<210> SEQ ID NO 365
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Trp Ile Asp Ser Ala Asn Asp Lys Thr Lys Tyr Ala Pro Lys Phe Gln
1               5                   10                  15

Asp

<210> SEQ ID NO 366
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Leu Ile Arg Asn Lys Ala Pro Gly Tyr Thr Thr Glu Tyr Ser Ala Ser
1               5                   10                  15

Val Lys Gly

<210> SEQ ID NO 367
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ala Ile Asn Ser Tyr Gly Val Asn Thr Tyr Tyr Pro Asp Thr Val Lys
1               5                   10                  15

Asp

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ser Arg Arg Val Tyr Ala Met Asp Tyr
1               5

<210> SEQ ID NO 369
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gly Asp Tyr Ser Asn Tyr Phe Tyr Trp Tyr Phe Asp Val
1               5                   10

<210> SEQ ID NO 370
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Glu Gly Trp Asp Ser Leu Thr Lys Val Trp Phe Gly Trp
1               5                   10

<210> SEQ ID NO 371
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Arg Tyr Tyr Ala Val Ser Ser Val Asp Tyr Ala Leu Asp Tyr
1               5                   10

<210> SEQ ID NO 372
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ile Gly Pro Ser Ile Thr Thr Val Ala Glu Gly Phe Ala Tyr
1               5                   10

<210> SEQ ID NO 373
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Val Gly Pro Ser Ile Ser Thr Val Ala Glu Gly Phe Pro Tyr
1               5                   10

<210> SEQ ID NO 374
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Val Gly Pro Ser Ile Ser Thr Ile Ala Glu Gly Phe Pro Tyr
1               5                   10

<210> SEQ ID NO 375
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ser Trp Glu Asp Leu Leu Leu Arg Ser Met Glu Asp Tyr Phe Asp Tyr
1               5                   10                  15

<210> SEQ ID NO 376
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Leu Tyr Tyr Asp Ser Leu Thr Lys Ile Leu Phe Ala Tyr
1               5                   10

<210> SEQ ID NO 377
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Leu Gly Pro Ser Ile Thr Thr Val Ala Glu Gly Phe Pro Tyr
1               5                   10

<210> SEQ ID NO 378
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gly Asp Phe Gly Asn Tyr Leu Ala Tyr Trp Tyr Phe Asp Val
1               5                   10

<210> SEQ ID NO 379
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Val Ala Ala Thr Ile Val Thr Thr Tyr Gly Ala Trp Phe Ala Tyr
1               5                   10                  15

<210> SEQ ID NO 380
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Ile Gly Pro Ser Ile Thr Thr Val Val Glu Gly Phe Pro Tyr
```

```
1               5                  10
```

<210> SEQ ID NO 381
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

```
Gly Ile Ile Tyr Tyr Tyr Asp Gly Ser Tyr Pro Tyr Ala Leu Asp Tyr
1               5                   10                  15
```

<210> SEQ ID NO 382
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

```
Asp Tyr Arg Arg Tyr Tyr Ala Ile Asp Tyr
1               5                  10
```

<210> SEQ ID NO 383
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

```
Asp Tyr Arg Arg Tyr Tyr Ala Met Asp Tyr
1               5                  10
```

<210> SEQ ID NO 384
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

```
Gly Ile Ile Tyr Tyr Tyr Asp Gly Thr Tyr Pro Tyr Ala Leu Asp Tyr
1               5                   10                  15
```

<210> SEQ ID NO 385
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

```
Glu Gly Arg Arg Tyr Tyr Ala Met Asp Tyr
1               5                  10
```

<210> SEQ ID NO 386
<211> LENGTH: 13
<212> TYPE: PRT
<213> ORGANISM: Artificial Sequence
<220> FEATURE:
<223> OTHER INFORMATION: Description of Artificial Sequence: Synthetic

```
                               peptide

<400> SEQUENCE: 386

Gly Asp Tyr Ser Asn Tyr Phe Tyr Trp Tyr Phe Asp Val
1               5                   10

<210> SEQ ID NO 387
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ile Glu Gly Pro Tyr Tyr Trp Tyr Phe Asp Val
1               5                   10

<210> SEQ ID NO 388
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Pro Ser Leu Tyr Tyr Tyr Asp Val Ala Trp Phe Pro Tyr
1               5                   10

<210> SEQ ID NO 389
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Val Gly Val Gln Asp Gly Tyr Tyr Val Arg Asp Phe Asp Tyr
1               5                   10

<210> SEQ ID NO 390
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Val Leu Arg Arg Ala Asp Cys Leu Asp Tyr
1               5                   10

<210> SEQ ID NO 391
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Leu Leu Ile Gly Pro Tyr Tyr Tyr Ala Met Asp Tyr
1               5                   10

<210> SEQ ID NO 392
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gly Phe Ser Leu Ser Thr Phe Gly Met Gly Val Gly
1               5                   10

<210> SEQ ID NO 393
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 393
gacatccaga tgacccagag cccaagcagc ctgagcgcca gcgtcggcga ccgcgtgacc    60
atcacctgcc gcgccagcca ggacatcggc aaccgcctga actggtacca gcagaagcca   120
ggcaaggccc caaagcgcct gatctacgcc accagcagcc tggacagcgg tgtcccaagc   180
cgcttcagcg gcagccgcag cggcaccgag ttcaccctga ccatcagcag cctgcaacca   240
gaggacttcg tcacctacta ctgcctgcaa tacgccagca gcccattcac cttcggccag   300
ggcaccaagc tggagatcaa g                                              321

<210> SEQ ID NO 394
<211> LENGTH: 320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 394
gacatccaga tgacccagag cccaagcagc ctgagcgcca gcgtcggcga ccgcgtgagc    60
atcacctgca aggccagcca gaacgccggc atcgacgtgg cttggttcca gcagaagcct   120
ggcaaggccc caaagctgct gatctacagc aagagcaacc gctacacggc gtgccaagcc   180
gcttcagcgg cagcggcagc ggcaccgact tcaccctgac catcagcagc tccagccag    240 aggacttcgc cacctactac tgcctccagt accgcagcta cccacgcacc ttcggccagg   300
gcaccaagct ggagatcaag                                                320

<210> SEQ ID NO 395
<211> LENGTH: 320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 395
gacatccaga tgacccagag cccaagcagc ctgagcgcca gcgtcggcga ccgcgtgagc    60
atcacctgca aggccagcca gaacgccggc atcgacgtgg cttggttcca gcagaagctg   120
gcaaggcccc aaagctgctg atctacagca agagcaaccg ctacaccggc gtgccaagcc   180
gcttcagcgg cagcggcagc ggcaccgact tcaccctgac catcagcagc tccagccag    240 aggacttcgc cgactactac tgcctccagt accgcagcta cccacgcacc ttcggcggcg   300
```

```
gcaccaagct ggagatcaag                                                  320
```

<210> SEQ ID NO 396
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396

```
caggtgcagc tggtgcagag cggcgccgag gtgaagaagc caggcagcag cgtgaaggtc     60
agctgcaagg cccccgacca catcttcagc atccactgga tgcagtgggt ccgccaagcc    120
ccaggccagg gcctggagtg gatgggcgag attttcccag gcagcggcac caccgactac    180
aacgagaagt tcaagggcaa ggtgaccatc accgtcgaca gagcaccag caccgcctac    240 atggagctga gcagcctgcg cagcgaggac accgccgtct actactgcgc cagcggcgcc    300
ttcgactact ggggccaggg caccaccgtg accgtgagca gc                       342
```

<210> SEQ ID NO 397
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 397

```
caggtgcagc tggtgcagag cggcgctgag gtgaagaagc caggcgccag cgtgaaggtg     60
agctgcaagg ccagcggcta cagcttcagc accttcttca tccactgggt ccgccaacgc    120
ccaggccagg gcctggagtg gatcggccgc atcgacccaa acagcggcgc caccaagtac    180
aacgagaagt tcgagagcaa ggtcaccctg accgcgaca ccagcatcag caccgcctac    240
atggagctga gccgcctgcg cagcgacgac accgccgtct actactgcgc ccgcggcgag    300
gacctgctga tccgcaccga cgccctggat tactggggtc agggtactag cgtgaccgtg    360
agcagc                                                              366
```

<210> SEQ ID NO 398
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 398

```
caggtgcagc tggtgcagag cggcgctgag gtgaagaagc caggcgccag cgtgaaggtg     60
agctgcaagg ccagcggcta cagcttcagc accttcttca tccactgggt ccgccaagcc    120
ccaggccagg gcctggagtg gatcggccgc atcgacccaa acagcggcgc caccaagtac    180
aacgagaagt tcgagagccg cgtcaccatg accgcgaca ccagcatcag caccgcctac    240
atggagctga gccgcctgcg cagcgacgac accgccgtct actactgcgc ccgcggcgag    300
gacctgctga tccgcaccga cgccctggat tactggggtc agggtactag cgtgaccgtg    360
agcagc                                                              366
```

<210> SEQ ID NO 399
<211> LENGTH: 227
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 399

```
His His His His His Glu Asn Leu Tyr Phe Gln Gly Leu Gln Gly
1               5                   10                  15

Asp Leu Ala Ser Leu Arg Ala Glu Leu Gln Gly His His Ala Glu Lys
            20                  25                  30

Leu Pro Ala Gly Ala Gly Ala Pro Lys Ala Gly Leu Glu Glu Ala Pro
        35                  40                  45

Ala Val Thr Ala Gly Leu Lys Ile Phe Glu Pro Pro Ala Pro Gly Glu
    50                  55                  60

Gly Asn Ser Ser Gln Asn Ser Arg Asn Lys Arg Ala Val Gln Gly Pro
65                  70                  75                  80

Glu Glu Thr Val Thr Gln Asp Cys Leu Gln Leu Ile Ala Asp Ser Glu
                85                  90                  95

Thr Pro Thr Ile Gln Lys Gly Ser Tyr Thr Phe Val Pro Trp Leu Leu
            100                 105                 110

Ser Phe Lys Arg Gly Ser Ala Leu Glu Glu Lys Glu Asn Lys Ile Leu
        115                 120                 125

Val Lys Glu Thr Gly Tyr Phe Phe Ile Tyr Gly Gln Val Leu Tyr Thr
    130                 135                 140

Asp Lys Thr Tyr Ala Met Gly His Leu Ile Gln Arg Lys Lys Val His
145                 150                 155                 160

Val Phe Gly Asp Glu Leu Ser Leu Val Thr Leu Phe Arg Cys Ile Gln
                165                 170                 175

Asn Met Pro Glu Thr Leu Pro Asn Asn Ser Cys Tyr Ser Ala Gly Ile
            180                 185                 190

Ala Lys Leu Glu Glu Gly Asp Glu Leu Gln Leu Ala Ile Pro Arg Glu
        195                 200                 205

Asn Ala Gln Ile Ser Leu Asp Gly Asp Val Thr Phe Phe Gly Ala Leu
    210                 215                 220

Lys Leu Leu
225
```

<210> SEQ ID NO 400
<211> LENGTH: 151
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 400

```
Ala Val Gln Gly Pro Glu Glu Thr Val Thr Gln Asp Cys Leu Gln Leu
1               5                   10                  15

Ile Ala Asp Ser Glu Thr Pro Thr Ile Gln Lys Gly Ser Tyr Thr Phe
            20                  25                  30

Val Pro Trp Leu Leu Ser Phe Lys Arg Gly Ser Ala Leu Glu Glu Lys
        35                  40                  45

Glu Asn Lys Ile Leu Val Lys Glu Thr Gly Tyr Phe Phe Ile Tyr Gly
    50                  55                  60

Val Leu Tyr Thr Asp Lys Thr Tyr Ala Met Gly His Leu Ile Gln Arg
65                  70                  75                  80

Lys Lys Val His Val Phe Gly Asp Glu Leu Ser Leu Val Thr Leu Phe
```

```
                    85                  90                  95

Arg Cys Ile Gln Asn Met Pro Glu Thr Leu Pro Asn Asn Ser Cys Tyr
                100                 105                 110

Ser Ala Gly Ile Ala Lys Leu Glu Glu Gly Asp Glu Leu Gln Leu Ala
            115                 120                 125

Ile Pro Arg Glu Asn Ala Gln Ile Ser Leu Asp Gly Asp Val Thr Phe
130                 135                 140

Phe Gly Ala Leu Lys Leu Leu
145                 150

<210> SEQ ID NO 401
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

His His His His His Glu Asn Leu Tyr Phe Gln Gly Ala Val Gln
1               5                   10                  15

Gly Pro Glu Glu Thr Val Thr Gln Asp Cys Leu Gln Leu Ile Ala Asp
            20                  25                  30

Ser Glu Thr Pro Thr Ile Gln Lys Gly Ser Tyr Thr Phe Val Pro Trp
        35                  40                  45

Leu Leu Ser Phe Lys Arg Gly Ser Ala Leu Glu Glu Lys Glu Asn Lys
    50                  55                  60

Ile Leu Val Lys Glu Thr Gly Tyr Phe Phe Ile Tyr Gly Val Leu Tyr
65                  70                  75                  80

Thr Asp Lys Thr Tyr Ala Met Gly His Leu Ile Gln Arg Lys Lys Val
                85                  90                  95

His Val Phe Gly Asp Glu Leu Ser Leu Val Thr Leu Phe Arg Cys Ile
                100                 105                 110

Gln Asn Met Pro Glu Thr Leu Pro Asn Asn Ser Cys Tyr Ser Ala Gly
            115                 120                 125

Ile Ala Lys Leu Glu Glu Gly Asp Glu Leu Gln Leu Ala Ile Pro Arg
        130                 135                 140

Glu Asn Ala Gln Ile Ser Leu Asp Gly Asp Val Thr Phe Phe Gly Ala
145                 150                 155                 160

Leu Lys Leu Leu

<210> SEQ ID NO 402
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Met Ala Val Gln Gly Pro Glu Glu Thr Val Thr Gln Asp Cys Leu Gln
1               5                   10                  15

Leu Ile Ala Asp Ser Glu Thr Pro Thr Ile Gln Lys Gly Ser Tyr Thr
            20                  25                  30

Phe Val Pro Trp Leu Leu Ser Phe Lys Arg Gly Ser Ala Leu Glu Glu
        35                  40                  45

Lys Glu Asn Lys Ile Val Lys Glu Thr Gly Tyr Phe Phe Ile Tyr Gly
    50                  55                  60
```

```
Gln Val Leu Tyr Thr Asp Lys Thr Tyr Ala Met Gly His Leu Ile Gln
 65                  70                  75                  80

Arg Lys Lys Val His Val Phe Gly Asp Glu Leu Ser Leu Val Thr Leu
                 85                  90                  95

Phe Arg Cys Ile Gln Asn Met Pro Glu Thr Leu Pro Asn Asn Ser Cys
            100                 105                 110

Tyr Ser Ala Gly Ile Ala Lys Leu Glu Glu Gly Asp Glu Leu Gln Leu
        115                 120                 125

Ala Ile Pro Arg Glu Asn Ala Gln Ile Ser Leu Asp Gly Asp Val Thr
    130                 135                 140

Phe Phe Gly Ala Leu Lys Leu Leu
145                 150

<210> SEQ ID NO 403
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Ile Ala Asp Ser Glu Thr Pro Thr Ile Gln Lys Gly Ser Tyr Thr
1               5                   10                  15

<210> SEQ ID NO 404
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Tyr Thr Asp Lys Thr Tyr Ala Met Gly His Leu Ile Gln Arg Lys Lys
1               5                   10                  15

Val His Val Phe Gly Asp Glu
            20

<210> SEQ ID NO 405
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Leu Gln Leu Ala Ile Pro Arg Glu Asn Ala Gln Ile
1               5                   10

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Ile Ser Leu Asp Gly Asp Val Thr Phe
1               5
```

```
<210> SEQ ID NO 407
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 407

His His His His His His
1               5
```